(12) United States Patent
Touti et al.

(10) Patent No.: US 11,604,193 B2
(45) Date of Patent: Mar. 14, 2023

(54) EX VIVO PROTEASE ACTIVITY DETECTION FOR DISEASE DETECTION/DIAGNOSTIC, STAGING, MONITORING AND TREATMENT

(71) Applicant: Glympse Bio, Inc., Cambridge, MA (US)

(72) Inventors: Faycal Touti, Belmont, MA (US); Wendy Winckler Adamovich, Melrose, MA (US); Sophie Cazanave, Cambridge, MA (US); Mehar Cheema, Medford, MA (US); Robert S. Langer, Newton, MA (US)

(73) Assignee: GLYMPSE BIO, INC., Cambridge, MA (US)

( * ) Notice: Subject to any disclaimer, the term of this patent is extended or adjusted under 35 U.S.C. 154(b) by 0 days.

(21) Appl. No.: 17/573,129

(22) Filed: Jan. 11, 2022

(65) Prior Publication Data
US 2022/0178935 A1    Jun. 9, 2022

Related U.S. Application Data

(63) Continuation-in-part of application No. PCT/US2021/049948, filed on Sep. 10, 2021.
(Continued)

(51) Int. Cl.
*G01N 33/58*       (2006.01)
*G01N 33/573*     (2006.01)
(Continued)

(52) U.S. Cl.
CPC ....... *G01N 33/573* (2013.01); *G01N 21/6428* (2013.01); *G01N 33/542* (2013.01);
(Continued)

(58) Field of Classification Search
CPC ............ G01N 33/582; G01N 21/6428; G01N 2021/6432; G01N 2021/6441; G01N 2800/085
See application file for complete search history.

(56) References Cited

U.S. PATENT DOCUMENTS 10,100,198 B2 * 10/2018 Kundu .................. C09B 23/083
10,619,219 B2 *  4/2020 McNamara ............ C12Q 1/689
(Continued)

FOREIGN PATENT DOCUMENTS

ES              2325584 T3 *  9/2009  ......... A61K 39/0011
WO      WO-2008018933 A2    2/2008
(Continued)

OTHER PUBLICATIONS

Fluorescent Labeling of (Oligo)Nucleotides by a New Fluoride Cleavable Linker Capable of Versatile Attachment Modes, to Knapp et al.; Bioconjugate Chem. 2010, 21, 1043-1055.*
(Continued)

*Primary Examiner* — Mohamed K Amara
(74) *Attorney, Agent, or Firm* — Wilson Sonsini Goodrich & Rosati

(57) ABSTRACT

The present application provides compositions and methods for determining a disease or condition in a subject. The method comprises contacting a body fluid with a molecule comprising a reporter thereof and the reported is cleaved by an agent in the body fluid. Diseases and conditions that can be determined by the method are also described.

17 Claims, 58 Drawing Sheets

Specification includes a Sequence Listing.

Related U.S. Application Data

(60) Provisional application No. 63/077,525, filed on Sep. 11, 2020.

(51) Int. Cl.
  *G01N 21/64* (2006.01)
  *G01N 33/542* (2006.01)

(52) U.S. Cl.
  CPC .............. *G01N 33/582* (2013.01); *G01N 2021/6432* (2013.01); *G01N 2021/6439* (2013.01); *G01N 2021/6441* (2013.01); *G01N 2333/95* (2013.01); *G01N 2800/085* (2013.01); *G01N 2800/26* (2013.01)

(56) References Cited

U.S. PATENT DOCUMENTS

| | | | |
|---|---|---|---|
| 2004/0236091 A1* | 11/2004 | Chicz | C07K 14/47 435/6.16 |
| 2005/0191680 A1 | 9/2005 | Bruno et al. | |
| 2010/0124757 A1 | 5/2010 | Kwon et al. | |
| 2011/0189680 A1 | 8/2011 | Keown et al. | |
| 2015/0133752 A1 | 5/2015 | Iverson et al. | |
| 2017/0114116 A1* | 4/2017 | Linderoth | A61P 3/04 |
| 2019/0064167 A1 | 2/2019 | Ahrens et al. | |
| 2019/0128873 A1 | 5/2019 | Bhatia et al. | |
| 2019/0345534 A1 | 11/2019 | Kwong et al. | |
| 2020/0096514 A1 | 3/2020 | Bhatia et al. | |
| 2021/0253734 A1* | 8/2021 | Lu | G01N 33/6893 |
| 2022/0128567 A1* | 4/2022 | Touti | G01N 33/542 |

FOREIGN PATENT DOCUMENTS

| | | | | |
|---|---|---|---|---|
| WO | WO-2009111470 A2 | 9/2009 | | |
| WO | WO-2015148622 A1 | 10/2015 | | |
| WO | WO-2017139254 A1 * | 8/2017 | ......... | G01N 33/6893 |
| WO | WO-2018064383 A1 | 4/2018 | | |
| WO | WO-2019236992 A9 * | 1/2020 | .............. | C12Q 1/37 |

OTHER PUBLICATIONS

"Barchetta, et al. "Circulating dipeptidyl peptidase-4 is independently associated with the presence and severtiy of NAFLD/NASH in individuals with and without obesity and metabolic disease" Journal of Endocrinological Inverstigation (2021) 44: 979-988".

"International Search Report and Written Opinion for PCT Application No. PCT/US2017/054105, dated Jan. 18, 2018".

"Kalubowilage, et al., "Early detection of pancreatic cancewrs in liquid biopsies by ultrasensitive fluorescence nanobiosensors" Nanomedicine: Nanotechnology, Biology, and Medicine 14 (2018) 1823-1832".

"Matheeussen, et al., "Method comparison of dipeptidyl peptidase IV activity assays and their applications in biological samples containing reversible inhibitors" Clinica Chimica Acta 413 (212) 456-462".

"Udukala, et al. "Early detection of non-small cell lung cancer in liquid biopsies by ultrasensitive protease activity analysis" J Cancer Metastasis Treat (2020); 6;25".

International Search Report and Written Opinion issued in PCT/US2021/049948 dated Feb. 28, 2022.

May 13, 2022 Non-Final Office Action U.S. Appl. No. 17/573,129.

Jun. 27, 2022 Non-Final Office Action U.S. Appl. No. 17/573,110.

Canal et al., Drug delivery properties of macroporous polystyrene solid foams. J Pharm Pharm Sci. 2012;15(1):197-207. doi: 10.18433/j3x884. PMID: 22365097.

Dovgan et al. On the use of DNA as a linker in antibody-drug conjugates: synthesis, stability and in vitro potency. Sci Rep 10, 7691 (2020).

Chi, Qingjia et al. "DNA Nanostructure as an Efficient Drug Delivery Platform for Immunotherapy." Frontiers in pharmacology vol. 10 1585. Jan. 28, 2020, doi:10.3389/fphar.2019.01585.

Gonzaga et al., Perspectives About Self-lmmolative Drug Delivery Systems. J Pharm Sci. Nov. 2020;109(11):3262-3281.doi: 10.1016/j.xphs.2020.08.014. Epub Aug. 27, 2020. PMID: 32860799.

Ho et al., A self-immolative reporter for beta-galactosidase sensing. Chembiochem. Mar. 26, 2007;8(5):560-6. doi: 10.1002/cbic.200600386. PMID: 17300128.

Karan et al., Near-Infrared Fluorescent Probe Activated by Nitroreductase for In Vitro and In Vivo Hypoxic Tumor Detection. J Med Chern. Mar. 25, 2021;64(6):2971-2981. doi: 10.1021/acs.jmedchem.0c02162. Epub Mar. 12, 2021. PMID: 33711229.

Knapp et al., Fluorescent labeling of (oligo)nucleotides by a new fluoride cleavable linker capable of versatile attachment modes. Bioconjug Chem. Jun. 16, 2010;21(6):1043-55. doi: 10.1021/bc900542f. PMID: 20509599.

Leriche et al., Cleavable linkers in chemical biology. Bioorg Med Chem. Jan. 15, 2012;20(2):571-82. doi: 10.1016/j.bmc.2011.07.048. Epub Jul. 30, 2011. PMID: 21880494.

Li et al., In Situ Imaging of Furin Activity with a Highly Stable Probe by Releasing of Precipitating Fluorochrome. Anal Chem. Oct. 2, 2018;90(19):11680-11687. doi: 10.1021/acs.analchem.8b03335. Epub Sep. 19, 2018. PMID: 30191711.

Liu et al., In Situ Localization of Enzyme Activity in Live Cells by a Molecular Probe Releasing a Precipitating Fluorochrome. Angew Chem Int Ed Engl. Sep. 18, 2017;56(39):11788-11792. doi: 10.1002/anie.201705747. Epub Aug. 15, 2017. PMID: 28755456.

Panchal, Rekha G et al. "Peptide conjugated phosphorodiamidate morpholino oligomers increase survival of mice challenged with Ames Bacillus anthracis." Nucleic acid therapeutics vol. 22,5 (2012): 316-22. doi:10.1089/nat.2012.0362.

S. Hong et al., Protein-Based Nanoparticles as Drug Delivery Systems. Pharmaceutics. Jun. 29, 2020;12(7):604.doi: 10.3390/pharmaceutics12070604. PMID: 32610448; PMCID: PMC7407889.

Tung et al., In vivo imaging of beta-galactosidase activity using far red fluorescent switch. Cancer Res. Mar. 1, 2004;64(5):1579-83. doi: 10.1158/0008-5472.can-03-3226. PMID: 14996712.

Y. Malam et al., Liposomes and nanoparticles: nanosized vehicles fordrug delivery in cancer. Trends Pharmacol Sci. Nov. 2009;30(11):592-9. doi: 10.1016/j.tips.2009.08.004. PMID: 19837467.

Yongchao Liu et al., Precipitated Fluorophore-Based Molecular Probe for In Situ Imaging of Aminopeptidase N in Living Cells and Tumors. Anal Chem. Apr. 27, 2021;93(16):6463-6471. doi: 10.1021/acs.analchem.1c00280. Epub Apr. 14, 2021. PMID: 33852265.

Zhe Li et al., Precipitated Fluorophore-Based Probe for Accurate Detection of Mitochondrial Analytes. Anal Chem. Feb. 2, 2021;93(4):2235-2243. doi: 10.1021/acs.analchem.0c04094. Epub Jan. 5, 2021. PMID: 33400485.

Nov. 7, 2022 Final Office Action U.S. Appl. No. 17/573,110.

* cited by examiner

| Substrate | Proteases |
|---|---|
| Probe#677 | None |
| Probe#102 | Major: CTSD, CTSK, CTSL, CTSS, ELA2, KLK2, KLK14, Trypsin3<br>Minor: ADAM10, ADAM17, CTSB, MMP1 |
| Probe#428 | CTSB, CTSH, CTSK, CTSL, CTSS, KLK14, MMP3, Trypsin3 |
| Probe#460 | Major: ELA2, KLK2, KLK14, CTSD, CTSK, CTSL, CTSS, Trypsin3<br>Minor: ADAM10, CAPN1, MMP13, MMP19, NAPSINA |
| Probe#48 | Major: ADAM10, CTSB, CTSD, CTSK, CTSS, KLK14, MMP13, MMP20, Trypsin3<br>Minor: ADAM17, CTSL, ELA2, MMP1, MMP3, PLAU |
| Probe#480 | CTSB, CTSL, GZMB, KLK14, Trypsin3 |
| Probe#492 | Major: CTSB, CTSS, ELA2, KLK14, Trypsin3<br>Minor: CTSK, CTSL, GzmA, MMP1, MMP3, MMP13, MMP20, PLAU |
| Probe#647 | Major: Caspase 1, Caspase 3, Caspase 5, Caspase 6, Caspase 8, GzmB<br>Minor: Caspase 10 |
| Probe#648 | Major: Caspase 6, KLK14<br>Minor: Caspase 3, Caspase 8, Caspase 10 |
| Probe#1 | Major: KLK14, PLAU, Trypsin3<br>Minor: CTSB |
| Probe#8 | Major: Caspase 3, Caspase 2, CTSB, CTSS<br>Minor: Caspase 7 |
| Probe#9 | Major: Caspase 1, Caspase 3, Caspase 8, CTSB<br>Minor: Caspase 6, Caspase 7, Caspase 10, CTSD, CTSK |
| Probe#12 | Major: Caspase 2, Caspase 3, Caspase 6, Caspase 7, Caspase 8, Caspase 10<br>Minor: CTSB |
| Probe#3 | Major: Caspase 1, Caspase 8, Caspase 10, GzmB<br>Minor: Caspase 5, Caspase 6, Caspase 7, CTSB |
| Probe#30 | Major: CTSB, CTSK, CTSS, MMP1, MMP13<br>Minor: CTSL, MMP14 |
| Probe#92 | Major: KLK6, KLK14, Trypsin3<br>Minor: CTSK |

Fig. 10

Group 1 – Probe#86
Group 2 – Probe#428
Group 3 – Probe#460
Group 4 – Probe#48
Group 5 – Probe#480
Group 6 – Probe#647
Group 7 – Probe#648
Group 8 – Probe#1
Group 9 – Probe#9
Group 10 – Probe#12
Group 11 – Probe#3
Group 12 – Probe#92
Group 13 – Probe#102
Group 14 – Probe#492
Group 15 – Probe#8
Group 16 – Probe#30

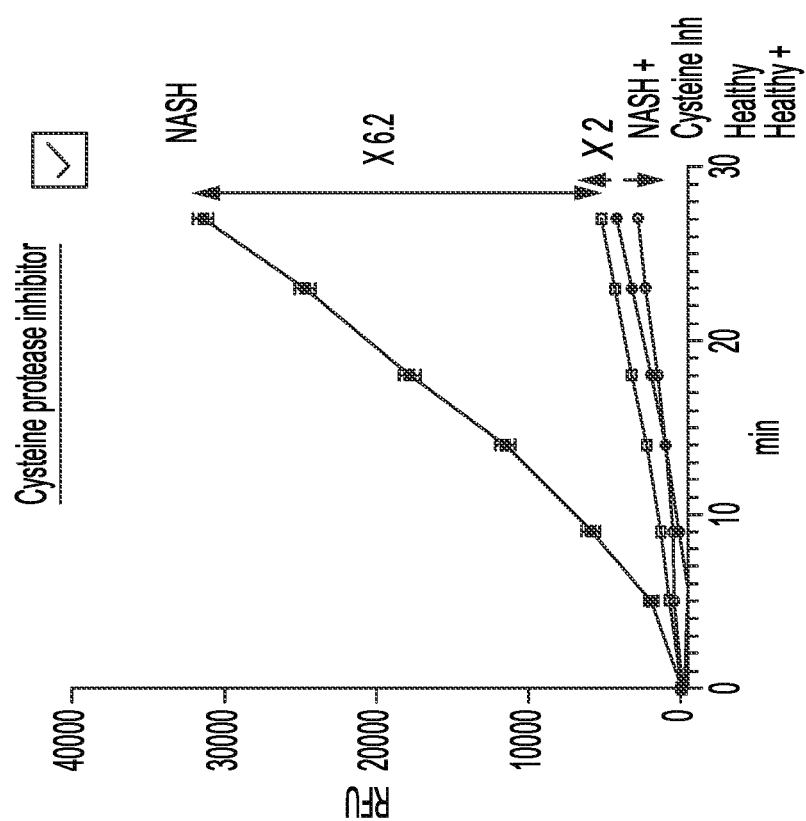
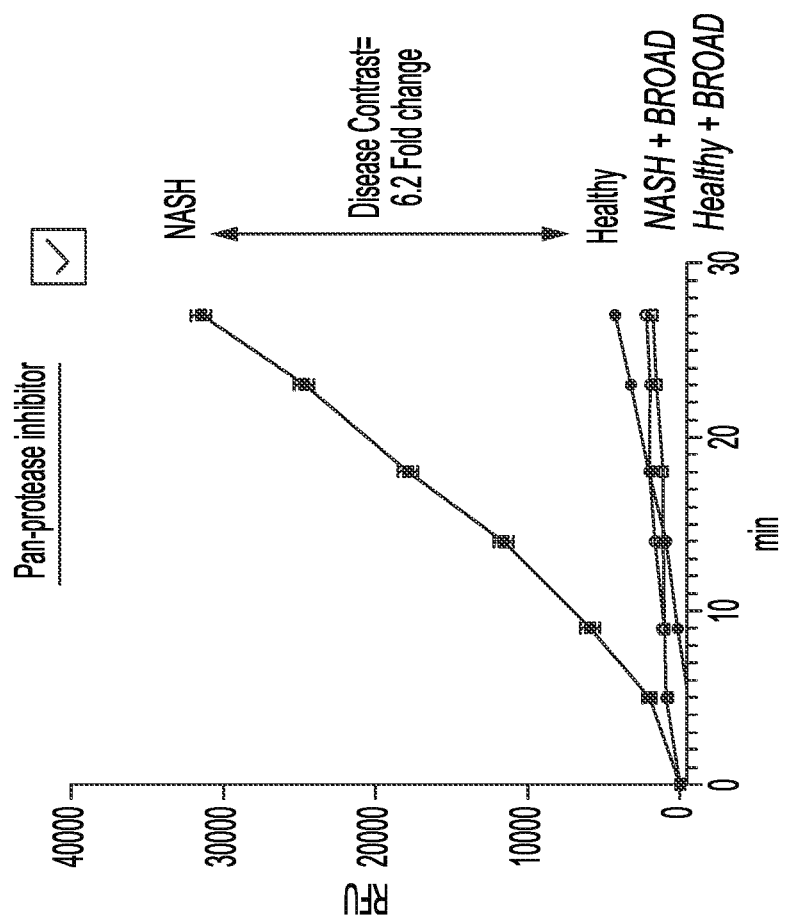
Fig. 30B
Fig. 30A

Examples of aminopeptidase/exopeptidase randomized stretch with n > 1
AMINOPEPTIDASE
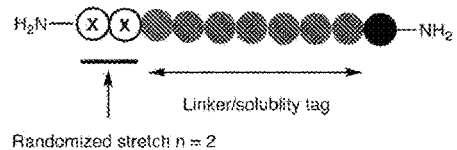
Randomized stretch n = 2
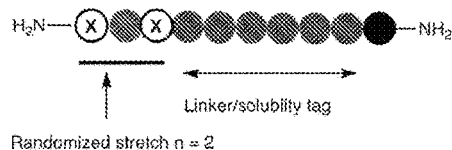
Randomized stretch n = 2
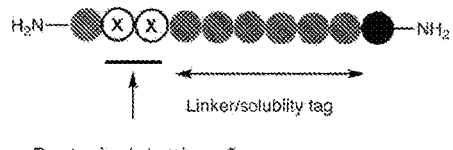
Randomized stretch n = 2
Generalization:
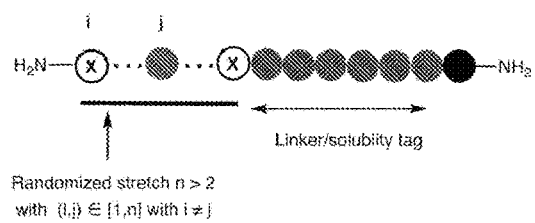
Randomized stretch n > 2
with (i,j) ∈ [1,n] with i ≠ j
Same generalization for carboxypeptidase:
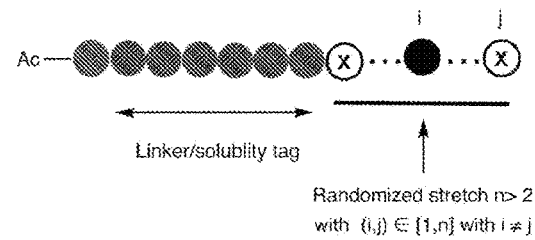
Randomized stretch n > 2
with (i,j) ∈ [1,n] with i ≠ j
Fig. 46C

EX VIVO PROTEASE ACTIVITY DETECTION FOR DISEASE DETECTION/DIAGNOSTIC, STAGING, MONITORING AND TREATMENT

CROSS REFERENCE

This application is a continuation-in-part of International Application No. PCT/US2021/049948, filed on Sep. 10, 2021 which claims the benefit of U.S. Provisional Application No. 63/077,525, filed on Sep. 11, 2020, each of which is entirely incorporated herein by reference for all purposes.

SEQUENCE LISTING

The instant application contains a Sequence Listing which has been submitted electronically in ASCII format and is hereby incorporated by reference in its entirety. Said ASCII copy, created on Jan. 11, 2022, is named 61226_702_503_SL.txt and is 393,420 bytes in size.

BRIEF SUMMARY

Provided herein is a method comprising contacting a plasma sample from a subject with a molecule ex vivo and detecting a rate of formation or an amount of said released reporter. Further provided herein is a method. Further provided herein is a method wherein said molecule comprises a cleavable linker and a reporter and wherein said cleavable linker is cleaved by an agent from said plasma, releasing said reporter from said molecule.

Further provided herein is a method further comprising introducing an anticoagulant to said plasma sample. Further provided herein is a method wherein said anticoagulant is an EDTA, a citrate, a heparin, an oxalate, any salt, solvate, enantiomer, tautomer and geometric isomer thereof, or any mixtures thereof.

Provided herein is a method comprising contacting a body fluid sample from a subject having a disease or condition with a molecule ex vivo. Further provided herein is a method wherein said molecule comprises a cleavable linker and a reporter and wherein said cleavable linker is cleaved by an agent from said body fluid, releasing said reporter from said molecule. Further provided herein is a method wherein said rate of formation or said amount of said released reporter is significantly different from a healthy subject.

Provided herein is a method comprising contacting a body fluid sample from a subject with a first molecule ex vivo wherein said first molecule comprises a first cleavable linker and a first reporter and wherein said first cleavable linker is cleaved by a first agent from said body fluid, releasing said first reporter from said first molecule. Further provided herein is a method detecting a rate of formation or an amount of said first released reporter. Further provided herein is a method contacting said body fluid sample from said subject with a second molecule ex vivo wherein said second molecule comprises a second cleavable linker and a second reporter, and wherein said second cleavable linker is cleaved by a second agent from said body fluid, releasing said second reporter from said second molecule. Further provided herein is a method detecting a rate of formation or an amount of said second released reporter and determining a disease or condition of said subject based on said detection of said first released reporter and said detection of said second released reporter.

Further provided herein is a method wherein said determination comprises a supervised Machine Learning classification algorithm, Logistic Regression, Naive Bayes, Support Vector Machine, Random Forest, Gradient Boosting, Neural Networks, a continuous regression approach, Ridge Regression, Kernel Ridge Regression, Support Vector Regression or any combination thereof.

Provided herein is a method comprising contacting a body fluid sample from a subject with a molecule ex vivo, wherein said molecule comprises a cleavable linker and a reporter and wherein said cleavable linker is cleaved by an agent from said body fluid, releasing said reporter from said molecule. Further provided herein is a method comprising detecting a rate of formation or an amount of said released reporter and determining a disease or condition of said subject based on said detection, wherein said disease or condition is a certain fibrosis stage or a certain nonalcoholic fatty liver disease activity score (NAS) of Non-alcoholic steatohepatitis (NASH).

Provided herein is a method comprising contacting a body fluid sample from a subject with a molecule ex vivo wherein said molecule comprises a cleavable linker and a reporter and wherein said cleavable linker is cleaved by an agent from said body fluid, releasing said reporter from said molecule. Further provided herein is a method detecting a rate of formation or an amount of said released reporter and determining a disease or condition of said subject based on said detection, wherein said disease or condition is selected from the group consisting of a liver disease a cancer, an organ transplant rejection, an infectious disease, an allergic disease, an autoimmunity, an Alzheimer's and a chronic inflammation; wherein said cancer is not pancreatic ductal adenocarcinoma or non-small cell lung cancer.

Further provided herein is a method wherein said liver disease comprises a Non-alcoholic steatohepatitis (NASH), a non-alcoholic fatty liver disease (NAFLD), a toxin mediated liver injury, a viral hepatitis, a fulminant hepatitis, an alcoholic hepatitis, an autoimmune hepatitis, a cirrhosis of the liver, a hepatocellular carcinoma (HCC), a primary biliary cholangitis (PBC), a cholangiocarcinoma, a primary sclerosing cholangitis, an acute or chronic rejection of a transplanted liver, an inherited liver disease or a combination thereof.

Further provided herein is a method wherein said body fluid sample is selected from the group consisting of blood, plasma, bone marrow fluid, lymphatic fluid, bile, amniotic fluid, mucosal fluid, saliva, urine, cerebrospinal fluid, spinal fluid, synovial fluid, semen, ductal aspirate, feces, stool, vaginal effluent, lachrymal fluid, tissue lysate and patient-derived cell line supernatant.

Further provided herein is a method wherein said body fluid sample comprises a rinse fluid, a conditioning media or buffer, a swab viral transport media, a saline, a culture media, or a cell culture supernatant.

Further provided herein is a method wherein said rinse fluid is selected from the group consisting of a mouthwash rinse, a bronchioalveolar rinse, a lavage fluid, a hair wash rinse, a nasal spray effluent, a swab of any bodily surface, orifice, organ structure or solid tumor biopsies applied to saline or any media or any derivatives thereof.

Further provided herein is a method wherein said agent is selected from the group consisting of a oxidoreductase, a transferase, a hydrolase, a lyase, a isomerase, a ligase, a protease (peptidase), a hydrolase, an esterase, a β-glycosidase, a phospholipase and a phosphodiesterase, peroxidase, lipase, amylase a nucleophilic reagent, a reducing reagent, a electrophilic/acidic reagent, an organometallic/metal catalyst, an oxidizing reagent, a hydroxyl ion, a thiols nucleophile, a nitrogen nucleophile, a sodium dithionite and a sodium periodate.

Further provided herein is a method wherein said agent is a protease. Further provided herein is a method wherein said protease is an endopeptidase or an exopeptidase. Further provided herein is a method wherein said protease is selected from the group consisting of an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh. binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase O, a carboxypeptidase U, a carboxypeptidase X1, a carboxypeptidase X2, a carboxypeptidase Z, a carnosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, a DDI-related protease, a DECYSIN, a Der1-like domain family, member 1, a Der1-like domain family, member 2, a Der1-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination thereof. Further provided herein is a method wherein said protease is selected from the group consisting of a T cell protease, a complement protease, a fibrosis protease, and an inflammation-related protease.

Further provided herein is a method wherein said cleavable linker is a peptide, a carbohydrate, a nucleic acid, a lipid, an ester, a glycoside, a phospholipid, a phosphodiester, a nucleophile/base sensitive linker, a reduction sensitive linker, an electrophile/acid sensitive linker, a metal cleavable linker, an oxidation sensitive linker or a combination thereof. Further provided herein is a method wherein said cleavable linker is a peptide. Further provided herein is a method wherein said peptide comprises an amino acid sequence selected from the group consisting of SEQ ID Nos: 1-677.

Further provided herein is a method wherein said cleavable linker is directly connected to said reporter through a covalent bond. Further provided herein is a method wherein said reporter comprises a fluorescent label, a mass tag, a chromophore, an electrochemically active molecule, a bio-Layer interferometry or surface plasmon resonance detectable molecule, a precipitating substance, a mass spectrometry and liquid chromatography substrate, a magnetically active molecule, a gel forming and/or viscosity changing molecule, an immunoassay detectable molecule, a cell-based amplification detectable or a nucleic acid barcode, or any combinations thereof. Further provided herein is a method wherein said reporter comprises a fluorescent label. Further provided herein is a method wherein said fluorescent label is selected from a group consisting of a 5-carboxyfluorescein (5-FAM), a 7-amino-4-carbamoylmethylcoumarin (ACC), a 7-Amino-4-methylcoumarin (AMC), a 2-Aminobenzoyl (Abz), a Cy7, a Cy5, a Cy3 and a (5-((2-Aminoethyl)amino)naphthalene-1-sulfonic acid) (EDANS).

Further provided herein is a method wherein said molecule further comprises a fluorescent quencher. Further provided herein is a method wherein said fluorescent quencher is selected from the group consisting of BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl]azo)benzoyl), Dnp (2,4-dinitrophenyl) and Eclipse. Further provided herein is a method wherein said fluorescent quencher is directly connected to said cleavable linker through a covalent bond.

Further provided herein is a method wherein said molecule further comprises a carrier. Further provided herein is a method wherein said carrier comprises a native, labeled or synthetic protein, a synthetic chemical polymer of precisely known chemical composition or with a distribution around a mean molecular weight, an oligonucleotide, a phosphorodiamidate morpholino oligomer (PMO), a foldamer, a lipid, a lipid micelle, a nanoparticle, a solid support made of polystyrene, polypropylene or any other type of plastic, or any combination thereof.

Further provided herein is a method wherein said subject is a mammal. Further provided herein is a method wherein said mammal is a human.

Further provided herein is a method wherein said reporter is linked to said cleavable linker through a self-immolative spacer. Further provided herein is a method wherein said self-immolative spacer is selected from the group consisting of a disulfide, a hetheroaminebifuncional disulfide, a thiol-based pirydazinediones, a p-aminebenzyloxycarbonyl, a dipeptide, a Gly-Pro (SEQ ID NO: 530), a L-Phe-Sar, a trans-cyclooctene tetrazine, a ortho Hydroxy-protected Aryl sulfate, a phosphoramidate-based spacer, a hydroxybenzyl, a trimethyl carbamate and a quinone methide-based spacer.

Further provided herein is a method wherein said detection comprises fluorescent detection, spectroscopic detection, mass spectrometry, immunological detection or imaging detection. Further provided herein is a method wherein said detection comprises fluorescent detection. Further provided herein is a method wherein said fluorescent detection is fluorescence resonance energy transfer (FRET).

Further provided herein is a method wherein said cleaved reporter comprises a precipitating fluorophore. Further provided herein is a method wherein said precipitating fluorophore comprises HPQ, Cl-HPQ, HTPQ, HBPQ, or HQPQ.

Provided herein is a method comprising measuring activity of two or more agents in a body fluid sample from a subject and determining a disease or condition of said subject based on said activity wherein said disease or condition is selected from the group consisting of a liver disease, an organ transplant rejection, an infectious disease, an allergic disease, an autoimmunity, an Alzheimer's and a chronic inflammation.

Further provided herein is a method wherein said liver disease comprises a Non-alcoholic steatohepatitis (NASH), a non-alcoholic fatty liver disease (NAFLD), a toxin mediated liver injury, a viral hepatitis, a fulminant hepatitis, an alcoholic hepatitis, an autoimmune hepatitis, a cirrhosis of the liver, a hepatocellular carcinoma (HCC), a primary biliary cholangitis (PBC), a cholangiocarcinoma, a primary sclerosing cholangitis, an acute or chronic rejection of a transplanted liver, an inherited liver disease or a combination thereof.

Provided herein is a method comprising measuring activity of two or more agents in a body fluid sample from a subject and determining a disease or condition of said subject based on said activity wherein said disease or condition is a certain fibrosis stage or a certain nonalcoholic fatty liver disease activity score (NAS) of Non-alcoholic steatohepatitis (NASH).

Further provided herein is a method which further comprises contacting said body fluid sample from said subject with a molecule ex vivo, wherein said molecule comprises a cleavable linker and a reporter and wherein said cleavable linker is cleaved by said protease from said plasma, releasing said reporter from said molecule, and detecting a rate of formation or an amount of said released reporter.

Further provided herein is a method wherein said agent is selected from the group consisting of a oxidoreductase, a transferase, a hydrolase, a lyase, a isomerase, a ligase, a protease (peptidase), a hydrolase, an esterase, a β-glycosidase, a phospholipase and a phosphodiesterase, peroxidase, lipase, amylase a nucleophilic reagent, a reducing reagent, a electrophilic/acidic reagent, an organometallic/metal catalyst, an oxidizing reagent, a hydroxyl ion, a thiols nucleophile, a nitrogen nucleophile, a sodium dithionite and a sodium periodate. Further provided herein is a method wherein said agent is a protease. Further provided herein is a method wherein said protease is an endopeptidase or an exopeptidase. Further provided herein is a method wherein said protease is selected from the group consisting of an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh. binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase O, a carboxypeptidase U, a carboxypeptidase X1, a carboxypeptidase X2, a carboxypeptidase Z, a carnosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, a DDI-related protease, a DECYSIN, a Der1-like domain family, member 1, a Der1-like domain family, member 2, a Der1-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination thereof.

Further provided herein is a method wherein said protease is selected from the group consisting of a T cell protease, a complement protease, a fibrosis protease, and an inflammation-related protease. Further provided herein is a method wherein said cleavable linker is a peptide, a carbohydrate, a nucleic acid, a lipid, an ester, a glycoside, a phospholipid, a phosphodiester, a nucleophile/base sensitive linker, a reduction sensitive linker, an electrophile/acid sensitive linker, a metal cleavable linker, an oxidation sensitive linker or a combination thereof. Further provided herein is a method wherein said cleavable linker is a peptide. Further provided herein is a method wherein said peptide comprises an amino acid sequence selected from the group consisting of SEQ ID Nos: 1-677. Further provided herein is a method wherein said cleavable linker is directly connected to said reporter through a covalent bond.

Further provided herein is a method wherein said reporter comprises a fluorescent label, a mass tag, a chromophore, an electrochemically active molecule, a bio-Layer interferometry or surface plasmon resonance detectable molecule, a precipitating substance, a mass spectrometry and liquid chromatography substrate, a magnetically active molecule, a gel forming and/or viscosity changing molecule, an immunoassay detectable molecule, a cell-based amplification detectable or a nucleic acid barcode, or any combinations thereof. Further provided herein is a method wherein said reporter comprises a fluorescent label. Further provided herein is a method wherein said fluorescent label is selected from a group consisting of a 5-carboxyfluorescein (5-FAM), a 7-amino-4-carbamoylmethylcoumarin (ACC), a 7-Amino-4-methylcoumarin (AMC), a 2-Aminobenzoyl (Abz), a Cy7, a Cy5, a Cy3 and a (5-((2-Aminoethyl)amino)naphthalene-1-sulfonic acid) (EDANS).

Further provided herein is a method wherein said molecule further comprises a fluorescent quencher. Further provided herein is a method wherein said fluorescent quencher is selected from the group consisting of BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl]azo)benzoyl), Dnp (2,4-dinitrophenyl) and Eclipse. Further provided herein is a method wherein said fluorescent quencher is directly connected to said cleavable linker through a covalent bond.

Further provided herein is a method wherein said molecule further comprises a carrier. Further provided herein is a method wherein said carrier comprises a native, labeled or synthetic protein, a synthetic chemical polymer of precisely known chemical composition or with a distribution around a mean molecular weight, an oligonucleotide, a phosphorodiamidate morpholino oligomer (PMO), a foldamer, a lipid, a lipid micelle, a nanoparticle, a solid support made of polystyrene, polypropylene or any other type of plastic, or any combination thereof.

Further provided herein is a method wherein said subject is a mammal. Further provided herein is a method wherein said mammal is a human.

Further provided herein is a method wherein said reporter is linked to said cleavable linker through a self-immolative spacer. Further provided herein is a method wherein said self-immolative spacer is selected from the group consisting of a disulfide, a hetheroaminebifuncional disulfide, a thiol-based pirydazinediones, a p-aminebenzyloxycarbonyl, a dipeptide, a Gly-Pro (SEQ ID NO: 530), a L-Phe-Sar, a trans-cyclooctene tetrazine, a ortho Hydroxy-protected Aryl sulfate, a phosphoramidate-based spacer, a hydroxybenzyl, a trimethyl carbamate and a quinone methide-based spacer.

Further provided herein is a method wherein said detection comprises fluorescent detection, spectroscopic detection, mass spectrometry, immunological detection or imaging detection. Further provided herein is a method wherein said detection comprises fluorescent detection. Further provided herein is a method wherein said fluorescent detection is fluorescence resonance energy transfer (FRET).

Further provided herein is a method wherein said cleaved reporter comprises a precipitating fluorophore. Further provided herein is a method wherein said precipitating fluorophore comprises HPQ, Cl-HPQ, HTPQ, HBPQ, or HQPQ.

Further provided herein is a method wherein said body fluid sample is selected from the group consisting of blood, plasma, bone marrow fluid, lymphatic fluid, bile, amniotic fluid, mucosal fluid, saliva, urine, cerebrospinal fluid, spinal fluid, synovial fluid, semen, ductal aspirate, feces, stool, vaginal effluent, lachrymal fluid, tissue lysate and patient-derived cell line supernatant. Further provided herein is a method wherein said body fluid sample comprises a rinse fluid, a conditioning media or buffer, a swab viral transport media, a saline, a culture media, or a cell culture supernatant. Further provided herein is a method wherein said rinse fluid is selected from the group consisting of a mouthwash rinse, a bronchioalveolar rinse, a lavage fluid, a hair wash rinse, a nasal spray effluent, a swab of any bodily surface, orifice, organ structure or solid tumor biopsies applied to saline or any media or any derivatives thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings ("FIGURE." or "FIGURES." herein), of which:

FIG. 6A shows that the probe 601 includes a fluorescent reporter 603 and a quencher 605. The probe 601 may also include a spacer 507, a solubility tag 509, and/or a covalent or non-covalent attachment site 511. FIG. 6B shows the cleavage process of two components probe. FIG. 6C shows the cleavage process of three components probe.

FIG. 7A shows a probe 701 with an auto-immolative spacer 705 and precipitating fluorescent reporter 703. The spacer 705 connects the precipitating fluorophore reporter to an exopeptidase substrate 707, which is surrounded by the rectangle for clarity. A specific, predetermined exopeptidase cleaves the exopeptidase substrate 707. As a result, the auto-immolative spacer 705 dissociates from the precipitating fluorophore reporter 703. This allows establishment of a particular hydrogen bond 709 in the reporter 703, such that it enters a solid state, precipitates from the fluid sample, and provides an intense fluorescent signal. FIG. 7B shows de detailed process. FIG. 7C shows the reaction process with both endopeptidase and exopeptidase.

FIG. 10 shows in vivo probes used to detect protease activity.

FIG. 15A shows the results from healthy samples. FIG. 15B shows results from NASH+ samples.

FIG. 19A shows the results of testing for protease abundance levels and FIG. 19B shows the results of testing for protease activity levels.

FIG. 21A shows the results of Probe #428, FIG. 21B shows the results of Probe #520, FIG. 21C shows the results of Probe #96, FIG. 21D shows the results of Probe #102, FIG. 21E shows the results of Probe #492, and FIG. 21F shows the results of Probe #647.

FIG. 30A-F provide experimental results demonstrating the association of specific proteases in the detection of disease-specific activity differences in NASH samples in mice K2EDTA plasma. FIG. 30A shows the results when testing with a pan-protease inhibitor. FIG. 30B shows the results when testing with a cysteine protease family inhibitor. FIG. 30C shows the results when testing with a cathepsin family inhibitor. FIG. 30D shows the results when testing with a CTSB specific inhibitor.

FIG. 30E shows the results when testing with a CTSK specific inhibitor. FIG. 30F shows the results when testing with a CTSL specific inhibitor. These results show that this substrate is cleaved by CTSL.

FIG. 31A shows the results of testing with a trypsin specific inhibitor and FIG. 31B shows the results when testing with a thrombin specific inhibitor.

FIG. 32A shows the results of testing pooled samples of healthy and NASH plasma when comparing protease activity.

FIG. 32B shows the quantitation ratio for protease activity between healthy and NASH samples.

FIG. 33A shows the results of testing for CTSL abundance levels and FIG. 33B shows that testing for CTSL activity levels is superior to testing for CTSL abundance.

FIG. 34A shows the results from the K2EDTA plasma cohort while FIG. 34B shows the results from the LiHeparin plasma cohort. Probe #18 is a Neutrophil elastase substrate. Probe #409 is a SARS-COV2 3C protease. Probe #462 is a MMP8 substrate. Probe #84 is a Furin substrate. Probe #26 is a Cathepsin K/B, Trypsin, Thrombin, Tryptase substrate.

FIG. 36A shows the results from saliva samples while FIG. 36B shows the results from swab samples conditioned in VTM (Viral Transport Media containing up to 10% FBS).

FIG. 39A shows the results of inhibition experiments involving Granzyme B while FIG.

39B shows the results of inhibition experiments involving caspases. Differential protease activity is more sensitive to the GzmB specific inhibitor than the caspase inhibitor, implicating GzmB, a hallmark of T-cell activity, in the disease signal detected in swabs.

Figure 40:
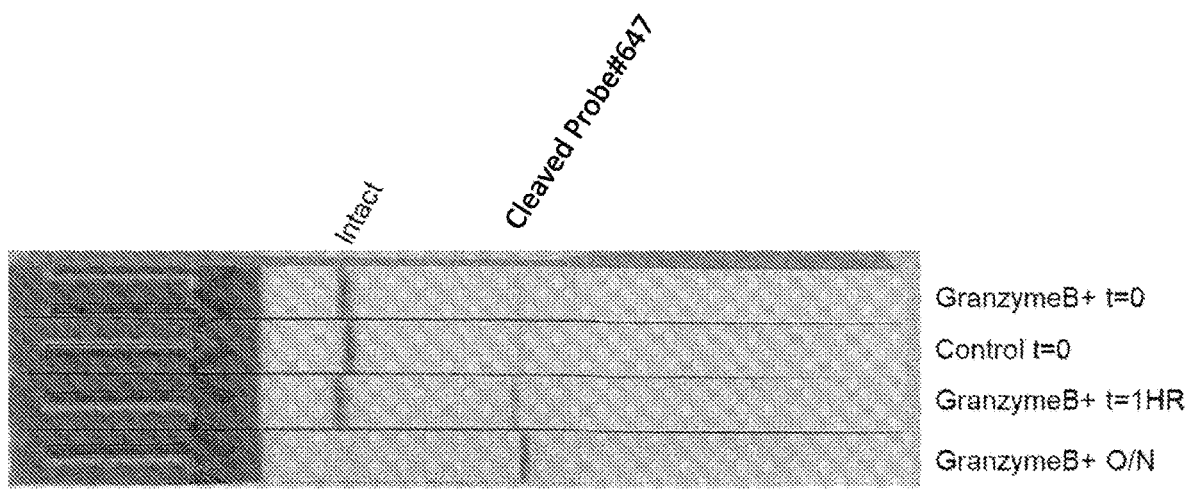

FIG. 40 shows a paper strip test capable of monitoring Granzyme B activity.

Figure 41A:
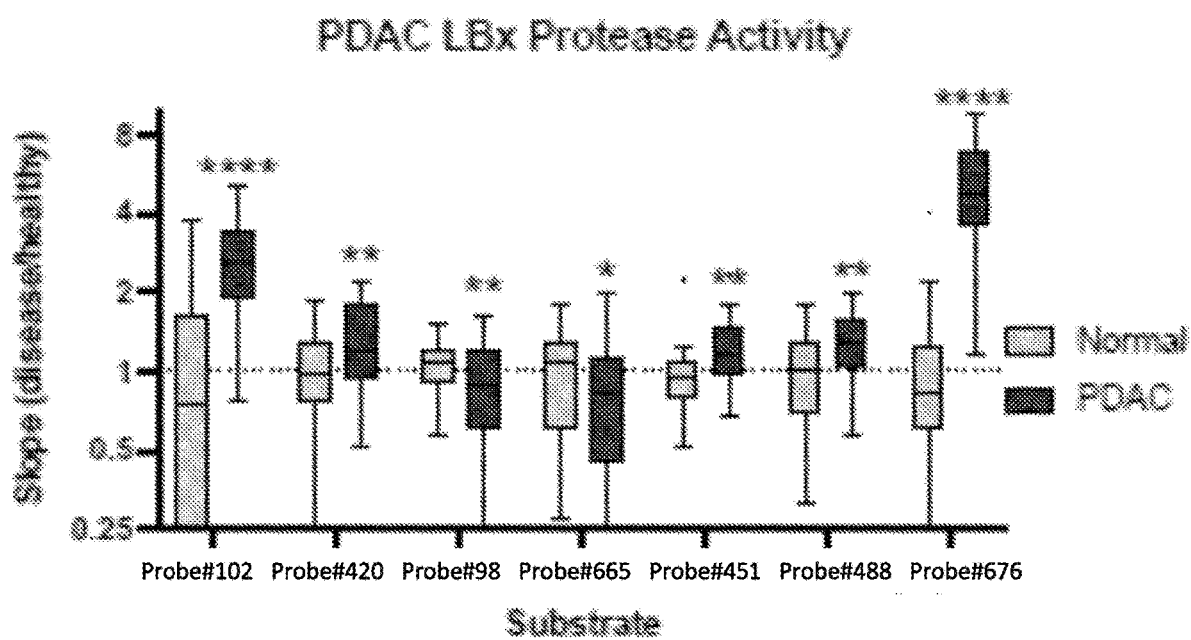
Figure 41B:
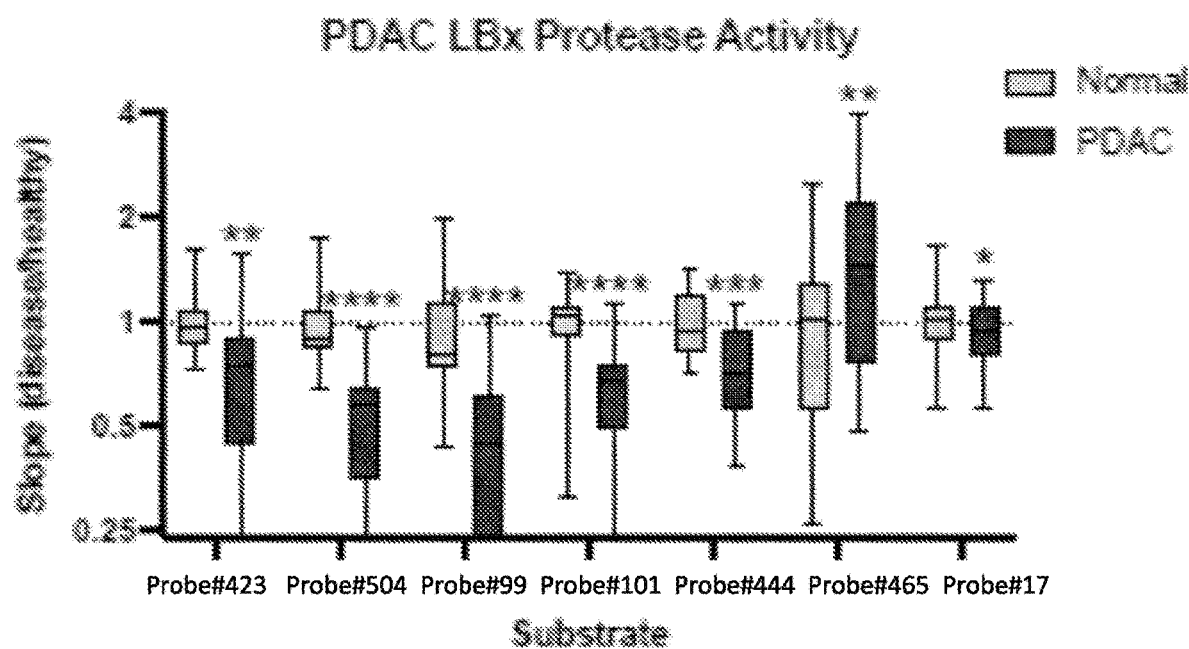

FIG. 41A-B provides experimental evidence showing that the peptide fragments can distinguish between healthy and pancreatic ductal adenocarcinoma (PDAC) samples. FIG. 41A shows the results of first set of experiments, while FIG. 41B shows the results of second set of experiments.

Figure 42:
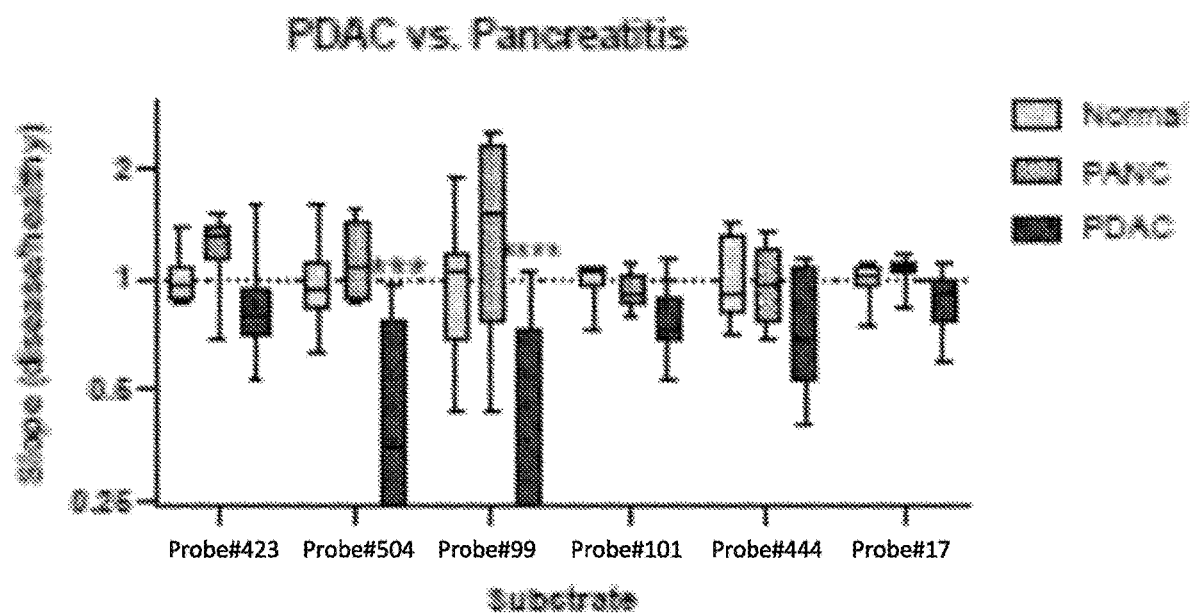

FIG. 42 provides experimental evidence showing that the peptide fragments can distinguish between healthy samples, PDAC samples, and pancreatitis samples.

Figure 43:
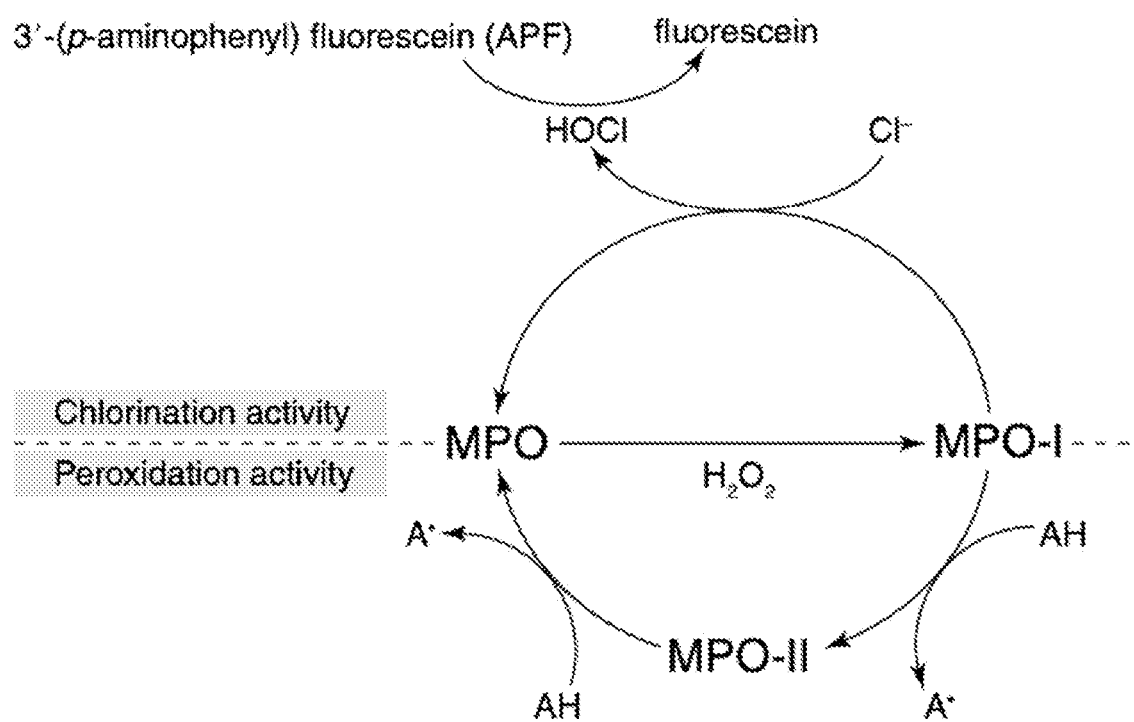

FIG. 43 shows a schematic diagram for detection of Chlorination and peroxidation activity of MPO using the EnzChek® Myeloperoxidase Activity Assay Kit. AH represents the nonfluorescent Amplex® UltraRed substrate, and A represents its fluorescent oxidation product. Hydrogen peroxide converts MPO to MPO-I and MPO is inactive without the presence of hydrogen peroxide. Amplex® UltraRed is then oxidized by MPO-I and creates the fluorescent oxidation product A which can be read at Ex/Em=530/590.

Figure 44A:
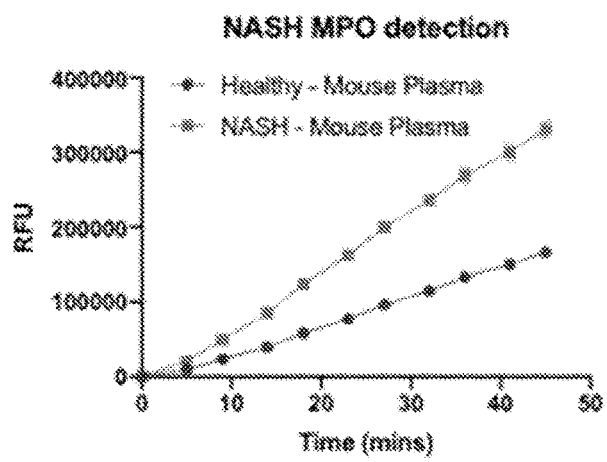
Figure 44B:
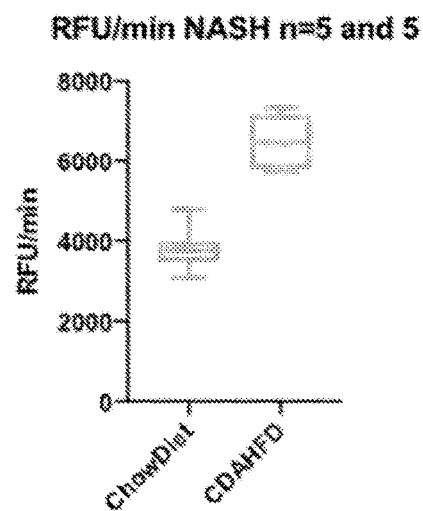
Figure 44C:
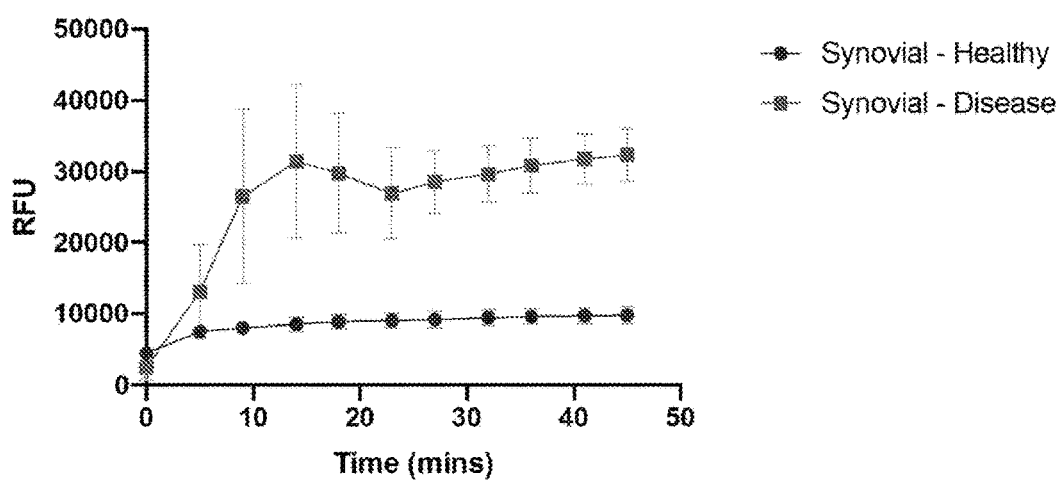

FIG. 44A-C shows the results for detecting peroxidases. FIG. 44A shows that MPO activities are different between healthy mice and mice with NASH. FIG. 44B shows that MPO activities are different between mice fed on a standard ChowDiet (CD), mice feed on a choline-deficient, L-amino acid-defined, high-fat diet (CDAHFD). FIG. 44C shows that MPO activities are different between healthy human subject and subjects with rheumatoid arthritis.

Figure 45A:
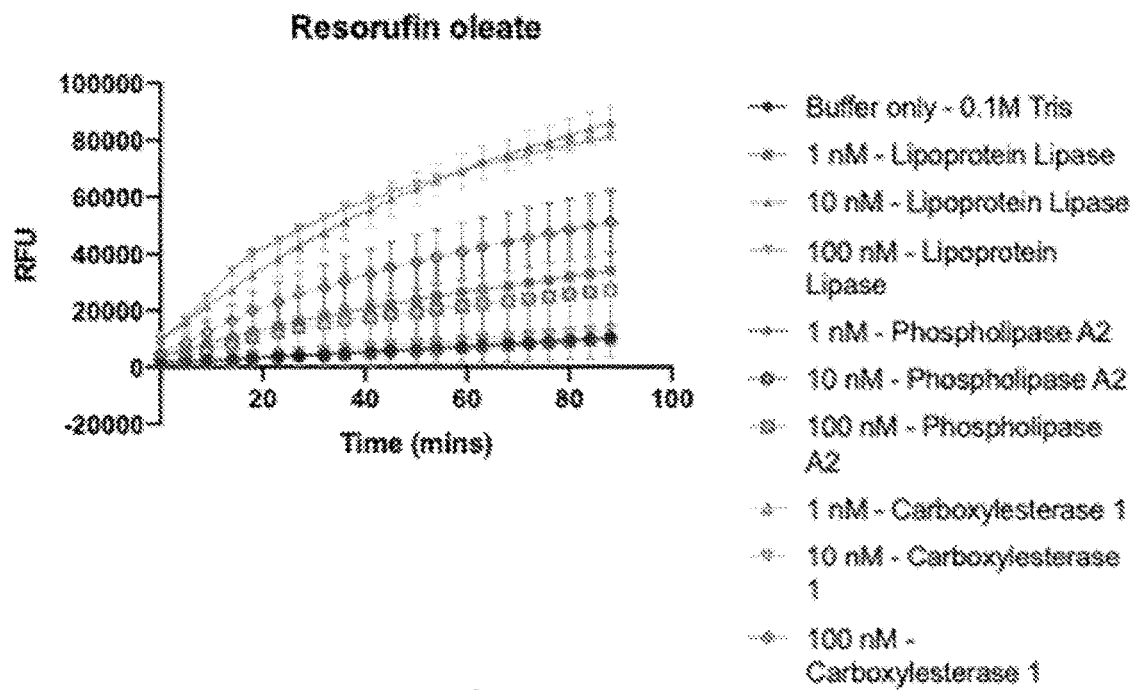
Figure 45B:
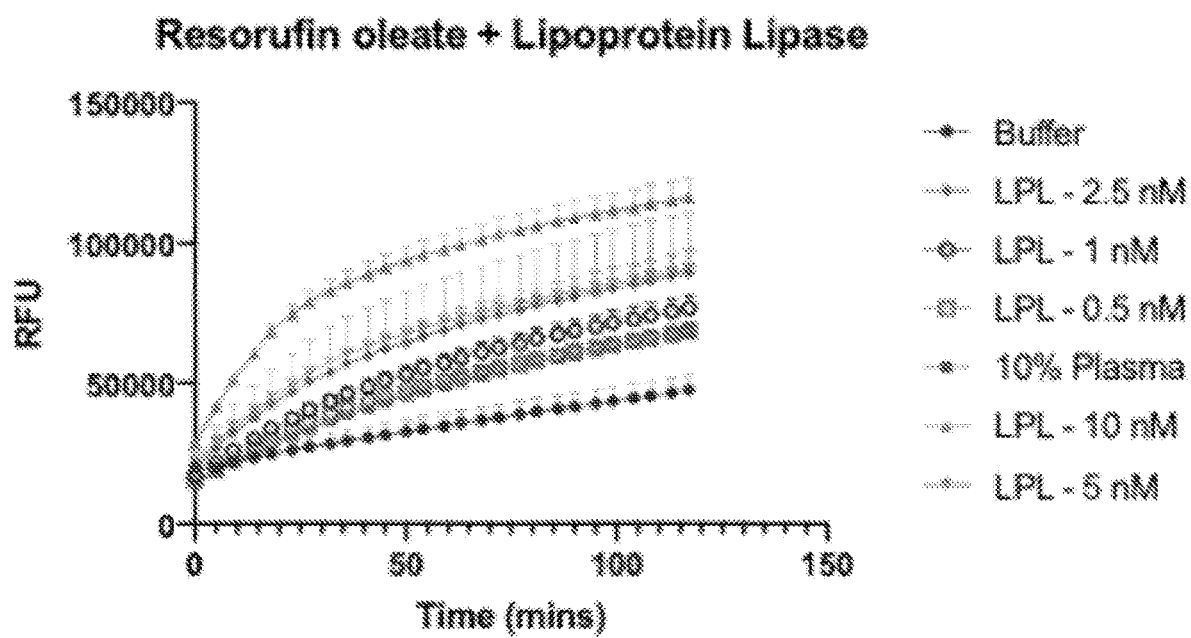
Figure 46A:
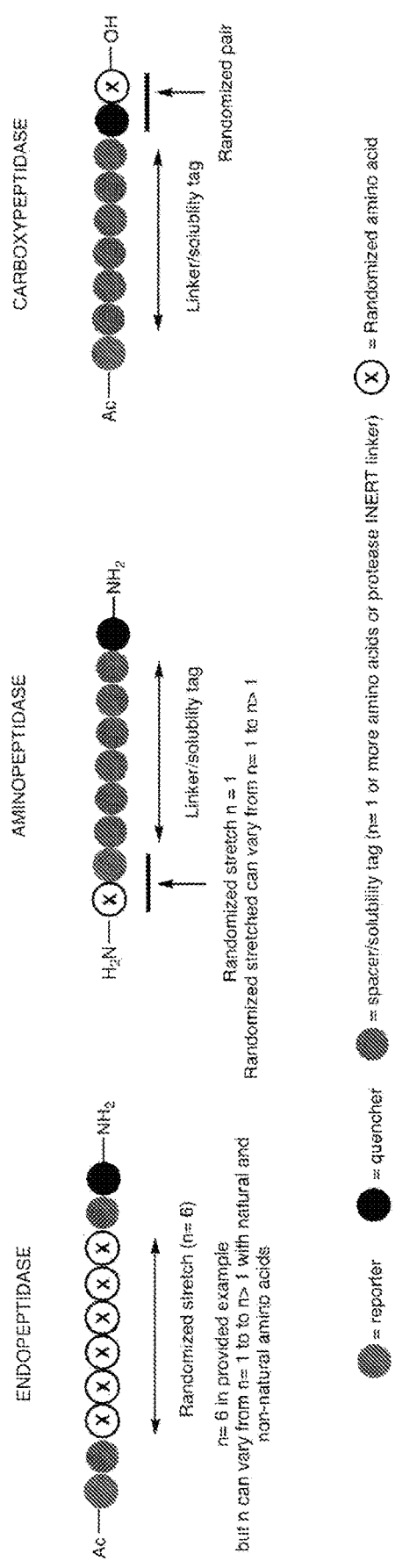
Figure 46B:
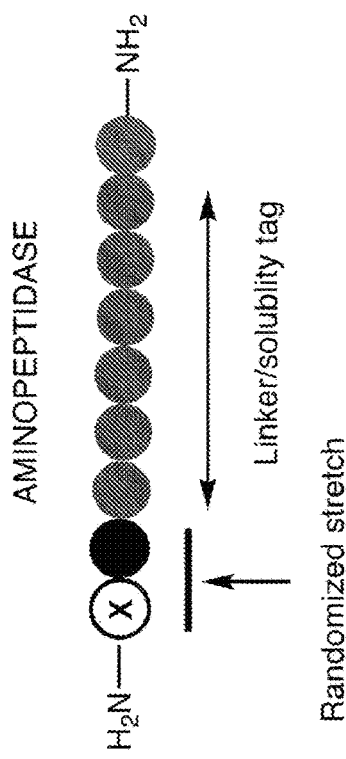
Figure 1:
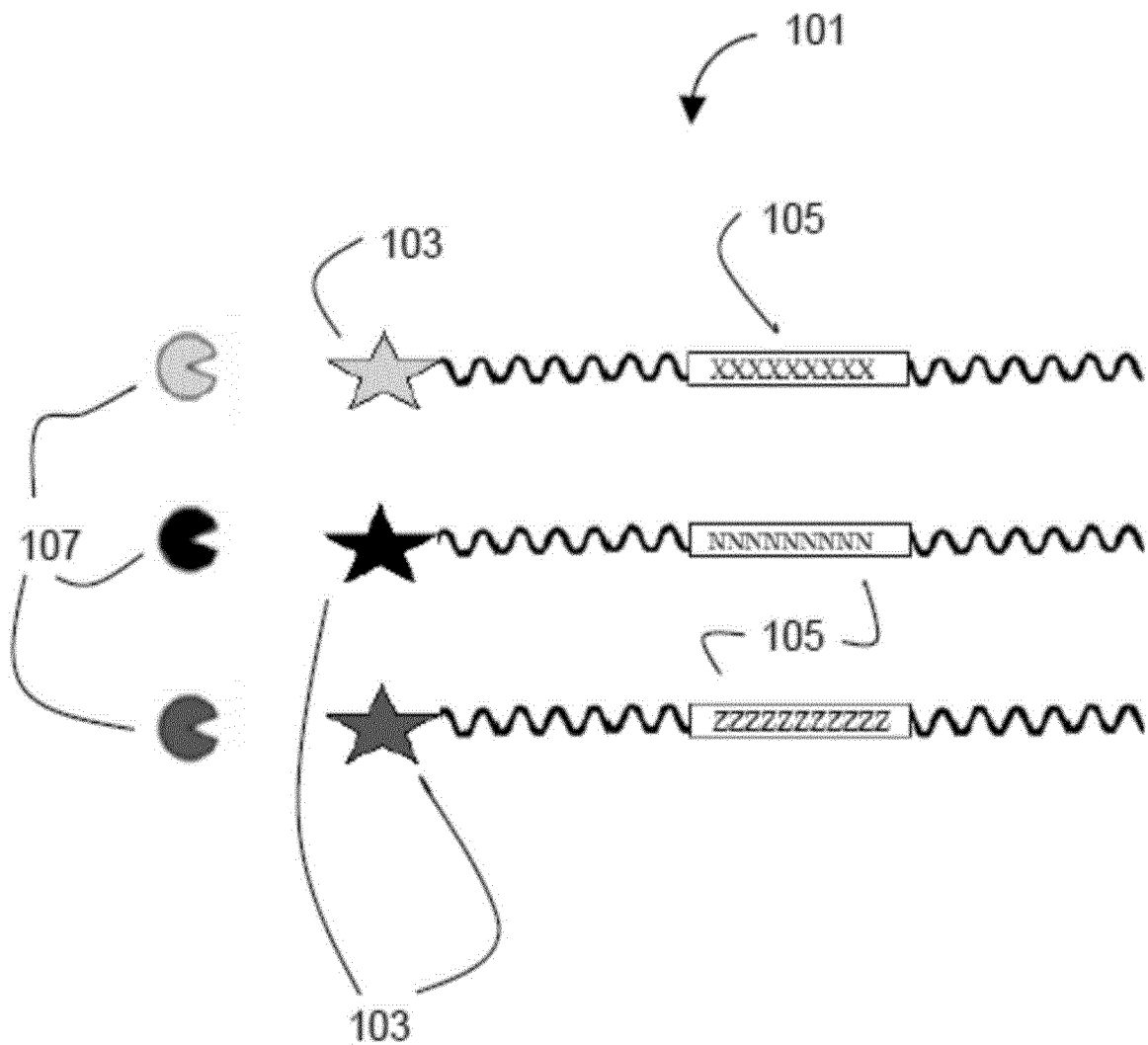

FIG. 45A-B shows the pooled results of spiked recombinant protease in human plasma using resorufin oleate as substrate. FIG. 46A shows result of 3 recombinant enzymes—carboxylesterase 1, phospholipase A2 and lipoprotein lipase. FIG. 46B shows the result of various concentrations of lipoprotein lipase.

FIG. 46A-C shows general designs of the exemplary cleavable linkers for FRET substrates. FIG. 46A shows general designs for endopeptidase, aminopeptidase and carboxypeptidase substrates. FIG. 46B shows an example that reporter and quencher can be inverted. FIG. 46C shows the generalized substrate designs for aminopeptidase and carboxypeptidase.

DETAILED DESCRIPTION

Provided herein are methods comprising contacting a body fluid sample from a subject with a molecule ex vivo. In some embodiments, the molecule comprises a cleavable linker and a reporter, and the cleavable linker is cleaved by an agent from the body fluid, releasing the reporter from the molecule. In some embodiments, the method further comprises detecting a rate of formation or an amount of the released reporter. In some embodiments, the rate of formation or amount of the released report is significantly different from a healthy subject. In some embodiments, the body fluid may be plasma. In some embodiments, the method further comprises determining a disease or condition of the subject based on the detection.

In one aspect, the body fluid sample is contacted by a second molecule with a second cleavable linker and a second reporter. In some embodiments, the second cleavable linker is cleaved by a second agent from the body fluid, releasing the second reporter from the second molecule. In some embodiments, the method further comprises detecting a rate of formation or an amount of the second released reporter. In some embodiments, the method further comprises determining a disease or condition of the subject based on the detection of the first released reporter and the detection of the second released reporter. In some embodiments, the method described herein can be used in a multiplexed format, such that a single body fluid sample can be used to ascertain the activity of multiple, select agents. This allows diagnostic panels to be created for specific pathologies and conditions, which leverage the activity of multiple agents to provide a more complete and accurate assessment of a certain condition. These panels can be used to correlate the activity of multiple agents with a particular condition or disease-state. These signatures can be saved, for example, in a database and used to assess the conditions or disease-state for subsequent individuals assessed by a particular protease activity panel. In some embodiments, a classification tool is used in the analysis to differentiate between healthy and diseased patients, or between discrete stages of disease. The classification tool may be supervised Machine Learning classification algorithms including but not limited to Logistic Regression, Naive Bayes, Support Vector Machine, Random Forest, Gradient Boosting or Neural Networks. Furthermore, if the modeled variable is continuous in nature (e.g. tumor volume), one could use continuous regression approaches such as Ridge Regression, Kernel Ridge Regression, or Support Vector Regression. These algorithms would operate on the multi-dimensional feature space defined by the measurements of multiple probes (or a mathematical function of those measurements such as probe ratios) in order to learn the relationship between probe measurements and disease status. Finally, one could combine probe measurements with clinical variables such as age, gender, or patients" comorbid status. In that case, one could either incorporate clinical features in the classifier directly or, alternatively, learn a second-order classifier which combines a probe-only prediction with clinical features to produce a result that is calibrated for those variables.

In some embodiments, the disease or condition may be a certain fibrosis stage or a certain nonalcoholic fatty liver disease activity score (NAS) of Non-alcoholic steatohepatitis (NASH). In some embodiments, the disease or condition may be a liver disease, a cancer, an organ transplant rejection, an infectious disease, an allergic disease, an autoimmunity and a chronic inflammation.

In another aspect, the methods described herein comprises ex vivo, multiplex detection of enzyme activity to diagnose and monitor pathologies and treatments in a subject. This enzyme activity can be used to diagnose and monitor a disease and condition in an internal organ of the subject.

Detection Probe/Molecule

Determination of the disease or condition is based on the rate of formation or amount of the released reporter detected in the sample. A probe/molecule is introduced to the body fluid samples. The probe/molecule comprises a cleavable linker and a reporter, and an agent of from the body fluid cleave the cleavable linker, releasing a cleaved reporter. The probe/molecule may have any structure that can fulfill this function. In some embodiments, the reporter may be covalently linked to a cleavable linker. In some embodiments, the reporter may be a fluorescent label, a mass tag, a chromophore, an electrochemically active molecule, a bio-Layer interferometry or surface plasmon resonance detectable molecule, a precipitating substance, a mass spectrometry and liquid chromatography substrate (including size exclusion, reverse phase, isoelectric point, etc.), a magnetically active molecule, a gel forming and/or viscosity changing molecule, an immunoassay detectable molecule, a cell-based amplification detectable molecule, a nucleic acid barcode, or any combinations thereof.

In some embodiments, the reporter may be a fluorescent label and the molecule also comprises a quencher. In some embodiments, the quencher is covalently linked to the cleavable linker. In some embodiments an internally quenched fluorophore is linked to the cleavable linker. In some embodiments, the molecule further comprises a self-immolative spacer. In some other embodiments, the molecule further comprises a carrier.

Cleavable Linker

In some aspects, the probe/molecule described herein comprises a cleavable linker. The cleavable linker as described herein may be in any structure that is capable of being cleaved by an agent. In some embodiments, the cleavable linker may be a peptide, a carbohydrate, a nucleic acid, a lipid, an ester, a glycoside, a phospholipid, a phosphodiester, a nucleophile/base sensitive linker, a reduction sensitive linker, an electrophile/acid sensitive linker, a metal cleavable linker, an oxidation sensitive linker, an auto-immolable linker (three component probe=enzyme substrate+linker+reporter) or a combination thereof. In some embodiments, the reporter can be in an inactive form and under disease activity becomes detectable. Geoffray Leriche, Louise Chisholm, Alain Wagner, Cleavable linkers in chemical biology, Bioorganic & Medicinal Chemistry, Volume 20, Issue 2, 2012, Pages 571-582, ISSN 0968-0896, https://doi.org/10.1016/j.bmc.2011.07.048.

Cross-linking agents aim to form a covalent bond between two spatially adjacent residues within one or two polymer chains. To identify protein binding partners, the cross-linking agents need to be able to detect and stabilize transient interactions. The crosslinking agents frequently form covalent links between lysine or cysteine residues in the proteins. Alternatively, the cross-linking agent can be photoreactive. Cross-linking cleavable linkers can be used to distinguish between inter- and intra-protein interactions of receptors, signaling cascades, and the structure of multi-protein complexes.

In some embodiments, the cleavable linker may be a peptide. The core structure of a peptide linker sometimes comprises of either a di-peptide or a tetra-peptide that is recognized and cleaved by lysosomal enzymes. Proteases (also called peptidases) catalyze the breakdown of peptide bonds by hydrolysis, and is restricted to a specific sequence of amino acids recognizable by the proteases. Commonly used proteases comprise pepsin, trypsin or chymotrypsin. Since proteases have key roles in many diseases, peptide linkers are widely used in drug release systems or in diagnostic tools. In some embodiments, the peptide linkers comprise a short peptide sequence. In some embodiments, the peptide linkers may include at least one non-naturally occurring amino acid.

In some embodiments, the peptide linkers may be less than about 20 amino acids in length. In some embodiments, the peptide linkers may be between 10 and 100 amino acids in length. In some embodiments, the peptide linkers may be 1 to 5, 1 to 10, 1 to 20, 1 to 30, 1 to 50, 1 to 70, 1 to 90, 1 to 100, 5 to 10, 5 to 20, 5 to 30, 5 to 50, 5 to 70, 5 to 90, 5 to 100, 10 to 20, 10 to 30, 10 to 50, 10 to 70, 10 to 90, 10 to 100, 20 to 30, 20 to 50, 20 to 70, 20 to 90, 20 to 100, 30 to 50, 30 to 70, 30 to 90, 30 to 100, 50 to 70, 50 to 90, 50 to 100, 70 to 90, 70 to 100, or 90 to 100 amino acids in length.

TABLE 1

Exemplary sequences for peptide linkers and corresponding probe construct designs

| SEQ ID NO | Sequence | Exemplary probe name | Exemplary probe construct | SEQ ID NO |
|---|---|---|---|---|
| 1 | SGRSG | Probe #1 | 5-FAM-GSGRSGGK(CPQ2)-PEG2-kk-GC | 678 |
| 2 | PGPREG | Probe #2 | 5-FAM-GPGPREGGK(CPQ2)-PEG2-kk-GC | 679 |
| 3 | IEPDSGSQ | Probe #3 | 5-FAM-GIEPDSGSQGK(CPQ2)-PEG2-kk-GC | 680 |
| 4 | VVADSSMES | Probe #4 | 5-FAM-GVVADSSMESGK(CPQ2)-PEG2-kk-GC | 681 |
| 5 | PTSY | Probe #5 | 5-FAM-GPTSYGK(CPQ2)-PEG2-kk-GC | 682 |
| 6 | YRFK | Probe #6 | 5-FAM-GYRFKGK(CPQ2)-PEG2-kk-GC | 683 |
| 7 | KVPL | Probe #7 | 5-FAM-GKVPLGK(CPQ2)-PEG2-kk-GC | 684 |
| 8 | VDVAD | Probe #8 | 5-FAM-GVDVADGK(CPQ2)-PEG2-kk-GC | 685 |
| 9 | LETD | Probe #9 | 5-FAM-GLETDGK(CPQ2)-PEG2-kk-GC | 686 |
| 10 | LEHD | Probe #10 | 5-FAM-GLEHDGK(CPQ2)-PEG2-kk-GC | 687 |
| 11 | REQD | Probe #11 | 5-FAM-GREQDGK(CPQ2)-PEG2-kk-GC | 688 |
| 12 | DEVD | Probe #12 | 5-FAM-GDEVDGK(CPQ2)-PEG2-kk-GC | 689 |
| 13 | VEID | Probe #13 | 5-FAM-GVEIDGK(CPQ2)-PEG2-kk-GC | 690 |
| 14 | VQVDGW | Probe #14 | 5-FAM-GVQVDGWGK(CPQ2)-PEG2-kk-GC | 691 |
| 15 | YEVDGW | Probe #15 | 5-FAM-GYEVDGWGK(CPQ2)-PEG2-kk-GC | 692 |
| 16 | LEVD | Probe #16 | 5-FAM-GLEVDGK(CPQ2)-PEG2-kk-GC | 693 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 17 | IEVE | Probe #17 | 5-FAM-GIEVEGK(CPQ2)-PEG2-kk-GC | 694 |
| 18 | AAPV | Probe #18 | 5-FAM-GAAPVGK(CPQ2)-PEG2-kk-GC | 695 |
| 19 | FFKF | Probe #19 | 5-FAM-GFFKFGK(CPQ2)-PEG2-kk-GC | 696 |
| 20 | GRRGKGG | Probe #20 | 5-FAM-GGRRGKGGGK(CPQ2)-PEG2-kk-GC | 697 |
| 21 | VKKR | Probe #21 | 5-FAM-GVKKRGK(CPQ2)-PEG2-kk-GC | 698 |
| 22 | FAAF(NO2)FVL | Probe #22 | 5-FAM-GFAAF(NO2)FVLGK(CPQ2)-PEG2-kk-GC | 699 |
| 23 | VVR | Probe #23 | 5-FAM-GVVRGK(CPQ2)-PEG2-kk-GC | 700 |
| 24 | KQKLR | Probe #24 | 5-FAM-GKQKLRGK(CPQ2)-PEG2-kk-GC | 701 |
| 25 | RPPGFSAF | Probe #25 | 5-FAM-GRPPGFSAFGK(CPQ2)-PEG2-kk-GC | 702 |
| 26 | GPR | Probe #26 | 5-FAM-GGPRGK(CPQ2)-PEG2-kk-GC | 703 |
| 27 | FR | Probe #27 | 5-FAM-GFRGK(CPQ2)-PEG2-kk-GC | 704 |
| 28 | LPLGL | Probe #28 | 5-FAM-GLPLGLGK(CPQ2)-PEG2-kk-GC | 705 |
| 29 | KPLGL | Probe #29 | 5-FAM-GKPLGLGK(CPQ2)-PEG2-kk-GC | 706 |
| 30 | (Gaba)PQGLE | Probe #30 | 5-FAM-G(Gaba)PQGLEGK(CPQ2)-PEG2-kk-GC | 707 |
| 31 | PKPLAL | Probe #31 | 5-FAM-GPKPLALGK(CPQ2)-PEG2-kk-GC | 708 |
| 32 | GPSGIHV | Probe #32 | 5-FAM-GGPSGIHVGK(CPQ2)-PEG2-kk-GC | 709 |
| 33 | WAHRTTFYRRGA | Probe #33 | 5-FAM-GWAHRTTFYRRGAGK(CPQ2)-PEG2-kk-GC | 710 |
| 34 | WKLRSSKQ | Probe #34 | 5-FAM-GWKLRSSKQGK(CPQ2)-PEG2-kk-GC | 711 |
| 35 | PFR | Probe #35 | 5-FAM-GPFRGK(CPQ2)-PEG2-kk-GC | 712 |
| 36 | SYRIF | Probe #36 | 5-FAM-GSYRIFGK(CPQ2)-PEG2-kk-GC | 713 |
| 37 | RPY | Probe #37 | 5-FAM-GRPYGK(CPQ2)-PEG2-kk-GC | 714 |
| 38 | TAFRSAYG | Probe #38 | 5-FAM-GTAFRSAYGGK(CPQ2)-PEG2-kk-GC | 715 |
| 39 | WAAFRFSQA | Probe #39 | 5-FAM-GWAAFRFSQAGK(CPQ2)-PEG2-kk-GC | 716 |
| 40 | VPR | Probe #40 | 5-FAM-GVPRGK(CPQ2)-PEG2-kk-GC | 717 |
| 41 | G | Probe #41 | 5-FAM-GGK(CPQ2)-PEG2-kk-GC | 718 |
| 42 | KLRSSKQ | Probe #42 | 5-FAM-GKLRSSKQGK(CPQ2)-PEG2-kk-GC | 719 |
| 43 | YASR | Probe #43 | 5-FAM-GYASRGK(CPQ2)-PEG2-kk-GC | 720 |
| 44 | RFAQAQQQLP | Probe #44 | 5-FAM-GRFAQAQQQLPGK(CPQ2)-PEG2-kk-GC | 721 |
| 45 | KPAKFFRL | Probe #45 | 5-FAM-GKPAKFFRLGK(CPQ2)-PEG2-kk-GC | 722 |
| 46 | PRAAA(hF)TSP | Probe #46 | 5-FAM-GPRAAA(hF)TSPGK(CPQ2)-PEG2-kk-GC | 723 |
| 47 | VGPQRFSGAP | Probe #47 | 5-FAM-GVGPQRFSGAPGK(CPQ2)-PEG2-kk-GC | 724 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 48 | FFLAQA(hF)RS | Probe #48 | 5-FAM-GFFLAQA(hF)RSGK(CPQ2)-PEG2-kk-GC | 725 |
| 49 | PLAQAV | Probe #49 | 5-FAM-GPLAQAVGK(CPQ2)-PEG2-kk-GC | 726 |
| 50 | RTAAVFRP | Probe #50 | 5-FAM-GRTAAVFRPGK(CPQ2)-PEG2-kk-GC | 727 |
| 51 | DVQEFRGVTAVIR | Probe #51 | 5-FAM-GDVQEFRGVTAVIRGK(CPQ2)-PEG2-kk-GC | 728 |
| 52 | TEGEARGSVI | Probe #52 | 5-FAM-GTEGEARGSVIGK(CPQ2)-PEG2-kk-GC | 729 |
| 53 | l-TR | Probe #53 | 5-FAM-G-l-TRGK(CPQ2)-PEG2-kk-GC | 730 |
| 54 | PLFAERK | Probe #54 | 5-FAM-GPLFAERKGK(CPQ2)-PEG2-kk-GC | 731 |
| 55 | LLVY | Probe #55 | 5-FAM-GLLVYGK(CPQ2)-PEG2-kk-GC | 732 |
| 56 | QQKRKIVL | Probe #56 | 5-FAM-GQQKRKIVLGK(CPQ2)-PEG2-kk-GC | 733 |
| 57 | ASHLGLAR | Probe #57 | 5-FAM-GASHLGLARGK(CPQ2)-PEG2-kk-GC | 734 |
| 58 | LPSRSSKI | Probe #58 | 5-FAM-GLPSRSSKIGK(CPQ2)-PEG2-kk-GC | 735 |
| 59 | STGRNGFK | Probe #59 | 5-FAM-GSTGRNGFKGK(CPQ2)-PEG2-kk-GC | 736 |
| 60 | SLLRSEET | Probe #60 | 5-FAM-GSLLRSEETGK(CPQ2)-PEG2-kk-GC | 737 |
| 61 | HRGRTLEI | Probe #61 | 5-FAM-GHRGRTLEIGK(CPQ2)-PEG2-kk-GC | 738 |
| 62 | YLGRSYKV | Probe #62 | 5-FAM-GYLGRSYKVGK(CPQ2)-PEG2-kk-GC | 739 |
| 63 | EKQRIIGG | Probe #63 | 5-FAM-GEKQRIIGGGK(CPQ2)-PEG2-kk-GC | 740 |
| 64 | QRQRIIGG | Probe #64 | 5-FAM-GQRQRIIGGGK(CPQ2)-PEG2-kk-GC | 741 |
| 65 | LQRIYK | Probe #65 | 5-FAM-GLQRIYKGK(CPQ2)-PEG2-kk-GC | 742 |
| 66 | SLGRKIQI | Probe #66 | 5-FAM-GSLGRKIQIGK(CPQ2)-PEG2-kk-GC | 743 |
| 67 | HAAPRSADIQIDI | Probe #67 | 5-FAM-GHAAPRSADIQIDIGK(CPQ2)-PEG2-kk-GC | 744 |
| 68 | FGR | Probe #68 | 5-FAM-GFGRGK(CPQ2)-PEG2-kk-GC | 745 |
| 69 | SLGR | Probe #69 | 5-FAM-GSLGRGK(CPQ2)-PEG2-kk-GC | 746 |
| 70 | GLQR | Probe #70 | 5-FAM-GGLQRGK(CPQ2)-PEG2-kk-GC | 747 |
| 71 | SVARTLLV | Probe #71 | 5-FAM-GSVARTLLVGK(CPQ2)-PEG2-kk-GC | 748 |
| 72 | GRIFG | Probe #72 | 5-FAM-GGRIFGGK(CPQ2)-PEG2-kk-GC | 749 |
| 73 | APK | Probe #73 | 5-FAM-GAPKGK(CPQ2)-PEG2-kk-GC | 750 |
| 74 | GFSPY | Probe #74 | 5-FAM-GGFSPYGK(CPQ2)-PEG2-kk-GC | 751 |
| 75 | WELRHAGH | Probe #75 | 5-FAM-GWELRHAGHGK(CPQ2)-PEG2-kk-GC | 752 |
| 76 | RQSRIVGGE | Probe #76 | 5-FAM-GRQSRIVGGEGK(CPQ2)-PEG2-kk-GC | 753 |
| 77 | EQAVYQTI | Probe #77 | 5-FAM-GEQAVYQTIGK(CPQ2)-PEG2-kk-GC | 754 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 78 | VAYSGENTFGF | Probe #78 | 5-FAM-GVAYSGENTFGFGK(CPQ2)-PEG2-kk-GC | 755 |
| 79 | GGR | Probe #79 | 5-FAM-GGGRGK(CPQ2)-PEG2-kk-GC | 756 |
| 80 | ATAD | Probe #80 | 5-FAM-GATADGK(CPQ2)-PEG2-kk-GC | 757 |
| 81 | RPLESNAV | Probe #81 | 5-FAM-GRPLESNAVGK(CPQ2)-PEG2-kk-GC | 758 |
| 82 | RPLGLAR | Probe #82 | 5-FAM-GRPLGLARGK(CPQ2)-PEG2-kk-GC | 759 |
| 83 | AAFF | Probe #83 | 5-FAM-GAAFFGK(CPQ2)-PEG2-kk-GC | 760 |
| 84 | RVKRGLA | Probe #84 | 5-FAM-GRVKRGLAGK(CPQ2)-PEG2-kk-GC | 761 |
| 85 | AAL | Probe #85 | 5-FAM-GAALGK(CPQ2)-PEG2-kk-GC | 762 |
| 86 | CGGmeGVndneeGFFsAr | Probe #86 | 5-FAM-CGGmeGVndneeGFFsArGK(CPQ2) | 763 |
| 87 | GPQGIWGQ | Probe #87 | 5FAM-GGPQGIWGQK(CPQ2)-PEG2-C | 764 |
| 88 | GLVPRGS | Probe #88 | 5FAM-GGLVPRGSGK(CPQ2)-PEG2-C | 765 |
| 89 | GPVGLI | Probe #89 | 5FAM-GGPVGLIGK(CPQ2)-PEG2-C | 766 |
| 90 | GPWGIWGQ | Probe #90 | 5FAM-GGPWGIWGQGK(CPQ2)-PEG2-C | 767 |
| 91 | GPVPLSLVM | Probe #91 | 5FAM-GGPVPLSLVMK(CPQ2)-PEG2-C | 768 |
| 92 | Gf-Pip-RSGG | Probe #92 | 5FAM-GGf-Pip-RSGGGK(CPQ2)-PEG2-C | 769 |
| 93 | PLGMRG | Probe #93 | 5FAM-GGf-Pip-KSGGGK(CPQ2)-PEG2-C | 770 |
| 94 | PLGMRG | Probe #94 | (FAM)-GPLGMRGG-K(CPQ2)-PEG2-k-GC | 771 |
| 95 | P-(Cha)-G-Cys(Me)-HA | Probe #95 | (FAM)-GP-(Cha)-G-Cys(Me)-HAG-K(CPQ2)-PEG2-kk-GC | 772 |
| 96 | RPLALWESQ | Probe #96 | (FAM)-GRPLALWESQG-K(CPQ2)-PEG2-k-GC | 773 |
| 97 | SGKGPRQITA | Probe #97 | (FAM)-SGKGPRQITA-K(CPQ2)-PEG2-k-GC | 774 |
| 98 | SGPLFYSVTA | Probe #98 | (FAM)-SGPLFYSVTA-K(CPQ2)-PEG2-kk-GC | 775 |
| 99 | SGRIFLRTA | Probe #99 | (FAM)-SGRIFLRTA-K(CPQ2)-PEG2-GC | 776 |
| 100 | SGRSENIRTA | Probe #100 | (FAM)-SGRSENIRTA-K(CPQ2)-PEG2-GC | 777 |
| 101 | GSGGS | Probe #101 | (FAM)-GGSGGS-K(CPQ2)-PEG2-kk-GC | 778 |
| 102 | KPILFFRLKG | Probe #102 | (FAM)-GKPILFFRLKG-K(CPQ2)-PEG2-kk-GC | 779 |
| 103 | AWESR(Nle) | Probe #103 | (FAM)-GAWESR(Nle)GK(CPQ2)-NH2 | 780 |
| 104 | NEKSG(Nle) | Probe #104 | (FAM)-GNEKSG(Nle)GK(CPQ2)-NH2 | 781 |
| 105 | NATIVY | Probe #105 | (FAM)-GNATIVYGK(CPQ2)-PEG2-k-NH2 | 782 |
| 106 | DPFVVS | Probe #106 | (FAM)-GDPFVVSGK(CPQ2)-PEG2-k-NH2 | 783 |
| 107 | FH(Nle)FTK | Probe #107 | (FAM)-GFH(Nle)FTKGK(CPQ2)-PEG2-k-NH2 | 784 |
| 108 | (Nle)NWHKH | Probe #108 | (FAM)-G(Nle)NWHKHGK(CPQ2)-NH2 | 785 |
| 109 | FARRWG | Probe #109 | (FAM)-GFARRWGGK(CPQ2)-PEG2-k-NH2 | 786 |
| 110 | PGKWSK | Probe #110 | (FAM)-GPGKWSKGK(CPQ2)-PEG2-k-NH2 | 787 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 111 | YEEAQP | Probe #111 | (FAM)-GYEEAQPGK(CPQ2)-PEG2-k-NH2 | 788 |
| 112 | YGAIKK | Probe #112 | (FAM)-GYGAIKKGK(CPQ2)-PEG2-k-NH2 | 789 |
| 113 | TS(Nle)EGY | Probe #113 | (FAM)-GTS(Nle)EGYGK(CPQ2)-PEG2-k | 790 |
| 114 | PNNFGS | Probe #114 | (FAM)-GPNNFGSGK(CPQ2)-PEG2-k-NH2 | 791 |
| 115 | EDTRNT | Probe #115 | (FAM)-GEDTRNTGK(CPQ2)-NH2 | 792 |
| 116 | KDLEQS | Probe #116 | (FAM)-GKDLEQSGK(CPQ2)-NH2 | 793 |
| 117 | AALHND | Probe #117 | (FAM)-GAALHNDGK(CPQ2)-PEG2-kk-NH2 | 794 |
| 118 | ADSFFK | Probe #118 | (FAM)-GADSFFKGK(CPQ2)-NH2 | 795 |
| 119 | ITFWRA | Probe #119 | (FAM)-GITFWRAGK(CPQ2)-NH2 | 796 |
| 120 | LSD(Nle)RL | Probe #120 | (FAM)-GLSD(Nle)RLGK(CPQ2)-NH2 | 797 |
| 121 | EVGWTY | Probe #121 | (FAM)-GEVGWTYGK(CPQ2)-PEG2-k-NH2 | 798 |
| 122 | IAFRQ(Nle) | Probe #122 | (FAM)-GIAFRQ(Nle)GK(CPQ2)-NH2 | 799 |
| 123 | YNIHT(Nle) | Probe #123 | (FAM)-GYNIHT(Nle)GK(CPQ2)-PEG2-kk-NH2 | 800 |
| 124 | (Nle)LWANH | Probe #124 | (FAM)-G(Nle)LWANHGK(CPQ2)-PEG2-kk-NH2 | 801 |
| 125 | LYSVQV | Probe #125 | (FAM)-GLYSVQVGK(CPQ2)-PEG2-k-NH2 | 802 |
| 126 | SHI(Nle)SN | Probe #126 | (FAM)-GSHI(Nle)SNGK(CPQ2)-PEG2-kk-NH2 | 803 |
| 127 | KLLIDV | Probe #127 | (FAM)-GKLLIDVGK(CPQ2)-NH2 | 804 |
| 128 | E(Nle)GVFD | Probe #128 | (FAM)-GE(Nle)GVFDGK(CPQ2)-PEG2-k-NH2 | 805 |
| 129 | HQAYTL | Probe #129 | (FAM)-GHQAYTLGK(CPQ2)-PEG2-kk-NH2 | 806 |
| 130 | YVRKIQ | Probe #130 | (FAM)-GYVRKIQGK(CPQ2)-PEG2-k-NH2 | 807 |
| 131 | DRENSP | Probe #131 | (FAM)-GDRENSPGK(CPQ2)-NH2 | 808 |
| 132 | KYDKPR | Probe #132 | (FAM)-GKYDKPRGK(CPQ2)-NH2 | 809 |
| 133 | RPWKQL | Probe #133 | (FAM)-GRPWKQLGK(CPQ2)-PEG2-k-NH2 | 810 |
| 134 | APLQRY | Probe #134 | (FAM)-GAPLQRYGK(CPQ2)-NH2 | 811 |
| 135 | YQGQK(Nle) | Probe #135 | (FAM)-GYQGQK(Nle)GK(CPQ2)-NH2 | 812 |
| 136 | GRISSI | Probe #136 | (FAM)-GGRISSIGK(CPQ2)-NH2 | 813 |
| 137 | HSLTNV | Probe #137 | (FAM)-GHSLTNVGK(CPQ2)-PEG2-kk-NH2 | 814 |
| 138 | EWDFPE | Probe #138 | (FAM)-GEWDFPEGK(CPQ2)-PEG2-k-NH2 | 815 |
| 139 | YLA(Nle)DG | Probe #139 | (FAM)-GYLA(Nle)DGGK(CPQ2)-PEG2-k-NH2 | 816 |
| 140 | FIY(Nle)PT | Probe #140 | (FAM)-GFIY(Nle)PTGK(CPQ2)-PEG2-k-NH2 | 817 |
| 141 | GHETWV | Probe #141 | (FAM)-GGHETWVGK(CPQ2)-PEG2-kk-NH2 | 818 |
| 142 | DYIGDE | Probe #142 | (FAM)-GDYIGDEGK(CPQ2)-PEG2-k-NH2 | 819 |
| 143 | AGTAHP | Probe #143 | (FAM)-GAGTAHPGK(CPQ2)-PEG2-kk-NH2 | 820 |
| 144 | V(Nle)TEIW | Probe #144 | (FAM)-GV(Nle)TEIWGK(CPQ2)-PEG2-k-NH2 | 821 |
| 145 | PDDWQN | Probe #145 | (FAM)-GPDDWQNGK(CPQ2)-PEG2-k-NH2 | 822 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 146 | GLNQEY | Probe #146 | (FAM)-GGLNQEYGK(CPQ2)-PEG2-k-NH2 | 823 |
| 147 | YRDAVA | Probe #147 | (FAM)-GYRDAVAGK(CPQ2)-NH2 | 824 |
| 148 | TGPKGN | Probe #148 | (FAM)-GTGPKGNGK(CPQ2)-NH2 | 825 |
| 149 | DHVPQI | Probe #149 | (FAM)-GDHVPQIGK(CPQ2)-PEG2-kk-NH2 | 826 |
| 150 | NKEPIL | Probe #150 | (FAM)-GNKEPILGK(CPQ2)-NH2 | 827 |
| 151 | VWN(Nle)VH | Probe #151 | (FAM)-GVWN(Nle)VHGK(CPQ2)-PEG2-kk-NH2 | 828 |
| 152 | PVIIEH | Probe #152 | (FAM)-GPVIIEHGK(CPQ2)-PEG2-kk-NH2 | 829 |
| 153 | FQTDNL | Probe #153 | (FAM)-GFQTDNLGK(CPQ2)-PEG2-k-NH2 | 830 |
| 154 | RF(Nle)HGI | Probe #154 | (FAM)-GRF(Nle)HGIGK(CPQ2)-PEG2-k-NH2 | 831 |
| 155 | YAERTT | Probe #155 | (FAM)-GYAERTTGK(CPQ2)-NH2 | 832 |
| 156 | NRGELP | Probe #156 | (FAM)-GNRGELPGK(CPQ2)-NH2 | 833 |
| 157 | HHYFNY | Probe #157 | (FAM)-GHEYFNYGK(CPQ2)-PEG2-k-NH2 | 834 |
| 158 | STPYYH | Probe #158 | (FAM)-GSTPYYHGK(CPQ2)-PEG2-kk-NH2 | 835 |
| 159 | WFYPSA | Probe #159 | (FAM)-GWFYPSAGK(CPQ2)-PEG2-k-NH2 | 836 |
| 160 | SEFLFS | Probe #160 | (FAM)-GSEFLFSGK(CPQ2)-PEG2-k-NH2 | 837 |
| 161 | WYKTQY | Probe #161 | (FAM)-GWYKTQYGK(CPQ2)-NH2 | 838 |
| 162 | VTHLKV | Probe #162 | (FAM)-GVTHLKVGK(CPQ2)-PEG2-k-NH2 | 839 |
| 163 | INGGFS | Probe #163 | (FAM)-GINGGFSGK(CPQ2)-PEG2-k-NH2 | 840 |
| 164 | TVLGLD | Probe #164 | (FAM)-GTVLGLDGK(CPQ2)-PEG2-k-NH2 | 841 |
| 165 | SYWP(Nle)Q | Probe #165 | (FAM)-GSYWP(Nle)QGK(CPQ2)-PEG2-k-NH2 | 842 |
| 166 | ASQQHR | Probe #166 | (FAM)-GASQQHRGK(CPQ2)-PEG2-k-NH2 | 843 |
| 167 | KNPAKA | Probe #167 | (FAM)-GKNPAKAGK(CPQ2)-PEG2-k-NH2 | 844 |
| 168 | (Nle)YWLVE | Probe #168 | (FAM)-G(Nle)YWLVEGK(CPQ2)-PEG2-k-NH2 | 845 |
| 169 | SWWIFE | Probe #169 | (FAM)-GSWWIFEGK(CPQ2)-PEG2-k-NH2 | 846 |
| 170 | VNYEQD | Probe #170 | (FAM)-GVNYEQDGK(CPQ2)-PEG2-k-NH2 | 847 |
| 171 | HFF(Nle)AE | Probe #171 | (FAM)-GHFF(Nle)AEGK(CPQ2)-PEG2-kk-NH2 | 848 |
| 172 | DIPPHW | Probe #172 | (FAM)-GDIPPHWGK(CPQ2)-PEG2-kk-NH2 | 849 |
| 173 | VDQW(Nle)W | Probe #173 | (FAM)-GVDQW(Nle)WGK(CPQ2)-PEG2-k-NH2 | 850 |
| 174 | LRSL(Nle)K | Probe #174 | (FAM)-GLRSL(Nle)KGK(CPQ2)-PEG2-k-NH2 | 851 |
| 175 | (Nle)(Nle)IRHA | Probe #175 | (FAM)-G(Nle)(Nle)IRHAGK(CPQ2)-PEG2-k-NH2 | 852 |
| 176 | HDVKFI | Probe #176 | (FAM)-GHDVKFIGK(CPQ2)-PEG2-kk-NH2 | 853 |
| 177 | KRVQFL | Probe #177 | (FAM)-GKRVQFLGK(CPQ2)-PEG2-k-NH2 | 854 |
| 178 | RD(Nle)YAE | Probe #178 | (FAM)-GRD(Nle)YAEGK(CPQ2)-NH2 | 855 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 179 | L(Nle)IYFE | Probe #179 | (FAM)-GL(Nle)IYFEGK(CPQ2)-PEG2-k-NH2 | 856 |
| 180 | LRTKQS | Probe #180 | (FAM)-GLRTKQSGK(CPQ2)-PEG2-k-NH2 | 857 |
| 181 | WHGQQY | Probe #181 | (FAM)-GWHGQQYGK(CPQ2)-PEG2-kk-NH2 | 858 |
| 182 | GPEGTI | Probe #182 | (FAM)-GGPEGTIGK(CPQ2)-PEG2-k-NH2 | 859 |
| 183 | ELDPIP | Probe #183 | (FAM)-GELDPIPGK(CPQ2)-PEG2-k-NH2 | 860 |
| 184 | GRAADF | Probe #184 | (FAM)-GGRAADFGK(CPQ2)-NH2 | 861 |
| 185 | HFIDYI | Probe #185 | (FAM)-GHFIDYIGK(CPQ2)-PEG2-kk-NH2 | 862 |
| 186 | S(Nle)(Nle)RVH | Probe #186 | (FAM)-GS(Nle)(Nle)RVHGK(CPQ2)-PEG2-k-NH2 | 863 |
| 187 | SFRKII | Probe #187 | (FAM)-GSFRKIIGK(CPQ2)-PEG2-k-NH2 | 864 |
| 188 | TYE(Nle)FS | Probe #188 | (FAM)-GTYE(Nle)FSGK(CPQ2)-PEG2-k-NH2 | 865 |
| 189 | HLLGFY | Probe #189 | (FAM)-GHLLGFYGK(CPQ2)-PEG2-kk-NH2 | 866 |
| 190 | (Nle)WTALT | Probe #190 | (FAM)-G(Nle)WTALTGK(CPQ2)-PEG2-k-NH2 | 867 |
| 191 | IWN(Nle)VY | Probe #191 | (FAM)-GIWN(Nle)VYGK(CPQ2)-PEG2-k-NH2 | 868 |
| 192 | RRNPLW | Probe #192 | (FAM)-GRRNPLWGK(CPQ2)-PEG2-k-NH2 | 869 |
| 193 | RWYGGI | Probe #193 | (FAM)-GRWYGGIGK(CPQ2)-NH2 | 870 |
| 194 | KTGDAR | Probe #194 | (FAM)-GKTGDARGK(CPQ2)-PEG2-k-NH2 | 871 |
| 195 | NYWEAN | Probe #195 | (FAM)-GNYWEANGK(CPQ2)-PEG2-k-NH2 | 872 |
| 196 | (Nle)QFDTS | Probe #196 | (FAM)-G(Nle)QFDTSGK(CPQ2)-PEG2-k-NH2 | 873 |
| 197 | KRGAVE | Probe #197 | (FAM)-GKRGAVEGK(CPQ2)-PEG2-k-NH2 | 874 |
| 198 | SLKPTE | Probe #198 | (FAM)-GSLKPTEGK(CPQ2)-NH2 | 875 |
| 199 | ENDRLP | Probe #199 | (FAM)-GENDRLPGK(CPQ2)-NH2 | 876 |
| 200 | NSYQVQ | Probe #200 | (FAM)-GNSYQVQGK(CPQ2)-NH2 | 877 |
| 201 | YPKEYL | Probe #201 | (FAM)-GYPKEYLGK(CPQ2)-NH2 | 878 |
| 202 | INNKWQ | Probe #202 | (FAM)-GINNKWQGK(CPQ2)-NH2 | 879 |
| 203 | (Nle)EFQGW | Probe #203 | (FAM)-G(Nle)EFQGWGK(CPQ2)-PEG2-k-NH2 | 880 |
| 204 | PVRSTN | Probe #204 | (FAM)-GPVRSTNGK(CPQ2)-NH2 | 881 |
| 205 | SQAIKV | Probe #205 | (FAM)-GSQAIKVGK(CPQ2)-NH2 | 882 |
| 206 | WA(Nle)LYH | Probe #206 | (FAM)-GWA(Nle)LYHGK(CPQ2)-PEG2-kk-NH2 | 883 |
| 207 | ISWIHA | Probe #207 | (FAM)-GISWIHAGK(CPQ2)-PEG2-kk-NH2 | 884 |
| 208 | AHDIV | Probe #208 | (FAM)-GAHDIVNGK(CPQ2)-PEG2-kk-NH2 | 885 |
| 209 | RHNVAS | Probe #209 | (FAM)-GRHNVASGK(CPQ2)-PEG2-k-NH2 | 886 |
| 210 | SVFVIE | Probe #210 | (FAM)-GSVFVIEGK(CPQ2)-PEG2-k-NH2 | 887 |
| 211 | FAKYYK | Probe #211 | (FAM)-GFAKYYKGK(CPQ2)-PEG2-k-NH2 | 888 |
| 212 | PYNTLQ | Probe #212 | (FAM)-GPYNTLQGK(CPQ2)-PEG2-k-NH2 | 889 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 213 | (Nle)DWGH(Nle) | Probe #213 | (FAM)-G(Nle)DWGH(Nle)GK(CPQ2)-PEG2-kk-NH2 | 890 |
| 214 | SNREWF | Probe #214 | (FAM)-GSNREWFGK(CPQ2)-NH2 | 891 |
| 215 | GKSEHT | Probe #215 | (FAM)-GGKSEHTGK(CPQ2)-PEG2-kk-NH2 | 892 |
| 216 | FP(Nle)TDQ | Probe #216 | (FAM)-GFP(Nle)TDQGK(CPQ2)-PEG2-k-NH2 | 893 |
| 217 | WSKFW(Nle) | Probe #217 | (FAM)-GWSKFW(Nle)GK(CPQ2) | 894 |
| 218 | RFTRPH | Probe #218 | (FAM)-GRFTRPHGK(CPQ2)-NH2 | 895 |
| 219 | QET(Nle)KD | Probe #219 | (FAM)-GQET(Nle)KDGK(CPQ2)-NH2 | 896 |
| 220 | HWWDVL | Probe #220 | (FAM)-GHWWDVLGK(CPQ2)-PEG2-kk-NH2 | 897 |
| 221 | FNLV(Nle)S | Probe #221 | (FAM)-GFNLV(Nle)SGK(CPQ2)-PEG2-k-NH2 | 898 |
| 222 | SAWRQR | Probe #222 | (FAM)-GSAWRQRGK(CPQ2)-PEG2-k-NH2 | 899 |
| 223 | TFHIFL | Probe #223 | (FAM)-GTFHIFLGK(CPQ2)-PEG2-kk-NH2 | 900 |
| 224 | WPQHVK | Probe #224 | (FAM)-GWPQHVKGK(CPQ2)-PEG2-k-NH2 | 901 |
| 225 | LI(Nle)HKN | Probe #225 | (FAM)-GLI(Nle)HKNGK(CPQ2)-PEG2-k-NH2 | 902 |
| 226 | QDLEQP | Probe #226 | (FAM)-GQDLEQPGK(CPQ2)-PEG2-k-NH2 | 903 |
| 227 | HQKK(Nle)P | Probe #227 | (FAM)-GHQKK(Nle)PGK(CPQ2)-NH2 | 904 |
| 228 | GVTWLN | Probe #228 | (FAM)-GGVTWLNGK(CPQ2)-PEG2-k-NH2 | 905 |
| 229 | AGEPFK | Probe #229 | (FAM)-GAGEPFKGK(CPQ2)-NH2 | 906 |
| 230 | SR(Nle)ATT | Probe #230 | (FAM)-GSR(Nle)ATTGK(CPQ2)-NH2 | 907 |
| 231 | LAF(Nle)NH | Probe #231 | (FAM)-GLAF(Nle)NHGK(CPQ2)-PEG2-kk-NH2 | 908 |
| 232 | PPSGLS | Probe #232 | (FAM)-GPPSGLSGK(CPQ2)-PEG2-k-NH2 | 909 |
| 233 | YTHSSP | Probe #233 | (FAM)-GYTHSSPGK(CPQ2)-PEG2-kk-NH2 | 910 |
| 234 | DGSHYR | Probe #234 | (FAM)-GDGSHYRGK(CPQ2)-PEG2-kk-NH2 | 911 |
| 235 | Y(Nle)GNGY | Probe #235 | (FAM)-GY(Nle)GNGYGK(CPQ2)-PEG2-k-NH2 | 912 |
| 236 | DSITVS | Probe #236 | (FAM)-GDSITVSGK(CPQ2)-PEG2-k-NH2 | 913 |
| 237 | QTPNIQ | Probe #237 | (FAM)-GQTPNIQGK(CPQ2)-PEG2-k-NH2 | 914 |
| 238 | KLFFGY | Probe #238 | (FAM)-GKLFFGYGK(CPQ2)-NH2 | 915 |
| 239 | TQNFNW | Probe #239 | (FAM)-GTQNFNWGK(CPQ2)-PEG2-k-NH2 | 916 |
| 240 | YSDHEV | Probe #240 | (FAM)-GYSDHEVGK(CPQ2)-PEG2-kk-NH2 | 917 |
| 241 | RYVVPA | Probe #241 | (FAM)-GRYVVPAGK(CPQ2)-NH2 | 918 |
| 242 | ILHRIR | Probe #242 | (FAM)-GILHRIRGK(CPQ2)-NH2 | 919 |
| 243 | ESDNQ(Nle) | Probe #243 | (FAM)-GESDNQ(Nle)GK(CPQ2)-PEG2-k-NH2 | 920 |
| 244 | YDDKG(Nle) | Probe #244 | (FAM)-GYDDKG(Nle)GK(CPQ2)-NH2 | 921 |
| 245 | QLS(Nle)VW | Probe #245 | (FAM)-GQLS(Nle)VWGK(CPQ2)-PEG2-k-NH2 | 922 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 246 | PGGER(Nle) | Probe #246 | (FAM)-GPGGER(Nle)GK(CPQ2)-NH2 | 923 |
| 247 | WKHHPD | Probe #247 | (FAM)-GWKHHPDGK(CPQ2)-NH2 | 924 |
| 248 | QWVDED | Probe #248 | (FAM)-GQWVDEDGK(CPQ2)-PEG2-k-NH2 | 925 |
| 249 | NAYNEI | Probe #249 | (FAM)-GNAYNEIGK(CPQ2)-PEG2-k-NH2 | 926 |
| 250 | EEKAPR | Probe #250 | (FAM)-GEEKAPRGK(CPQ2)-PEG2-kk-NH2 | 927 |
| 251 | PWQIGK | Probe #251 | (FAM)-GPWQIGKGK(CPQ2)-NH2 | 928 |
| 252 | IAQVGN | Probe #252 | (FAM)-GIAQVGNGK(CPQ2)-PEG2-k-NH2 | 929 |
| 253 | V(Nle)RQSE | Probe #253 | (FAM)-GV(Nle)RQSEGK(CPQ2)-NH2 | 930 |
| 254 | TERVDA | Probe #254 | (FAM)-GTERVDAGK(CPQ2)-NH2 | 931 |
| 255 | WLRWRL | Probe #255 | (FAM)-GWLRWRLGK(CPQ2)-PEG2-k-NH2 | 932 |
| 256 | WKTKGQ | Probe #256 | (FAM)-GWKTKGQGK(CPQ2)-PEG2-k-NH2 | 933 |
| 257 | QSNGDV | Probe #257 | (FAM)-GQSNGDVGK(CPQ2)-PEG2-k-NH2 | 934 |
| 258 | TLFYAL | Probe #258 | (FAM)-GTLFYALGK(CPQ2)-PEG2-k-NH2 | 935 |
| 259 | TVTLNP | Probe #259 | (FAM)-GTVTLNPGK(CPQ2)-PEG2-k-NH2 | 936 |
| 260 | YAFGRK | Probe #260 | (FAM)-GYAFGRKGK(CPQ2)-PEG2-k-NH2 | 937 |
| 261 | DYNYWD | Probe #261 | (FAM)-GDYNYWDGK(CPQ2)-PEG2-k-NH2 | 938 |
| 262 | EWHEII | Probe #262 | (FAM)-GEWHEIIGK(CPQ2)-PEG2-kk-NH2 | 939 |
| 263 | QKAAWD | Probe #263 | (FAM)-GQKAAWDGK(CPQ2)-NH2 | 940 |
| 264 | DNTSAD | Probe #264 | (FAM)-GDNTSADGK(CPQ2)-PEG2-k-NH2 | 941 |
| 265 | HEGEYV | Probe #265 | (FAM)-GHEGEYVGK(CPQ2)-PEG2-kk-NH2 | 942 |
| 266 | WSPSFK | Probe #266 | (FAM)-GWSPSFKGK(CPQ2)-NH2 | 943 |
| 267 | HDEHWT | Probe #267 | (FAM)-GHDEHWTGK(CPQ2)-PEG2-kk-NH2 | 944 |
| 268 | YVW(Nle)RD | Probe #268 | (FAM)-GYVW(Nle)RDGK(CPQ2)-NH2 | 945 |
| 269 | (Nle)DP(Nle)KF | Probe #269 | (FAM)-G(Nle)DP(Nle)KFGK(CPQ2)-NH2 | 946 |
| 270 | (Nle)R(Nle)FWD | Probe #270 | (FAM)-G(Nle)R(Nle)FWDGK(CPQ2)-NH2 | 947 |
| 271 | DIAIT(Nle) | Probe #271 | (FAM)-GDIAIT(Nle)GK(CPQ2)-PEG2-k-NH2 | 948 |
| 272 | PI(Nle)RFH | Probe #272 | (FAM)-GPI(Nle)RFHGK(CPQ2)-PEG2-k-NH2 | 949 |
| 273 | VWQGYI | Probe #273 | (FAM)-GVWQGYIGK(CPQ2)-PEG2-k-NH2 | 950 |
| 274 | KK(Nle)SNP | Probe #274 | (FAM)-GKK(Nle)SNPGK(CPQ2)-PEG2-k-NH2 | 951 |
| 275 | GHPLSP | Probe #275 | (FAM)-GGHPLSPGK(CPQ2)-PEG2-kk-NH2 | 952 |
| 276 | VRQHKP | Probe #276 | (FAM)-GVRQHKPGK(CPQ2)-NH2 | 953 |
| 277 | AQNFYR | Probe #277 | (FAM)-GAQNFYRGK(CPQ2)-NH2 | 954 |
| 278 | VAGKSI | Probe #278 | (FAM)-GVAGKSIGK(CPQ2)-NH2 | 955 |
| 279 | LVGQVN | Probe #279 | (FAM)-GLVGQVNGK(CPQ2)-PEG2-k-NH2 | 956 |
| 280 | QVKHFT | Probe #280 | (FAM)-GQVKHFTGK(CPQ2)-PEG2-k-NH2 | 957 |
| 281 | QKSVVS | Probe #281 | (FAM)-GQKSVVSGK(CPQ2)-NH2 | 958 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 282 | Y(Nle)QEWL | Probe #282 | (FAM)-GY(Nle)QEWLGK(CPQ2)-PEG2-k-NH2 | 959 |
| 283 | G(Nle)YIDE | Probe #283 | (FAM)-GG(Nle)YIDEGK(CPQ2)-PEG2-k-NH2 | 960 |
| 284 | NAGSKF | Probe #284 | (FAM)-GNAGSKFGK(CPQ2)-NH2 | 961 |
| 285 | EFVHNP | Probe #285 | (FAM)-GEFVHNPGK(CPQ2)-PEG2-kk-NH2 | 962 |
| 286 | WE(Nle)VKI | Probe #286 | (FAM)-GWE(Nle)VKIGK(CPQ2)-NH2 | 963 |
| 287 | WVGASH | Probe #287 | (FAM)-GWVGASHGK(CPQ2)-PEG2-kk-NH2 | 964 |
| 288 | ITTLY(Nle) | Probe #288 | (FAM)-GITTLY(Nle)GK(CPQ2)-PEG2-k-NH2 | 965 |
| 289 | GHIDEY | Probe #289 | (FAM)-GGHIDEYGK(CPQ2)-PEG2-kk-NH2 | 966 |
| 290 | KV(Nle)DYG | Probe #290 | (FAM)-GKV(Nle)DYGGK(CPQ2)-NH2 | 967 |
| 291 | QEKQT(Nle) | Probe #291 | (FAM)-GQEKQT(Nle)GK(CPQ2)-NH2 | 968 |
| 292 | EVGHEA | Probe #292 | (FAM)-GEVGHEAGK(CPQ2)-PEG2-kk-NH2 | 969 |
| 293 | AWEGQY | Probe #293 | (FAM)-GAWEGQYGK(CPQ2)-PEG2-k-NH2 | 970 |
| 294 | FLVQWT | Probe #294 | (FAM)-GFLVQWTGK(CPQ2)-PEG2-k-NH2 | 971 |
| 295 | SKWGYW | Probe #295 | (FAM)-GSKWGYWGK(CPQ2)-NH2 | 972 |
| 296 | TWIS(Nle)Q | Probe #296 | (FAM)-GTWIS(Nle)QGK(CPQ2)-PEG2-k-NH2 | 973 |
| 297 | VIDKDF | Probe #297 | (FAM)-GVIDKDFGK(CPQ2)-NH2 | 974 |
| 298 | VKFAIY | Probe #298 | (FAM)-GVKFAIYGK(CPQ2)-NH2 | 975 |
| 299 | HNQ(Nle)KS | Probe #299 | (FAM)-GHNQ(Nle)KSGK(CPQ2)-PEG2-k-NH2 | 976 |
| 300 | QYVFF(Nle) | Probe #300 | (FAM)-GQYVFF(Nle)GK(CPQ2)-PEG2-k-NH2 | 977 |
| 301 | YNPRE(Nle) | Probe #301 | (FAM)-GYNPRE(Nle)GK(CPQ2)-NH2 | 978 |
| 302 | KHG(Nle)PE | Probe #302 | (FAM)-GKHG(Nle)PEGK(CPQ2)-PEG2-kk-NH2 | 979 |
| 303 | WSREYW | Probe #303 | (FAM)-GWSREYWGK(CPQ2)-NH2 | 980 |
| 304 | IDRVDK | Probe #304 | (FAM)-GIDRVDKGK(CPQ2)-PEG2-kk-NH2 | 981 |
| 305 | GDRENSPK(CPQ2)L-OH | Probe #305 | (FAM)-kkGDRENSPK(CPQ2)L-OH | 982 |
| 306 | GDRENSPLK(CPQ2)-OH | Probe #306 | (FAM)-kkGDRENSPLK(CPQ2)-OH | 983 |
| 307 | NAGSKFK(CPQ2)Q-OH | Probe #307 | (FAM)-GNAGSKFK(CPQ2)Q-OH | 984 |
| 308 | NAGSKFQK(CPQ2)-OH | Probe #308 | (FAM)-GNAGSKFQK(CPQ2)-OH | 985 |
| 309 | GHLLGFYK(CPQ2)V-OH | Probe #309 | (FAM)-kkGHLLGFYK(CPQ2)V-OH | 986 |
| 310 | GHLLGFYVK(CPQ2)-OH | Probe #310 | (FAM)-kkGHLLGFYVK(CPQ2)-OH | 987 |
| 311 | GQEKQT(Nle)K(CPQ2)(Nle)-OH | Probe #311 | (FAM)-kkGQEKQT(Nle)K(CPQ2)(Nle)-OH | 988 |
| 312 | GQEKQT(Nle)(Nle)K(CPQ2)-OH | Probe #312 | (FAM)-kkGQEKQT(Nle)(Nle)K(CPQ2)-OH | 989 |
| 313 | kGDPFVVSK(CPQ2)W-OH | Probe #313 | (FAM)-kGDPFVVSK(CPQ2)W-OH | 990 |
| 314 | kGDPFVVSWK(CPQ2)-OH | Probe #314 | (FAM)-kGDPFVVSWK(CPQ2)-OH | 991 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 315 | NAYNEIK(CPQ2)R-OH | Probe #315 | (FAM)-GNAYNEIK(CPQ2)R-OH | 992 |
| 316 | NAYNEIRK(CPQ2)-OH | Probe #316 | (FAM)-GNAYNEIRK(CPQ2)-OH | 993 |
| 317 | V(Nle)RQSEK(CPQ2)N-OH | Probe #317 | (FAM)-GV(Nle)RQSEK(CPQ2)N-OH | 994 |
| 318 | V(Nle)RQSENK(CPQ2)-OH | Probe #318 | (FAM)-GV(Nle)RQSENK(CPQ2) | 995 |
| 319 | YNPRE(Nle)K(CPQ2)I-OH | Probe #319 | (FAM)-GYNPRE(Nle)K(CPQ2)I-OH | 996 |
| 320 | YNPRE(Nle)IK(CPQ2)-OH | Probe #320 | (FAM)-GYNPRE(Nle)IK(CPQ2)-OH | 997 |
| 321 | EFVHNPK(CPQ2)K-OH | Probe #321 | (FAM)-kGEFVHNPK(CPQ2)K-OH | 998 |
| 322 | EFVHNPKK(CPQ2)-OH | Probe #322 | (FAM)-kGEFVHNPKK(CPQ2)-OH | 999 |
| 323 | KRVQFLK(CPQ2)H-OH | Probe #323 | (FAM)-GKRVQFLK(CPQ2)H-OH | 1000 |
| 324 | KRVQFLHK(CPQ2)-OH | Probe #324 | (FAM)-GKRVQFLHK(CPQ2)-OH | 1001 |
| 325 | LI(Nle)HKNK(CPQ2)G-OH | Probe #325 | (FAM)-kGLI(Nle)HKNK(CPQ2)G-OH | 1002 |
| 326 | LI(Nle)HKNGK(CPQ2)-OH | Probe #326 | (FAM)-kGLI(Nle)HKNGK(CPQ2)-OH | 1003 |
| 327 | WA(Nle)LYHK(CPQ2)S-OH | Probe #327 | (FAM)-kkGWA(Nle)LYHK(CPQ2)S-OH | 1004 |
| 328 | WA(Nle)LYHSK(CPQ2)-OH | Probe #328 | (FAM)-kkGWA(Nle)LYHSK(CPQ2)-OH | 1005 |
| 329 | AHDIVNK(CPQ2)Y-OH | Probe #329 | (FAM)-kkGAHDIVNK(CPQ2)Y-OH | 1006 |
| 330 | AHDIVNYK(CPQ2)-OH | Probe #330 | (FAM)-kkGAHDIVNYK(CPQ2)-OH | 1007 |
| 331 | SVFVIEK(CPQ2)P-OH | Probe #331 | (FAM)-kGSVFVIEK(CPQ2)P-OH | 1008 |
| 332 | SVFVIEPK(CPQ2)-OH | Probe #332 | (FAM)-kGSVFVIEPK(CPQ2)-OH | 1009 |
| 333 | PPSGLSK(CPQ2)E-OH | Probe #333 | (FAM)-kGPPSGLSK(CPQ2)E-OH | 1010 |
| 334 | PPSGLSEK(CPQ2)-OH | Probe #334 | (FAM)-kGPPSGLSEK(CPQ2)-OH | 1011 |
| 335 | RWYGGIK(CPQ2)F-OH | Probe #335 | (FAM)-kkGRWYGGIK(CPQ2)F-OH | 1012 |
| 336 | RWYGGIFK(CPQ2)-OH | Probe #336 | (FAM)-kkGRWYGGIFK(CPQ2)-OH | 1013 |
| 337 | QYVFF(Nle)K(CPQ2)D-OH | Probe #337 | (FAM)-kGQYVFF(Nle)K(CPQ2)D-OH | 1014 |
| 338 | QYVFF(Nle)DK(CPQ2)-OH | Probe #338 | (FAM)-kGQYVFF(Nle)DK(CPQ2)-OH | 1015 |
| 339 | FAKYYKK(CPQ2)T-OH | Probe #339 | (FAM)-kGFAKYYKK(CPQ2)T-OH | 1016 |
| 340 | FAKYYKTK(CPQ2)-OH | Probe #340 | (FAM)-kGFAKYYKTK(CPQ2)-OH | 1017 |
| 341 | QVKHFTK(CPQ2)A-OH | Probe #341 | (FAM)-kGQVKHFTK(CPQ2)A-OH | 1018 |
| 342 | QVKHFTAK(CPQ2)-OH | Probe #342 | (FAM)-kGQVKHFTAK(CPQ2)-OH | 1019 |
| 343 | APK(CPQ2)-OH | Probe #343 | FAM-APK(CPQ2)-OH | 1020 |
| 344 | NH2-HK(FAM)DRENSP | Probe #344 | NH2-HK(FAM)DRENSPGK(CPQ2)-NH2 | 1021 |
| 345 | NH2-K(FAM)HDRENSP | Probe #345 | NH2-K(FAM)HDRENSPGK(CPQ2)-NH2 | 1022 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 346 | NH2-WK(FAM)NAGSKF | Probe #346 | NH2-WK(FAM)NAGSKFGkK(CPQ2)-NH2 | 1023 |
| 347 | NH2-K(FAM)WNAGSKF | Probe #347 | NH2-K(FAM)WNAGSKFGkK(CPQ2)-NH2 | 1024 |
| 348 | NH2-SK(FAM)HLLGFY | Probe #348 | NH2-SK(FAM)HLLGFYGkK(CPQ2)-NH2 | 1025 |
| 349 | NH2-K(FAM)SHLLGFY | Probe #349 | NH2-K(FAM)SHLLGFYGkK(CPQ2)-NH2 | 1026 |
| 350 | NH2-KK(FAM)QEKQT(Nle) | Probe #350 | NH2-KK(FAM)QEKQT(Nle)GK(CPQ2)-NH2 | 1027 |
| 351 | NH2-K(FAM)KQEKQT(Nle) | Probe #351 | NH2-K(FAM)KQEKQT(Nle)GK(CPQ2)-NH2 | 1028 |
| 352 | NH2-GK(FAM)DPFVVS | Probe #352 | NH2-GK(FAM)DPFVVSGK(CPQ2)-NH2 | 1029 |
| 353 | NH2-K(FAM)GDPFVVS | Probe #353 | NH2-K(FAM)GDPFVVSGK(CPQ2)-NH2 | 1030 |
| 354 | NH2-PK(FAM)NAYNEI | Probe #354 | NH2-PK(FAM)NAYNEIGK(CPQ2)-NH2 | 1031 |
| 355 | NH2-K(FAM)PNAYNEI | Probe #355 | NH2-K(FAM)PNAYNEIGK(CPQ2)-NH2 | 1032 |
| 356 | NH2-DK(FAM)V(Nle)RQSE | Probe #356 | NH2-DK(FAM)V(Nle)RQSEGkK(CPQ2)-NH2 | 1033 |
| 357 | NH2-K(FAM)DV(Nle)RQSE | Probe #357 | NH2-K(FAM)DV(Nle)RQSEGkK(CPQ2)-NH2 | 1034 |
| 358 | NH2-EK(FAM)YNPRE(Nle) | Probe #358 | NH2-EK(FAM)YNPRE(Nle)GkK(CPQ2)-NH2 | 1035 |
| 359 | NH2-K(FAM)EYNPRE(Nle) | Probe #359 | NH2-K(FAM)EYNPRE(Nle)GkK(CPQ2)-NH2 | 1036 |
| 360 | NH2-TK(FAM)EFVHNP | Probe #360 | NH2-TK(FAM)EFVHNPG1cK(CPQ2)-NH2 | 1037 |
| 361 | NH2-K(FAM)TEFVHNP | Probe #361 | NH2-K(FAM)TEFVHNPG1cK(CPQ2)-NH2 | 1038 |
| 362 | NH2-QK(FAM)KRVQFL | Probe #362 | NH2-QK(FAM)KRVQFLGK(CPQ2)-NH2 | 1039 |
| 363 | NH2-K(FAM)QKRVQFL | Probe #363 | NH2-K(FAM)QKRVQFLGK(CPQ2)-NH2 | 1040 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 364 | NH2-YK(FAM)LI(Nle)HKN | Probe #364 | NH2-YK(FAM)LI(Nle)HKNGK(CPQ2)-NH2 | 1041 |
| 365 | NH2-K(FAM)YLI(Nle)HKN | Probe #365 | NH2-K(FAM)YLI(Nle)HKNGK(CPQ2)-NH2 | 1042 |
| 366 | NH2-FK(FAM)WA(Nle)LYH | Probe #366 | NH2-FK(FAM)WA(Nle)LYHG1cK(CPQ2)-NH2 | 1043 |
| 367 | NH2-K(FAM)FWA(Nle)LYH | Probe #367 | NH2-K(FAM)FWA(Nle)LYHG1cK(CPQ2)-NH2 | 1044 |
| 368 | NH2-IK(FAM)AHDIVN | Probe #368 | NH2-IK(FAM)AHDIVNG1cK(CPQ2)-NH2 | 1045 |
| 369 | NH2-K(FAM)IAHDIVN | Probe #369 | NH2-K(FAM)IAHDIVNG1cK(CPQ2)-NH2 | 1046 |
| 370 | NH2-VK(FAM)SVFVIF | Probe #370 | NH2-VK(FAM)SVFVIEGK(CPQ2)-NH2 | 1047 |
| 371 | NH2-K(FAM)VSVFVIF | Probe #371 | NH2-K(FAM)VSVFVIEGK(CPQ2)-NH2 | 1048 |
| 372 | NH2-(Nle)K(FAM)PPSGLS | Probe #372 | NH2-(Nle)K(FAM)PPSGLSGK(CPQ2)-NH2 | 1049 |
| 373 | NH2-K(FAM)(Nle)PPSGLS | Probe #373 | NH2-K(FAM)(Nle)PPSGLSGK(CPQ2)-NH2 | 1050 |
| 374 | NH2-LK(FAM)RWYGGI | Probe #374 | NH2-LK(FAM)RWYGGIG1cK(CPQ2)-NH2 | 1051 |
| 375 | NH2-K(FAM)LRWYGGI | Probe #375 | NH2-K(FAM)LRWYGGIG1cK(CPQ2)-NH2 | 1052 |
| 376 | NH2-NK(FAM)QYVFF(Nle) | Probe #376 | NH2-NK(FAM)QYVFF(Nle)GK(CPQ2)-NH2 | 1053 |
| 377 | NH2-K(FAM)NQYVFF(Nle) | Probe #377 | NH2-K(FAM)NQYVFF(Nle)GK(CPQ2)-NH2 | 1054 |
| 378 | NH2-AK(FAM)FAKYYK | Probe #378 | NH2-AK(FAM)FAKYYKGK(CPQ2)-NH2 | 1055 |
| 379 | NH2-K(FAM)AFAKYYK | Probe #379 | NH2-K(FAM)AFAKYYKGK(CPQ2)-NH2 | 1056 |
| 380 | NH2-RK(FAM)QVKHFT | Probe #380 | NH2-RK(FAM)QVKHFTGK(CPQ2)-NH2 | 1057 |
| 381 | NH2-K(FAM)RQVKHFT | Probe #381 | NH2-K(FAM)RQVKHFTGK(CPQ2)-NH2 | 1058 |
| 382 | NH2-K(FAM)PP | Probe #382 | NH2-K(FAM)PPK(CPQ2)-NH2 | 1059 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 383 | kpilffrlk | Probe #383 | 5FAM-GkpilffrlkGK(CPQ2)-PEG2-kk-NH2 | 1060 |
| 384 | LRR | Probe #384 | Boc-Leu-Arg-Arg-AMC | 1061 |
| 385 | R | Probe #385 | Arg-AMC | 1062 |
| 386 | VR | Probe #386 | Boc-Val-Arg-AMC | 1063 |
| 387 | RR | Probe #387 | Z-Arg-Arg-AMC | 1064 |
| 388 | GR | Probe #388 | Gly-Arg-AMC | 1065 |
| 389 | FR | Probe #389 | Z-Phe-Arg-AMC | 1066 |
| 390 | RGK | Probe #390 | Ac-Arg-Gly-Lys-AMC | 1067 |
| 391 | GGR | Probe #391 | Z-Gly-Gly-Arg-AMC | 1068 |
| 392 | F | Probe #392 | Glutaryl-Phe-AMC | 1069 |
| 393 | D | Probe #393 | H-Asp-AMC | 1070 |
| 394 | RR | Probe #394 | H-Arg-Arg-AMC | 1071 |
| 395 | R | Probe #395 | Z-Arg-AMC | 1072 |
| 396 | Bz-R | Probe #396 | Bz-Arg-AMC | 1073 |
| 397 | Bz-R | Probe #397 | Bz-Arg-AMC | 1073 |
| 398 | PR | Probe #398 | Z-Pro-Arg-AMC | 1074 |
| 399 | GPR | Probe #399 | Z-Gly-Pro-Arg-AMC | 1075 |
| 400 | LR | Probe #400 | Z-Leu-Arg-AMC | 1076 |
| 401 | PFR | Probe #401 | H-Pro-Phe-Arg-AMC | 1077 |
| 402 | LLR | Probe #402 | Z-Leu-Leu-Arg-AMC | 1078 |
| 403 | QRR | Probe #403 | Boc-Gln-Arg-Arg-AMC | 1079 |
| 404 | GR | Probe #404 | Glutaryl-Gly-Arg-AMC | 1080 |
| 405 | GRR | Probe #405 | Boc-Gly-Arg-Arg-AMC | 1081 |
| 406 | LRGG | Probe #406 | Z-Leu-Arg-Gly-Gly-AMC | 1082 |
| 407 | RLRGG | Probe #407 | 5-FAM-GRLRGGGK(CPQ2)-PEG2-kk-GC | 1083 |
| 408 | RELNGGAPI | Probe #408 | 5-FAM-GRELNGGAPIGK(CPQ2)-PEG2-kk-GC | 1084 |
| 409 | TSAVLQSGFRK | Probe #409 | 5-FAM-GTSAVLQSGFRKGK(CPQ2)-PEG2-kk-GC | 1085 |
| 410 | SGVTFQGKFKK | Probe #410 | 5-FAM-GSGVTFQGKFKKGK(CPQ2)-PEG2-kk-GC | 1086 |
| 411 | AAFA | Probe #411 | 5-FAM-GAAFAGK(CPQ2)-PEG2-kk-GC | 1087 |
| 412 | HGDQMAQKS | Probe #412 | 5FAM-GHGDQMAQKS-K(CPQ2)-PEG2-DLys-DLys-GC-NH2 | 1088 |
| 413 | GPLGMR | Probe #413 | 5FAM-GGPLGMRG-K(CPQ2)-PEG2-DLys-DLys-GC-NH2 | 1089 |
| 414 | FFLAQA-HomoPhe-RSK | Probe #414 | 5FAM-GFFLAQA-HomoPhe-RSK-K(CPQ2)-PEG2-DLys-DLys-GC-NH2 | 1090 |
| 415 | AHAVSRIRIYLLPAK | Probe #415 | 5FAM-GAHAVSRIRIYLLPAK-K(CPQ2)-PEG2-DLys-DLys-GC-NH2 | 1091 |
| 416 | PLALWAR | Probe #416 | 5FAM-GPLALWAR-K(CPQ2)-PEG2-DLys-DLys-GC-NH2 | 1092 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 417 | PLA-C(OMeBzl)-WAR | Probe #417 | 5FAM-GPLA-C(OMeBzl)-WAR-K(CPQ2)-PEG2-DLys-DLys-GC-NH2 | 1093 |
| 418 | APRWIQD | Probe #418 | 5FAM-GAPRWIQD-K(CPQ2)-PEG2-DLys-DLys-GC-NH2 | 1094 |
| 419 | LREQQRLKS | Probe #419 | 5FAM-GLREQQRLKS-K(CPQ2)-PEG2-DLys-DLys-GC-NH2 | 1095 |
| 420 | EFPIYVFLPAKK | Probe #420 | 5FAM-GEFPIYVFLPAKK-K(CPQ2)-PEG2-DLys-DLys-GC-NH2 | 1096 |
| 421 | GAANLVRGG | Probe #421 | 5FAM-GGAANLVRGG-K(CPQ2)-PEG2-DLys-DLys-GC-NH2 | 1097 |
| 422 | GYAELRMG | Probe #422 | 5FAM-GGYAELRMGG-K(CPQ2)-PEG2-DLys-DLys-GC-NH2 | 1098 |
| 423 | AAGAMFLEA | Probe #423 | 5FAM-GAAGAMFLEA-K(CPQ2)-PEG2-DLys-DLys-GC-NH2 | 1099 |
| 424 | LGGSGQRGRKALE | Probe #424 | (FAM)-GLGGSGQRGRKALEG-K(CPQ2)-(PEG2)-DLys-DLys-GC | 1100 |
| 425 | LGGSGHYGRSGLE | Probe #425 | (FAM)-GLGGSGHYGRSGLEG-K(CPQ2)-(PEG2)-DLys-DLys-GC | 1101 |
| 426 | YGRS | Probe #426 | (FAM)-GYGRSG-K(CPQ2)-(PEG2)-DLys-DLys-GC | 1102 |
| 427 | FRGRK | Probe #427 | (FAM)-GFRGRKG-K(CPQ2)-(PEG2)-DLys-DLys-GC | 1103 |
| 428 | DRRKKLTQ | Probe #428 | (FAM)-GDRRKKLTQG-K(CPQ2)-(PEG2)-DLys-DLys-GC | 1104 |
| 429 | HPGGPQ | Probe #429 | (FAM)-GHPGGPQG-K(CPQ2)-(PEG2)-DLys-DLys-GC | 1105 |
| 430 | KLRFSKQ | Probe #430 | (FAM)-GKLRFSKQG-K(CPQ2)-(PEG2)-DLys-DLys-GC | 1106 |
| 431 | AIKFFSAQ | Probe #431 | (FAM)-GAIKFFSAQG-K(CPQ2)-(PEG2)-DLys-DLys-GC | 1107 |
| 432 | AIKFFVRQ | Probe #432 | (FAM)-GAIKFFVRQG-K(CPQ2)-(PEG2)-DLys-DLys-GC | 1108 |
| 433 | RPPGFSAFK | Probe #433 | (FAM)-GRPPGFSAFKG-K(CPQ2)-(PEG2)-DLys-DLys-GC | 1109 |
| 434 | FAP-QLS | Probe #434 | (FAM)-GFAP-QLSG-K(CPQ2)-(PEG2)-DLys-DLys-GC | 1110 |
| 435 | FAA-QMA | Probe #435 | (FAM)-GFAA-QMAG-K(CPQ2)-(PEG2)-DLys-DLys-GC | 1111 |
| 436 | GMP-ANQ | Probe #436 | (FAM)-GGMP-ANQG-K(CPQ2)-(PEG2)-DLys-DLys-GC | 1112 |
| 437 | LSGRSDNH | Probe #437 | (FAM)-GLSGRSDNHG-K(CPQ2)-(PEG2)-DLys-DLys-GC | 1113 |
| 438 | MAALITRPDF | Probe #438 | (FAM)-GMAALITRPDFG-K(CPQ2)-(PEG2)-DLys-DLys-GC | 1114 |
| 439 | MAAAITRPRF | Probe #439 | (FAM)-GMAAAITRPRFG-K(CPQ2)-(PEG2)-DLys-DLys-GC | 1115 |
| 440 | MAALIVRPDL | Probe #440 | (FAM)-GMAALIVRPDLG-K(CPQ2)-(PEG2)-DLys-DLys-GC | 1116 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 441 | TSGPNQEQE | Probe #441 | (FAM)-GTSGPNQEQEG-K(CPQ2)-(PEG2)-DLys-DLys-GC | 1117 |
| 442 | TAGPNQEQE | Probe #442 | (FAM)-GTAGPNQEQEG-K(CPQ2)-(PEG2)-DLys-DLys-GC | 1118 |
| 443 | GPGPNQA | Probe #443 | (FAM)-GGPGPNQAG-K(CPQ2)-(PEG2)-DLys-DLys-GC | 1119 |
| 444 | ASGPAGPA | Probe #444 | (FAM)-GASGPAGPAG-K(CPQ2)-(PEG2)-DLys-DLys-GC | 1120 |
| 445 | ERGETGPSG | Probe #445 | (FAM)-GERGETGPSGG-K(CPQ2)-(PEG2)-DLys-DLys-GC | 1121 |
| 446 | VSQELGQR | Probe #446 | (FAM)-GVSQELGQRG-K(CPQ2)-(PEG2)-DLys-DLys-GC | 1122 |
| 447 | TGPPGYPTG | Probe #447 | (FAM)-GTGPPGYPTGG-K(CPQ2)-(PEG2)-DLys-DLys-GC | 1123 |
| 448 | TRLPVYQ | Probe #448 | (FAM)-GTRLPVYQG-K(CPQ2)-(PEG2)-DLys-DLys-GC | 1124 |
| 449 | RQARVVGG | Probe #449 | (FAM)-GRQARVVGGG-K(CPQ2)-(PEG2)-DLys-DLys-GC | 1125 |
| 450 | RQRRVVGG | Probe #450 | (FAM)-GRQRRVVGGG-K(CPQ2)-(PEG2)-DLys-DLys-GC | 1126 |
| 451 | RQARAVGG | Probe #451 | (FAM)-GRQARAVGGG-K(CPQ2)-(PEG2)-DLys-DLys-GC | 1127 |
| 452 | RKRRGSRG | Probe #452 | (FAM)-GRKRRGSRGG-K(CPQ2)-(PEG2)-DLys-DLys-GC | 1128 |
| 453 | KQSRKFVP | Probe #453 | (FAM)-GKQSRKFVPG-K(CPQ2)-(PEG2)-DLys-DLys-GC | 1129 |
| 454 | VTGRS | Probe #454 | (FAM)-GVTGRSG-K(CPQ2)-(PEG2)-DLys-DLys-GC | 1130 |
| 455 | LKSRVK | Probe #455 | (FAM)-GLKSRVKG-K(CPQ2)-(PEG2)-DLys-DLys-GC | 1131 |
| 456 | GIGAVLKVLT | Probe #456 | (FAM)-GGIGAVLKVLTG-K(CPQ2)-(PEG2)-DLys-DLys-GC | 1132 |
| 457 | GLPALISWIK | Probe #457 | (FAM)-GGLPALISWIKG-K(CPQ2)-(PEG2)-DLys-DLys-GC | 1133 |
| 458 | SEVNLDAEF | Probe #458 | (FAM)-GSEVNLDAEFG-K(CPQ2)-(PEG2)-DLys-DLys-GC | 1134 |
| 459 | EEKPICFFRLGKE | Probe #459 | (FAM)-GEEKPICFFRLGKEG-K(CPQ2)-(PEG2)-DLys-DLys-GC | 1135 |
| 460 | EEKPILFFRLGKE | Probe #460 | (FAM)-GEEKPILFFRLGKEG-K(CPQ2)-(PEG2)-DLys-DLys-GC | 1136 |
| 461 | APSSVIAA | Probe #461 | (FAM)-GAPSSVIAAG-K(CPQ2)-(PEG2)-DLys-DLys-GC | 1137 |
| 462 | KKAKRNAL | Probe #462 | (FAM)-GKKAKRNALG-K(CPQ2)-(PEG2)-DLys-DLys-GC | 1138 |
| 463 | WTNTSANYNL | Probe #463 | (FAM)-GWTNTSANYNLG-K(CPQ2)-(PEG2)-DLys-DLys-GC | 1139 |
| 464 | RVRR | Probe #464 | (FAM)-GRVRRG-K(CPQ2)-(PEG2)-DLys-DLys-GC | 1140 |
| 465 | ERTKR | Probe #465 | (FAM)-GERTKRG-K(CPQ2)-(PEG2)-DLys-DLys-GC | 1141 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 466 | RYQIKPLKSTDE | Probe #466 | (FAM)-GRYQIKPLKSTDEG-K(CPQ2)-(PEG2)-DLys-DLys-GC | 1142 |
| 467 | WELRHQA-(Hfe)-RSK | Probe #467 | (FAM)-GWELRHQA-(Hfe)-RSKG-K(CPQ2)-(PEG2)-DLys-DLys-GC | 1143 |
| 468 | SGAFK-C(Me)-LKDGAG | Probe #468 | (FAM)-GSGAFK-C(Me)-LKDGAGG-K(CPQ2)-(PEG2)-DLys-DLys-GC | 1144 |
| 469 | YVADGW | Probe #469 | (FAM)-GYVADGWG-K(CPQ2)-(PEG2)-DLys-DLys-GC | 1145 |
| 470 | WEHDGW | Probe #470 | (FAM)-GWEHDGWG-K(CPQ2)-(PEG2)-DLys-DLys-GC | 1146 |
| 471 | YVADAPV | Probe #471 | (FAM)-GYVADAPVG-K(CPQ2)-(PEG2)-DLys-DLys-GC | 1147 |
| 472 | RPPGFSA | Probe #472 | (FAM)-GRPPGFSAG-K(CPQ2)-(PEG2)-DLys-DLys-GC | 1148 |
| 473 | GSPAFLA | Probe #473 | (FAM)-GGSPAFLAG-K(CPQ2)-(PEG2)-DLys-DLys-GC | 1149 |
| 474 | AGFSLPA | Probe #474 | (FAM)-GAGFSLPAG-K(CPQ2)-(PEG2)-DLys-DLys-GC | 1150 |
| 475 | RWHTVGLRWE | Probe #475 | (FAM)-GRWHTVGLRWEG-K(CPQ2)-(PEG2)-DLys-DLys-GC | 1151 |
| 476 | LEQ | Probe #476 | (FAM)-GLEQG-K(CPQ2)-(PEG2)-DLys-DLys-GC | 1152 |
| 477 | RWPPMGLPWE | Probe #477 | (FAM)-GRWPPMGLPWEG-K(CPQ2)-(PEG2)-DLys-DLys-GC | 1153 |
| 478 | RPKPVE | Probe #478 | (FAM)-GRPKPVEG-K(CPQ2)-(PEG2)-DLys-DLys-GC | 1154 |
| 479 | IETD | Probe #479 | (FAM)-GIETDG-K(CPQ2)-(PEG2)-DLys-DLys-GC | 1155 |
| 480 | VGPDFGR | Probe #480 | (FAM)-GVGPDFGRG-K(CPQ2)-(PEG2)-DLys-DLys-GC | 1156 |
| 481 | GIEFDSGGC | Probe #481 | (FAM)-GGIEFDSGGCG-K(CPQ2)-(PEG2)-DLys-DLys-GC | 1157 |
| 482 | GDFLRRV | Probe #482 | (FAM)-GGDFLRRVG-K(CPQ2)-(PEG2)-DLys-DLys-GC | 1158 |
| 483 | AAL | Probe #483 | (FAM)-GAALG-K(CPQ2)-(PEG2)-DLys-DLys-GC | 1159 |
| 484 | YATWSMIAAH | Probe #484 | (FAM)-GYATWSMIAAHG-K(CPQ2)-(PEG2)-DLys-DLys-GC | 1160 |
| 485 | VIMWRLTVGT | Probe #485 | (FAM)-GVIMWRLTVGTG-K(CPQ2)-(PEG2)-DLys-DLys-GC | 1161 |
| 486 | RRVLALQQEL | Probe #486 | (FAM)-GRRVLALQQELG-K(CPQ2)-(PEG2)-DLys-DLys-GC | 1162 |
| 487 | LATWPLSGLW | Probe #487 | (FAM)-GLATWPLSGLWG-K(CPQ2)-(PEG2)-DLys-DLys-GC | 1163 |
| 488 | NTPNWLVNAV | Probe #488 | (FAM)-GNTPNWLVNAVG-K(CPQ2)-(PEG2)-DLys-DLys-GC | 1164 |
| 489 | SPLAQAVRSSSRK | Probe #489 | (FAM)-GSPLAQAVRSSSRKG-K(CPQ2)-(PEG2)-DLys-DLys-GC | 1165 |
| 490 | QMPGRLSMAF | Probe #490 | (FAM)-GQMPGRLSMAFG-K(CPQ2)-(PEG2)-DLys-DLys-GC | 1166 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 491 | PLGLR | Probe #491 | (FAM)-GPLGLRG-K(CPQ2)-(PEG2)-DLys-DLys-GC | 1167 |
| 492 | QRANSIRVTW | Probe #492 | (FAM)-GQRANSIRVTWG-K(CPQ2)-(PEG2)-DLys-DLys-GC | 1168 |
| 493 | PLAVR | Probe #493 | (FAM)-GPLAVRG-K(CPQ2)-(PEG2)-DLys-DLys-GC | 1169 |
| 494 | LLAVPAANTV | Probe #494 | (FAM)-GLLAVPAANTVG-K(CPQ2)-(PEG2)-DLys-DLys-GC | 1170 |
| 495 | GPQGLRGQ | Probe #495 | (FAM)-GGPQGLRGQG-K(CPQ2)-(PEG2)-DLys-DLys-GC | 1171 |
| 496 | RTGLYLYNST | Probe #496 | (FAM)-GRTGLYLYNSTG-K(CPQ2)-(PEG2)-DLys-DLys-GC | 1172 |
| 497 | RKKLTQSKFVGGAE | Probe #497 | (FAM)-GRKKLTQSKFVGGAEG-K(CPQ2)-(PEG2)-DLys-DLys-GC | 1173 |
| 498 | KHYR | Probe #498 | (FAM)-GKHYRG-K(CPQ2)-(PEG2)-DLys-DLys-GC | 1174 |
| 499 | QAR | Probe #499 | (FAM)-GQARG-K(CPQ2)-(PEG2)-DLys-DLys-GC | 1175 |
| 500 | PRPFNYL | Probe #500 | (FAM)-GPRPFNYLG-K(CPQ2)-(PEG2)-DLys-DLys-GC | 1176 |
| 501 | APFEMSA | Probe #501 | (FAM)-GAPFEMSAG-K(CPQ2)-(PEG2)-DLys-DLys-GC | 1177 |
| 502 | APFEFSA | Probe #502 | (FAM)-GAPFEFSAG-K(CPQ2)-(PEG2)-DLys-DLys-GC | 1178 |
| 503 | PLGFRV | Probe #503 | (FAM)-GPLGFRVG-K(CPQ2)-(PEG2)-DLys-GC | 1179 |
| 504 | RPLALWRS | Probe #504 | (FAM)-GRPLALWRSG-K(CPQ2)-(PEG2)-GC | 1180 |
| 505 | RPLALEESQ | Probe #505 | (FAM)-GRPLALEESQG-K(CPQ2)-(PEG2)-DLys-GC | 1181 |
| 506 | RPLALWRSQ | Probe #506 | (FAM)-GRPLALWRSQG-K(CPQ2)-(PEG2)-GC | 1182 |
| 507 | RNALAVERTAS | Probe #507 | (FAM)-GRNALAVERTASG-K(CPQ2)-(PEG2)-GC | 1183 |
| 508 | RPKPQQFW | Probe #508 | (FAM)-GRPKPQQFWG-K(CPQ2)-(PEG2)-DLys-GC | 1184 |
| 509 | SGSNPYKYTA | Probe #509 | (FAM)-SGSNPYKYTA-K(CPQ2)-(PEG2)-DLys-DLys-GC | 1185 |
| 510 | SGSNPYGYTA | Probe #510 | (FAM)-SGSNPYGYTA-K(CPQ2)-(PEG2)-DLys-DLys-GC | 1186 |
| 511 | SGTLSELHTA | Probe #511 | (FAM)-SGTLSELHTA-K(CPQ2)-(PEG2)-DLys-DLys-GC | 1187 |
| 512 | SGTISHLHTA | Probe #512 | (FAM)-SGTISHLHTA-K(CPQ2)-(PEG2)-DLys-DLys-GC | 1188 |
| 513 | SG-(Orn)-RSHP-(Hfe)-TLYTA | Probe #513 | (FAM)-SG-(Orn)-RSHP-(Hfe)-TLYTA-K(CPQ2)-(PEG2)-DLys-GC | 1189 |
| 514 | SG-(Orn)-RSHG-(Hfe)-FLYTA | Probe #514 | (FAM)-SG-(Orn)-RSHG-(Hfe)-FLYTA-K(CPQ2)-(PEG2)-DLys-GC | 1190 |
| 515 | SGESLAYYTA | Probe #515 | (FAM)-SGESLAYYTA-K(CPQ2)-(PEG2)-DLys-DLys-GC | 1191 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 516 | SGHMHAALTA | Probe #516 | (FAM)-SGHMHAALTA-K(CPQ2)-(PEG2)-DLys-DLys-GC | 1192 |
| 517 | ILSR-(DIle)-VGG | Probe #517 | (FAM)-GILSR-(DIle)-VGGG-K(CPQ2)-(PEG2)-DLys-GC | 1193 |
| 518 | ILS-(DArg)-(DIle)-(DVal)-GG | Probe #518 | (FAM)-GILS-(DArg)-(DIle)-(DVal)-GGG-K(CPQ2)-(PEG2)-DLys-GC | 1194 |
| 519 | RQRRALEK | Probe #519 | 5FAM-GRQRRALEKG-K(CPQ2)-PEG2-GC | 1195 |
| 520 | KPISLISS | Probe #520 | 5FAM-GKPISLISSG-K(CPQ2)-PEG2-GC | 1196 |
| 521 | QKGRYKQE | Probe #521 | 5FAM-GQKGRYKQEG-K(CPQ2)-PEG2-GC | 1197 |
| 522 | GPLGLRSW | Probe #522 | 5FAM-GGPLGLRSWK(CPQ2)-PEG2-C | 1198 |
| 523 | GPLGVRGK | Probe #523 | 5FAM-GGPLGVRGKK(CPQ2)-PEG2-C | 1199 |
| 524 | GfPRSGG | Probe #524 | 5FAM-GGfPRSGGGK(CPQ2)-PEG2-C | 1200 |
| 525 | Pyr | Probe #525 | Pyr-AMC | 1201 |
| 526 | SY | Probe #526 | H-Ser-Tyr-AMC | 1202 |
| 527 | GF | Probe #527 | H-Gly-Phe-AMC | 1203 |
| 528 | Y | Probe #528 | H-Tyr-AMC | 1204 |
| 529 | Cit | Probe #529 | H-Cit-AMC Hydrobromide salt | 1205 |
| 530 | GP | Probe #530 | Suc-Gly-Pro-AMC | 1206 |
| 531 | T | Probe #531 | H-Thr-AMC | 1207 |
| 532 | I | Probe #532 | H-Ile-AMC | 1208 |
| 533 | GA | Probe #533 | H-Gly-Ala-AMC hydrochloride salt | 1209 |
| 534 | Cys(Bzl) | Probe #534 | H-Cys(Bzl)-AMC | 1210 |
| 535 | A | Probe #535 | H-Ala-AMC | 1211 |
| 536 | K | Probe #536 | Ac-Lys-AMC acetate salt | 1212 |
| 537 | GLF | Probe #537 | MeOSuc-Gly-Leu-Phe-AMC | 1213 |
| 538 | L | Probe #538 | H-Leu-AMC | 1214 |
| 539 | VAN | Probe #539 | Z-Val-Ala-Asn-AMC | 1215 |
| 540 | AAA | Probe #540 | Suc-Ala-Ala-Ala-AMC | 1216 |
| 541 | K | Probe #541 | H-Lys-AMC acetate salt | 1217 |
| 542 | F | Probe #542 | H-Phe-AMC trifluoroacetate salt | 1218 |
| 543 | FSR | Probe #543 | Boc-Phe-Ser-Arg-AMC | 1219 |
| 544 | VVR | Probe #544 | Z-Val-Val-Arg-AMC hydrochloride salt | 1220 |
| 545 | KA | Probe #545 | H-Lys-Ala-AMC hydrochloride salt | 1221 |
| 546 | PR | Probe #546 | H-Pro-Arg-AMC hydrochloride salt | 1222 |
| 547 | MGP | Probe #547 | H-Met-Gly-Pro-AMC hydrochloride salt | 1223 |
| 548 | KP | Probe #548 | H-Lys-Pro-AMC hydrochloride salt | 1224 |
| 549 | QGR | Probe #549 | Boc-Gln-Gly-Arg-AMC hydrochloride salt | 1225 |
| 550 | Glu(OBzl)-AR | Probe #550 | Boc-Glu(OBzl)-Ala-Arg-AMC hydrochloride salt | 1226 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 551 | WEHD | Probe #551 | Ac-Trp-Glu-His-Asp-AMC | 1227 |
| 552 | QAR | Probe #552 | Boc-Gln-Ala-Arg-AMC hydrochloride salt | 1228 |
| 553 | AAF | Probe #553 | H-Ala-Ala-Phe-AMC (free base) | 1229 |
| 554 | GPK | Probe #554 | Tos-Gly-Pro-Lys-AMC trifluoroacetate salt | 1230 |
| 555 | AAPM | Probe #555 | MeOSuc-Ala-Ala-Pro-Met-AMC | 1231 |
| 556 | AEPF | Probe #556 | Suc-Ala-Glu-Pro-Phe-AMC | 1232 |
| 557 | GG | Probe #557 | H-Gly-Gly-AMC hydrochloride salt | 1233 |
| 558 | VLK | Probe #558 | Boc-Val-Leu-Lys-AMC acetate salt | 1234 |
| 559 | EKK | Probe #559 | Boc-Glu-Lys-Lys-AMC acetate salt | 1235 |
| 560 | VPR | Probe #560 | Boc-Val-Pro-Arg-AMC hydrochloride salt | 1236 |
| 561 | GKR | Probe #561 | Boc-Gly-Lys-Arg-AMC hydrochloride salt | 1237 |
| 562 | Glu(OBzl)-GR | Probe #562 | Boc-Glu(OBzl)-Gly-Arg-AMC hydrochloride salt | 1238 |
| 563 | LR | Probe #563 | Z-Leu-Arg-AMC hydrochloride salt | 1239 |
| 564 | AFK | Probe #564 | MeOSuc-Ala-Phe-Lys-AMC trifluoroacetate salt | 1240 |
| 565 | LGR | Probe #565 | Boc-Leu-Gly-Arg-AMC acetate salt | 1241 |
| 566 | PFR | Probe #566 | H-Pro-Phe-Arg-AMC acetate salt | 1242 |
| 567 | AAPV | Probe #567 | Suc-Ala-Ala-Pro-Val-AMC | 1243 |
| 568 | AFK | Probe #568 | H-Ala-Phe-Lys-AMC trifluoroacetate salt | 1244 |
| 569 | VKM | Probe #569 | Z-Val-Lys-Met-AMC acetate salt | 1245 |
| 570 | GPLGP | Probe #570 | Suc-Gly-Pro-Leu-Gly-Pro-AMC | 1246 |
| 571 | KQKER | Probe #571 | Ac-Lys-Gln-Lys-Leu-Arg-AMC trifluoroacetate salt | 1247 |
| 572 | RVRR | Probe #572 | Boc-Arg-Val-Arg-Arg-AMC acetate salt | 1248 |
| 573 | IEGR | Probe #573 | Boc-Ile-Glu-Gly-Arg-AMC acetate salt | 1249 |
| 574 | GP | Probe #574 | H-Gly-Pro-AMC HBr | 1250 |
| 575 | AAPV | Probe #575 | MeOSuc-Ala-Ala-Pro-Val-AMC | 1251 |
| 576 | RPFHLLVY | Probe #576 | Suc-Arg-Pro-Phe-His-Leu-Leu-Val-Tyr-AMC trifluoroacetate salt | 1252 |
| 577 | Anb-WS-Gnf-TVF | Probe #577 | H-Anb-Trp-Ser-Gnf-Thr-Val-Phe-AMC | 1253 |
| 578 | HSSKLQ | Probe #578 | Mu-His-Ser-Ser-Lys-Leu-Gln-AMC | 1254 |
| 579 | RPY | Probe #579 | MeO-Succ-Arg-Pro-Tyr-AMC | 1255 |
| 580 | DRENSPK(Dnp)L-OH | Probe #580 | (ACC)-kkDRENSPK(Dnp)L | 1256 |
| 581 | kkDRENSPLK(Dnp)-OH | Probe #581 | (ACC)-kkDRENSPLK(Dnp) | 1257 |
| 582 | NAGSKFK(Dnp)Q-OH | Probe #582 | (ACC)-NAGSKFK(Dnp)Q | 1258 |
| 583 | NAGSKFQK(Dnp)-OH | Probe #583 | (ACC)-NAGSKFQK(Dnp) | 1259 |
| 584 | HLLGFYK(Dnp)V-OH | Probe #584 | (ACC)-kkHLLGFYK(Dnp)V | 1260 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 585 | HLLGFYVK(Dnp)-OH | Probe #585 | (ACC)-kkHLLGFYVK(Dnp) | 1261 |
| 586 | QEKQT(Nle)K(Dnp)(Nle)-OH | Probe #586 | (ACC)-kkQEKQT(Nle)K(Dnp)(Nle) | 1262 |
| 587 | QEKQT(Nle)(Nle)K(Dnp)-OH | Probe #587 | (ACC)-kkQEKQT(Nle)(Nle)K(Dnp) | 1263 |
| 588 | DPFVVSK(Dnp)W-OH | Probe #588 | (ACC)-kDPFVVSK(Dnp)W | 1264 |
| 589 | DPFVVSWK(Dnp)-OH | Probe #589 | (ACC)-kDPFVVSWK(Dnp) | 1265 |
| 590 | NAYNEIK(Dnp)R-OH | Probe #590 | (ACC)-NAYNEIK(Dnp)R | 1266 |
| 591 | NAYNEIRK(Dnp)-OH | Probe #591 | (ACC)-NAYNEIRK(Dnp) | 1267 |
| 592 | V(Nle)RQSEK(Dnp)N-OH | Probe #592 | (ACC)-V(Nle)RQSEK(Dnp)N | 1268 |
| 593 | V(Nle)RQSENK(Dnp)-OH | Probe #593 | (ACC)-V(Nle)RQSENK(Dnp) | 1269 |
| 594 | YNPRE(Nle)K(Dnp)I-OH | Probe #594 | (ACC)-YNPRE(Nle)K(Dnp)I | 1270 |
| 595 | YNPRE(Nle)IK(Dnp)-OH | Probe #595 | (ACC)-YNPRE(Nle)IK(Dnp) | 1271 |
| 596 | EFVHNPK(Dnp)K-OH | Probe #596 | (ACC)-kEFVHNPK(Dnp)K | 1272 |
| 597 | EFVHNPKK(Dnp)-OH | Probe #597 | (ACC)-kEFVHNPKK(Dnp) | 1273 |
| 598 | KRVQFLK(Dnp)H-OH | Probe #598 | (ACC)-KRVQFLK(Dnp)H | 1274 |
| 599 | KRVQFLHK(Dnp)-OH | Probe #599 | (ACC)-KRVQFLHK(Dnp) | 1275 |
| 600 | LI(Nle)HKNK(Dnp)G-OH | Probe #600 | (ACC)-kLI(Nle)HKNK(Dnp)G | 1276 |
| 601 | LI(Nle)HKNGK(Dnp)-OH | Probe #601 | (ACC)-kLI(Nle)HKNGK(Dnp) | 1277 |
| 602 | WA(Nle)LYHK(Dnp)S-OH | Probe #602 | (ACC)-kkWA(Nle)LYHK(Dnp)S | 1278 |
| 603 | WA(Nle)LYHSK(Dnp)-OH | Probe #603 | (ACC)-kkWA(Nle)LYHSK(Dnp) | 1279 |
| 604 | AHDIVNK(Dnp)Y-OH | Probe #604 | (ACC)-kkAHDIVNK(Dnp)Y | 1280 |
| 605 | AHDIVNYK(Dnp)-OH | Probe #605 | (ACC)-kkAHDIVNYK(Dnp) | 1281 |
| 606 | SVFVIEK(Dnp)P-OH | Probe #606 | (ACC)-kSVFVIEK(Dnp)P | 1282 |
| 607 | SVFVIEPK(Dnp)-OH | Probe #607 | (ACC)-kSVFVIEPK(Dnp) | 1283 |
| 608 | PPSGLSK(Dnp)E-OH | Probe #608 | (ACC)-kPPSGLSK(Dnp)E | 1284 |
| 609 | PPSGLSEK(Dnp)-OH | Probe #609 | (ACC)-kPPSGLSEK(Dnp) | 1285 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 610 | RWYGGIK(Dnp)F-OH | Probe #610 | (ACC)-kkRWYGGIK(Dnp)F | 1286 |
| 611 | RWYGGIFK(Dnp)-OH | Probe #611 | (ACC)-kkRWYGGIFK(Dnp) | 1287 |
| 612 | QYVFF(Nle)K(Dnp)D-OH | Probe #612 | (ACC)-kQYVFF(Nle)K(Dnp)D | 1288 |
| 613 | QYVFF(Nle)DK(Dnp)-OH | Probe #613 | (ACC)-kQYVFF(Nle)DK(Dnp) | 1289 |
| 614 | FAKYYKK(Dnp)T-OH | Probe #614 | (ACC)-kFAKYYKK(Dnp)T | 1290 |
| 615 | FAKYYKTK(Dnp)-OH | Probe #615 | (ACC)-kFAKYYKTK(Dnp) | 1291 |
| 616 | QVKHFTK(Dnp)A-OH | Probe #616 | (ACC)-kQVKHFTK(Dnp)A | 1292 |
| 617 | QVKHFTAK(Dnp)-OH | Probe #617 | (ACC)-kQVKHFTAK(Dnp) | 1293 |
| 618 | YVADAPK(Dnp)-OH | Probe #618 | (ACC)-kYVADAPK(Dnp) | 1294 |
| 619 | KGISSQY | Probe #619 | ACC-GKGISSQYK(Dnp)-NH2 | 1295 |
| 620 | ALPALQN | Probe #620 | ACC-GALPALQNK(Dnp)-PEG2-Dlys-Dlys-NH2 | 1296 |
| 621 | HRFRG | Probe #621 | ACC-GHRFRGK(Dnp)-NH2 | 1297 |
| 622 | APEEIMDQQ | Probe #622 | ACC-GAPEEIMDQQK(Dnp)-PEG2-Dlys-Dlys-NH2 | 1298 |
| 623 | SRKSQQY | Probe #623 | ACC-GSRKSQQYK(Dnp)-NH2 | 1299 |
| 624 | SKGRSLI | Probe #624 | ACC-GSKGRSLIGK(Dnp)-NH2 | 1300 |
| 625 | FAQSIPK | Probe #625 | ACC-GFAQSIPKK(Dnp)-PEG2-Dlys-Dlys-NH2 | 1301 |
| 626 | RQRRVVG | Probe #626 | ACC-GRQRRVVGGK(Dnp)-NH2 | 1302 |
| 627 | ERGETGPS | Probe #627 | ACC-GERGETGPSGK(Dnp)-NH2 | 1303 |
| 628 | ASGPSS | Probe #628 | ACC-GASGPSSGK(Dnp)-PEG2-Dlys-Dlys-NH2 | 1304 |
| 629 | YRFR | Probe #629 | ACC-GYRFRGK(Dnp)-NH2 | 1305 |
| 630 | KLFSSKQ | Probe #630 | ACC-GKLFSSKQK(Dnp)-NH2 | 1306 |
| 631 | IVPRG | Probe #631 | ACC-GIVPRGK(Dnp)-NH2 | 1307 |
| 632 | IRRSSYFK | Probe #632 | ACC-GIRRSSYFKK(Dnp)-NH2 | 1308 |
| 633 | His(Bzl)-Tle-PSD-Met(O) | Probe #633 | ACC-Gly-His(Bzl)-Tle-Pro-Ser-Asp-Met(O)-Gly-K(Dnp)-Gly-PEG2-Dlys-Dlys-NH2 | 1309 |
| 634 | Nva-IE-Oic-DFGR | Probe #634 | ACC-Nva-Ile-Glu-Oic-Asp-Phe-Gly-Arg-Lys(Dnp)-NH2 | 1310 |
| 635 | H-DThr-Phe(F5)-R | Probe #635 | Ac-His-DThr-Phe(F5)-Arg-ACC | 1311 |
| 636 | Dap-Orn-Phe(3Cl)-Cys(MeOBzl) | Probe #636 | Ac-Dap-Orn-Phe(3Cl)-Cys(MeOBzl)-ACC | 1312 |
| 637 | Cha-L-hSer(Bzl)-R | Probe #637 | Ac-Cha-Leu-hSer(Bzl)-Arg-ACC | 1313 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 638 | His(Bzl)-Tle-PSD-Met(O) | Probe #638 | ACC-Gly-His(Bzl)-Tle-Pro-Ser-Asp-Met(O)-Gly-K(Dnp)-Gly-PEG2-Dlys-Dlys-NH2 | 1309 |
| 639 | hCha-Phe(guan)-Oic-R | Probe #639 | Ac-hCha-Phe(guan)-Oic-Arg-ACC | 1314 |
| 640 | Abu-Nle(O-Bzl) | Probe #640 | NH2-Abu-Nle(O-Bzl)-ACC | 1315 |
| 641 | Nle(O-Bzl)-Met(O)2-Oic-Abu | Probe #641 | Ac-Nle(O-Bzl)-Met(O)2-Oic-Abu-ACC | 1316 |
| 642 | Dap-Orn-Phe(3Cl)-Cys(MeOBz) | Probe #642 | ACC-G-Dap-Orn-Phe(3Cl)-Cys(MeOBz)-G-K(Dnp)-NH2 | 1317 |
| 643 | Cha-L-hSer-R | Probe #643 | ACC-Gly-Cha-Leu-hSer-Arg-Gly-K(Dnp)-NH2 | 1318 |
| 644 | FVT-Gnf-SW | Probe #644 | ACC-Phe-Val-Thr-Gnf-Ser-Trp-K(Dnp)-NH2 | 1319 |
| 645 | hCha-Phe(guan)-Oic-R | Probe #645 | ACC-Gly-hCha-Phe(guan)-Oic-Arg-Gly-K(Dnp)-NH2 | 1320 |
| 646 | Nle(OBz)-Met(O2)-Oic-Abu | Probe #646 | ACC-Gly-Nle(OBz)-Met(O2)-Oic-Abu-Gly-K(Dnp)-NH2 | 1321 |
| 647 | AIEPDSG | Probe #647 | 5FAM-GAIEPDSGG-Lys(CPQ2)-PEG2-Dlys-Dlys-GC-NH2 | 1322 |
| 648 | AIEFDSG | Probe #648 | 5FAM-GAIEFDSGG-Lys(CPQ2)-Dlys-Dlys-GC-NH2 | 1323 |
| 649 | AAEAISD | Probe #649 | 5FAM-GGAAEAISDAK(CPQ2)-kk-PEG2-C | 1324 |
| 650 | AGGAQMGA | Probe #650 | 5FAM-GGAGGAQMGAK(CPQ2)-kk-PEG2-C | 1325 |
| 651 | AQPDALNV | Probe #651 | 5FAM-GGAQPDALNVK(CPQ2)-kk-PEG2-C | 1326 |
| 652 | ATDVTTTP | Probe #652 | 5FAM-GGATDVTTTPK(CPQ2)-kk-PEG2-C | 1327 |
| 653 | DIVTVANA | Probe #653 | 5FAM-GGDIVTVANAK(CPQ2)-kk-PEG2-C | 1328 |
| 654 | DLGLKSVP | Probe #654 | 5FAM-GGDLGLKSVPK(CPQ2)-kk-PEG2-C | 1329 |
| 655 | DVMASNKR | Probe #655 | 5FAM-GGDVMASNKRK(CPQ2)-kk-PEG2-C | 1330 |
| 656 | ESDELNTI | Probe #656 | 5FAM-GGESDELNTIK(CPQ2)-kk-PEG2-C | 1331 |
| 657 | FHPLHSKI | Probe #657 | 5FAM-GGFHPLHSKIK(CPQ2)-kk-PEG2-C | 1332 |
| 658 | HARLVHV | Probe #658 | 5FAM-GGGHARLVHVK(CPQ2)-kk-PEG2-C | 1333 |
| 659 | HIANVERV | Probe #659 | 5FAM-GGHIANVERVK(CPQ2)-kk-PEG2-C | 1334 |
| 660 | KAAATQKK | Probe #660 | 5FAM-GGKAAATQKKK(CPQ2)-kk-PEG2-C | 1335 |
| 661 | LATASTMD | Probe #661 | 5FAM-GGLATASTMDK(CPQ2)-kk-PEG2-C | 1336 |
| 662 | LGPKGQT | Probe #662 | 5FAM-GGLGPKGQTGK(CPQ2)-kk-PEG2-C | 1337 |
| 663 | LSLPETGE | Probe #663 | 5FAM-GGLSLPETGEK(CPQ2)-kk-PEG2-C | 1338 |
| 664 | NLAGILKE | Probe #664 | 5FAM-GGNLAGILKEK(CPQ2)-kk-PEG2-C | 1339 |
| 665 | NPGMSEPV | Probe #665 | 5FAM-GGNPGMSEPVK(CPQ2)-kk-PEG2-C | 1340 |

TABLE 1-continued

Exemplary sequences for peptide linkers and corresponding probe construct designs

| SEQ ID NO | Sequence | Exemplary probe name | Exemplary probe construct | SEQ ID NO |
|---|---|---|---|---|
| 666 | PFGCHAK | Probe #666 | 5FAM-GGPFGCHAKK(CPQ2)-kk-PEG2-C | 1341 |
| 667 | PLGLRWW | Probe #667 | 5FAM-GGPLGLRWWK(CPQ2)-kk-PEG2-C | 1342 |
| 668 | QMGVMQGV | Probe #668 | 5FAM-GGQMGVMQGVK(CPQ2)-kk-PEG2-C | 1343 |
| 669 | QTCKCSCK | Probe #669 | 5FAM-GGQTCKCSCKK(CPQ2)-kk-PEG2-C | 1344 |
| 670 | QWAGLVEK | Probe #670 | 5FAM-GGQWAGLVEKK(CPQ2)-kk-PEG2-C | 1345 |
| 671 | RPAVMTSP | Probe #671 | 5FAM-GGRPAVMTSPK(CPQ2)-kk-PEG2-C | 1346 |
| 672 | TLRELHLD | Probe #672 | 5FAM-GGTLRELHLDK(CPQ2)-kk-PEG2-C | 1347 |
| 673 | TPPPSQGK | Probe #673 | 5FAM-GGTPPPSQGKK(CPQ2)-kk-PEG2-C | 1348 |
| 674 | TSEDLVVQ | Probe #674 | 5FAM-GGTSEDLVVQK(CPQ2)-kk-PEG2-C | 1349 |
| 675 | VWAAEAIS | Probe #675 | 5FAM-GGVWAAEAISK(CPQ2)-kk-PEG2-C | 1350 |
| 676 | R | Probe #676 | H-R-AMC | 1351 |
| 677 | GC | Probe #677 | FAM-GGC-PEG8 | 1352 |

```
Nle = norleucine
K(FAM) = carboxy-fluorescein-L-lysine
HomoPhe = Hfe = L-homophenylalanine
Cys(OMeBzl) = C(OMeBzl) = S-paramethoxybenzyl cysteine
DIle = d-isoleucine
DArg = D-arginine
DVal = D-valine
Pyr = pyroglutamic acid
Cit = citrulline
C(Bzl) = S-benzyl-L-cysteine
Glu(OBzl) = benzyl-L-glutamate
Anb = amino-n-butyric acid
Gnf = guamidine-L-phenylalanine
K(Dnp) = dinitrobenzylation of lysine
His(Bzl) = benzyl-L-histidine
Tle = L-tert-leucine
Met(O) = L-methionine-sulfoxide
Bz = Benzoyl
Oic = L-octahydroindole-2-carboxylic acid
Nva = norvaline (click to see farther down list)
DThr = d-threonine
Phe(F5) = 2,3,4,5,6-pentafluoro-L-penylalanine
Phe(3Cl) = 3-chloro-L-phenylalanine
hSer(Bzl) = benzyl homoserine
hCha = homocyclohexylalnine
Phe(guan) = phenylalanine derivative with a guanidine group in the para position
Nle(O-Bzl) = Nle(OBz) = benzyloxy-L-norleucine
Met(O)2 = L-methionine sulfone
Dap = 2,3-diaminopropionic acid
hSer = homoserine
Met(O2) = methylsulfonylbutanoic acid
Abu = L-alpha-aminobutyric acid
Cha = L-cyclohexylalanine
Cys(Me) = L- Methyl cysteine
Orn = L-Ornithine
hF = L-Homophenylalanine
GABA = gamma aminobutyric acid
Pip = piperidine carboxylic acid
lower case = D-amino acids
```

The peptide linkers described herein for endoproteases may follow a design: $X_mAY_n$ or $AX_nB$, wherein respectively, A is a single amino acid and A and B are amino acid pairs recognized by a particular endoprotease, X and Y are any amino acid labeled or not with a reporter, and m, n are zero or any integer. This design is for exemplification only and should not be construed as the only possible design for the peptide linker.

The peptide linkers described herein for exoproteases may follow a design: $X_mAY_n$, wherein A is amino acid pairs recognized by a particular exoprotease, X and Y are any amino acid labeled or not with a reporter, and n is zero or any integer. This design is for exemplification only and should not be construed as the only possible design for the peptide linker.

TABLE 2

Exemplary peptide linker designs.

| amino acid in P1' | amino acid in P1 | amino acid in P2 | amino acid in P3 | amino acid in P4 | Example probe name | Example prob design | SEQ ID NO | Protease family | Critical amino acid (single or pair) |
|---|---|---|---|---|---|---|---|---|---|
|  | R/K |  |  |  | Probe #161 | (FAM)-GWYKTQYGK(CPQ2)-NH2 | 1353 | Endo | Single |
|  | R/K |  |  |  | Probe #109 | (FAM)-GFARRWGGK(CPQ2)-PEG2-k-NH2 | 1354 | Endo | Single |
|  |  | F/Y/L/W |  |  | Probe #165 | (FAM)-GSYWP(Nle)QGK(CPQ2)-PEG2-k-NH2 | 1355 | Endo | Single |
|  |  | F/Y |  |  | Probe #140 | (FAM)-GFIY(Nle)PTGK(CPQ2)-PEG2-k-NH2 | 1356 | Endo | Single |
|  |  | P |  |  | #148 Probe | (FAM)-GTGPKGNGK(CPQ2)-NH2 | 825 | Endo | Single |
| F | K |  |  |  | Probe #217 | (FAM)-GWSKFW(Nle)GK(CPQ2) | 894 | Endo | Pair (AB) |
|  | D | G |  |  | Probe #194 | (FAM)-GKTGDARGK(CPQ2)-PEG2-k-NH2 | 871 | Endo | Pair (AB) |
|  | L | P |  |  | Probe #275 | (FAM)-GGHPLSPGK(CPQ2)-PEG2-kk-NH2 | 952 | Endo | Pair (AB) |
|  | D | T/I/V |  |  | Probe #297 | (FAM)-GVIDKDFGK(CPQ2)-NH2 | 1357 | Endo | Pair (AB) |
|  | R | K/R |  |  | Probe #109 | (FAM)-GFARRWGGK(CPQ2)-PEG2-k-NH2 | 1358 | Endo | Pair (AB) |
| S | R |  |  |  | Probe #204 | (FAM)-GPVRSTNGK(CPQ2)-NH2 | 881 | Endo | Pair (AB) |
|  | D | E |  |  | Probe #199 | (FAM)-GENDRLPGK(CPQ2)-NH2 | 876 | Endo | Pair (near neighbor AXB) |
|  | D | V |  |  | Probe #248 | (FAM)-GQWVDEDGK(CPQ2)-PEG2-k-NH2 | 925 | Endo | Pair (near neighbor AXXE3) |
|  | K/R at C-terminus |  |  |  | Probe #321 | (FAM)-kGEFVHNPK(CPQ2)K-OH | 1359 | Exo | Single |
|  | K/R/H at C-terminus |  |  |  | Probe #315 | (FAM)-GNAYNEIK(CPQ2)R-OH | 1360 | Exo | Single |
|  | W/G/F at N-terminus |  |  |  | Probe #346 | NH2-WK(FAM)NAGSKFGkK(CPQ2)-NH2 | 1361 | Exo | Single |
|  | Q/K at N-terminus |  |  |  | Probe #362 | NH2-QK(FAM)KRVQFLGK(CPQ2)-NH2 | 1362 | Exo | Single |

In some embodiments, the cleavable linker may be a carbohydrate. Tung et al. reported a conjugate of β-galactoside and 7-hydroxy-9H-(1,3-dichloro-9,9-dimethylacridin-2-one), which has far-red fluorescence properties after a cleavage by β-galactosidase. Tung C H, Zeng Q, Shah K, Kim D E, Schellingerhout D, Weissleder R. In vivo imaging of beta-galactosidase activity using far red fluorescent switch. Cancer Res. 2004 Mar. 1; 64(5):1579-83. Ho et al. reported combining β-galactosidase substrate with p-benzyloxycarbonyl as a self-immolative linker. β-D-Galactopyranoside, the substrate of β-galactosidase, was conjugated to an optical probe through a para-substituted benzyloxycarbonyl group (serves as a first self-immolative linker) and a glycine residue (serves as a quencher and a second self-immolative linker). Enzymatic cleavage of the β-D-Galactopyranoside triggered a series of spontaneous reactions that resulted in a release of optically active probe. Ho, N.-H., Weissleder, R. and Tung, C.-H. (2007), A Self-Immolative Reporter For β-Galactosidase Sensing. ChemBioChem, 8: 560-566. Some carbohydrate linkers are commercially available.

In some embodiments, the cleavable linker may be a nucleic acid. The effect of a DNA linker on the behavior of its conjugate both reduces the toxicity of the free drug by reducing its cell penetration, which is positive in case of premature deconjugation in the bloodstream and increases the off-target toxicity on low antigen-expressing cells, presumably due to nonspecific interaction of the nucleic acid-based linker with the cell surface. For example, in an antibody-drug conjugates, the antibody and drug can be non-covalently connected using complementary DNA linkers. Dovgan, I., Ehkirch, A., Lehot, V. et al. On the use of DNA as a linker in antibody-drug conjugates: synthesis, stability and in vitro potency. Sci Rep 10, 7691 (2020). Dovgan et al. disclosed a trastuzumab to be connected to monomethyl auristatin E (MMAE) through a 37-mer oligonucleotide.

In some embodiments, the cleavable linker may be a lipid. In some embodiments, the cleavable linker may be a phospholipid. The insertion of phospholipid groups between two fluorescent dyes or a dye/quencher pair allows the detection of phospholipase cleavage activity. In some embodiments, the cleavable linker may be a phosphodiester. The insertion of phosphodiester groups between two fluorescent dyes or a dye/quencher pair allows the detection of phosphodiesterase cleavage activity. In some embodiments, the lipid is directly attached to the fluorophore: once the covalent bond between the lipid and fluorophore is cleaved, the increase of fluorescent activity allows for the detection of the enzyme presence In some embodiments, the cleavable linker may be an ester. Ester groups are often cleaved by saponification. The reactivity of the ester to cleavage can be enhanced by the use of electron-withdrawing groups or stabilized by the use of auto-immolative spacers to precluded spontaneous hydrolysis. In chemical biology, ester-based cleavable compounds were initially used for protein purification and in structural biology. FRET-based probes were designed to image esterase activities.

In some embodiments, the cleavable linker may be a glycoside. For example, cellulase enzymes deconstruct cellulose to glucose, and are often comprised of glycosylated linkers connecting glycoside hydrolases (GHs) to carbohydrate-binding modules (CBMs).

In some embodiments, the cleavable linker may be a nucleophile/base sensitive linker. These can include, but are not limited to, halogen nucleophiles, oxygen nucleophiles, safety-catch linkers, thiol nucleophiles, nitrogen nucleophiles, and phenacyl ester derivatives.

In some embodiments, the cleavable linker may be sensitive to activity from all enzyme families, including but is not limited to oxidoreductases, transferases, hydrolases, lyases, isomerases, and ligases.

Fluoridolyzable linkers are widely used in organic chemistry as silicon-based protecting groups for alcohols. The high thermodynamic affinity of fluorine for silicon allows their removal in orthogonal and mild conditions using a fluorine source. In this reaction a fluoride ion reacts with silicon as nucleophilic species and the cleavage conditions depend on the steric hindrance of the silicon"s alkyl group. Fluoride ions can also trigger bond cleavage due to their basic properties.

Oxygen nucleophiles include sulfone and ester linkers while safety-catch linkers allow greater control over the timing of the bond breakage, because the linker will remain stable until it is activated for cleavage by a chemical modification.

In secondary amine synthesis or solid phase synthesis, nitrobenzenesulfonamides are known to be cleaved with a thiol nucleophile, like b-mercaptoethanol. Cysteines can be modified by electron-deficient alkynes to form a vinyl sulfide linkage.

Displacement reactions involving a specific nitrogen species as a nucleophile can occur in mild cleavable conditions. These reactions can be classified into two groups; cleavage by aminolysis or exchange reaction. For aminolysis cleavage, examples include the cleavage of a malondialdehyde (MDA) indole derivative by either pyrrolidine or hydrazine, and the cleavage of an ester linker by hydroxylamine or hydrazine. Acylhydrazones44 and hydrazones45,156 can be used as cleavable linkers through transimination in a mildly acidic medium. An amine catalyst (e.g., aniline, p-anisidine or hydroxylamine) accelerates hydrolysis and enables the effective transition between stable and dynamic states, which is required for cleavage and exchange.

In some embodiments, the cleavable linker may be a reduction sensitive linker. Reduction sensitive linkages have been used in chemical biology for a long time and it is a commonly used class of cleavable linker. Examples of cleavable linkers sensitive to reductive conditions include: nitroreductases, disulfide bridges and azo compounds. Karan et al. reported a fluorescent probe to detect nitroreductase. Sanu Karan, Mi Young Cho, Hyunseung Lee, Hwunjae Lee, Hye Sun Park, Mahesh Sundararajan, Jonathan L. Sessler, and Kwan Soo Hong. Near-Infrared Fluorescent Probe Activated by Nitroreductase for In Vitro and In Vivo Hypoxic Tumor Detection. Journal of Medicinal Chemistry 2021 64 (6), 2971-2981. In naturally occurring proteins, disulfide bridges generally play a role in maintaining the protein structure. They are known to be efficiently and rapidly cleaved by mild reducing agents like dithiothreitol (DTT), b-mercaptoethanol or tris(2-carboxyethyl)phosphine (TCEP). In chemical biology, disulfide bridges have been used in a wide range of applications including functional and structural proteomics, drug delivery, tumor imaging, DNA and protein-DNA complex purifications. The disulfide-based cleavable linker is commonly used due to its straightforward synthesis and rapid cleavage. Azo linkers are very appealing to chemical biologists since they are able to undergo cleavage following treatment with sodium dithionite, a mild and potentially bio-orthogonal reducing agent. The azo compound is reduced into two aniline moieties via an electrochemical reduction mechanism and this allows the use of reducing agents that are commonly used in many biological protocols, such as TCEP, DTT. In chemical biology, azo compounds have been used to cross-link proteins for over a decade and more recently for protein affinity purification.

In some embodiments, the cleavable linker may be an electrophile/acid sensitive linker. Acid sensitive linkers can be combined with other type of linkers. For example, a first β-galactosidase cleavage of the β-D-Galactopyranoside triggers the self-immolation of a benzyloxycarbonyl group, resulting in a release of optically active probe. Ho, N.-H., Weissleder, R. and Tung, C.-H. (2007), A Self-Immolative Reporter For β-Galactosidase Sensing. ChemBioChem, 8: 560-566. Two different modes of electrophilic cleavage are used in chemical biology: acidic sensitive linkers that are sensitive to proton sources, and alkyl 2-(diphenylphosphino) benzoate derivatives sensitive to azide compounds. Proton sensitive bonds are among the most frequently used cleavable functions in organic chemistry; illustrated by the development of the BOC group which protects amines, or the Merrifield resin used in solid phase synthesis. In organic chemistry, the cleavage conditions that can be tolerated are very flexible regarding the acids" reagents, solvents, temperatures and pH. In contrast, biocompatible acid cleavable linkers must be responsive to minor changes in pH. Strong acidic conditions can lead to the denaturation of proteins and DNA. Biocompatible acid cleavable linkers are chosen for their instability near physiological pH and are often different from the classical protecting groups, which are cleaved with strong acids. Chemical reactions that can break or form bonds in water can be used as the basis of a cleavable linker, for example the Staudinger ligation. This reaction is proceeded by the nucleophilic attack of an alkyl 2-(diphenylphosphino)benzoate derivative on an azide, to form an aza-ylide intermediate. Then the ester traps the aza-ylide, which leads to the formation of an amide. In this process, the ester acts as a cleavable linker, and the azide as a bioorthogonal chemical agent, which guarantees a chemoselective and bioorthogonal cleavage.

In some embodiments, the cleavable linker may be a metal cleavable linker. Organometallic compounds are used to catalyze the modification of proteins containing non-natural amino acids, but their use as cleavage reagent in chemical biology has only been reported a few times. The allyl function is a commonly used protecting group for alcohols in organic synthesis and it is also used as a cleavable linker in DNA sequencing by synthesis Metal cleavable linkers were also used in the design of peptide nucleic acids (PNAs), which were developed for enzyme-independent DNA/RNA hybridization methods.

In some embodiments, the cleavable linker may be an oxidation sensitive linker. Sodium periodate is undoubtedly the most frequently used biocompatible oxidizing agent due to its ability to cleave vicinal diols to form two aldehydes compounds. One example of this type of cleavable linker consists of a vicinal diol with a tartaric acid spacer and two functional groups at both ends. Selenium based linkers also contain cleavable bonds sensitive to oxidizing agents, such as sodium periodate or N-chlorobenzenesulfonamide immobilized on polystyrene beads (iodo-beads). The trigger agent oxidizes the labile bond to selenium oxide, which is then cleaved directly via intramolecular b-elimination or rearrangement.

Reporter and Detection Methods

In some aspects, the probe/molecule described herein comprises a reporter. The reporter as described herein may be in any structure that may be capable of being detected by any method, including but not limited to fluorescent detection, spectroscopic detection, immunological detection or imaging detection. In some embodiments, the reporter may be a fluorescent label, a mass tag or a nucleic acid barcode.

In some embodiments, the reporter may be a fluorescent label. Labels, tags and probes containing small compounds such as florescence can be used to label proteins and nucleic acids. Bio-affinity towards other molecules (biotin, digoxygenin), enzymatic (AP, HRP) or chemiluminescent (esters or acridine) can be used as well. Genetically encoded markers like the fluorescent proteins of the GFP family have become a reporter of choice for gene expression studies and protein localization. In combination with subcellular tags, GFP can be used to label subcellular structures like synapses allowing novel approaches to study developmental processes like synapse formation. Other fluorescent labels include but are not limited to small organic dyes and lipophilic dyes. The fluorescence label may serve itself as the activity substrate without addition of linkers.

Some reporters are "internally quenched", thus does not require a quencher, wherein the cleavage of a bond linking the internally quenched fluorophore to the substrate linker directly yields a fluorescent molecule. Many described probes for proteases, esterases, peroxidases and others function this way.

In some embodiments, the reporter may be a mass tag. Mass tag reagents are designed to enable identification and quantitation of proteins in different samples using mass spectrometry (MS). Mass tagging reagents within a set typically have the same nominal mass (i.e., are isobaric) and chemical structure composed of an amine-reactive NHS ester group, a spacer arm (mass normalizer), and a mass reporter.

In some embodiments, the reporter may be a nucleic acid barcode. For example, DNA barcoding is a system for species identification focused on the use of a short, standardized genetic region acting as a "barcode" in a similar way that Universal Product Codes are used by supermarket scanners to distinguish commercial products.

In some embodiments, the reporter may be detected using a ligand binding assay. A ligand binding assay often involves a detection step, such as an ELISA, including fluorescent, colorimetric, bioluminescent and chemiluminescent ELISAs, a paper test strip or lateral flow assay, or a bead-based fluorescent assay. In some embodiments, a paper-based ELISA test may be used to detect the cleaved reporter in the fluid sample. The paper-based ELISA may be created inexpensively, such as by reflowing wax deposited from a commercial solid ink printer to create an array of test spots on a single piece of paper. When the solid ink is heated to a liquid or semi-liquid state, the printed wax permeates the paper, creating hydrophobic barriers. The space between the hydrophobic barriers may then be used as individual reaction wells. The ELISA assay may be performed by drying the detection antibody on the individual reaction wells, constituting test spots on the paper, followed by blocking and washing steps. Fluid from a sample taken from the subject may then be added to the test spots. Then, for example, a streptavidin alkaline phosphate (ALP) conjugate may be added to the test spots, as the detection antibody. Bound ALP may then be exposed to a color reacting agent, such as BCIP/NBT (5-bromo-4-chloro-3"-indolyphosphate p-toluidine salt/nitro-blue tetrazolium chloride), which causes a purple colored precipitate, indicating presence of the reporter.

In some embodiments, the reporter can be detected using volatile organic compounds. Volatile organic compounds may be detected by analysis platforms such as gas chromatography instrument, a breathalyzer, a mass spectrometer, or use of optical or acoustic sensors. Gas chromatography may be used to detect compounds that can be vaporized without decomposition (e.g., volatile organic compounds). A gas chromatography instrument includes a mobile phase (or moving phase) that is a carrier gas, for example, an inert gas such as helium or an unreactive gas such as nitrogen, and a stationary phase that is a microscopic layer of liquid or polymer on an inert solid support, inside a piece of glass or metal tubing called a column. The column is coated with the stationary phase and the gaseous compounds analyzed interact with the walls of the column, causing them to elute at different times (i.e., have varying retention times in the column). Compounds may be distinguished by their retention times.

Mass spectrometry and enrichment/chromatography methods may be used to separate and distinguish/detect cleaved from intact reporters used in the present invention based on differences in mass and or presence of a label. For example, enzymatic reactions can result in the fragmentation of a parent molecule resulting in a mass shift of the starting substrate, this can be exploited in different chromatography/ enrichment methods such as size exclusion chromatography and affinity enrichments. In mass spectrometry, a sample is ionized, for example by bombarding it with electrons. The sample may be solid, liquid, or gas. By ionizing the sample, some of the sample"s molecules are broken into charged fragments. These ions may then be separated according to their mass-to-charge ratio. This is often performed by accelerating the ions and subjecting them to an electric or magnetic field, where ions having the same mass-to-charge ratio will undergo the same amount of deflection. When deflected, the ions may be detected by a mechanism capable of detecting charged particles, for example, an electron multiplier. The detected results may be displayed as a spectrum of the relative abundance of detected ions as a function of the mass-to-charge ratio. The molecules in the sample can then be identified by correlating known masses, such as the mass of an entire molecule to the identified masses or through a characteristic fragmentation pattern.

When the reporter includes a nucleic acid, the reporter may be detected by various sequencing methods known in the art, for example, traditional Sanger sequencing methods or by next-generation sequencing (NGS). NGS generally refers to non-Sanger-based high throughput nucleic acid sequencing technologies, in which many (i.e., thousands, millions, or billions) of nucleic acid strands can be sequenced in parallel. Examples of such NGS sequencing includes platforms produced by Illumina (e.g., HiSeq, MiSeq, NextSeq, MiniSeq, and iSeq 100), Pacific Biosciences (e.g., Sequel and RSII), and Ion Torrent by ThermoFisher (e.g., Ion S5, Ion Proton, Ion PGM, and Ion Chef systems). It is understood that any suitable NGS sequencing platform may be used for NGS to detect nucleic acid of the detectable analyte as described herein.

Analysis may be performed directly on the biological sample or the detectable cleaved reporters may be purified to some degree first. For example, a purification step may involve isolating the detectable analyte from other components in the biological sample. Purification may include methods such as affinity chromatography. The isolated or purified detectable analyte does not need to be 100% pure or even substantially pure prior to analysis. Detecting the cleaved reporters may provide a qualitative assessment (e.g., whether the detectable cleaved reporters, and thus the predetermined protease is present or absent) or a quantitative assessment (e.g., the amount of the detectable cleaved reporters present) to indicate a comparative activity level of the predetermined proteases in the fluid sample. The quantitative value may be calculated by any means, such as, by determining the percent relative amount of each fraction present in the sample. Methods for making these types of calculations are known in the art.

The cleaved reporters may be detected by any detection method that may be suitable for the particular reporter. In some aspects, the detection method comprises fluorescent detection, spectroscopic detection, mass spectrometry, immunological detection or imaging detection. In some aspects, the detection method may be fluorescence resonance energy transfer (FRET).

In some embodiments, the detection method may be spectroscopic detection. Spectroscopic methods of detection are very commonly employed in ion chromatography (IC) and are second only to conductivity detection in their frequency of usage. These methods can be divided broadly into the categories of molecular spectroscopic techniques and atomic spectroscopic techniques. Molecular spectroscopy includes UV-visible spectrophotometry, refractive index measurements, and photoluminescence techniques (fluorescence and phosphorescence). Atomic spectroscopy includes atomic emission spectroscopy (using various excitation sources) and atomic absorption spectroscopy. Many of the spectroscopic detection methods can operate in a direct or indirect mode. The definitions of these terms are the same as those used to describe the electrochemical detection modes. That is, direct spectroscopic detection results when the solute ion has a greater value of the measured detection parameter than does the eluent ion. Indirect detection results when the reverse is true.

In some embodiments, the detection method may be mass spectrometry. Mass spectrometry (MS) is an analytical technique that is used to measure the mass-to-charge ratio of ions. The results are typically presented as a mass spectrum, a plot of intensity as a function of the mass-to-charge ratio.

In some embodiments, the detection method may be fluorescence resonance energy transfer (FRET). FRET (Fluorescence Resonance Energy Transfer) is a distance dependent dipole-dipole interaction without the emission of a photon, which results in the transfer of energy from an initially excited donor molecule to an acceptor molecule. It allows the detection of molecular interactions in the nanometer range. FRET peptides are labeled with a donor molecule and an acceptor (quencher) molecule. In most cases, the donor and acceptor pairs are two different dyes. The transferred energy from a fluorescent donor is converted into molecular vibrations if the acceptor is a non-fluorescent dye (quencher). When the FRET is terminated (by separating donor and acceptor), an increase of donor fluorescence can be detected. When both the donor and acceptor dyes are fluorescent, the transferred energy is emitted as light of longer wavelength so that the intensity ratio change of donor and acceptor fluorescence can be measured. In order for efficient FRET quenching to take place, the fluorophore and quencher molecules must be close to each other (approximately 10-100 Å) and the absorption spectrum of the quencher must overlap with the emission spectrum of the fluorophore.

Precipitating Fluorophore

In some aspects, the cleaved reporter may be a precipitating fluorophore. In some embodiments, the precipitating fluorophore may be HPQ, Cl-HPQ, HTPQ, HTPQA, HBPQ, or HQPQ.

In some embodiments, the precipitating fluorophore may be HPQ, also known as 2-(2"-hydroxyphenyl)-4(3H)-quinazolinone. HPQ is a small organic dye known for its classic luminescence mechanism through excited-state intramolecular proton transfer (ESIPT), shows strong light emission in the solid state, but no emission in solution. HPQ is found to be strictly insoluble in water and exhibits intense solid-state fluorescence similar to that of tetraphenyl ethylene. Moreover, its essential properties of insolubility and intense solid-state fluorescence can be countered and reversed, by prohibiting the establishment of an internal hydrogen bond between the imine nitrogen and phenolic hydroxyl group.

In some embodiments, the precipitating fluorophore may be Cl-HPQ. Cl-HPQ is released when HPQF, a water soluble and non-fluorescent molecule, reacts with furin. Cl-HPQ starts to precipitate near the enzyme activity site, and the precipitates emit bright solid-state fluorescence with more than 60-fold fluorescence enhancement. Li et al. In Situ Imaging of Furin Activity with a Highly Stable Probe by Releasing of Precipitating Fluorochrome. Anal. Chem. 2018, 90, 19, 11680-11687.

In some embodiments, the precipitating fluorophore may be HTPQ. HTPQ is found to be strictly insoluble in water and shows intense fluorescence in the solid state with maximum excitation and emission wavelengths at 410 nm and 550 nm respectively. This makes it far better suited to the use with a confocal microscope. The large Stokes shift of HTPQ contributes additional and highly desirable advantages: increased sensitivity, minimized background fluorescence and enhanced bioimaging contrast. Liu et al. In Situ Localization of Enzyme activity in Live Cells by a Molecular Probe Releasing a Precipitating Fluorochrome. Angew Chem Int Ed Engl. 2017 Sep. 18; 56(39):11788-11792.

In some embodiments, the precipitating fluorophore may be HTPQA. HTPQA is another enzyme-responsive fluorogenic probe derived from HTPQ. When converted by ALP, the probe releases free HTPQ which starts to precipitate after a very short delay; the precipitate emits bright solid-state fluorescence with more than 100-fold fluorescence enhancement.

In some embodiments, the precipitating fluorophore may be HBPQ. HBPQ is completely insoluble in water and shows strong yellow solid emission when excited with a 405 nm laser. Liu et al. Precipitated Fluorophore-Based Molecular Probe for In Situ Imaging of Aminopeptidase N in Living Cells and Tumors. Anal. Chem. 2021, 93, 16, 6463-6471, Publication Date: Apr. 14, 2021.

In some embodiments, the precipitating fluorophore may be HQPQ. HQPQ is, a novel solid-state fluorophore that is insoluble in water. Li et al. Precipitated Fluorophore-Based Probe for Accurate Detection of Mitochondrial Analytes. Anal. Chem. 2021, 93, 4, 2235-2243. Publication Date: Jan. 5, 2021.

The precipitating and non-precipitating fluorophores can be separated from the enzyme substrate by a self-immolative substrate to stabilize the initial probe and ensure that the enzymatic cleavage is transduced via the immolative spacer into the formation of the precipitating fluorophore or the non-internally quenched soluble fluorophore.

Fluorescent Quencher

In some aspects, the probe/molecule described herein comprises a fluorescent quencher. The fluorescent quencher as described herein may be in any structure that is capable of decreasing the fluorescence intensity of a given substance. In some embodiments, the fluorescent quencher may be BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl]azo)benzoyl), Dnp (2,4-dinitrophenyl) or Eclipse®.

In some embodiments, the fluorescent quencher may be a BHQ quencher including, but not limited to, BHQ0, BHQ1, BHQ2, BHQ3, or BBQ650. BHQ, or black hole quencher, dyes work through a combination of FRET and static quenching to enable avoidance of the residual background signal common to fluorescing quenchers such as TAMRA, or low signal-to-noise ratio. The different types of BHQ dyes are used to quench different colored dyes with BHQ1 used to quench green and yellow dyes such as FAM, TET, or HEX and BHQ2 used for quenching orange and red dyes. BHQ dyes are true dark quenchers with no native emission due to their polyacromatic-azo backbone. Substituting electron-donating and withdrawing groups on the aromatic rings produces a complete series of quenchers with broad absorption curves that span the visible spectrum.

In some embodiments, the fluorescent quencher may be an ATTO quencher including, but not limited to ATTO 540Q, ATTO 580Q, or ATTO 612Q. ATTO quenchers have characteristic properties of strong absorption (high extinction coefficient) and high photo-stability. ATTO quenchers are often utilized as fluorescent quenchers on amine-labeled nucleotides for FRET experiments.

In some embodiments, the fluorescent quencher may be CPQ2. The quencher CPQ2 is often used as a pair with the fluorescent donor 5-carboxylfluorescein.

In some embodiments, the fluorescent quencher may be a QSY quencher including but not limited to QSY-21, QSY-35, QSY-7, or QSY-9. QSY probes are dark quenchers, substances that absorb excitation energy from a fluorophore and dissipate the energy as heat.

In some embodiments, the fluorescent quencher may be DABCYL (4-([4'-dimethylamino)phenyl]azo)benzoyl). DABCYL is one of the most popular acceptors for developing FRET-based nucleic acid probes and protease substrates. DABCYL dyes are often paired with EDANS in FRET-based fluorescent probes. DABCYL has a broad and intense visible absorption but no fluorescence.

In some embodiments, the fluorescent quencher may be Dnp (2,4-dinitrophenyl). Dnp is a stable quencher and its absorption spectrum does not change with pH, which makes this group a convenient marker for substrate quantitation in solutions.

In some embodiments, the fluorescent quencher may be Eclipse®. Eclipse® is a non-fluorescent chromophore and a dark quencher often used in dual-labelled probes. As dark quenchers, Eclipse® absorbs energy without emitting fluorescence. Eclipse® has an absorption range from 390 nm to 625 nm and is capable of effective performance in a wide range of colored FRET probes.

Carrier

In some aspects, the probe/molecule described herein comprises a carrier. The fluorescent quencher as described herein may be in any structure. In some embodiments, the carrier may be a native, labeled or synthetic protein, a synthetic chemical polymer of precisely known chemical composition or with a distribution around a mean molecular weight (e.g. a linear or branched PEG polymers), an oligonucleotide, a phosphorodiamidate morpholino oligomer (PMO), or a foldamer, a lipid, a lipid micelle, a nanoparticle (e.g., iron oxide, gold, and non-metallic nanoparticles), a solid support made of polystyrene, polypropylene or any other type of plastic or polymer. In some embodiments, the carrier may be a peptide longer than the peptide linker. A carrier can be covalently or non-covalently attached to the cleavable linker.

In some embodiments, the carrier may be a nanoparticle. The transport of insoluble drugs via nanoparticles is improving because of their small particle size. Nanoparticle carrier is a kind of sub-micro particle delivery system, which belongs to a nanoscale microscope. Drugs encapsulated in sub-particles can adjust the speed of drug release, increase the permeability of biofilm, change the distribution in vivo, and improve the bioavailability. Nanoparticles are solid colloidal particles ranging in size from 10 to 100 nm used as a core in functionalization systems. They are generally composed of natural or synthetic macromolecule substances and can be used as carriers for conducting or transporting drugs. Nanospheres and nanocapsules can be formed. The chemical materials of nanomaterials are chitosan, gelatin, branched polymers, carbon-based carriers, etc. Gold nanoparticles consist of a core of gold atoms that can be functionalized by addition of a monolayer of moieties containing a thiol (SH) group.

In some embodiments, the carrier may be a native, labeled or synthetic protein. Proteins can be used as carriers for the delivery of chemicals and biomolecular drugs, such as anticancer drugs and therapeutic proteins. Protein nanoparticles have several advantages as a drug delivery system, such as biodegradability, stability, surface modification of particles, ease of particle size control, and they have less problems associated with toxicity issues, such as immunogenicity. Protein nanoparticles can be generated using proteins, such as fibroins, albumin, gelatin, gliadine, legumin, 30Kc19, lipoprotein, and ferritin proteins, and are prepared through emulsion, electrospray, and desolvation methods. Hong S, Choi D W, Kim H N, Park C G, Lee W, Park H H. Protein-Based Nanoparticles as Drug Delivery Systems. Pharmaceutics. 2020; 12(7):604. Published 2020 Jun. 29. For example, albumin, a plasma protein with a molecular weight of 66 kDa, has been extensively investigated as a drug carrier In some embodiments, the carrier may be a synthetic chemical polymer. Polymeric nanoparticles have been extensively investigated as drug nanocarriers. Drug loading is achieved either by (i) entrapment of an aqueous drug phase using the polymer to form nanoscale structures such as cages and capsules or (ii) chemical linking of the drug molecules to the polymer backbone by means of a simple ester or amide bond that can be hydrolyzed in vivo. The most widely researched synthetic polymers include polylactide (PLA), poly(D,L-lactide-co-glycolide) (PLGA) and PEG. All three polymers are hydrolyzed in vivo and are biodegradable. Malam Y, Loizidou M, Seifalian A M. Liposomes and nanoparticles: nanosized vehicles for drug delivery in cancer. Trends Pharmacol Sci. 2009 November; 30(11):592-9.

In some embodiments, the carrier may be a polyethylene glycol (PEG). PEG has been studied comprehensively as a carrier because it is soluble in both organic and hydrophilic solvents. Unlike many other synthetic polymers, PEG is relatively hydrophilic. Conjugation with PEG increases the solubility of hydrophobic molecules and prolongs the circulation time in the organism. PEG also minimizes the nonspecific absorption of a molecule, such as a drug, provides specific affinity toward the targeted tissue, and increases the drug accumulation in malignant tissue. PEG can be conjugated to other polymers to make them less hydrophobic (i.e., PEGylation). The changes in surface hydrophilicity prevent protein adsorption, thereby enabling cell adhesion and proliferation on biomaterial scaffolds. The PMO backbone is made of morpholino rings with phosphorodiamidate linkage, which protects them from nuclease degradation while still maintaining the complementary base pairing. The potential application of PMO-based antisense technology targeting bacterial pathogens is being explored for the development of a new class of antibacterial drugs. Panchal R G, Geller B L, Mellbye B, Lane D, Iversen P L, Bavari S. Peptide conjugated phosphorodiamidate morpholino oligomers increase survival of mice challenged with Ames *Bacillus anthracis*. Nucleic Acid Ther. 2012; 22(5): 316-322. Fluorescein-tagged Morpholinos combined with fluorescein-specific antibodies can be used as probes for in-situ hybridization to miRNAs.

In some embodiments, the carrier may be an oligonucleotide. Biostable, high-payload DNA nanoassemblies of various structures, including cage-like DNA nanostructure, DNA particles, DNA polypods, and DNA hydrogel, have been reported. Cage-like DNA structures hold drug molecules firmly inside the structure and leave a large space within the cavity. These DNA nanostructures use their unique structure to carry abundant CpG, and their biocompatibility and size advantages to enter immune cells to achieve immunotherapy for various diseases. Part of the DNA nanostructures can also achieve more effective treatment in conjunction with other functional components such as aPD1, RNA, TLR ligands. DNA-based nanoparticles, such as spherical nucleic acids, hybrid DNA-based nanoparticles, polypod-like DNA nanostructure, DNA hydrogels have been reported. Chi Q, Yang Z, Xu K, Wang C and Liang H (2020) DNA Nanostructure as an Efficient Drug Delivery Platform for Immunotherapy. Front. Pharmacol. 10:1585.

In some embodiments, the carrier may be a phosphorodiamidate Morpholino oligomer (PMO). Antisense phosphorodiamidate morpholino oligomers (PMOs) and their derivatives downregulate target gene expression in a sequence-dependent manner by interfering with the binding of ribosome to mRNA and thereby inhibiting protein translation.

In some embodiments, the carrier may be a lipid or a lipid micelle. The liposome bilayer can be composed of either synthetic or natural phospholipids. The predominant physical and chemical properties of a liposome are based on the net properties of the constituent phospholipids, including permeability, charge density and steric hindrance. The lipid bilayer closes in on itself due to interactions between water molecules and the hydrophobic phosphate groups of the phospholipids. This process of liposome formation is spontaneous because the amphiphilic phospholipids self-associate into bilayers. Drug loading into liposomes can be achieved through (i) liposome formation in an aqueous solution saturated with soluble drug; (ii) the use of organic solvents and solvent exchange mechanisms; (iii) the use of lipophilic drugs; and (iv) pH gradient methods. Malam Y, Loizidou M, Seifalian AM. Liposomes and nanoparticles: nanosized vehicles for drug delivery in cancer. Trends Pharmacol Sci. 2009 November; 30(11):592-9.

In some embodiments, the carrier may be a solid support made of polystyrene, polypropylene or any other type of plastic. For example, drug delivery properties of microporous polystyrene solid foams have been reported by Canal et al. These materials were obtained by polymerization in the continuous phase of highly concentrated emulsions prepared by the phase inversion temperature method. Their porosity, specific surface and surface topography are associated with drug incorporation and release characteristics. Canal, Cristina & Aparicio, Rosa & Vilchez, Alejandro & Esquena, Jordi & Garcia-Celma, Maria. (2012). Drug Delivery Properties of Macroporous Polystyrene Solid Foams. Journal of pharmacy & pharmaceutical sciences: a publication of the Canadian Society for Pharmaceutical Sciences, Socite canadienne des sciences pharmaceutiques. 15. 197-207.

In some embodiments, the carrier may be a foldamer. Foldamer, is a folded oligomer or polymer with a well-defined conformation. The conformation of foldamers is highly predictable from their primary sequences, therefore, it is possible to arrange functional groups at target positions and it may be possible to design functional foldamers, such as for efficient cellular uptake. For example, Cell-penetrating peptide (CPP) foldamers are peptide-based foldamers equipped with cell membrane permeabilities. Peptide foldamers contain unnatural amino acids, non-proteinogenic amino acids, which make the peptide adopt a stable secondary structure, especially helical structures, even in short sequences. This property is helpful for the design of amphipathic CPPs with a stable helical structure. Furthermore, peptides containing unnatural amino acids generally exhibit resistance to hydrolysis by proteases, which are abundant throughout the body and in the cells. High stability of the peptide foldamers against enzymatic degradation can lead to their prolonged function in vivo. Makoto Oba, Cell-Penetrating Peptide Foldamers: Drug Delivery Tools. ChemBioChem 10.1002/cbic.201900204.

Self-Immolative Spacer

In some aspects, the probe/molecule described herein comprises a self-immolative spacer. In some embodiments, the self-immolative spacer comprise a disulfide, a p-amino benzyl alcohol, an a-quinone methide spacer, a hetheroaminebifuncional disulfide, a thiol-based pirydazinediones, a p-aminebenzyloxycarbonyl, a dipeptide, a Gly-Pro (SEQ ID NO: 530), a L-Phe-Sar, a trans-cyclooctene tetrazine, a ortho Hydroxy-protected Aryl sulfate, a phosphoramidate-based spacer, a hydroxybenzyl, a trimethyl carbamate, a quinone methide-based spacer, a cyclizing spacer, a Trimethyl lock, a 2-amino methyl piperidine or an ethylene diamine derived cyclizing spacer. Gonzaga et al. Perspective about self-immolative drug delivery systems. Journal of Pharmaceutical Sciences 109 (2020) 3262-3281.

Cleavage of the cleavable linker by a predetermined protease or enzyme makes the self-immolative spacer dissociate from the precipitating fluorescent or non-fluorescent reporter, thereby resulting in a detectable signal. The cleavable linker of the plurality of probes/molecules may be cleavable by a predetermined endoprotease in the body fluid sample resulting in auto immolation and reporter release or results in a protease substrate that can be cleaved by a predetermined exopeptidase. In some embodiments, the predetermined exopeptidase is added to the body fluid sample. In some embodiments, the predetermined exopeptidase cleaves the protease substrate, thereby causing the self-immolative spacer to dissociate from the precipitating fluorescent reporter, thereby resulting in a detectable signal.

Body Fluid Samples

Determination of the disease or condition is based on the rate of formation or amount of the released reporter detected in the body fluid sample. In some embodiments, the body fluid sample may be blood, serum, plasma, bone marrow fluid, lymphatic fluid, bile, amniotic fluid, mucosal fluid, saliva, urine, cerebrospinal fluid, synovial fluid, semen, ductal aspirate, feces, vaginal effluent, cyst fluid, tissue homogenate, tissue-derived fluid, lachrymal fluid and patient-derived cell line supernatant. In some embodiments, the body fluid sample comprises a rinse fluid. In some embodiments, the rinse fluid may be a mouthwash rinse, a bronchioalveolar rinse, a lavage fluid, a hair wash rinse, a nasal spray effluent, a swab of any bodily surface, orifice or organ structure applied to saline or any media or any derivatives thereof.

In some embodiments, the body fluid sample may be blood. Blood is a constantly circulating fluid providing the body with nutrition, oxygen, and waste removal. Blood is mostly liquid, with numerous cells and proteins suspended in it. Blood is made of several main factors including plasma, red blood cells, white blood cells, and platelets.

In some embodiments, the body fluid sample may be a plasma. Plasma is the liquid that remains when clotting is prevented with the addition of an anticoagulant. Serum is the conventional term in the art for the fluid that remains when clotting factors are removed from plasma. Anticoagulants are medicines that help prevent blood clots. Examples of anticoagulants include, but are not limited to, an ethylenediamine tetraacetic acid (EDTA), a citrate, a heparin, an oxalate, any salt, solvate, enantiomer, tautomer and geometric isomer thereof, or any mixtures thereof.

In some embodiments, the anticoagulant may be EDTA. The main property of EDTA, a polyprotic acid containing four carboxylic acid groups and two amine groups with lone pair electrons, is the ability to chelate or complex metal ions in 1:1 metal-EDTA complexes. Owing to its strong complexation with metal ions that are cofactors for enzymes, EDTA is widely used as a sequestering agent to prevent some enzyme reactions from occurring. When blood is collected with no additives within an appropriate container (blood tube), it clots fairly quickly. As calcium ions are necessary for this process, the specific association between the carboxylic groups of EDTA and calcium is a reliable solution to prevent clotting, stabilizing whole blood in a fluid form, as required for some laboratory analyses. Moreover, EDTA showed optimal extended stabilization of blood cells and particles. Three EDTA formulations can be employed as anticoagulants: $Na_2EDTA$, K2EDTA and K3EDTA, choice of which mostly depends on the type of analyses to be performed.

In some embodiments, the anticoagulant may be a citrate. Citrate (C6H707) is a small negatively charged molecule with a molecular weight of 191 Daltons. Citrate can be used as the anticoagulant of choice for stored blood products, typically as acid citrate dextrose (ACD), (3.22% citrate, 112.9 mmol/l citrate, 123.6 mmol/l glucose, 224.4 mmol/l sodium and 114.2 mmol/l hydrogen ions), or trisodium citrate (TCA) $Na_3C_3H_5O(COO)_3$, (4% TCA, 136 mmol/l citrate, 420 mmol/l sodium). Citrate chelates calcium, and at a concentration of 4-6 mmol/l with an ionized calcium of <0.2 mmol/l prevents activation of both coagulation cascades and platelets. As such, citrate has been the standard anticoagulant used by hematologists and blood transfusion services for stored blood products and also as an extracorporeal anticoagulant for centrifugal platelet and leucopheresis techniques and plasma exchange.

In some embodiments, the anticoagulant may be a heparin. The molecular basis for the anticoagulant action of heparin lies in its ability to bind to and enhance the inhibitory activity of the plasma protein antithrombin against several serine proteases of the coagulation system, most importantly factors IIa (thrombin), Xa and IXa. Two major mechanisms underlie heparin"s potentiation of antithrombin. The conformational changes induced by heparin binding cause both expulsion of the reactive loop and exposure of exosites of the surface of antithrombin, which bind directly to the enzyme target; and a template mechanism exists in which both inhibitor and enzyme bind to the same heparin molecule. The relative importance of these two modes of action varies between enzymes. In addition, heparin can act through other serine protease inhibitors such as heparin co-factor II, protein C inhibitor and tissue factor plasminogen inhibitor. The antithrombotic action of heparin in vivo, though dominated by anticoagulant mechanisms, is more complex, and interactions with other plasma proteins and cells play significant roles in the living vasculature.

In some embodiments, the anticoagulant may be an oxalate. Sodium, potassium, ammonium, and lithium oxalates inhibit blood coagulation by forming insoluble complex with calcium. Potassium oxalate at concentration of 1-2 mg/ml of blood is widely used. Combined ammonium and/or potassium oxalate does not cause shrinkage of erythrocytes. It consists of three parts by weight of ammonium oxalate, which causes swelling of the erythrocytes, balanced by two parts of potassium oxalate which causes shrinkage.

NH4+ & K+ oxalate mixture in the ratio of 3:2, and 2 mg/ml of blood is the required amount.

In some embodiments, the body fluid sample may be bone marrow fluid. Bone marrow is found in the center of most bones and has many blood vessels. There are two types of bone marrow: red and yellow. Red marrow contains blood stem cells that can become red blood cells, white blood cells, or platelets. Yellow marrow is made mostly of fat.

In some embodiments, the body fluid sample may be lymphatic fluid. Lymphatic fluid, also called lymph, is a collection of the extra fluid that drains from cells and tissues, that is not reabsorbed into the capillaries.

In some embodiments, the body fluid sample may be bile. Bile is a digestive fluid produced by the liver and stored in the gallbladder. During bile reflux, digestive fluid backs up into the stomach and, in some cases, the esophagus.

In some embodiments, the body fluid sample may be amniotic fluid. Amniotic fluid is a clear, slightly yellowish liquid that surrounds the unborn baby (fetus) during pregnancy. It is contained in the amniotic sac.

In some embodiments, the body fluid sample may be mucosal fluid. Mucosal fluid, also called mucus, is a thick protective fluid that is secreted by mucous membranes and used to stop pathogens and dirt from entering the body. Mucus is also used to prevent bodily tissues from being dehydrated.

In some embodiments, the body fluid sample may be saliva. Saliva is an extracellular fluid produced and secreted by salivary glands in the mouth.

In some embodiments, the body fluid sample may be urine. Urine is a liquid by-product of metabolism in humans and in many other animals. Urine flows from the kidneys through the ureters to the urinary bladder.

In some embodiments, the body fluid sample may be cerebrospinal fluid. Cerebrospinal fluid is a clear fluid that surrounds the brain and spinal cord. It cushions the brain and spinal cord from injury and also serves as a nutrient delivery and waste removal system for the brain In some embodiments, the body fluid sample may be synovial fluid. Synovial fluid, also known as joint fluid, is a thick liquid located between your joints. The fluid cushions the ends of bones and reduces friction when joints are moved.

In some embodiments, the body fluid sample may be semen. Semen is the male reproductive fluid which contains spermatozoa in suspension.

In some embodiments, the body fluid sample may be ductal aspirate. Ductal aspirate, also known as ductal lavage, ductal fluid, or lavage fluid, is fluid collected from a duct, such as the milk duct of the breast.

In some embodiments, the body fluid sample may be feces. Feces, also known as excrement or stool is waste matter discharged from the bowels after food has been digested.

In some embodiments, the body fluid sample may be vaginal effluent. Vaginal effluent, also known as vaginal discharge, is a clear or whitish fluid that comes out of the vagina.

In some embodiments, the body fluid sample may be lachrymal fluid. Lachrymal fluid, also known as lacrimal fluid, is secreted by the lacrimal glands to lubricate the eye and fight bacteria.

In some embodiments, the body fluid sample may be tissue homogenate. A tissue homogenate is obtained through mechanical micro-disruption of fresh tissue and the cell membranes are mechanically permeabilized.

Proteases and Other Agents

The probe/molecule described herein may be cleaved by a protease from the body fluid. In some embodiments, the protease comprises an endopeptidase or an exopeptidase.

In some embodiments, the protease comprises an endopeptidase. An endopeptidase is an enzyme which breaks peptide bonds other than terminal ones in a peptide chain.

In some embodiments, the protease comprises an exopeptidase. An exopeptidase is an enzyme that catalyzes the cleavage of the terminal or penultimate peptide bond; the process releases a single amino acid or dipeptide from the peptide chain.

In some embodiments, the protease comprises an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh. binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, or a combination hereof.

In some embodiments, the protease comprises a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), or a combination hereof.

In some embodiments, the protease comprises a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase O, a carboxypeptidase U, a carboxypeptidase X1, a carboxypeptidase X2, a carboxypeptidase Z, a carnosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, or a combination hereof.

In some embodiments, the protease comprises a DDI-related protease, a DECYSIN, a Der1-like domain family, member 1, a Der1-like domain family, member 2, a Der1-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination hereof.

In some embodiments, the protease comprises an enamelysin, an endopeptidase C1p, an endoplasmic reticulum metallopeptidase 1, an endothelin-converting enzyme 1, an endothelin-converting enzyme 2, an enteropeptidase, an epidermis-specific SP-like, an epilysin, an epithelial cell transforming sequence 2 oncogene-like, an epitheliasin, an epoxide hydrolase, an epoxyde hydrolase related protein, an eukar. translation initiation F3SF, an eukar. translation initiation F3SH, or a combination hereof.

In some embodiments, the protease comprises a Factor VII activating protease, a FACE-1/ZMPSTE24, a FACE-2/RCE1, a family with sequence similarity 108, member A1, a family with sequence similarity 108, member B1, a family with sequence similarity 108, member C1, a family with sequence similarity 111, A, a family with sequence similarity 111, B, a furin, or a combination hereof.

In some embodiments, the protease comprises a gamma-glutamyl hydrolase, a gamma-glutamyltransferase 1, a gamma-glutamyltransferase 2, a gamma-glutamyltransferase 5, a gamma-glutamyltransferase 6, a gamma-glutamyltransferase m-3, a gamma-glutamyltransferase-like 3, a GCDFP15, a gelatinase A, a gelatinase B, a Gln-fructose-6-P transamidase 1, a Gln-fructose-6-P transamidase 2, a Gln-fructose-6-P transamidase 3, a Gln-PRPP amidotransferase, a glutamate carboxypeptidase II, a glutaminyl cyclase, a glutaminyl cyclase 2, a glycosylasparaginase, a glycosylasparaginase-2, a granzyme, a granzyme A, a granzyme B, a granzyme H, a granzyme K, a granzyme M, a haptoglobin-1, or a combination hereof.

In some embodiments, the protease comprises a histone deacetylase (HDAC), a haptoglobin-related protein, a HAT-like 2, a HAT-like 3, a HAT-like 4, a HAT-like 5, a HAT-related protease, HSP90AA1? (a heat shock 90 kDa protein 1, alpha), HSP90AB1? (a heat shock 90 kDa protein 1, beta), a heat shock protein 75, a heat shock protein 90 kDa beta (Grp94), member 1/tumor rejection antigen (gp96), a hepatocyte growth factor, a hepsin, a HetF-like, a HGF activator, a hGPI8, a Hin-1/OTU domain containing 4, a homologue ICEY, a HP43.8KD, a HTRA1 serine protease, a HTRA2, a HTRA3, a HTRA4, a hyaluronan-binding ser-protease, a implantation serine protease 2, a indian hedgehog protein, a insulysin, a intestinal serine protease 1, a josephin-1, a josephin-2, or a combination hereof.

In some embodiments, the protease comprises a Kallikrein (KLK), a kallikrein hK1, a kallikrein hK2, a kallikrein hK3, a kallikrein hK4, a kallikrein hK5, a kallikrein hK6, a kallikrein hK7, a kallikrein hK8, a kallikrein hK9, a kallikrein hK10, a kallikrein hK11, a kallikrein hK12, a kallikrein hK13, a kallikrein hK14, a kallikrein hK15, a Kell blood-group protein, a KHNYN KH and NYN domain containing, a lactotransferrin, a legumain, a leishmanolysin-2, a leucyl aminopeptidase, a leucyl-cystinyl aminopeptidase, a leukotriene A4 hydrolase, a lysosomal carboxypeptidase A, a lysosomal Pro-X C-peptidase, or a combination hereof.

In some embodiments, the protease comprises a membrane metallo-endopeptidase (MME), a macrophage elastase, a macrophage-stimulating protein, a mammalian tolloid-like 1 protein, a mammalian tolloid-like 2 protein, a MAPiD methione aminopeptidase 1D, a marapsin, a marapsin 2, a MASP1/3 (a MBL associated serine protease 3), a MBL associated serine protease 2 (MASP2), a mastin, a matrilysin, a matrilysin-2, a matriptase, a matriptase-2, a matriptase-3, a membrane dipeptidase, a membrane dipeptidase 2, a membrane dipeptidase 3, a membrane-type mosaic Ser-protein, a meprin alpha subunit, a meprin beta subunit, a mesoderm-specific transcript, a mesotrypsin, a methionyl aminopeptidase I, a methionyl aminopeptidase IL, a methionyl aminopeptidase II-like, a mitochondrial inner membrane protease 2, a mitochondrial Intermediate peptidase, a mitochondrial Proc. peptidase b-subunit, a mitochondrial proc. protease, a mitochondrial signal peptidase, a matrix metalloproteinase (MMP), a MMP19, a MMP21, a MMP23A, a MMP23B, a MMP27, a MPND, a MT1-MMP, a MT2-MMP, a MT3-MMP, a MT4-MMP, a MT5-MMP, a MT6-MMP, a MYSM1, or a combination hereof.

In some embodiments, the protease comprises a NAALADASE II, a NAALADASE like 2, a NAALADASE like1, a napsin A, a napsin B, a nardilysin, a nasal embryonic LHRH factor, a NEDD4 binding protein 1, a neprilysin, a neprilysin-2, a neurolysin, a neurotrypsin, a neutrophil elastase (ELANE, ELA2), a NLRP1 self-cleaving protein, a nuclear recept. interacting protein 2, a nuclear recept. interacting protein 3, a nucleoporin 98, a NYN domain and retroviral integrase containing, a NY-REN-60, an OMA1, an O-sialoglycoprotein endopeptidase, an O-sialoglycoprotein endopeptidase like 1, an osteoblast serine protease, an OTU domain containing 6B, an OTU domain containing-1, an OTU domain containing-3, an OTU domain containing-5, an OTU domain containing-6A, an otubain-1, an otubain-2, an OTUD2/YOD1, an ovastacin, an oviductin-like/ovochymase-2, an ovochymase-like, or a combination hereof.

In some embodiments, the protease comprises a proteinase 3 (PRTN3), a papain, a PACE4 proprotein convertase, a pancreatic elastase, a pancreatic elastase II (IIA), a pancreatic elastase II form B, a pancreatic endopeptidase E (A), a pancreatic endopeptidase E (B), a pappalysin-1, a pappalysin-2, a paracaspase, a paraplegin, a pepsin A, a pepsin C, a PHEX endopeptidase, a PIDD auto-processing protein unit 1, a PIM1 endopeptidase, a PIM2 endopeptidase, a pitrilysin metalloproteinase 1, a plasma Glu-carboxypeptidase, a plasma kallikrein, a plasma-kallikrein-like 2, a plasma-kallikrein-like 3, a plasma-kallikrein-like 4, a plasmin (plasminogen), a PM20D2 peptidase, a POH1/PSMD14, a polyserase-2, a polyserase-3, a polyserase-I, a Ppnx, a presenilin 1, a presenilin 2, a presenilin homolog 1/SPPL3, a presenilin homolog 2, a presenilin homolog 3/SPP, a presenilin homolog 4/SPPL2B, a presenilin homolog 5, a presenilins-assoc. rhomboid like, a procollagen C-proteinase, a proliferation-association protein 1, a prolyl oligopeptidase, a prolyl oligopeptidase-like, a proprotein convertase 1, a proprotein convertase 2, a proprotein convertase 4, a proprotein convertase 5, a proprotein convertase 7, a proprotein convertase 9 (a proprotein convertase subtilisin/kexin type 9, PCSK9), a prostasin, (a protease, serine, 56), a proteasome alpha 1 subunit, a proteasome alpha 2 subunit, a proteasome alpha 3 subunit, a proteasome alpha 3-like subunit, a proteasome alpha 4 subunit, a proteasome alpha 5 subunit, a proteasome alpha 6 subunit, a proteasome alpha 7 subunit, a proteasome alpha 8 subunit, a proteasome b subunit LMP7-like, a proteasome beta 1 subunit, a proteasome beta 2 subunit, a proteasome beta 3 subunit, a proteasome beta 3-like subunit, a proteasome beta 4 subunit, a proteasome catalytic sub. 1-like, a proteasome catalytic subunit 1, a proteasome catalytic subunit 1i, a proteasome catalytic subunit 2, a proteasome catalytic subunit 2i, a proteasome catalytic subunit 3, a proteasome catalytic subunit 3i, a protein C, a protein C-like, a protein Z, a proteinase 3, a PRPF8, a PSMD7, a pyroglutamyl-peptidase I, a pyroglutamyl-peptidase II, or a combination hereof.

In some embodiments, the protease comprises a reelin, a renin, a retinol binding protein 3, a rhomboid 5 homolog 1, a rhomboid 5 homolog 2, a rhomboid domain containing 1, a rhomboid domain containing 2, a rhomboid, veinlet-like 2, a rhomboid, einlet-like 3, a rhomboid-like protein 1, or a combination hereof.

In some embodiments, the protease comprises a serine protease, a serine protease 3 (PRSS3), a S2P protease, a SAD1, a secernin-1, a secernin-2, a secernin-3, a sentrin (SUMO protease 1), a sentrin (SUMO protease 2), a sentrin (SUMO protease 3), a sentrin (SUMO protease 5), a sentrin (SUMO protease 5-like 1), a sentrin (SUMO protease 6), a sentrin (SUMO protease 7), a sentrin (SUMO protease 8), a sentrin (SUMO protease 9), a sentrin (SUMO protease 11), a sentrin (SUMO protease 12), a sentrin (SUMO protease 13), a sentrin (SUMO protease 14), a sentrin (SUMO protease 15), a sentrin (SUMO protease 16), a sentrin (SUMO protease 17), a sentrin (SUMO protease 18), a sentrin (SUMO protease 19), a separase, a seprase, a serine carboxypeptidase 1, a signalase 18 kDa component, a signalase 21 kDa component, a signalase-like 1, a similar to *Arabidopsis* Ser-prot., a similar to SPUVE, a site-1 protease, a sonic hedgehog protein, a spinesin, a SprT-like N-terminal domain, a stromelysin 1, a stromelysin 2, a stromelysin 3, a suppressor of Ty 16 homolog, or a combination hereof.

In some embodiments, the protease comprises a taspase, a TBP-associated factor 2, a TESP2, a TESP3, a testase 2, a testis serine protease 2, a testis serine protease 3, a testis serine protease 4, a testis serine protease 5, a testis serine protease 6, a testisin, a testis-specific protein tsp50, a thimet oligopeptidase, a thrombin, a thymus-specific serine peptidase, a TINAG related protein, a TMPRSS11A, a t-plasminogen activator, a TRAF-binding protein domain, a transferrin receptor 2 protein, a transferrin receptor protein, a transmembrane Ser-protease 3, a transmembrane Ser-protease 4, a transthyretin, a TRH-degrading ectoenzyme, a tripeptidyl-peptidase I, a tripeptidyl-peptidase IL, a trypsin, a trypsin 10, a trypsin 15, a trypsin C, a trypsin X2, a tryptase, a tryptase alpha/beta 1, a tryptase beta 2, a tryptase delta 1, a tryptase gamma 1, a tryptase homolog 2/EOS, a tryptase homolog 3, a tubulointerstitial nephritis antigen, or a combination hereof.

In some embodiments, the protease comprises a ubiquitin C-term. hydrolase BAP1, a ubiquitin C-terminal hydrolase 1, a ubiquitin C-terminal hydrolase 3, a ubiquitin C-terminal hydrolase 4, a ubiquitin C-terminal hydrolase 5, a ubiquitin specific peptidase like 1, a UCR1, a UCR2, a UDP-N-acetylglucosaminyltransferase subunit, a Ufm-1 specific protease 1, a Ufm-1 specific protease 2, a urokinase (PLAU, uPA) a umbelical vein proteinase, a u-plasminogen activator, a USP1, a USP2, a USP3, a USP4, a USP5, a USP6, a USP7, a USP8, a USP9X, a USP9Y, a USP10, a USP11, a USP12, a USP13, a USP14, a USP15, a USP16, a USP17, a USP17-like, a USP18, a USP19, a USP20, a USP21, a USP22, a USP24, a USP25, a USP26, a USP27, a USP28, a USP29, a USP30, a USP31, a USP34, a USP35, a USP36, a USP37, a USP40, a USP41, a USP42, a USP43, a USP44, a USP45, a USP46, a USP47, a USP48, a USP49, a USP50, a USP51, a USP52, a USP53, a USP54, or a combination hereof.

In some embodiments, the protease comprises a VCP (p97)/p47-interacting protein, a VDU1, a vitellogenic carboxypeptidase-L, a X-Pro dipeptidase, a X-prolyl aminopeptidase 2, a YME1-like 1, a zinc finger CCCH-type containing 12A, a zinc finger CCCH-type containing 12B, a zinc finger CCCH-type containing 12C, a zinc finger CCCH-type containing 12D, a Zinc finger containing ubiquitin peptidase 1, or a combination hereof.

In some embodiments, the protease comprises an A20 (Tumor necrosis factor, alpha-induced protein 3, TNF a-induced protein 3). A20 is a zinc finger protein and a deubiquitinating enzyme. A20 has been shown to inhibit NF-kappa B activation as well as TNF-mediated apoptosis, limit inflammation.

In some embodiments, the protease comprises an Angiotensin-converting enzyme 2 (ACE2). ACE2 is an enzyme attached to the membrane cells located to the membrane of cells located in the intestines, kidney, testis, gallbladder, and heart. ACE2 counters the activity of the related angiotensin-converting enzyme, ACE, by reducing the amount of angiostatin II.

In some embodiments, the protease comprises a cathepsin. The cathepsin may be, but is not limited to, a cathepsin A (CTSA), a cathepsin B (CTSB), a cathepsin C (CTSC), a cathepsin D (CTSD), a cathepsin E (CTSE), a cathepsin H (CTSH), a cathepsin K (CTSK), a cathepsin L (CTSL), a cathepsin S (CTSS), a cathepsin V (CTSV), and a cathepsin Z (CTSZ). Cathepsins are a subset of proteases, many of which become activated in low pH. Cathepsisns comprise serine proteases, cysteine proteases, and aspartyl proteases, among others. Cathepsins have been implicated in cancer, Alzheimer"s disease, arthritis, Ebola, pancreatitis, glaucoma, COPD, and other diseases.

In some embodiments, the protease comprises a caspase. The caspase may be, but is not limited to, a caspase 1, a caspase 2, a caspase 3, a caspase 4, a caspase 5, a caspase 6, a caspase 7, a caspase 8, a caspase 9, a caspase 10, a caspase 11, a caspase 12, a caspase 13, and a caspase 14.

In some embodiments, the protease comprises a calpain. The calpain may be, but is not limited to a calpain 1, a calpain 2, a calpain 3, a calpain 4, a calpain 5, a calpain 6, a calpain 7, a calpain 8, a calpain 9, a calpain 10, a calpain 11, a calpain 12, a calpain 13, a calpain 14, and a calpain 15. Caspases are a family of protease enzymes that play essential roles in programmed cell death and cell homeostasis.

In some embodiments, the protease comprises a cysteine protease. Cysteine proteases, also known as thiol proteases, are hydrolase enzymes that degrade proteins. These proteases share a common catalytic mechanism that involves a nucleophilic cysteine thiol in a catalytic triad or dyad. The cysteine protease family comprises Papain (*Carica papaya*), bromelain (*Ananas comosus*), cathepsin K (liverwort), calpain (*Homo sapiens*), aspase-1 (*Rattus norvegicus*), separase (*Saccharomyces cerevisiae*), Adenain (human adenovirus type 2), Pyroglutamyl-peptidase I (*Bacillus amyloliquefaciens*), Sortase A (*Staphylococcus aureus*), Hepatitis C virus peptidase 2 (hepatitis C virus), Sindbis virus-type nsP2 peptidase (sindbis virus), Dipeptidyl-peptidase VI (Lysinibacillus *sphaericus*), DeSI-1 peptidase (*Mus musculus*), TEV protease (tobacco etch virus), Amidophosphoribosyltransferase precursor (*Homo sapiens*), Gamma-glutamyl hydrolase (*Rattus norvegicus*), Hedgehog protein (*Drosophila melanogaster*) and DmpA aminopeptidase (*Ochrobactrum anthropi*), etc.

In some embodiments, the protease comprises a complement C1r serine protease (Complement component 1r). In some embodiments, the protease comprises a complement C1s serine protease (Complement component 1s). C1r along with C1q and C1s form the C1 complex. C1r has very narrow trypsin-like specificity that is responsible for activation of the C1 complex. C1 activation is a two-step process involving (1) C1r intramolecular autoactivation and (2) C1s cleavage by activated C1r. C1r contains a chymotrypsin-like serine protease domain at its C-terminal, and cleaves a single Arg-Ile bond in C1r and in C1s. Zvi Fishelson, in xPharm: The Comprehensive Pharmacology Reference, 2007.

In some embodiments, the protease comprises a chymotrypsin (chymotrypsins A and B, alpha-chymar ophth, avazyme, chymar, chymotest, enzeon, quimar, quimotrase, alpha-chymar, alpha-chymotrypsin A, alpha-chymotrypsin)). Chymotrypsin is a digestive enzyme component of pancreatic juice acting in the duodenum, where it performs proteolysis, the breakdown of proteins and polypeptides. Chymotrypsin preferentially cleaves peptide amide bonds where the side chain of the amino acid N-terminal to the scissile amide bond is a large hydrophobic amino acid (tyrosine, tryptophan, and phenylalanine).

In some embodiments, the protease comprises a chymase (mast cell protease 1, skeletal muscle protease, skin chymotryptic proteinase, mast cell serine proteinase, skeletal muscle protease). Chymases are a family of serine proteases found in mast cells, basophil granulocytes. Chymases show broad peptidolytic activity and are involved in inflammatory response, hypertension and atherosclerosis.

In some embodiments, the protease comprises a dipeptidyl peptidase (DPP). DPP comprises cathepsin C (DPP1), DPP2, DPP3, DPP4, DPP 6, DPP7, DPP8, DPP9, DPP10.

In some embodiments, the protease comprises a DPP4 (adenosine deaminase complexing protein 2, CD26). DPP4 is expressed on cell surface and is associated with immune regulation, signal transduction, and apoptosis. DPP4 is a serine exopeptidase that cleaves X-proline or X-alanine dipeptides from the N-terminus of polypeptides. DPP-4 is known to cleave a broad range of substrates including growth factors, chemokines, neuropeptides, and vasoactive peptides. DPP4 plays a major role in glucose metabolism, is responsible for the degradation of incretins such as GLP-1, and appears to work as a suppressor in the development of some tumors In some embodiments, the protease comprises a DPP1 (Cathepsin C, CTSC). DPP1 is a lysosomal exo-cysteine protease belonging to the peptidase C1 family. Cathepsin C appears to be a central coordinator for activation of many serine proteases in immune/inflammatory cells. Cathepsin C catalyzes excision of dipeptides from the N-terminus of protein and peptide substrates, In some embodiments, the protease comprises a disintegrin and metalloproteinase (ADAM). ADAMs are a family of single-pass transmembrane and secreted metalloendopeptidases. Not all human ADAMs have a functional protease domain. Those ADAMs which are active proteases are classified as sheddases because they cut off or shed extracellular portions of transmembrane proteins.

In some embodiments, the protease comprises an ADAM12 metalloprotease. ADAM12 binds insulin growth factor binding protein-3 (IGFBP-3), appears to be an early Down syndrome marker, and has been implicated in a variety of biological processes involving cell-cell and cell-matrix interactions, including fertilization, muscle development, and neurogenesis.

In some embodiments, the protease comprises a disintegrin and metalloproteinase with thrombospondin motifs (ADAMTS). ADAMTS is a family of multidomain extracellular protease enzymes, comprising ADAMTS1, ADAMTS2, ADAMTS3, ADAMTS4, ADAMTS5 (=ADAMTS11), ADAMTS6, ADAMTS7, ADAMTS8 (or METH-2), ADAMTS9, ADAMTS10, ADAMTS12, ADAMTS13, ADAMTS14, ADAMTS15, ADAMTS16, ADAMTS17, ADAMTS18, ADAMTS19, and ADAMTS20. Known functions of the ADAMTS proteases include processing of procollagens and von Willebrand factor as well as cleavage of aggrecan, versican, brevican and neurocan, making them key remodeling enzymes of the extracellular matrix. They have been demonstrated to have important roles in connective tissue organization, coagulation, inflammation, arthritis, angiogenesis and cell migration.

In some embodiments, the protease comprises an ADAMTS1. ADAMTS1 is a member of the ADAMTS protein family. The expression of ADAMTS1 may be associated with various inflammatory processes, development of cancer cachexia, normal growth, fertility, and organ morphology and function.

In some embodiments, the protease comprises a Factor VII activating protease (FSAP). FSAP is a circulating serine protease with high homology to fibrinolytic enzymes, and may be associated with the regulation of coagulation and fibrinolysis.

In some embodiments, the protease comprises a furin. Furin belongs to the subtilisin-like proprotein convertase family, and is a calcium-dependent serine endoprotease. Furin"s substrates includes: proparathyroid hormone, transforming growth factor beta 1 precursor, proalbumin, probeta-secretase, membrane type-1 matrix metalloproteinase, beta subunit of pro-nerve growth factor and von Willebrand factor.

In some embodiments, the protease comprises a histone deacetylase (HDAC). HDACs are a class of enzymes that remove acetyl groups (O═C—CH3) from an ε-N-acetyl lysine amino acid on a histone, allowing the histones to wrap the DNA more tightly.

In some embodiments, the protease comprises a HTRA1 serine protease. HTRA1 is a secreted enzyme that is proposed to regulate the availability of insulin-like growth factors (IGFs) by cleaving IGF-binding proteins. It has also been suggested to be a regulator of cell growth.

In some embodiments, the protease comprises a granzyme. Granzymes are serine proteases released by cytoplasmic granules within cytotoxic T cells and natural killer (NK) cells. Granzymes induce programmed cell death in the target cell. Granzymes also kill bacteria and inhibit viral replication.

In some embodiments, the protease comprises, a Kallikrein (KLK). Kallikreins are a subgroup of serine proteases. Kallikreins are responsible for the coordination of various physiological functions including blood pressure, semen liquefaction and skin desquamation.

In some embodiments, the protease comprises a matrix metalloproteinase (MMP, matrix metallopeptidases, matrixins). MPPs are calcium-dependent zinc-containing endopeptidases. MMPs have been implicated in cleavage of cell surface receptors, the release of apoptotic ligands, chemokine/cytokine inactivation, cell proliferation and cell migration.

In some embodiments, the protease comprises a membrane metallo-endopeptidase (MME). MME is a zinc-dependent metalloprotease that cleaves peptides at the amino side of hydrophobic residues and inactivates several peptide hormones including glucagon, enkephalins, substance P, neurotensin, oxytocin, and bradykinin. MME is expressed in a wide variety of tissues and is particularly abundant in kidney. MME is also a common acute lymphocytic leukemia antigen.

In some embodiments, the protease comprises a mannose-binding protein-associated serine protease 2 (MASP2, Mannan-binding lectin serine protease 2, MBL associated serine protease 2). MASP2 is involved in the complement system, cleaves complement components C4 and C2 into C4a, C4b, C2a, and C2b.

In some embodiments, the protease comprises a mannose-binding protein-associated serine protease 3 (MBL associated serine protease 3, MASP3). MASP3 originates from the MASP1 gene through differential splicing, it circulates in high serum concentrations predominantly in complex with Ficolin-3 and regulates Ficolin-3 mediated complement activation.

In some embodiments, the protease comprises a neutrophil elastase (ELANE, ELA2). ELANE is a serine proteinase secreted by neutrophils and microphages during inflammation and destroys bacteria and host tissue.

In some embodiments, the protease comprises a proteinase 3 (PRTN3). PRTN3 is a serine protease enzyme expressed mainly in neutrophil granulocytes and contributes to the proteolytic generation of antimicrobial peptides.

In some embodiments, the protease comprises a plasmin (a.k.a. plasminogen). Plasmin is a proteolytic enzyme derived from an inert plasma precursor known as plasminogen. It is present in blood that degrades many blood plasma proteins, including fibrin clots. In human, plasmin is encoded by PLG gene.

In some embodiments, the protease comprises a pepsin. Pepsin is an endopeptidase that cleaves proteins into smaller peptides. It is an aspartic protease, using a catalytic aspartate in its active site.

In some embodiments, the protease comprises a presenilin-1 (PS-1). PS-1 is a presenilin protein that is one of the four core proteins in the gamma secretase complex, which is considered to play an important role in generation of amyloid beta from amyloid precursor protein.

In some embodiments, the protease comprises a proprotein convertase subtilisin/kexin type 9 (PCSK9). PCSK9 is a member of the peptidase S8 family.

In some embodiments, the protease comprises a serine protease. Serine protease cleaves peptide bonds in proteins, in which serine serves as the nucleophilic amino acid at the enzyme's active site. Serine protease includes many subfamilies.

In some embodiments, the protease comprises a tryptase. Tryptase is a the most abundant secretory granule-derived serine proteinase contained in mast cells and has been used as aa marker for mast cell activation. It is released from mask cells when they are activated as part of a normal immune response as well as in allergic responses.

In some embodiments, the protease comprises, a trypsin. Trypsin is a serine protease from the PA clan superfamily, found in the digestive system. Trypsin cuts peptide chains mainly at the carboxyl side of the amino acids lysine or arginine.

In some embodiments, the protease comprises a urokinase (PLAU, uPA). Urokinase is a serine protease present in humans and other animals. It is present in human urine, blood and in the extracellular matrix of many tissues. It is involved in degradation of the extracellular matrix and possibly tumor cell migration and proliferation. Urokinase is a 411-residue protein, consisting of three domains: the serine protease domain, the kringle domain, and the EGF-like domain. Urokinase is synthesized as a zymogen form (prourokinase or single-chain urokinase), and is activated by proteolytic cleavage between Lys158 and Ile159. The two resulting chains are kept together by a disulfide bond.

Described herein are agents to be detected including but are not limited to a oxidoreductase, a transferase, a hydrolase, a lyase, a isomerase, a ligase, a protease, a hydrolase, an esterase, a β-glycosidase, a phospholipase and a phosphodiesterase, peroxidase, lipase, amylase a nucleophilic reagent, a reducing reagent, a electrophilic/acidic reagent, an organometallic/metal catalyst, an oxidizing reagent, a hydroxyl ion, a thiols nucleophile, a nitrogen nucleophile, a sodium dithionite and a sodium periodate.

As described herein, the activity detection of some agents does not rely on cleavage. For example, some oxidoreductases, transferases, hydrolases, lyases, isomerases, and ligases lead to the substrate linker modification and release or formation of a reporter molecule that can be detected. As a way of illustration, a certain oxidation processes can modify an inactive fluorophore and render it fluorescent/detectable without the need of a substrate linker or binding events (for non-covalent processes) can change magnetic/fluorescent physical-chemical properties of certain reporters and render them detectable.

Disease and Condition

The method described herein comprise determining a disease or condition of the subject. In some aspects, the disease or condition comprises a liver disease, a cancer, a metabolic disease, a fibrotic disease, an organ transplant rejection, an infectious disease, an allergic disease, an autoimmunity, Alzheimer"s or a chronic inflammation. In some embodiments, the liver disease may be a non-alcoholic steatohepatitis (NASH), a non-alcoholic fatty liver disease (NAFLD), a toxin mediated liver injury (drug/medication, alcohol, environmental), a viral hepatitis (HAV, HBV, HCV, HDV, HEV, other virus infecting the liver), an autoimmune hepatitis, a primary biliary cholangitis, a primary sclerosing cholangitis, a fulminant hepatitis, a cirrhosis of the liver, a hepatocellular carcinoma (HCC), a cholangiocarcinoma, an acute or chronic rejection of a transplanted liver, an inherited liver disease (e.g. Wilson disease, hemochromatosis, or alpha-1 antitrypsin) or a combination thereof.

In some embodiments, the cancer comprises adenoid cystic carcinoma, adrenal gland tumors, amyloidosis, anal cancer, appendix cancer, astrocytoma, ataxia-telangiectasia, Beckwith-Wiedemann syndrome, bile duct cancer (cholangiocarcinoma), Birt-Hogg-Dubé Syndrome, bladder cancer, bone cancer (sarcoma of the bone), brain stem glioma, brain tumors, breast cancer, Carney complex, central nervous system tumors, cervical cancer, colorectal cancer, Cowden Syndrome, craniopharyngioma, Desmoid tumors, desmoplastic infantile ganglioglioma, ependymoma, esophageal cancer, Ewing sarcoma, eye cancer, eyelid cancer, familial adenomatous polyposis, familial GIST, familial malignant melanoma, familial pancreatic cancer, gallbladder cancer, gastrointestinal stromal tumors (GIST), germ cell tumors, gestational trophoblastic disease, head and neck cancer, breast and ovarian cancer, diffuse gastric cancer, leiomyosarcoma and renal cell cancer, mixed polyposis syndrome, papillary renal carcinoma, juvenile polyposis syndrome, kidney cancer, lacrimal gland tumors, laryngeal and hypopharyngeal cancer, leukemia, myeloid leukemia, lymphoblastic leukemia, eosinophilic leukemia, Li-Fraumeni syndrome, liver cancer, lung cancer, Hodgkin lung cancer, non-Hodgkin lung cancer, Lynch syndrome, mastocytosis, medulloblastoma, melanoma, meningioma, mesothelioma, multiple endocrine neoplasia, multiple myeloma, myelodysplastic syndrome, nasal cavity and paranasal sinus cancer, nasopharyngeal cancer, neuroblastoma, neuroendocrine tumors, neurofibromatosis, nevoid basal cell carcinoma syndrome, oral and oropharyngeal cancer, osteosarcoma, ovarian cancer, fallopian tube cancer, peritoneal cancer, pancreatic cancer, parathyroid cancer, penile cancer, Peutz-Jeghers syndrome, phenochromocytoma, paraganglioma, pituitary gland tumors, pleuropulmonary blastoma, prostate cancer, retinoblastoma, rhabdomyosarcoma, salivary gland cancer, Kaposi sarcoma, soft tissue sarcoma, sarcoma, non-melanoma skin cancer, small bowel cancer, stomach cancer, testicular cancer, thymoma and thymic carcinoma, thyroid cancer, tuberous sclerosis complex, uterine cancer, vaginal cancer, von Hippel-Lindau syndrome, vulvar cancer, Waldenstrom macroglobulinemia, Werner syndrome, Wilms tumors, or xeroderma pigmentosum.

In some embodiments, the disease may be NASH. Non-alcoholic steatohepatitis, also called NASH, is a more active inflammatory form of non-alcoholic fatty liver disease (NAFLD). NAFLD is caused by buildup of fat in the liver. When this buildup causes inflammation and damage, it is known as NASH, which can lead to scarring of the liver. There are often no outward signs or symptoms associated with NASH, although the most common symptoms are fatigue or mild pain in the upper right abdomen. NASH may lead to cirrhosis of the liver, causing one or more of the following symptoms as the condition progresses: bleeding easily, bruising easily, itchy skin, jaundice, abdominal fluid accumulation, loss of appetite, nausea, leg swelling, confusion, drowsiness, slurred speech, or spider-like blood vessels.

NASH is most common in patients who are overweight or obese; other risk factors include diabetes, high cholesterol, high triglycerides, poor diet, metabolic syndrome, polycystic ovary syndrome, sleep apnea, and hyperthyroidism.

NAFLD encompasses the entire spectrum of fatty liver disease in individuals without significant alcohol consumption, ranging from fatty liver to steatohepatitis to cirrhosis. Non-alcoholic fatty liver is the presence of >5% hepatic steatosis without evidence of hepatocellular injury in the form of ballooning of the hepatocytes or evidence of fibrosis. The risk of progression to cirrhosis and liver failure is considered minimal. NASH is the presence of >5% hepatic steatosis with inflammation and hepatocyte injury (ballooning) with or without fibrosis. This can progress to cirrhosis, liver failure, and rarely liver cancer. NASH cirrhosis is presence of cirrhosis with current or previous histological evidence of steatosis or steatohepatitis.

NAS is an unweighted composite of steatosis, lobular inflammation, and ballooning scores. NAS is a useful tool to measure changes in liver histology in patients with NAFLD in clinical trials. Fibrosis is scored separately and can be classified as F1 through F4; specifically, stage 1 is zone 3 (perivenular), perisinusoidal, or periportal fibrosis; stage 2 is both zone 3 and periportal fibrosis; stage 3 is bridging fibrosis with nodularity; and stage 4 is cirrhosis.

TABLE 3

The histological scoring system for nonalcoholic fatty liver disease: components of NAFLD activity score (NAS) and fibrosis staging.
NAS Components (see scoring interpretation)

| Item | Score | Extent | Definition and Comment |
|---|---|---|---|
| Steatosis | 0 | <5% | Refers to amount of surface area involved by steatosis as evaluated on low to medium power examination. |
|  | 1 | 5-33% |  |
|  | 2 | >33-66% |  |
|  | 3 | >66% |  |
| Lobular Inflammation | 0 | No foci | Acidophil bodies are not included in this assessment, nor is portal inflammation |
|  | 1 | <2 foci/200x |  |
|  | 2 | 2-4 foci/200x |  |
|  | 3 | >4 foci/200x |  |
| Hepatocyte Ballooning | 0 | None |  |
|  | 1 | Few ballooned cells | "Few" means rare but definite ballooned hepatocytes as well as cases that are diagnostically borderline |
|  | 2 | Many cells/prominent ballooning | Most cases with prominent ballooning also had Mallory"s hyalin, but Mallory"s hyaline is not scored separately for the NAS |

TABLE 3-continued

| | | Fibrosis Stage (Evaluated separately from NAS) | |
|---|---|---|---|
| Item | Score | Extent | Definition and Comment |
| Fibrosis | 0 | None | |
| | 1 | Perisinusoidal or periportal | |
| | 1A | Mild, zone 3, perisinusoidal | "delicate" fibrosis |
| | 1B | Moderate, zone 3, perisinusoidal | "dense" fibrosis |
| | 1C | Portal/periportal | This category is included to accommodate cases with portal and/or peri portal fibrosis without accompanying pericellular/perisinusoidal fibrosis |
| | 2 | Perisinusoidal and portal/periportal | |
| | 3 | Bridging fibrosis | |
| | 4 | Cirrhosis | |

Scoring interpretation: Total NAS score represents the sum of scores for steatosis, lobular inflammation, and ballooning, and ranges from 0-8. Diagnosis of NASH (or, alternatively, fatty liver not diagnostic of NASH) should be made first, then NAS is used to grade activity. In the reference study, NAS scores of 0-2 occurred in cases largely considered not diagnostic of NASH, scores of 3-4 were evenly divided among those considered not diagnostic, borderline, or positive for NASH. Scores of 5-8 occurred in cases that were largely considered diagnostic of NASH In some embodiments, the disease may be NAFLD. Nonalcoholic fatty liver disease (NAFLD) is an umbrella term for a range of liver conditions affecting people who drink little to no alcohol. As the name implies, the main characteristic of NAFLD is too much fat stored in liver cells. There are often no outward signs or symptoms associated with NAFLD, although the most common symptoms are fatigue or mild pain in the upper right abdomen.

In some embodiments, the disease may be fulminant hepatitis. Fulminant hepatitis, or fulminant hepatic failure, is defined as a clinical syndrome of severe liver function impairment, which causes hepatic coma and the decrease in synthesizing capacity of liver. Then they rapidly develop severe, often life-threatening liver failure. This can happen within hours, days, or sometimes weeks. Symptoms of severe liver failure include confusion, extreme irritability, altered consciousness, blood clotting defects, and buildup of fluid in the abdominal cavity and multiorgan system failure.

In some embodiments, the disease may be a hepatocellular carcinoma (HCC). HCC is the most common type of primary liver cancer. HCC occurs most often in people with chronic liver diseases leading to advanced fibrosis or cirrhosis. The most common liver diseases associated with HCC are viral hepatitis B or C, alcohol related liver disease and NASH.

In some embodiments, the disease may be a primary biliary cholangitis (PBC). Primary biliary cholangitis, previously called primary biliary cirrhosis, is a chronic disease in which the bile ducts in the liver are slowly destroyed. Bile is a fluid made in the liver. Chronic inflammation in the liver can lead to bile duct damage, irreversible scarring of liver tissue (cirrhosis) and eventually, liver failure. PBC is considered an autoimmune disease, which means the body"s immune system is mistakenly attacking healthy cells and tissue. Researchers think a combination of genetic and environmental factors triggers the disease. It usually develops slowly. At this time, there"s no cure for primary biliary cholangitis, but medication can slow liver damage, especially if treatment begins early.

In some embodiments, the liver disease may be a toxin mediated liver injury (e.g., from drug/medication, alcohol, environmental). Toxin mediated liver injury is an inflammation of liver in reaction to certain substances, such as alcohol, chemicals, drugs/medication, environmental factors or nutritional supplements. The liver normally removes and breaks down most drugs and chemicals from the bloodstream, which creates byproducts that can damage the liver. Although the liver has a great capacity for regeneration, constant exposure to toxic substances can cause serious, sometimes irreversible harm.

In some embodiments, the liver disease may be a viral hepatitis (HAV, HBV, HCV, HDV, HEV, other virus infecting the liver). Viral hepatitis is a liver inflammation due to a viral infection. It may present in acute form as a recent infection with relatively rapid onset, or in chronic form. The most common causes of viral hepatitis are the five unrelated hepatotropic viruses hepatitis A, B, C, D, and E. Other viruses can also cause liver inflammation, including cytomegalovirus, Epstein-Barr virus, and yellow fever. There also have been scores of recorded cases of viral hepatitis caused by herpes simplex virus. Viral hepatitis is either transmitted through contaminated food or water (A, E) or via blood and body fluids (B, C). Hepatitis A and hepatitis B can be prevented by vaccination. Effective treatments for hepatitis C are available but costly.

In some embodiments, the liver disease may be an autoimmune hepatitis. Autoimmune hepatitis is liver inflammation that occurs when the immune system attacks liver cells. The exact cause of autoimmune hepatitis is unclear, but genetic and environmental factors appear to interact over time in triggering the disease. Untreated autoimmune hepatitis can lead to scarring of the liver (cirrhosis) and eventually to liver failure. When diagnosed and treated early, autoimmune hepatitis often can be controlled with drugs that suppress the immune system. A liver transplant may be an option when autoimmune hepatitis doesn"t respond to drug treatments or in cases of advanced liver disease. There are two main forms of autoimmune hepatitis: (1) Type 1 autoimmune hepatitis. Type I autoimmune hepatitis is the most common type and can occur at any age. About half the people with type 1 autoimmune hepatitis have other autoimmune disorders, such as celiac disease, rheumatoid arthritis or ulcerative colitis; (2) Type 2 autoimmune hepatitis. Although adults can develop type 2 autoimmune hepatitis, it"s most common in children and young people. Other autoimmune diseases may accompany type 2 autoimmune hepatitis.

In some embodiments, the liver disease may be a primary sclerosing cholangitis. Primary sclerosing cholangitis is a disease of the bile ducts. In primary sclerosing cholangitis, inflammation causes scars within the bile ducts. These scars make the ducts hard and narrow and gradually cause serious liver damage. A majority of people with primary sclerosing cholangitis also have inflammatory bowel disease, such as ulcerative colitis or Crohn"s disease. In most cases of primary sclerosing cholangitis, the disease progresses slowly. It can eventually lead to liver failure, repeated infections, and tumors of the bile duct or liver.

In some embodiments, the liver disease may be a cirrhosis of the liver. Cirrhosis is a late stage of scarring (fibrosis) of the liver caused by many forms of liver diseases and conditions, such as hepatitis and chronic alcoholism. In the process of liver self-repair, scar tissue forms. As cirrhosis progresses, more and more scar tissue forms, making it difficult for the liver to function (decompensated cirrhosis).

In some embodiments, the liver disease may be a cholangiocarcinoma. Cholangiocarcinoma (bile duct cancer) is a type of cancer that forms in the bile ducts. Risk factors for cholangiocarcinoma include primary sclerosing cholangitis (an inflammatory disease of the bile ducts), ulcerative colitis, cirrhosis, hepatitis C, hepatitis B, infection with certain liver flukes, and some congenital liver malformations. Cholangiocarcinoma can be categorized based on the location of the cancer occurs in the bile ducts: intrahepatic cholangiocarcinoma, hilar cholangiocarcinoma, distal cholangiocarcinoma. Cholangiocarcinoma is often diagnosed when it is advanced, making successful treatment difficult to achieve.

In some embodiments, the liver disease may be an inherited liver disease (e.g., Wilson disease, hemochromatosis, or alpha-1 antitrypsin, etc.) Inherited liver diseases are genetic disorders that can cause severe liver disease and other health problems. Wilson"s disease is a rare inherited disorder that causes copper to accumulate in your liver, brain and other vital organs. Hemochromatosis is a disease in which deposits of iron collect in the liver and other organs. The primary form of hemochromatosis is one of the most common inherited diseases in the U.S. The alpha-1 antitrypsin protein is synthesized mainly in the liver by hepatocytes, secreted into the blood stream, and acts as an inhibitor of neutrophil elastase released primarily in the lung during inflammation. Alpha-1 antitrypsin deficiency is caused when alpha-1 antitrypsin protein is either lacking or exists in lower than normal levels in the blood.

In some embodiments, the disease may be an organ transplant rejection. Transplant rejection occurs when transplanted tissue is rejected by the recipient"s immune system, which destroys the transplanted tissue. Transplant rejection can be lessened by determining the molecular similitude between donor and recipient and by use of immunosuppressant drugs after transplant.

In some embodiments, the disease may be an infectious disease, Infectious diseases are disorders caused by organisms—such as bacteria, viruses, fungi or parasites. Bacteria are one-cell organisms responsible for illnesses such as streptococcal upper respiratory infection, urinary tract infections and tuberculosis. Viruses cause a multitude of diseases ranging from the common cold to AIDS. Many skin diseases, such as ringworm and athlete"s foot, are caused by fungi. Other types of fungi can infect the lungs or nervous system. Malaria is caused by a tiny parasite that is transmitted by a mosquito bite. Other parasites may be transmitted to humans from animal feces. In some embodiments, the infectious disease is COVID-19.

In some embodiments, the disease may be an allergic disease. Allergic diseases are caused by allergen-induced unfavorable immune responses initiating various symptoms in different organs, which often cannot be completely controlled by modern medicine. The immunologic basis of allergic diseases is observed in two phases: sensitization and development of memory T and B cell responses, and IgE production and effector functions, which are related to eosinophils, innate lymphoid cells, dendritic cell subsets, epithelial cells and tissue inflammation/injury, epithelial barrier, tissue remodeling and chronicity in asthma, atopic dermatitis (AD) and allergic rhinitis (AR). Different disease phenotypes and endotypes may become apparent with different dominant molecular mechanisms, related biomarkers and responses to biologic therapy. Multiple mechanistic factors are complexly involved in the pathogenesis of allergic inflammations In some embodiments, the disease may be an autoimmune disease/autoimmunity. An autoimmune disease is a condition in which the immune system mistakenly attacks one"s own body. Normally, the immune system can tell the difference between foreign cells and one"s own cells. In an autoimmune disease, the immune system mistakes part of the body, like the joints or skin, as foreign. It releases proteins called autoantibodies that attack healthy cells. Some autoimmune diseases target only one organ. Type 1 diabetes damages the pancreas. Other diseases, like systemic lupus erythematosus (SLE), affect many different organ systems. In some embodiments, the autoimmune disease may be Rheumatoid arthritis, Crohns disease, Multiple sclerosis (MS) or psoriatic arthritis (PsA).

In some embodiments, the disease may be a chronic inflammation. Chronic inflammation is also referred to as slow, long-term inflammation lasting for prolonged periods of several months to years. Generally, the extent and effects of chronic inflammation vary with the cause of the injury and the ability of the body to repair and overcome the damage. Most of the features of acute inflammation continue as the inflammation becomes chronic, including the expansion of blood vessels (vasodilation), increase in blood flow, capillary permeability and migration of neutrophils into the infected tissue through the capillary wall (diapedesis). However, the composition of the white blood cells changes soon and the macrophages and lymphocytes begin to replace short-lived neutrophils. Thus the hallmarks of chronic inflammation are the infiltration of the primary inflammatory cells such as macrophages, lymphocytes, and plasma cells in the tissue site, producing inflammatory cytokines, growth factors, enzymes and hence contributing to the progression of tissue damage and secondary repair including fibrosis and granuloma formation, etc.

In some embodiments, the disease may be a fibrotic disease. Fibrotic disease is defined by the overgrowth, hardening, and/or scarring of various tissues and is attributed to excess deposition of extracellular matrix components including collagen. Fibrosis is the end result of chronic inflammatory reactions induced by a variety of stimuli including persistent infections, autoimmune reactions, allergic responses, chemical insults, radiation, and tissue injury. The fibrotic disorders include but are not limited to systemic fibrotic diseases such as systemic sclerosis (SSc), sclerodermatous graft vs. host disease, idiopathic pulmonary fibrosis (IPF), nephrogenic systemic fibrosis, and organ-specific disorders including radiation-induced fibrosis and cardiac, pulmonary, liver, and kidney fibrosis.

In some embodiments, the disease may be a metabolic disease. A metabolic disorder/disease occurs when abnormal chemical reactions in the body disrupt metabolism. When this happens, one might have too much of some substances or too little of other ones that an individual needs to stay healthy. There are different groups of disorders. Some affect the breakdown of amino acids, carbohydrates, or lipids. Another group, mitochondrial diseases, affects the parts of the cells that produce the energy. one can develop a metabolic disorder when some organs, such as the liver or pancreas, become diseased or do not function normally. Diabetes is an example.

In some embodiments, the disease may be Alzheimer"s. Alzheimer"s is a type of dementia that affects memory, thinking and behavior. Symptoms eventually grow severe enough to interfere with daily tasks. Alzheimer"s changes typically begin in the part of the brain that affects learning. As Alzheimer"s advances through the brain, it leads to increasingly severe symptoms, including disorientation, mood and behavior changes; deepening confusion about events, time and place; unfounded suspicions about family, friends and professional caregivers; more serious memory loss and behavior changes; and difficulty speaking, swallowing and walking.

EXAMPLES

These examples are provided for illustrative purposes only and not to limit the scope of the claims provided herein. It will be appreciated that variations in proportions and alternatives in elements of the components shown will be apparent to those skilled in the art and are within the scope of the embodiments presented herein.

Example 1. Diagnosing NASH Using Probes in Mice

In this experiment, the probes of the present application were shown to accurately detect the activity levels of proteases associated with non-alcoholic steatohepatitis (NASH) in a fluid sample to diagnose NASH in a subject.

Protease activity levels associated with NASH were assessed in vivo in two mice populations, one healthy and one with NASH. The probes used in vivo are shown in FIG. 10.

Figure 11:
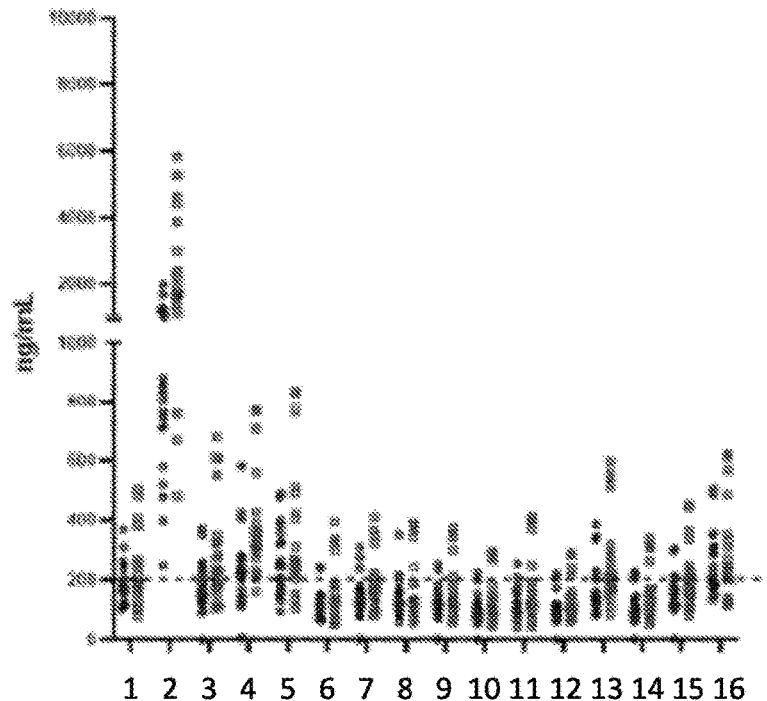
FIG. 11 shows the protease activities measured using the in vivo probes.

Mass-barcoded reporters urinary concentration levels obtained from proteolytic cleavage of these probes by proteases in healthy mice, which were fed on a standard Chow Diet (CD), and NASH mice, which were fed a choline-deficient, L-amino acid-defined, high-fat diet (CDAHFD) are shown in FIG. 11. NASH-related probes, cleaved by increased NASH-related protease activity, associated with higher mass-barcoded reporters accumulation in urine from NASH mice compared to healthy mice.

Figure 12:
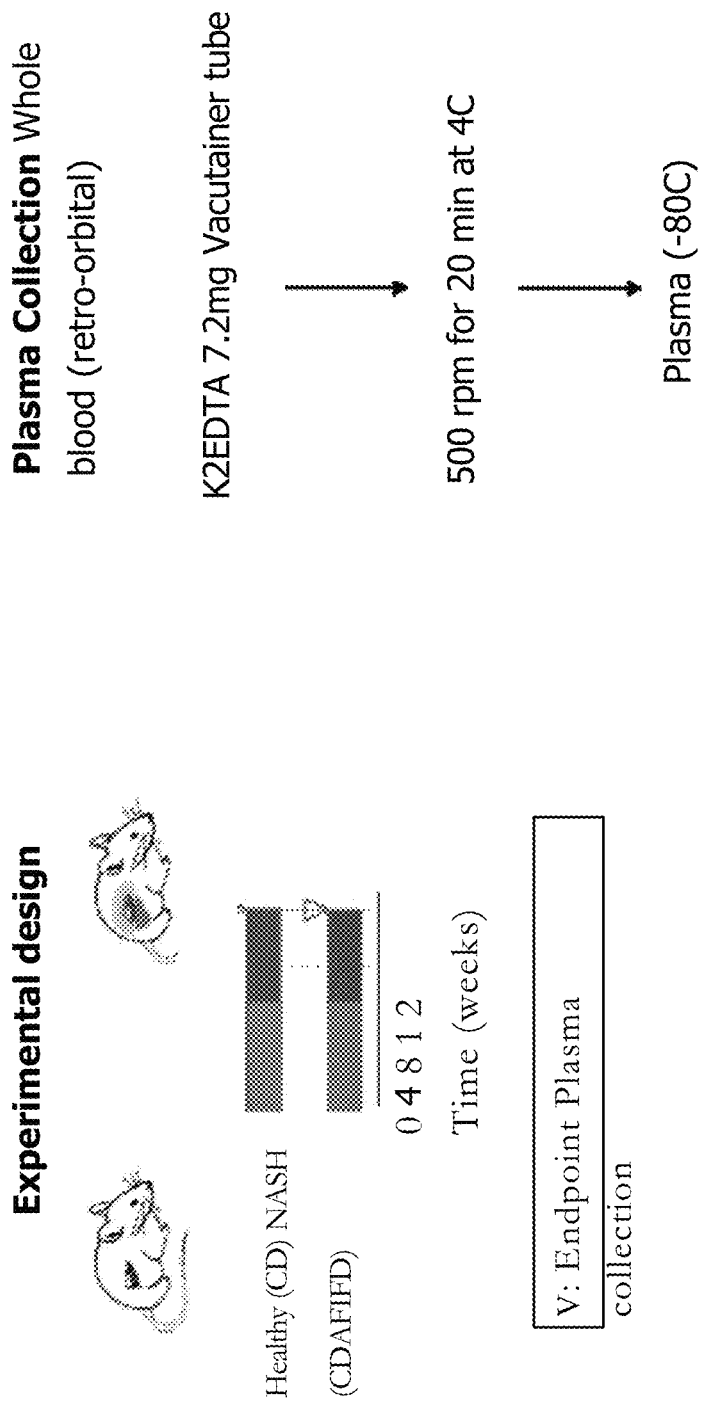
FIG. 12 outlines an experiment of present application.

As shown in FIG. 12, blood samples were collected in K2EDTA tubes from mice that were either healthy (CD) or had NASH (CDAHFD) after 12 weeks on their respective diet. All animals were used in accordance with animal care guidelines. Plasma was obtained from these blood samples by centrifugation at 3,500 RPM for 20 min at 4° C. The plasma was stored at −80° C. until it was needed for experimental purposes.

Figure 13:
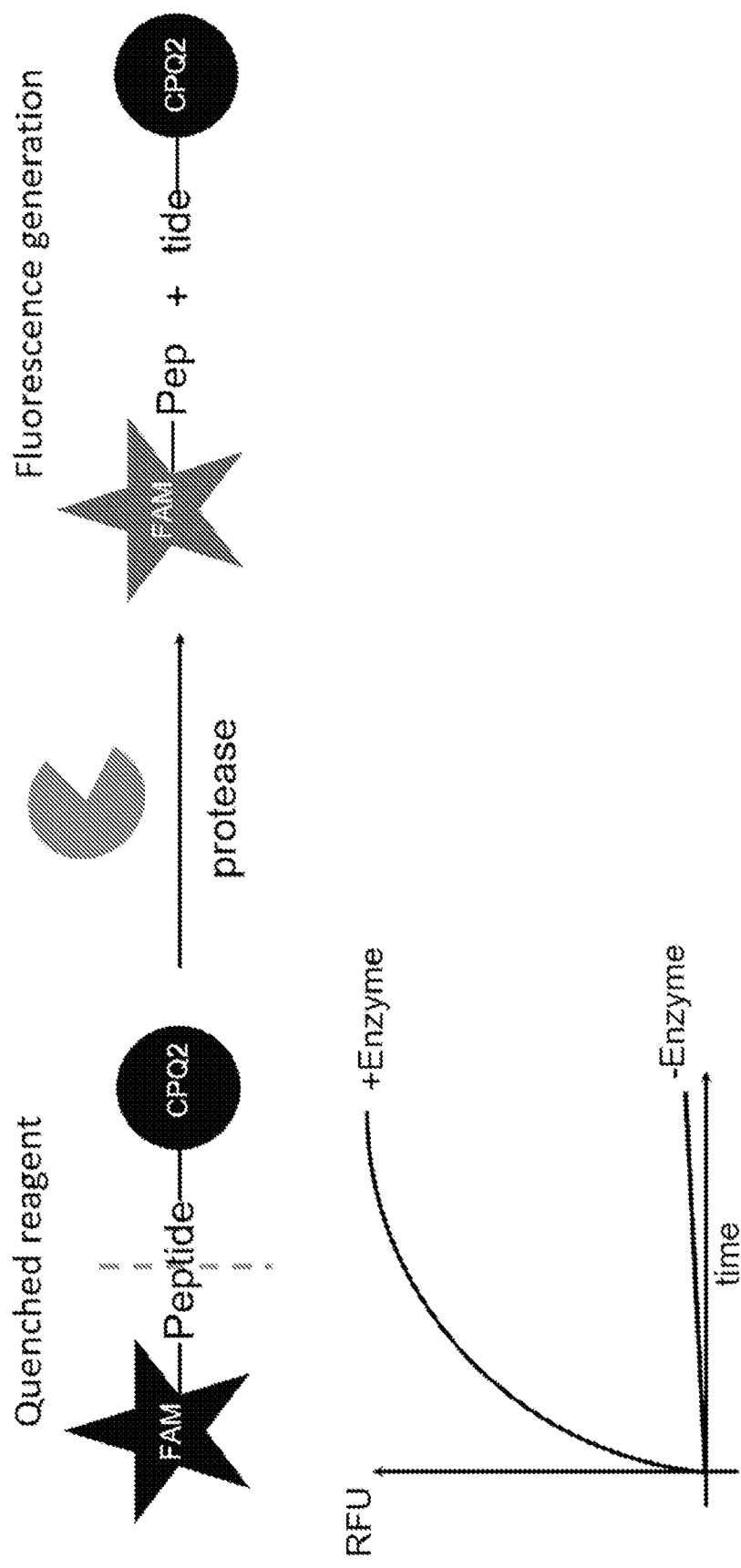
FIG. 13 outlines an experiment of present application.

As shown in FIG. 13, thawed plasma samples were pooled and contacted with probes with fluorescent quenchers and protease-cleavable fluorescent reporters at various peptide and serum concentrations. Samples were mixed with protease substrates and quenchers/reporters in 96-well plates. The 96-well plates were read on a Biotech Synergy H1, using 465,535 excitation/emission settings.

Figure 5:
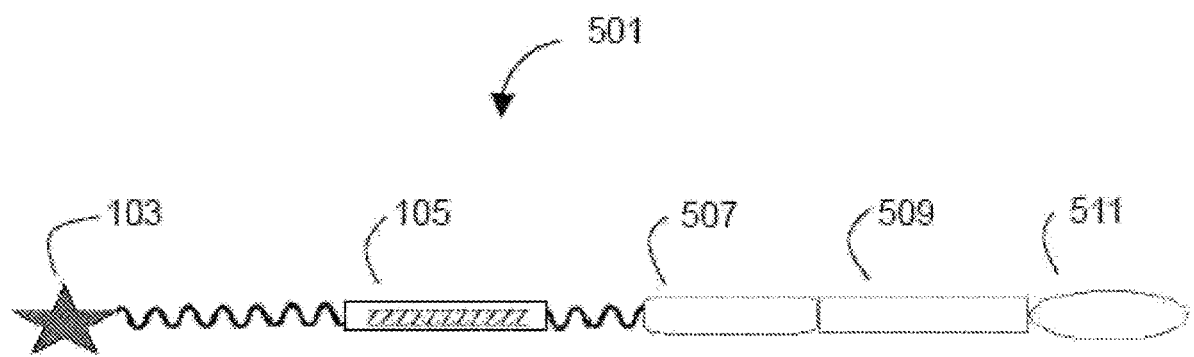
FIG. 5 shows a schematic of a probe 501 that includes a spacer 507, a solubility tag 509, a quencher and a covalent or non-covalent attachment site 511. The respective positions of these components can, in principle, be interconverted.
Figure 6A:
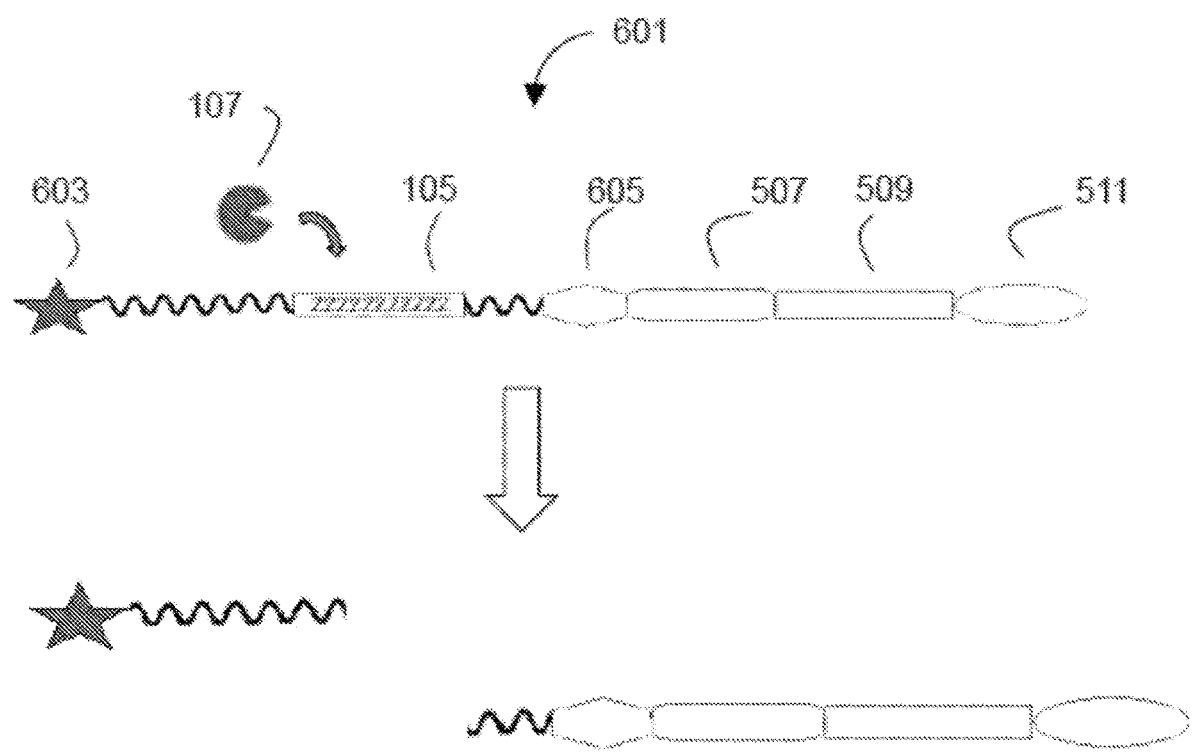
FIG. 6A-C shows cleavage of the probe.
Figure 6B:
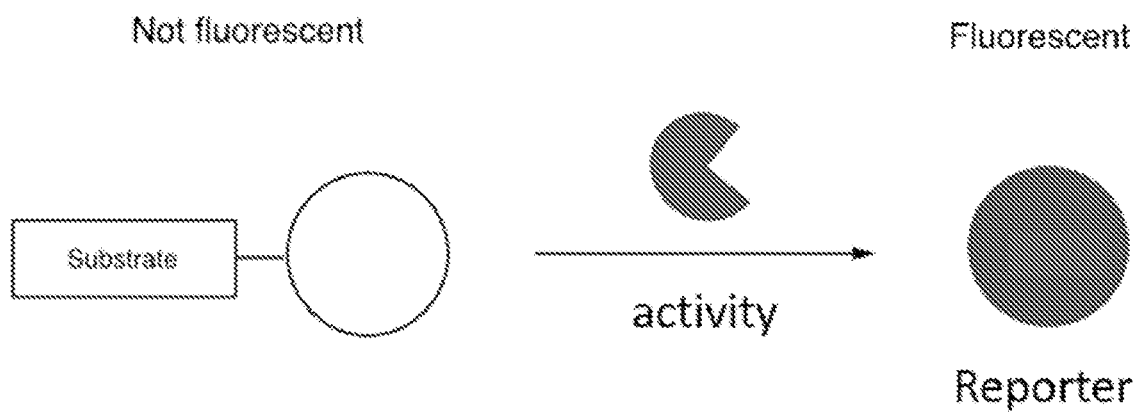
Figure 6C:
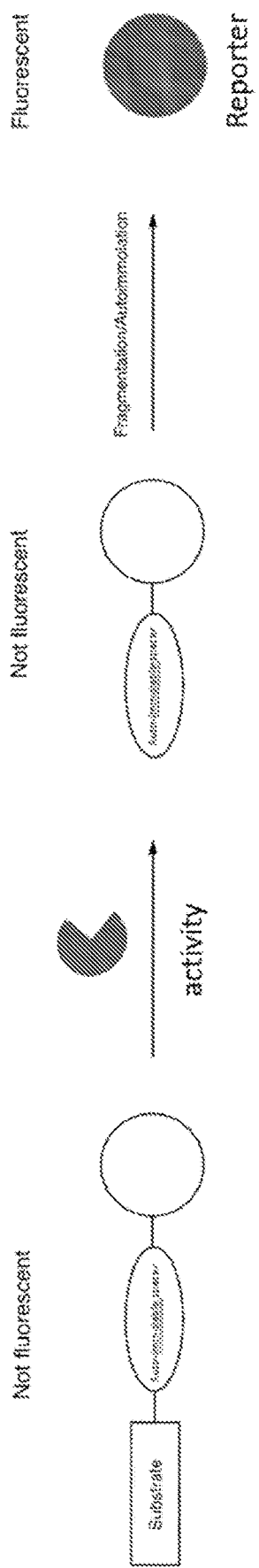
Figure 7A:
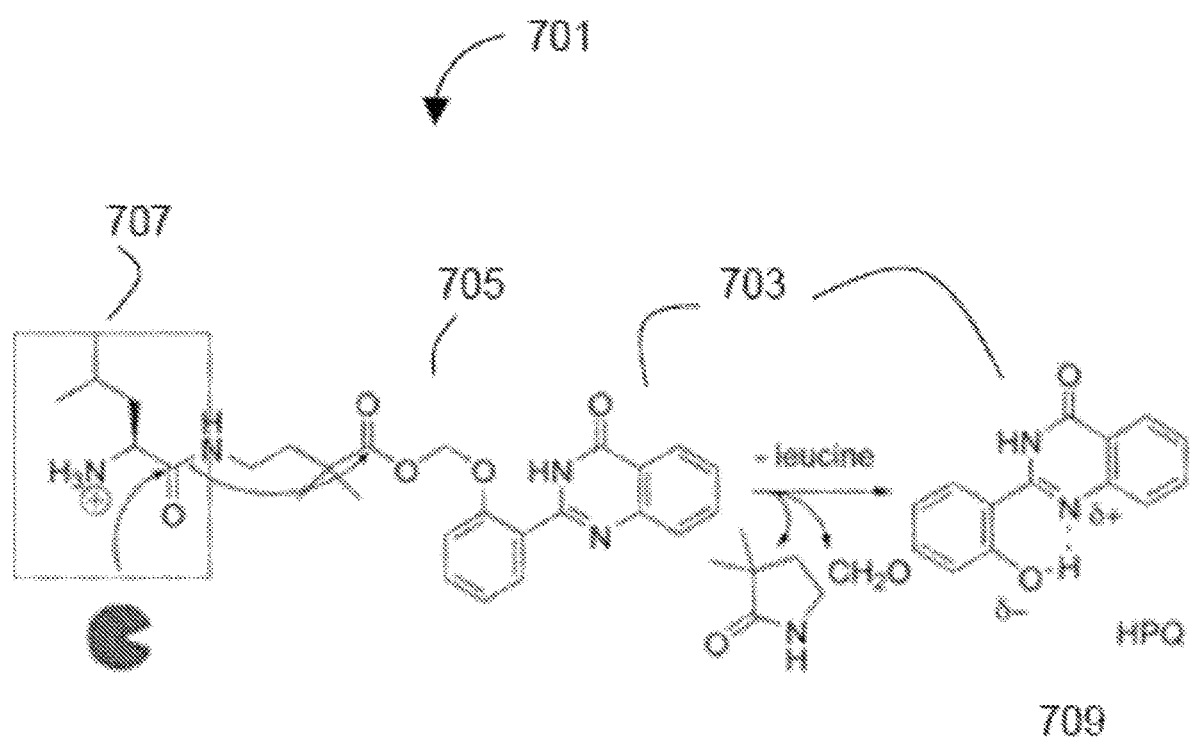
FIG. 7A-C shows reaction processes for HPQ fluorophore.
Figure 7B:
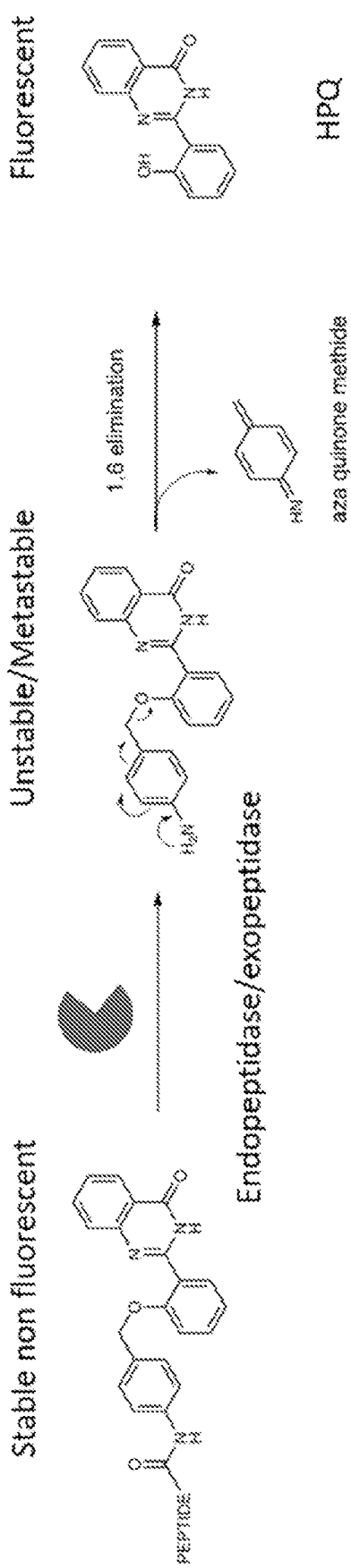
Figure 7C:
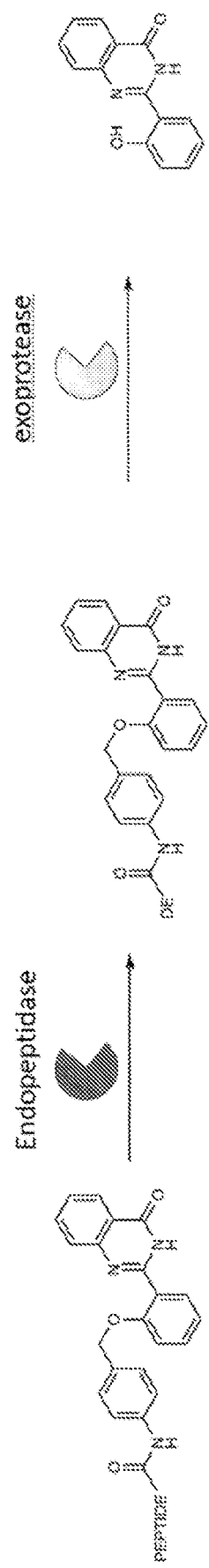
Figure 14:
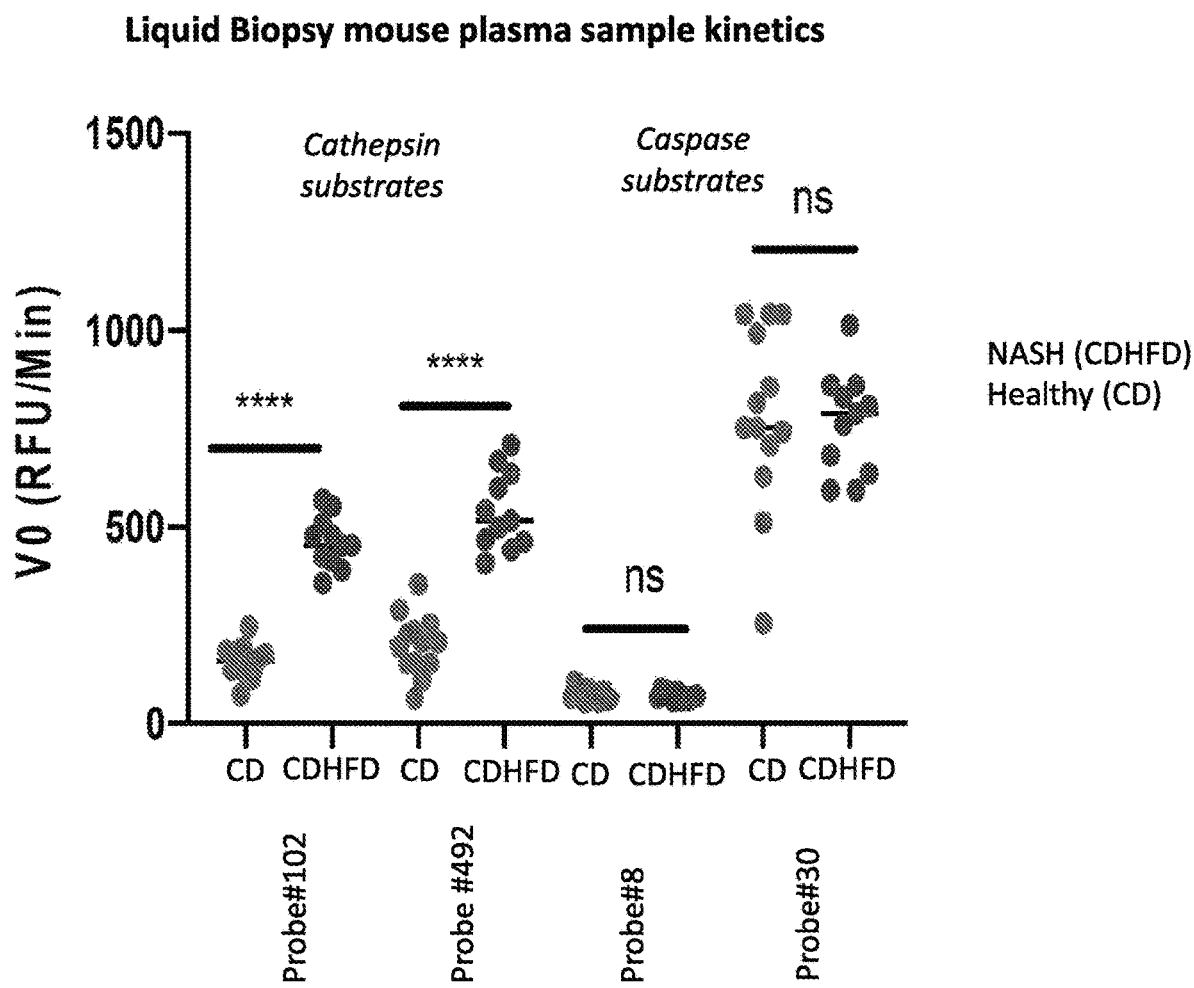
FIG. 14 shows that the probes can accurately detect and differentiate between samples from patients diagnosed with NASH via liver biopsy and healthy patient samples when encountering NASH-related proteases in mice K2EDTA plasma.
Figures 15A, 15B:
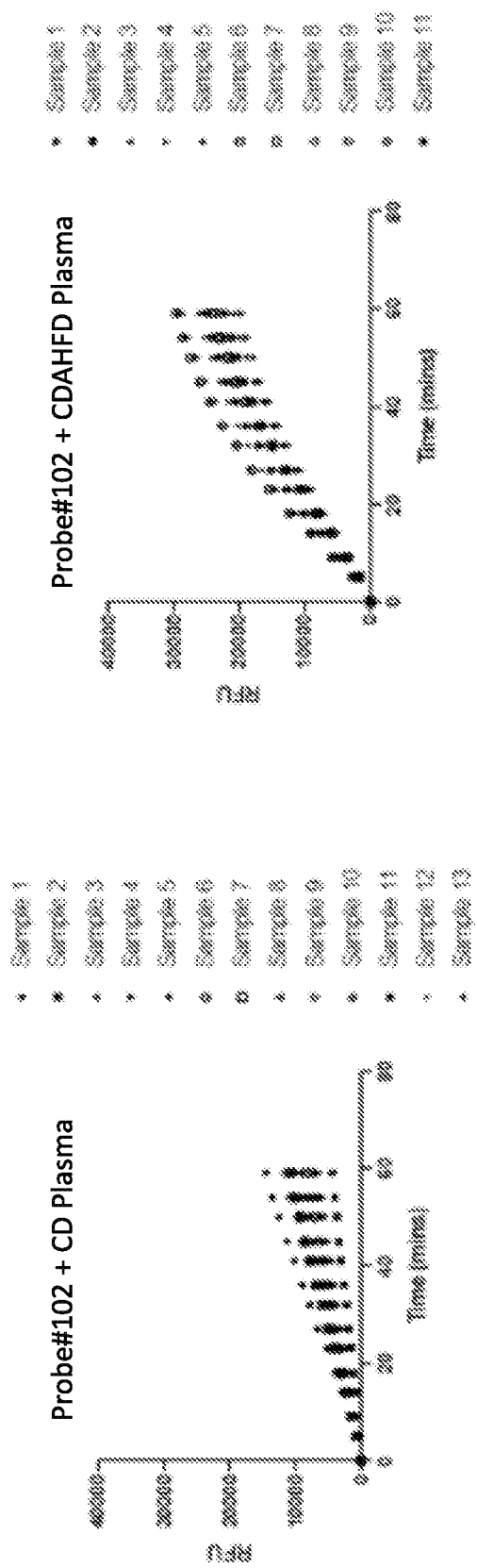
FIG. 15A-B provide experimental results showing that a specific peptide linker of the present application can differentiate between NASH-related protease activity in healthy mice and NASH+ samples from K2EDTA mice plasma.

As shown in FIG. 14, the probes of the present application were able to measure the activity of NASH-related proteases as expressed in Relative Fluorescent Unit (RFU) per minute in the two mouse populations. Probes measuring cathepsin activity were 3-fold higher in protease cleavage kinetics in mice with NASH compared to healthy mice. In contrast, probes sensing caspase activity showed no change in detectable activity between healthy and NASH mice. FIG. 15A and FIG. 15B show the subset of results for one probe, Probe #102, in detecting NASH-related protease activity; here, the use of the fluorescent reporter and quencher, like those discussed in FIG. 5, were shown to accurately measure the activity levels of NASH-related proteases in the plasma of healthy mice (FIG. 15A) and NASH mice (FIG. 15B).

Thus, probes of the present application can accurately detect the activity levels of proteases associated with a biological condition or disease-state in a subject, ex vivo, using a body fluid sample.

Example 2: Detection of NASH Protease Activity in Plasma in Mice

As shown in FIG. 14, the probes of the present application are able to accurately detect protease activity of NASH related proteases in the plasma samples taken from two mice populations, as explained in Example 1 and FIG. 13, in a multiplex format. A single plasma sample was contacted with the probes for each predetermined protease to provide a multiplex assessment of protease activity in the sample.

Figure 16:
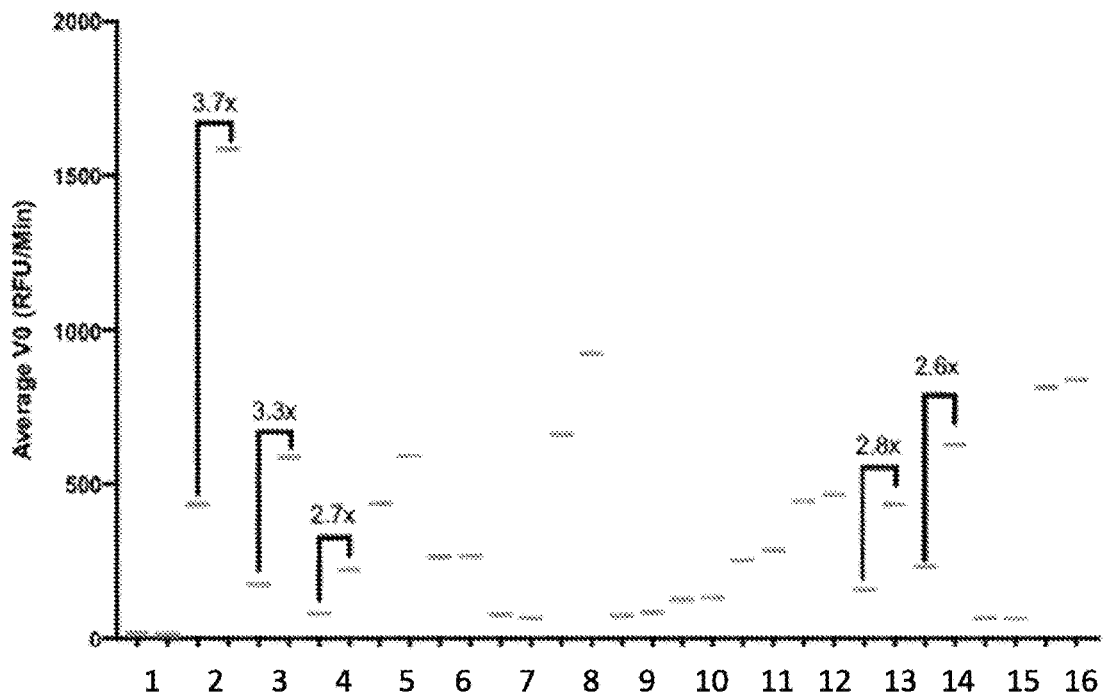
FIG. 16 provides experimental results comparing the ex vivo probes and their ability to distinguish between NASH (CDHFD) samples (the right data point) and healthy (CD) samples (the left data point).

In FIG. 16, for each set of probes, the protease activity in healthy mice is shown on the left, while the protease activity in NASH mice is shown on the right. As shown, the probes of the present application were able to measure increases in NASH-related protease activity.

Figure 17:
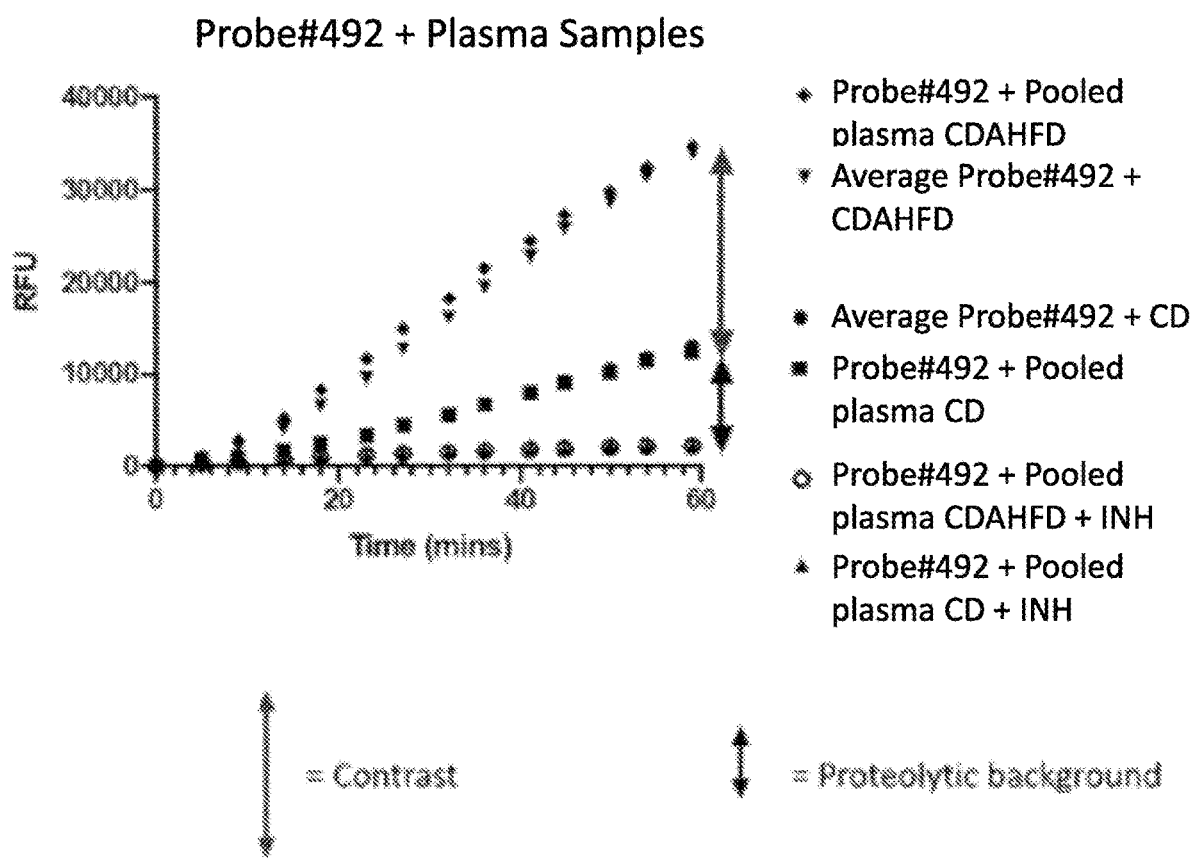
FIG. 17 provides raw experimental results showing that the measured rate of fluorescence increase for Probe #492 can be ascribed to protease activity and to NASH disease in K2EDTA mice plasma The average rate of fluorescence increase over n=10 samples matches pooled plasma (n=10) increase of fluorescence in both disease and healthy conditions.
Figure 18:
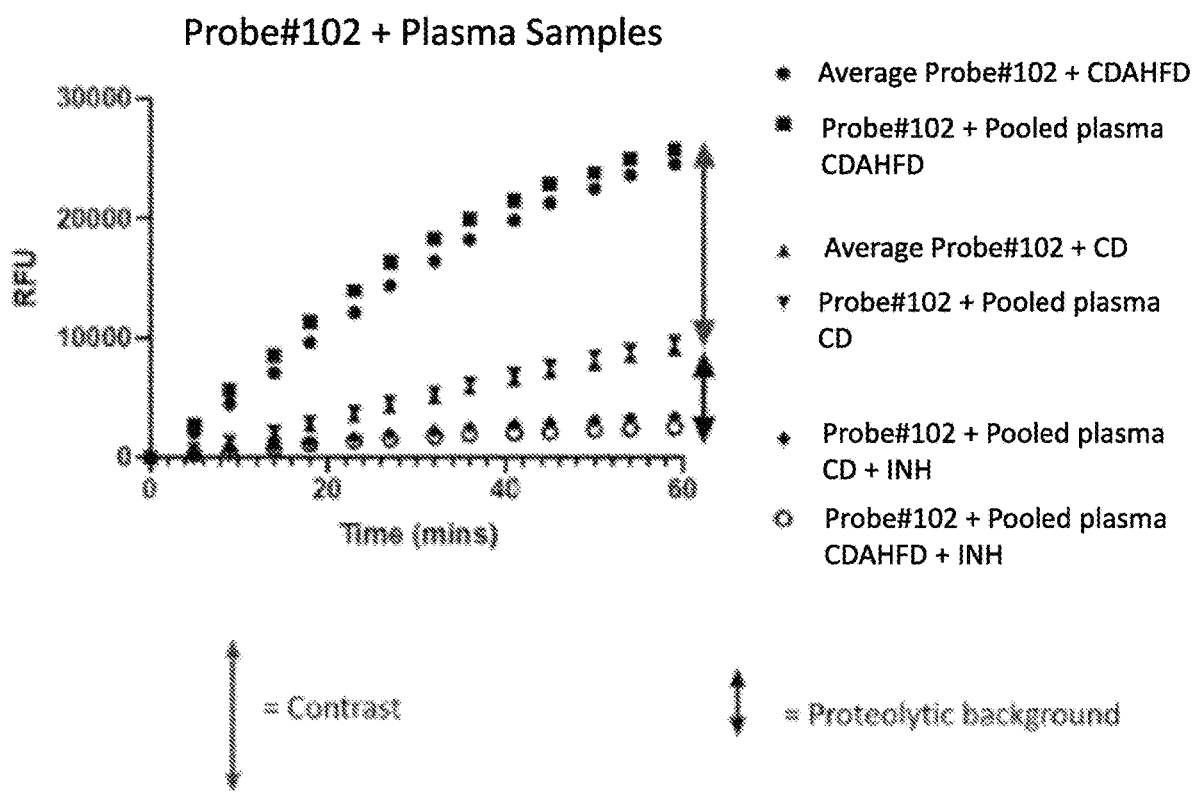
FIG. 18 provides experimental results showing that the measure rate of fluorescence increase for Probe #102 can be ascribed to protease activity and to NASH disease in K2EDTA mice plasma. The average rate of fluorescence increase over n=10 samples matches pooled plasma (n=10) increase of fluorescence in both disease and healthy conditions.

As shown in FIG. 17 and FIG. 18, protease activity measured as RFU/min was similar in pooled plasma samples within the same group of animals than the average of protease activity from each animal from that group. Furthermore, adding a broad protease inhibitor cocktail (INH) completely abrogated protease activity in both healthy and NASH animal groups, providing evidence that the fluorescent signal measured over time depends on proteolytic activities.

Figure 19B:
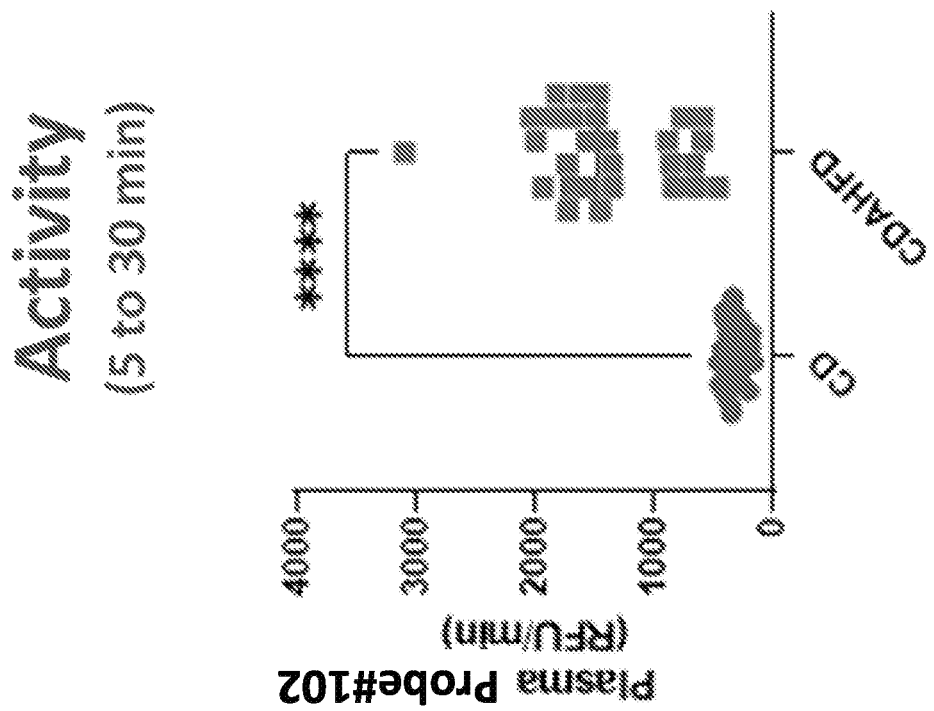
FIG. 19A-B provides experimental results showing that activity, not abundance, is responsible for determination of disease-based protease activity differences in K2EDTA mouse plasma samples.
Figure 19A:
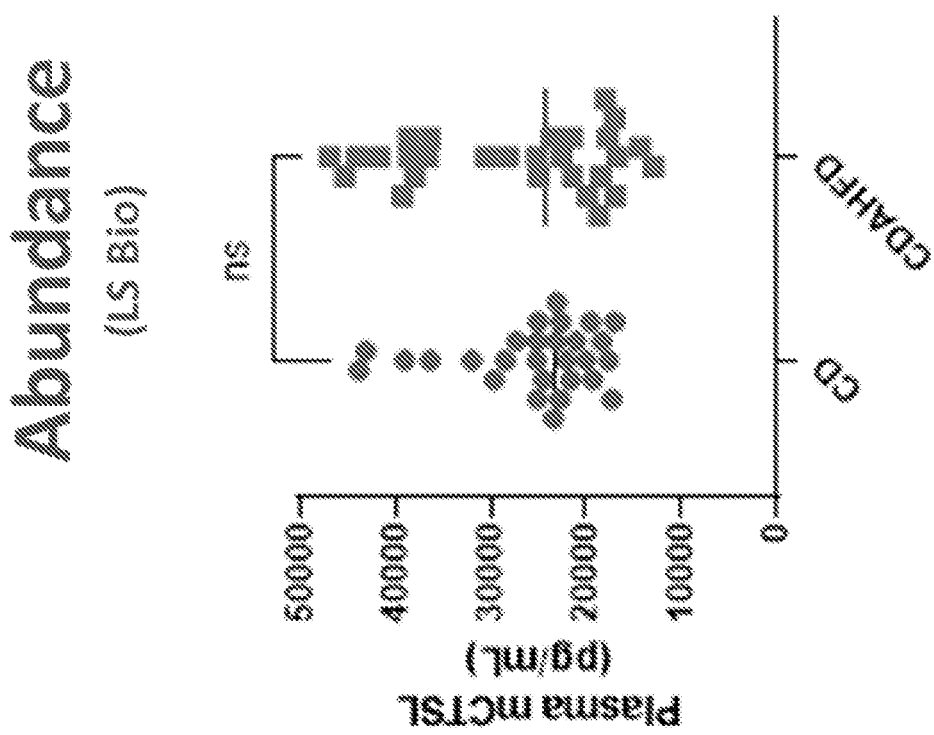

FIG. 19A and FIG. 19B show that, when studying samples of mouse plasma, activity, not abundance, is more important in differentiating between healthy samples and NASH samples. Although abundance of NASH-related proteases (here cathepsin L, or CTSL) may be comparable between healthy CD mice and NASH CDAHFD mice (FIG. 19A), the activity levels of these proteases are not (FIG. 19B). In this experiment, protease abundance was measured using an ELISA kit from LS Bio while activity was measured using the Probe #102 (a CTSL sensing probe) fluorescence assay described in Example 1.

Thus, probes of the present application can accurately detect the activity levels of proteases associated with a biological condition or disease-state in a subject, ex vivo, using a body fluid sample such as plasma in a multiplex format.

Example 3: Liquid Biopsy Determines Progression Versus Regression of NASH

In this experiment, the probes of the present application were able to differentiate among healthy mice, NASH mice, and NASH mice that were undergoing disease regression.

Figure 20:
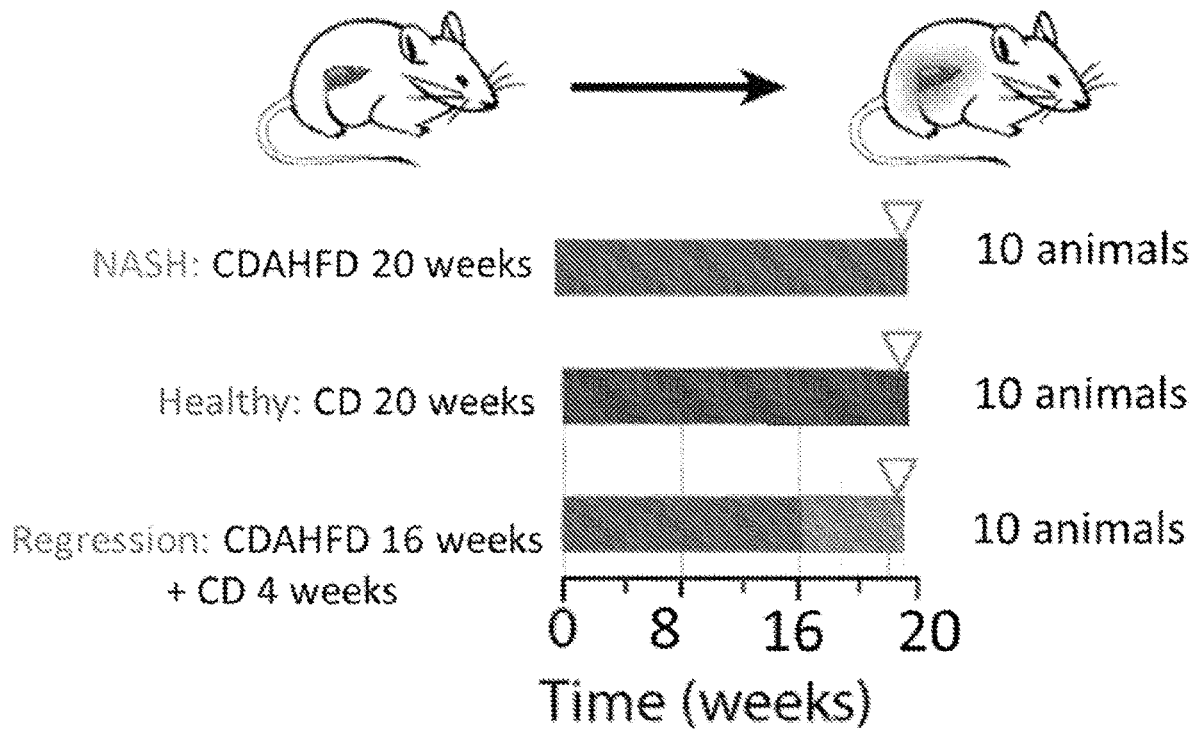
FIG. 20 outlines an experimental design of the present application.
Figures 21A, 21B, 21C:
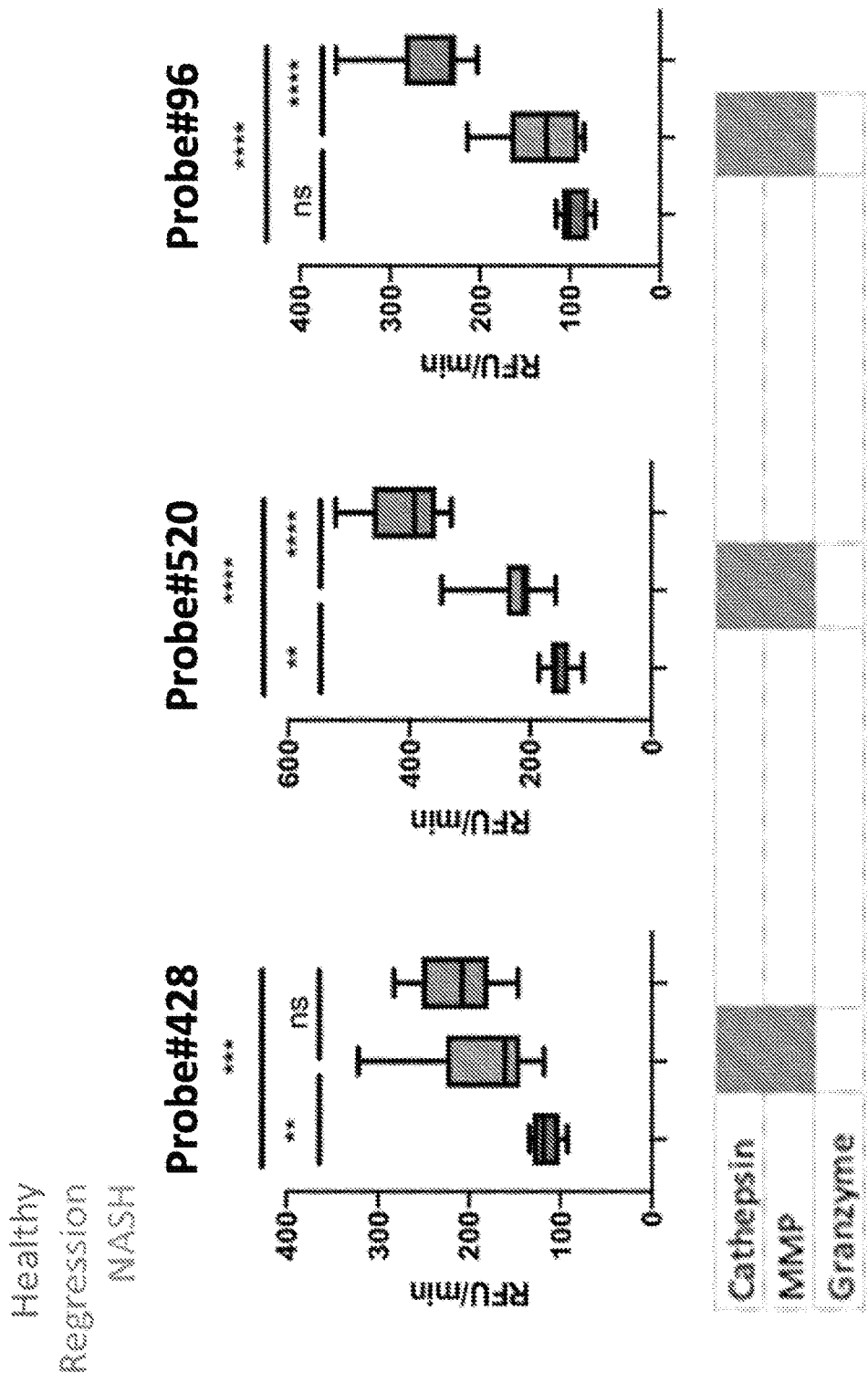
FIG. 21A-F provide experimental results showing that several probes can differentiate among healthy K2EDTA plasma samples (left), regression samples (center), and NASH samples (right).
Figures 21D, 21E, 21F:
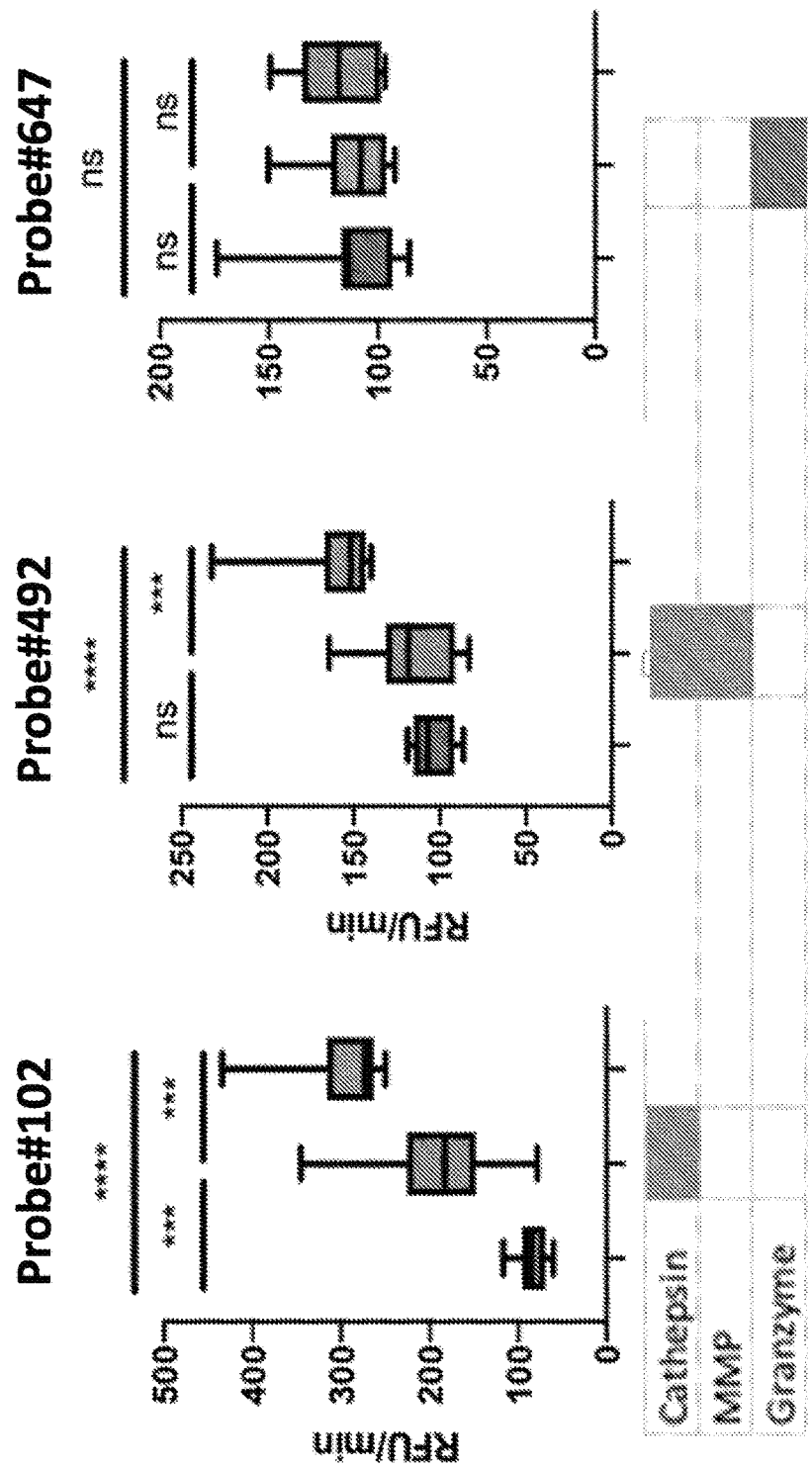

FIG. 20 shows the experimental design including three groups of mice: CDAHFD NASH mice for 20 weeks (NASH progression), healthy CD mice for 20 weeks, and mice fed a CDAHFD for 16 weeks before being switched to a chow diet for 4 weeks (NASH regression). Plasma samples were collected from all animals at 20 weeks.

As seen in FIGS. 21A-F, several probes were used to contact the thawed plasma, as described in Example 1, and this resulted in clear differentiation between the healthy, regression, and NASH samples. The probes showing the most differentiation in NASH were linked to cathepsin and/or MMP protease activities.

This experiment showed that not only can we differentiate between healthy and diseased samples, but it can also differentiate among healthy, disease-progressing, and disease-regressing samples.

Example 4: Liquid Biopsy Applications Towards Fulminant Hepatitis in Mice

In this experiment, another mouse liver-disease model—that for fulminant hepatitis—was studied to determine the wider uses of the present application. This experiment served to develop the ex vivo assay technology for applications in hepatitis models using plasma and existing sensors in the FRET substrate library.

Figure 22:
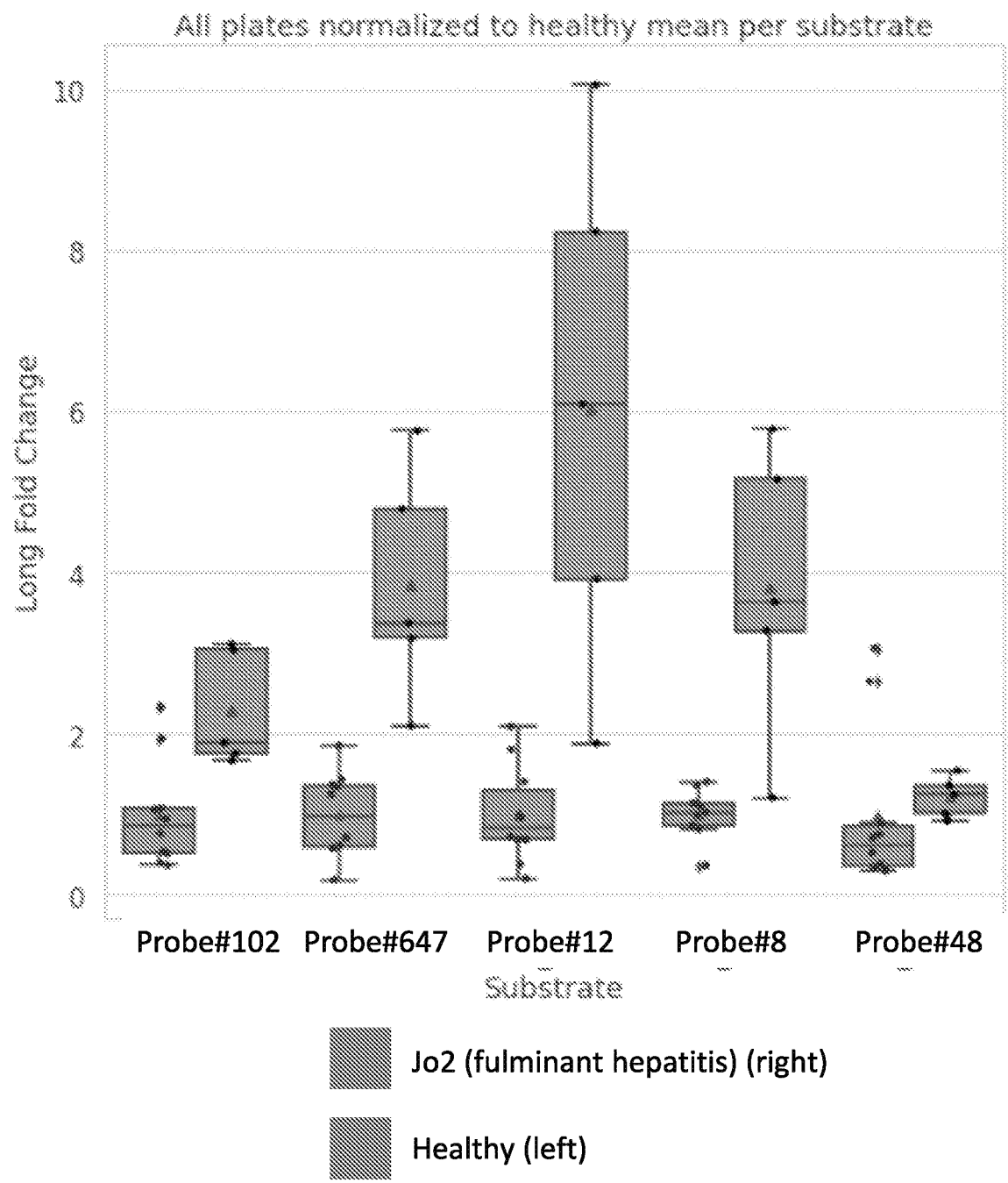
FIG. 22 provides experimental results showing the probes can distinguish between healthy and the JO2 mouse model of fulminant hepatitis samples ex vivo. The Jo2 antibody shows cytolytic activity against cell lines expressing mouse Fas by inducing apoptosis.
Figure 23:
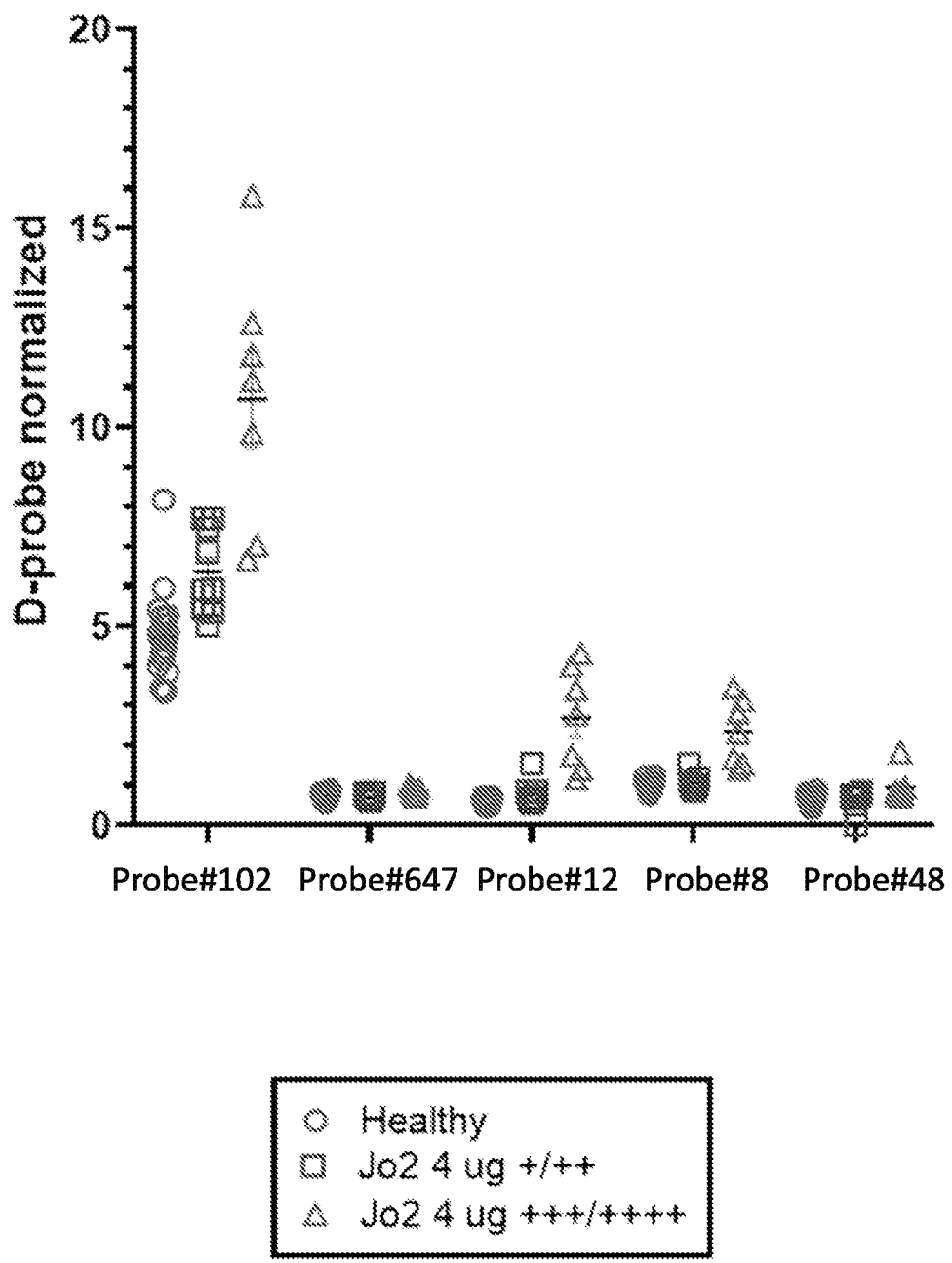
FIG. 23 provides experimental results showing the probes can distinguish between healthy and fulminant hepatitis samples in vivo in a mice model. +/++ group denotes mild hepatitis symptoms and +++/++++ group denotes fulminant hepatitis based on physio-pathological examination of mice. The Jo2 antibody shows cytolytic activity against cell lines expressing mouse Fas by inducing apoptosis.

Fulminant hepatitis is induced after injection intraperitoneal of monoclonal antibody anti-CD95 (Jo2, BD biosciences, 4 ug/animal), and mouse plasma samples were collected 3 hours after Jo2 injection. As shown in FIG. 22, when the probes contacted the mouse plasma samples using the method described previously in Example 1, the probes were able to differentiate between healthy and Jo2 samples ex vivo. FIG. 23 shows the same results in vivo, with the same mice receiving the injectable probe formulation for direct comparison with the ex vivo approach.

The Jo2 hepatitis model demonstrates differential probe cleavage compared to NASH liver model data in mice. Predominantly Caspase centric probes (Probe #647, Probe #8, Probe #12) show contrast that is specific and sensitive to the Jo2 model. The comparison with mass spectrometry data also aligns and confirms high concordance with the ex vivo approach, which is reassuring to confirm the existence of a biologically relevant signal.

Figure 24:
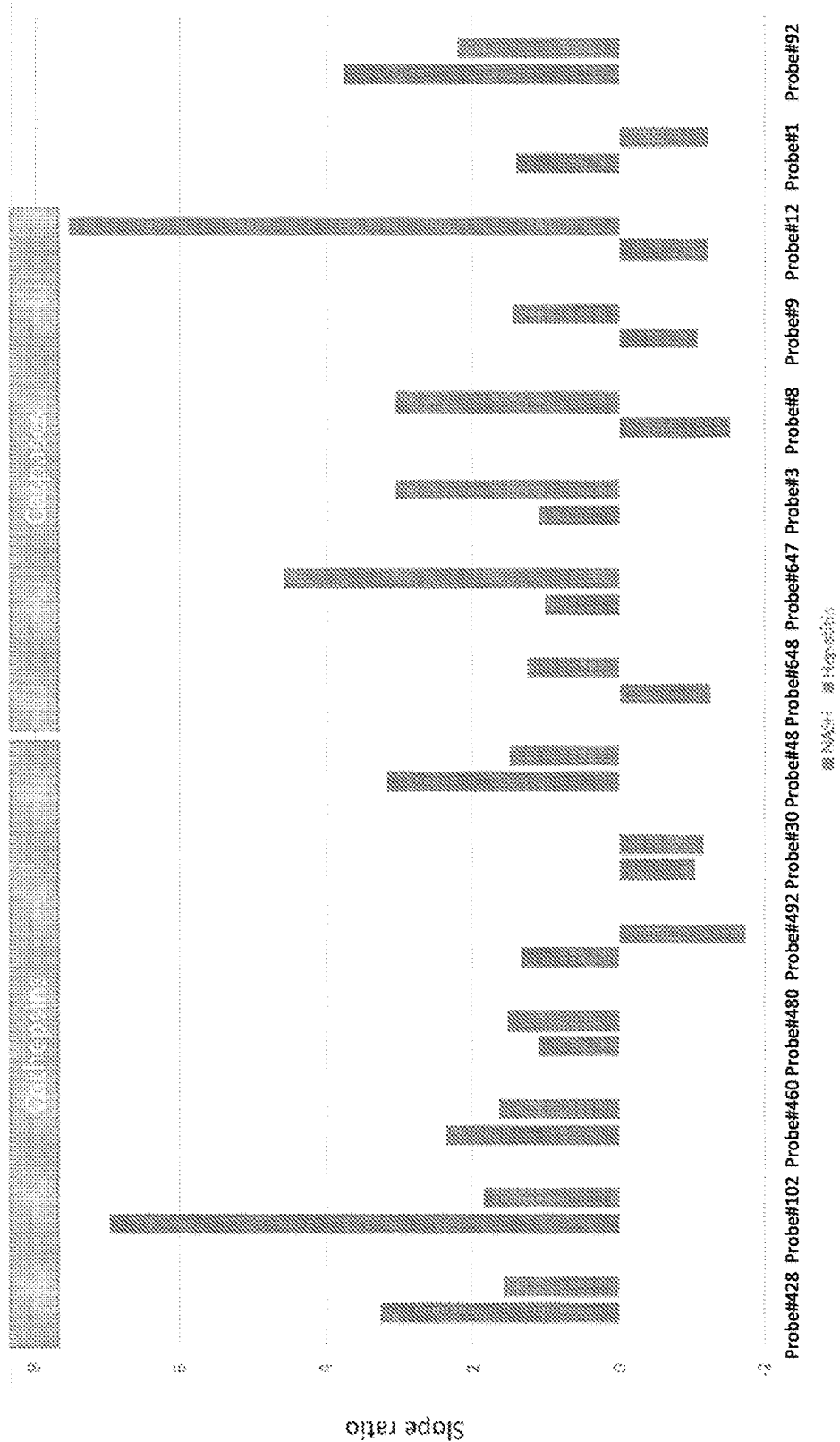
FIG. 24 shows that peptide fragments can distinguish between two different preclinical models of liver disease due to their distinct biological mechanisms.

FIG. 24 demonstrates that for two preclinical models of liver disease, the application can distinctly identify each disease due to the distinct biological mechanisms underlying protease activity of each disease (i.e., cathepsin activity in NASH and caspase activity in hepatitis).

Example 5: Detecting NASH in Human Plasma

This experiment relates to the detection of NASH in humans.

Figure 25:
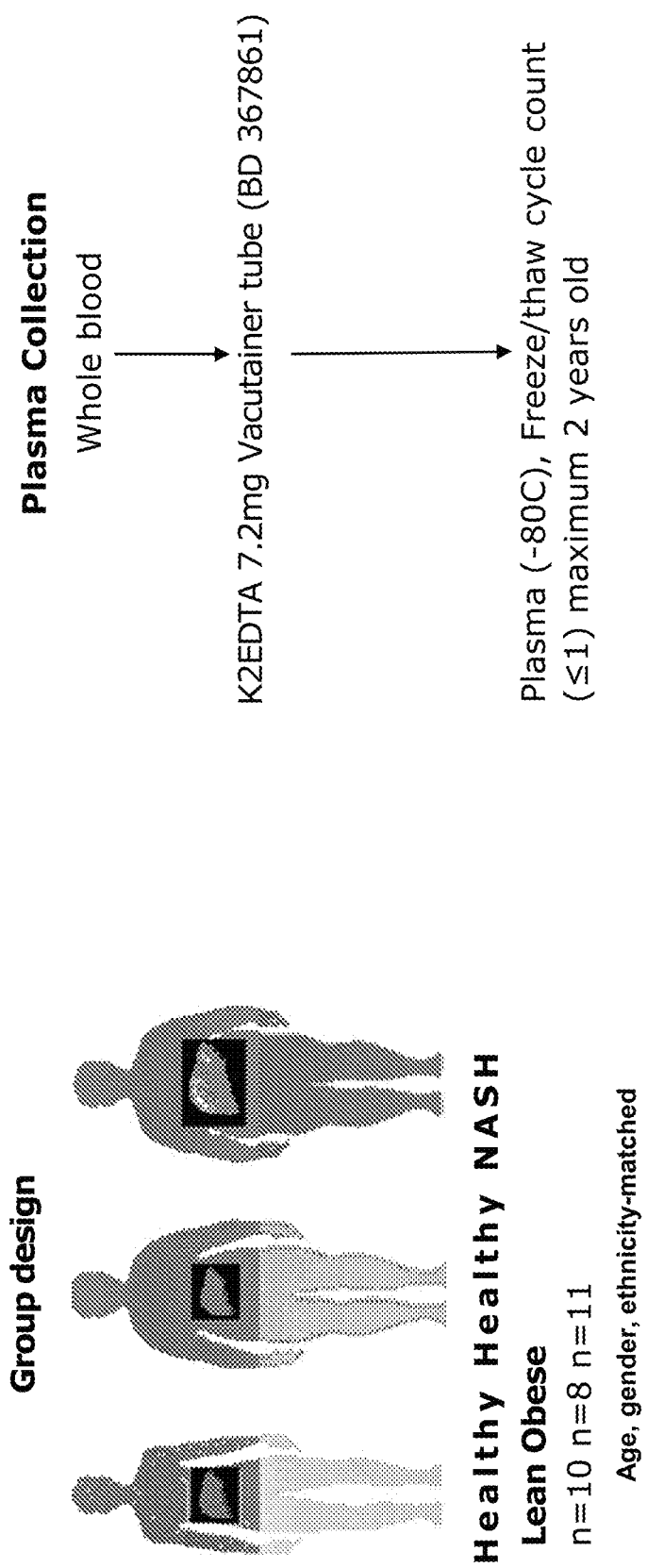
FIG. 25 outlines an experimental design of the present application.

As shown in FIG. 25, blood samples were collected from human subjects that were diagnosed as healthy/lean, healthy/obese, or NASH. Plasma was obtained from these blood samples in the same method as used in Example 1. The plasma was stored at −80C for no more than 2 years and with a freeze/thaw cycle count of <1 for each sample.

Figure 26:
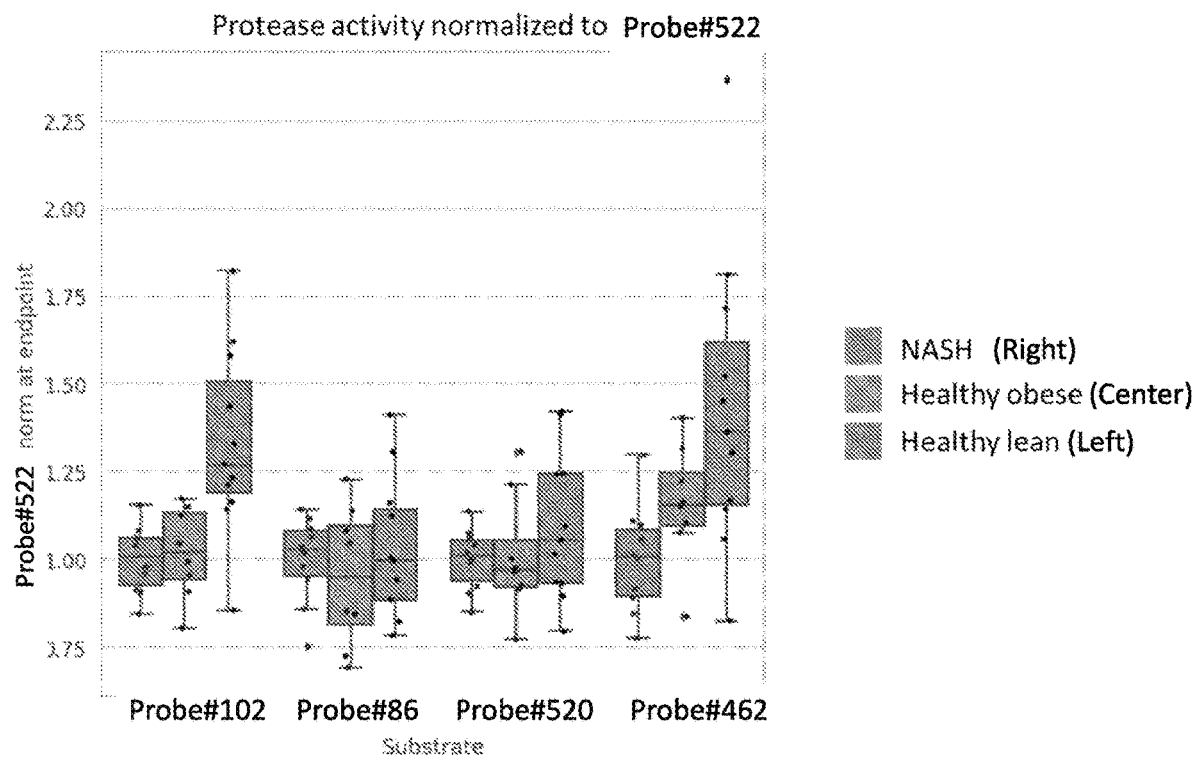
FIG. 26 provides experimental results showing the probes can distinguish between healthy, Obese and NASH human samples.

As shown in FIG. 26, when the probes contacted the human plasma samples using the method described in Example 1, increased fluorescence levels over time were observed in NASH samples when compared to healthy, allowing differentiation between the protease activity levels of healthy and NASH samples.

Figure 27:
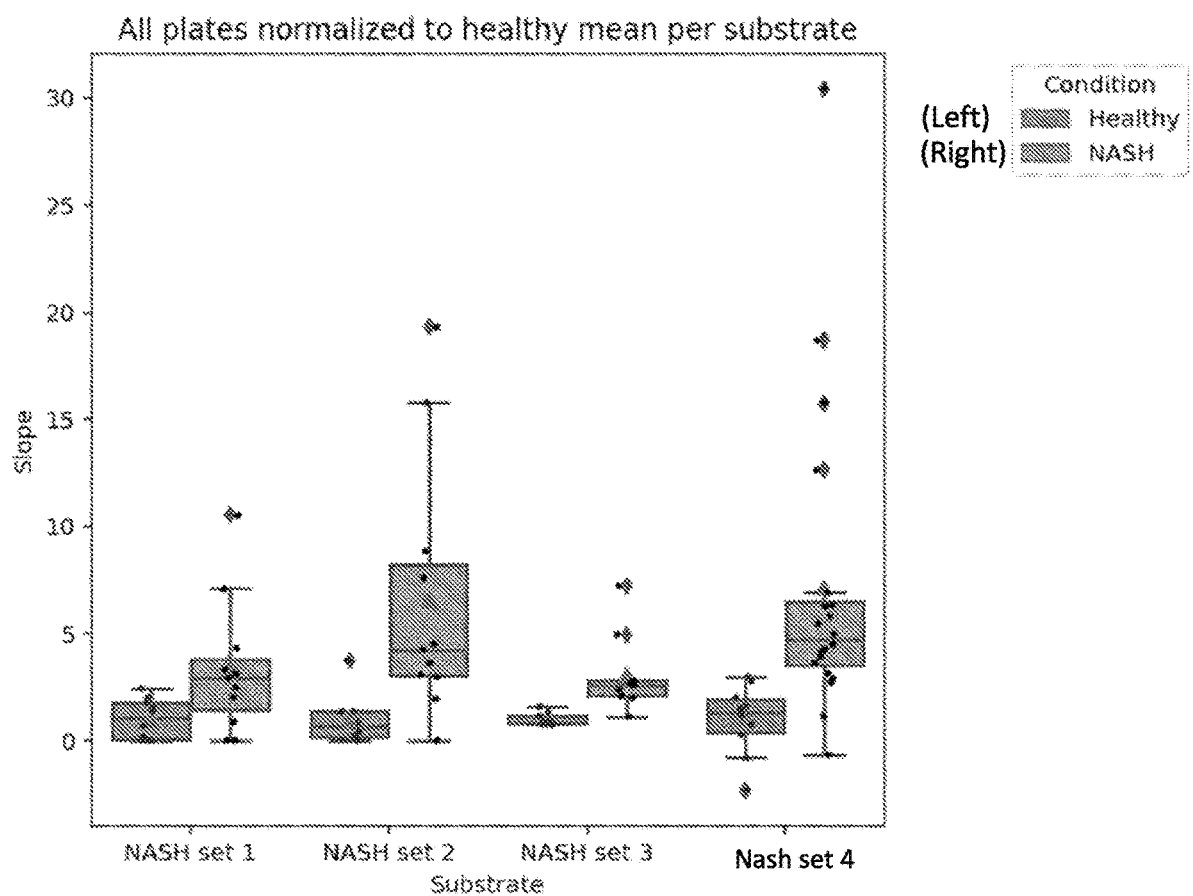
FIG. 27 provides experimental results that show reproducibility among independent sample cohorts with various collection dates, collection protocols, shipment etc.

FIG. 27 shows high levels of reproducibility in the application"s ability to differentiate between healthy and NASH samples when independent sample cohorts were tested.

Figure 28:
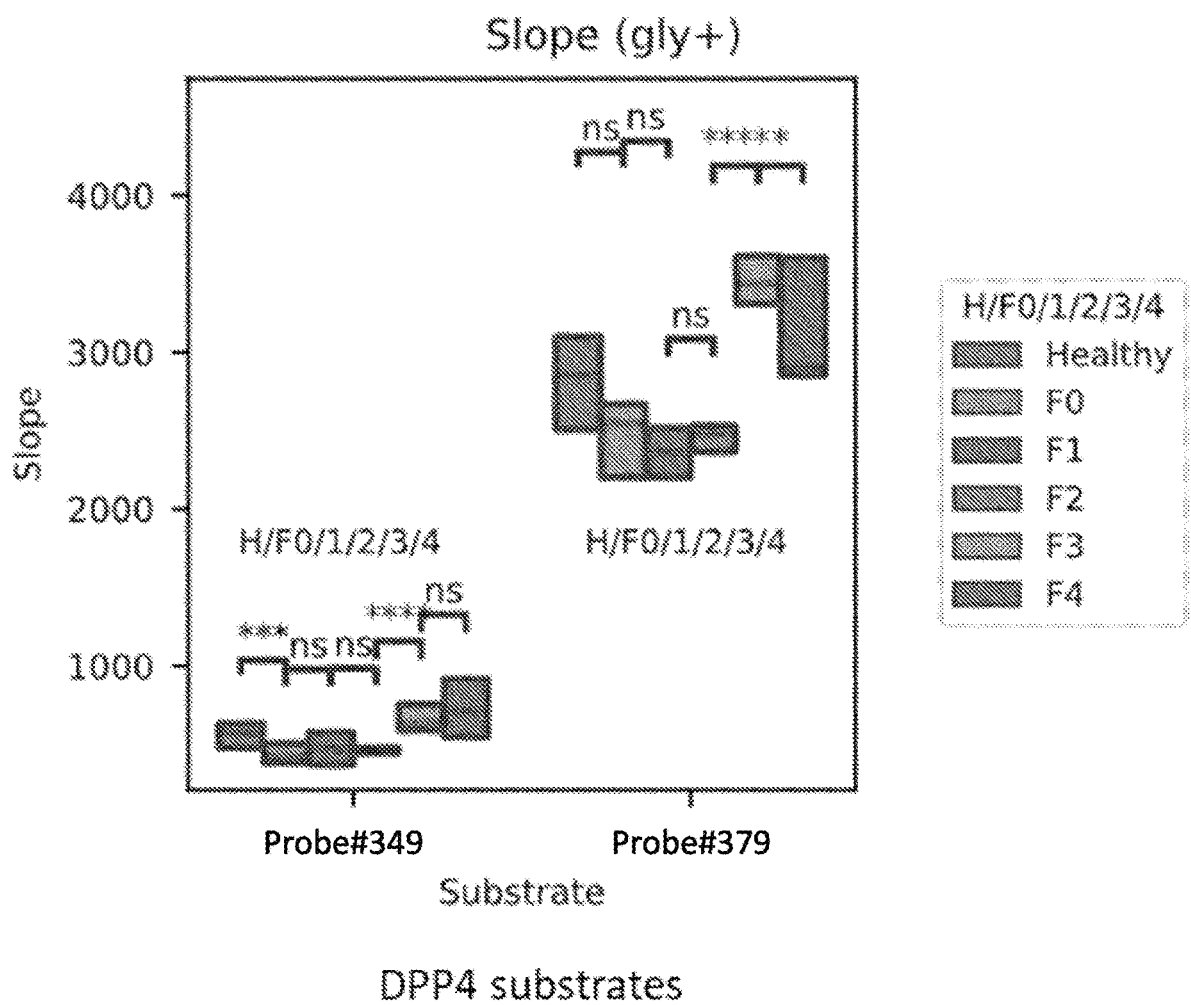
FIG. 28 provides experimental results showing the peptide fragments can distinguish between different stages of NASH disease progression in specific assay conditions.

FIG. 28 further demonstrates that the application is not only able to differentiate between healthy and NASH human samples, but it is, surprisingly, also able to differentiate between early-stage (F0-F2) and late-stage (F3+) NASH. The entire F0-F4 data set contains 100 NASH samples, and the experiment was conducted using the method from Example 1.

Figure 29:
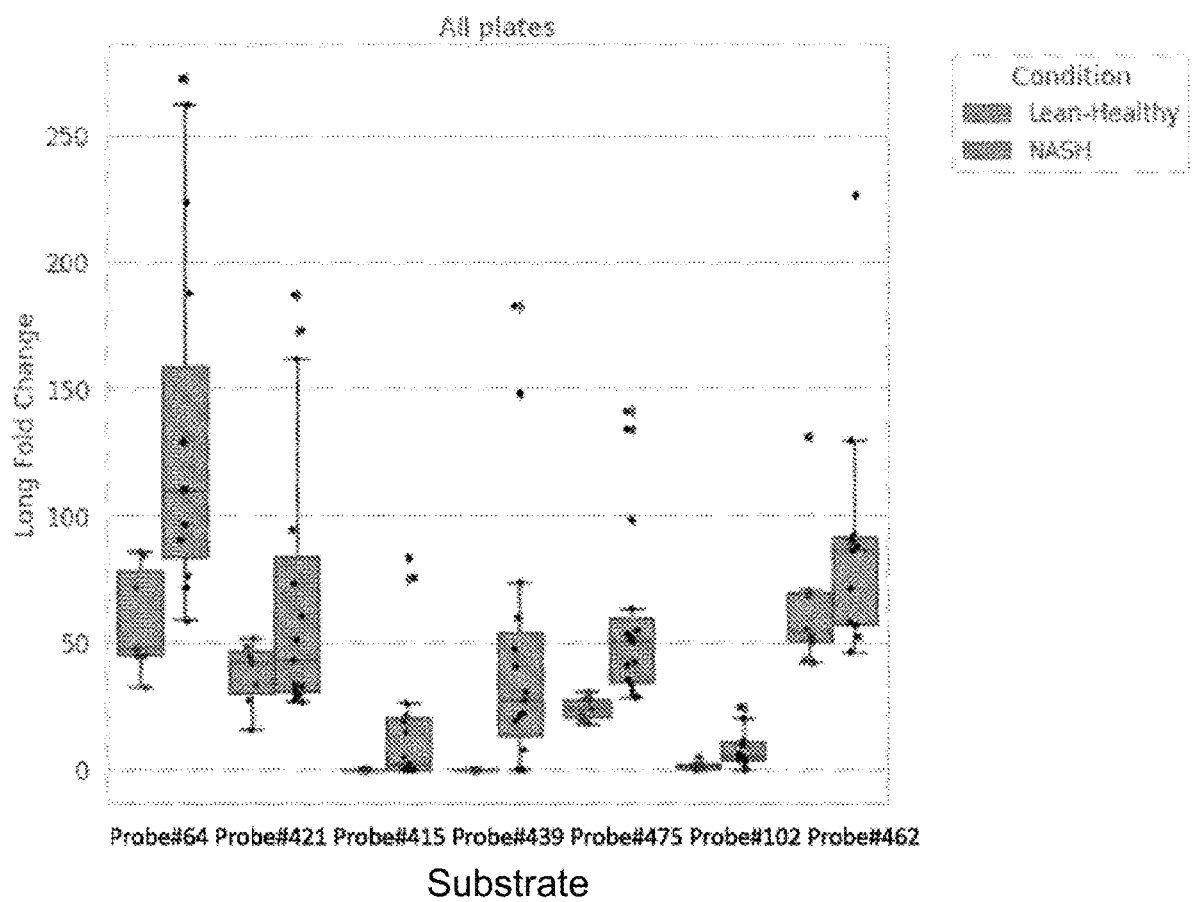
FIG. 29 provides experimental results showing the multiplicity of the peptide fragments able to distinguish between NASH and Healthy human K2EDTA plasma.

As shown in FIG. 29, multiple probes of the present application are able to differentiate between healthy and NASH samples in humans—this multiplicity furnishes a lower false-positive rate when testing samples This experiment demonstrates the application is highly adept at differentiating between healthy and NASH (and different fibrosis stages of NASH) in a non-invasive manner in human subjects.

Example 6: Mechanism of Function of Liquid Biopsy

In this experiment, the specific protease cleaved by a specific probe is determined in order to show the specificity of the application regarding the disease differences it detects. This experiment also shows that protease activity, not abundance, is the driving factor in the application"s determination of disease-markers in a sample.

For this experiment, all plasma samples were prepared individually and diluted 1/10e in PBS with inhibitor added directly to the samples. Inhibitor was prepared at 15× concentration to final. Substrates were diluted in DI water at 18 uM, such that the final concentration on the plate would be 6 uM. All samples were prepared such that their last dilution on the plate would not affect the desired final concentration. 10 ul of each individual sample was pipetted into their corresponding wells, and the plate was then spun down in the centrifuge at 1500 RPM for 30 seconds to coat the bottom of each well with the sample. 5 ul of the 18 uM substrate solution was pipetted into each well being used on a 384 well plate, and then the plate was spun down in the centrifuge at 1500 rpm for 30 seconds. The plate was placed immediately in the plate reader at 37° C. for a 30-minute-long fluorescence kinetic read at 485/535 extended gain.

To assess the proteolytic cleavage pattern of Probe #102, samples were tested using a pool of broad inhibitors for serine, cysteine, threonine, MMP and aspartic protease family members (broad inhibitor) to assess general protease activity, AEBSF for serine proteases, E64 for cysteine proteases, CTSi for broad cathepsin inhibition of cathepsins L, S, K and B, or specific inhibitors for cathepsin K (L00625), for cathepsin L (SID) or cathepsin B (CA074).

All E64 (broad cysteine), SID (CTSL) and the CTSi (CTSL, S, K, B) inhibitors decreased NASH signal significantly with less decrease in signal for healthy, indicating that the nature of the decrease in signal was disease-specific. When using the broad inhibitor or E64, we observed a greater than 6-fold decrease in the RFU signal contrast between NASH and healthy samples, indicating that a cysteine protease was responsible for the disease contrast. Broad cathepsin inhibitor CTSi decreased NASH by 47% while only decreasing healthy by 18%, demonstrating that a cathepsin was responsible for the disease contrast. A specific cathepsin inhibitor for CTSL (SID) decreased NASH by 60% while only decreasing healthy by 33%. Both NASH and healthy decreased with the addition of the serine inhibitor, AEBSF. NASH was inhibited 65%, while healthy was inhibited at 60%. The similar decrease in RFU for both NASH and healthy indicates that the AEBSF signal being sensed by Probe #102 is not a significant contributor to the disease specific signal and of a background nature.

Specific inhibitors for cathepsin K and B, L006235 and CA074, respectively, did not significantly decrease signal for NASH or healthy samples.

Figures 30C, 30D:
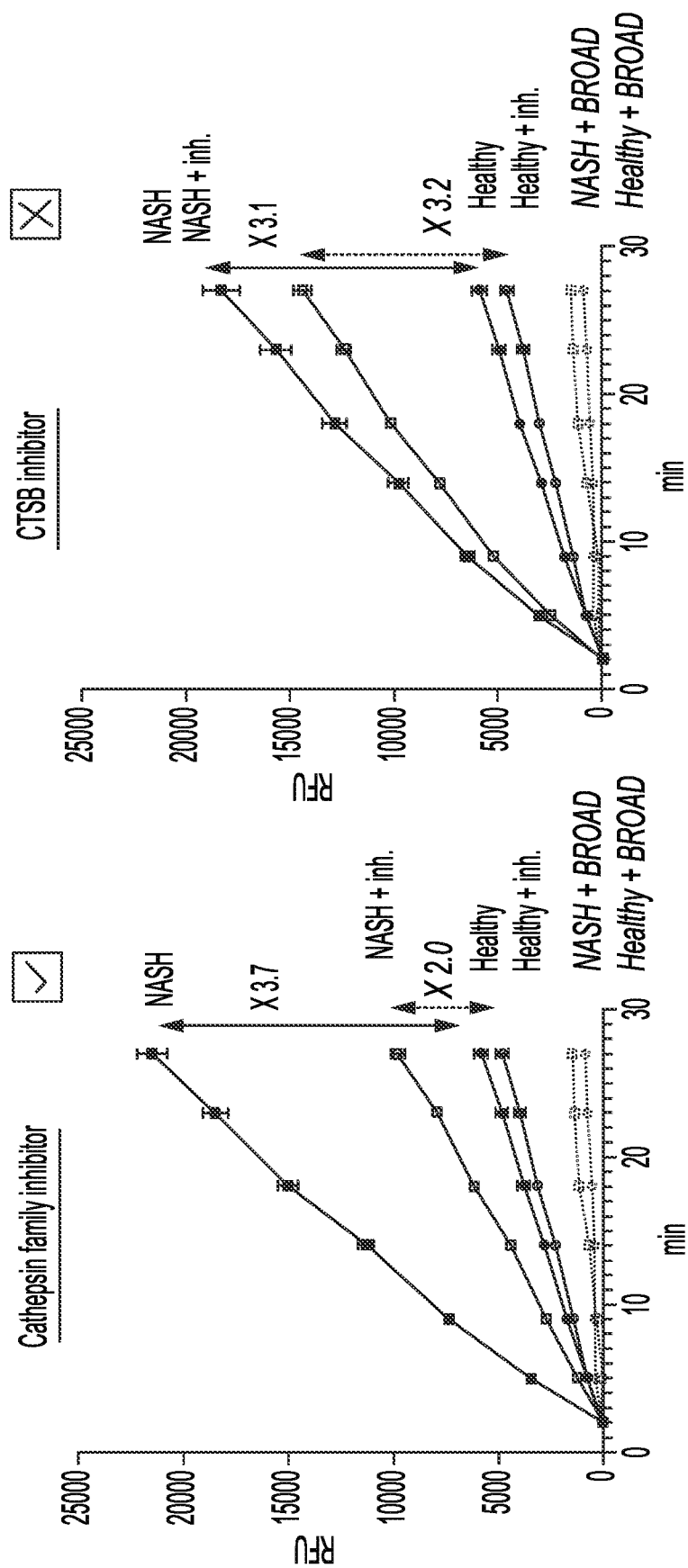
Figure 30F:
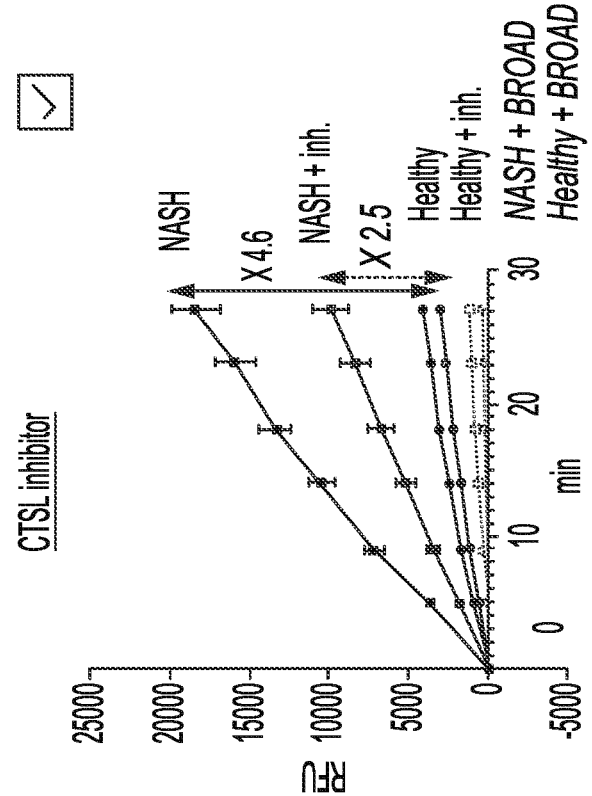
Figure 30E:
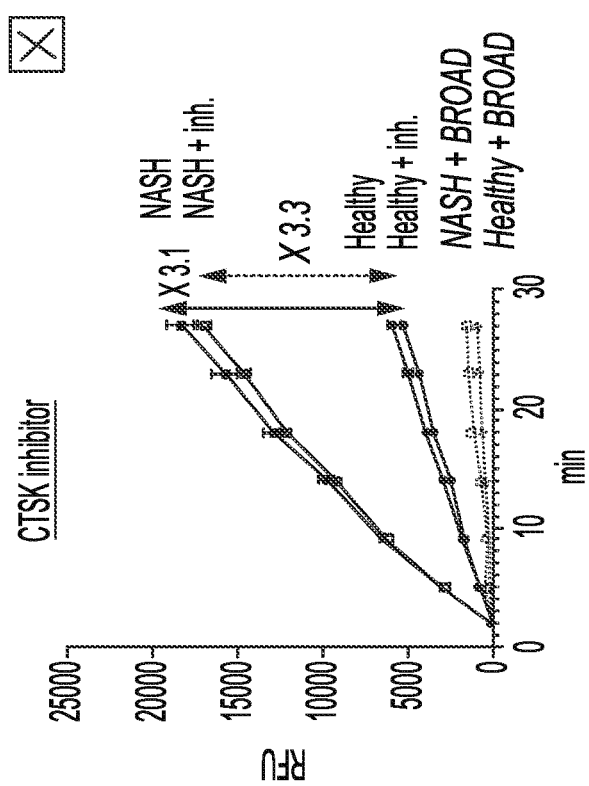

FIG. 30A demonstrates Probe #102 in combination with broad protease inhibitors to show that Probe #102 specifically contacts a protease in order to determine the difference between healthy and NASH samples. FIG. 30B shows that Probe #102 contacts a cysteine protease, and FIG. 30C further limits this to a cathepsin family protease. FIG. 30D-F test individual cathepsins to show that Probe #102 specifically responds to the activity of cathepsin L (CTSL), a NASH-related protease. Thus, cathepsin L activity is responsible for the disease vs. healthy differences in protease activity in samples as recognized by the application.

Figures 31A, 31B:
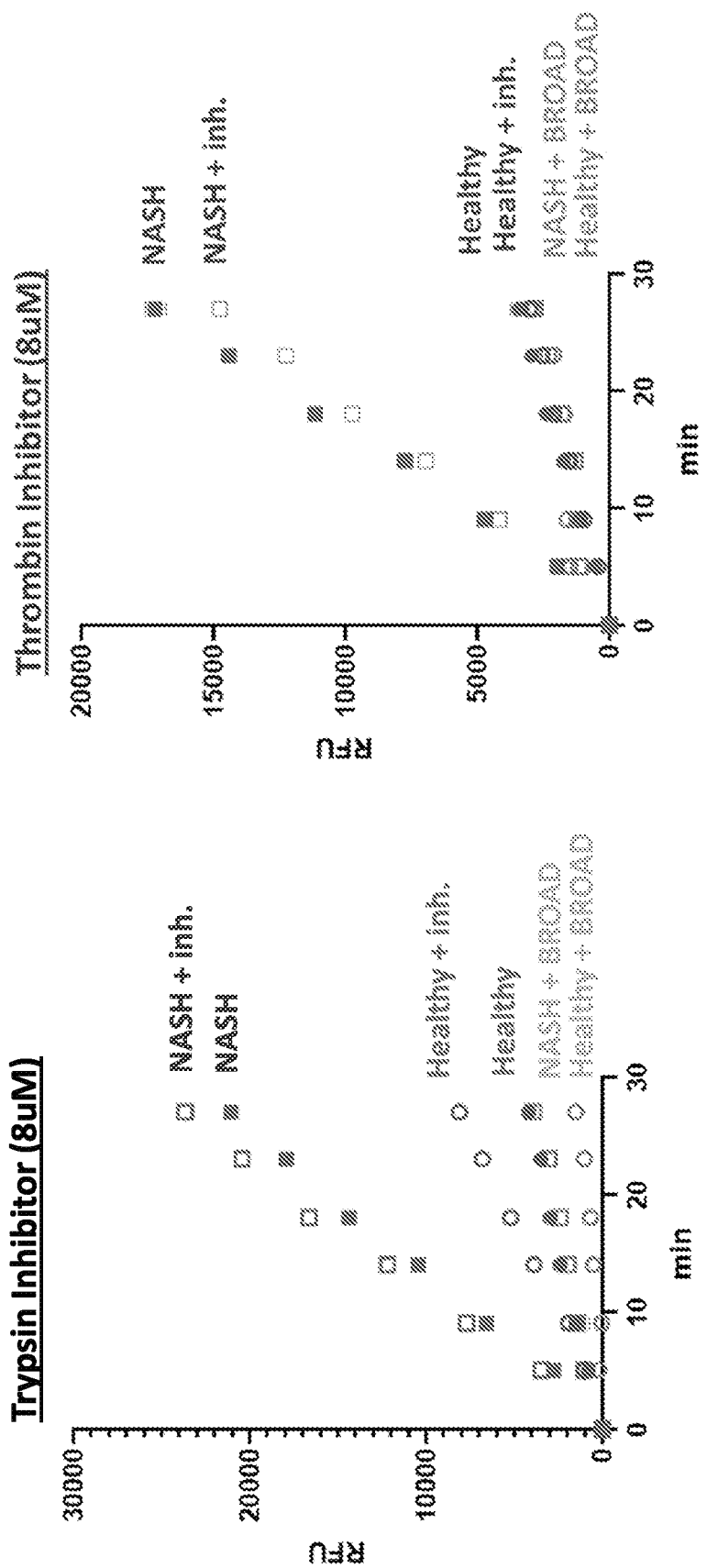
FIG. 31A-B provides experimental results showing that two common promiscuous proteases abundant in plasma are not responsible for determination of disease-based protease activity differences in NASH samples in K2EDTA mice plasma.

As shown in FIG. 31A-B, the application's discrimination between healthy and NASH tissue is not caused by either trypsin or thrombin, both promiscuous proteases that are constantly present in blood.

Figures 32A, 32B:
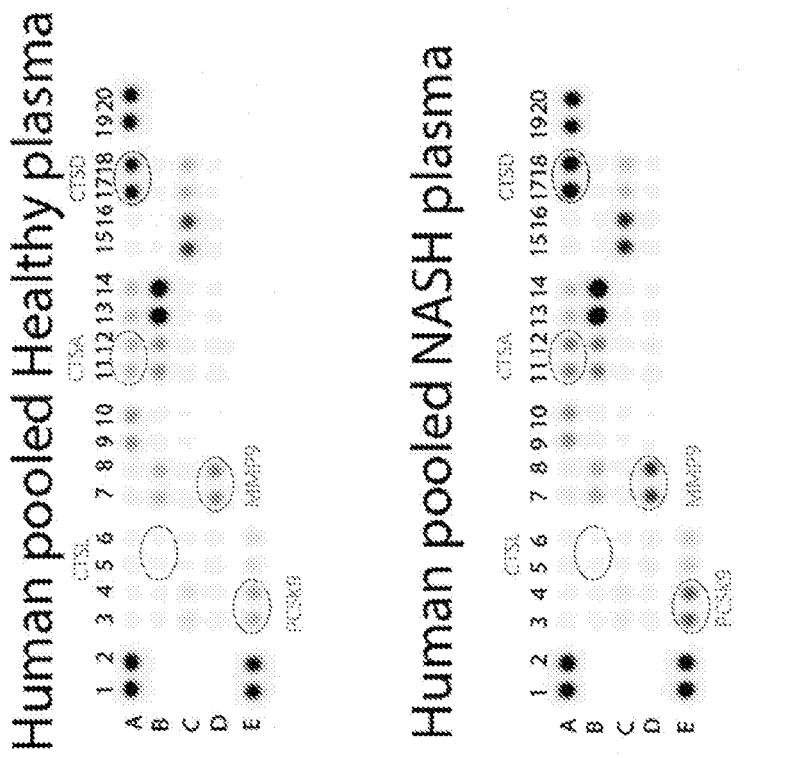
FIG. 32A-B provides experimental results showing that activity, not abundance, is responsible for determination of disease-based protease activity differences in human samples.

As shown in FIG. 32A-B, protease activity is the true measure of disease, rather than protease quantity. This corroborates the previous determination in mice that activity is more important than abundance as previously seen in Example 2 and as previously shown in FIG. 19.

Figures 33A, 33B:
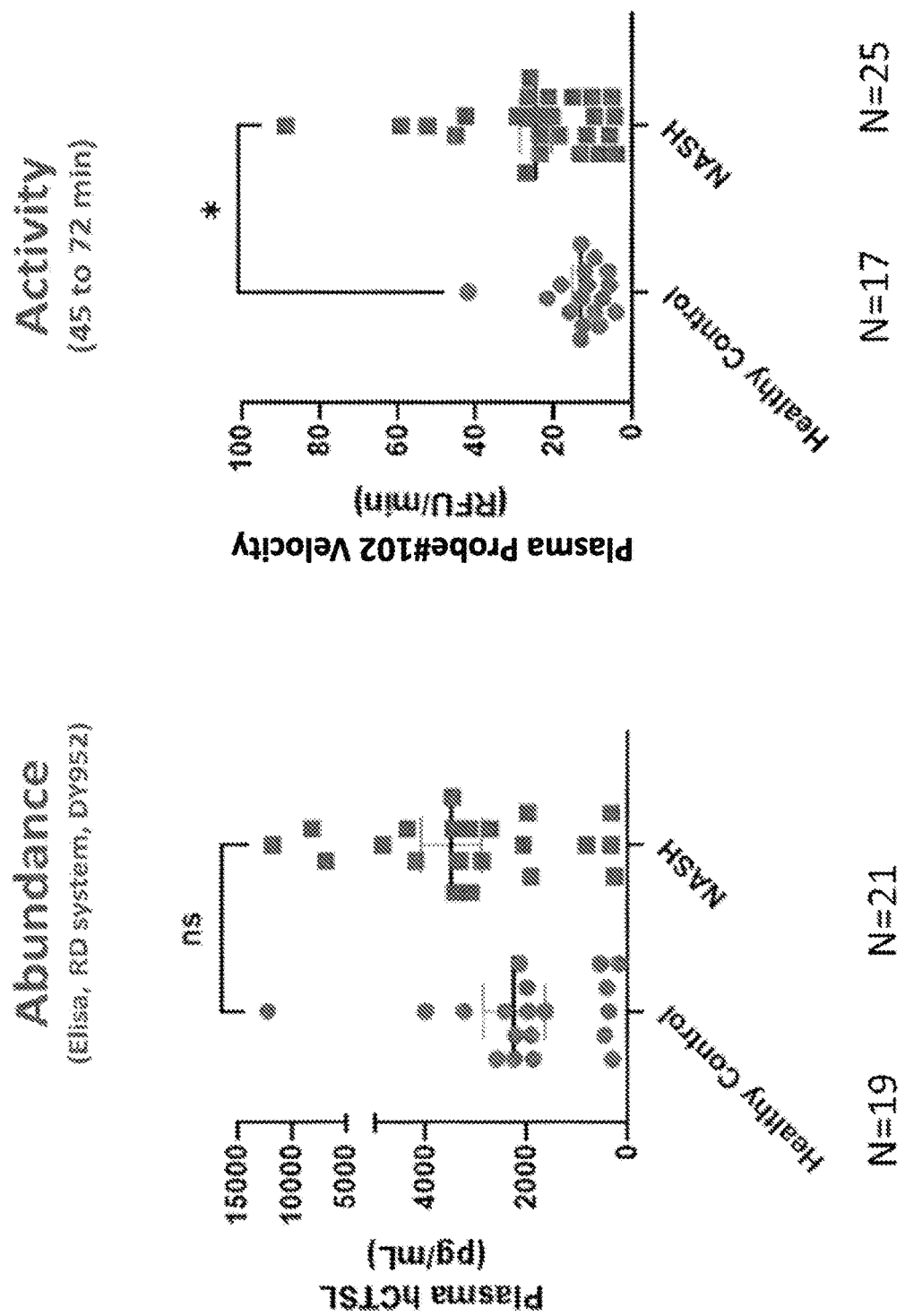
FIG. 33A-B shows that although Cathepsin-L is equally abundant in both healthy and NASH human samples, the differences in its activity levels allow for the differentiation between healthy and NASH samples.

More specifically, FIG. 33 demonstrates that although CTSL is equally abundant in both healthy and NASH human samples, CTSL activity is different between these two sample populations.

The application is shown to function by measuring the activity levels, rather than the abundance of specific disease-related proteases, to give an accurate determination of a specific disease in a sample.

Example 7: Liquid Biopsy Applications Toward COVID Diagnosis

In this example, the application is directed toward diagnosing COVID.

Initial experiments with COVID used K2EDTA and Lithium Heparin collected plasma. Samples were thawed on ice from storage in −80° C. and were then diluted to 10% in PBS. After the samples were prepared, the volume was split in half and broad protease inhibitors were added to one tube—100× dilution final, 67× in the tube. 10 uL of each sample were placed into a well in a 96-well plate, and the plates were stored on ice. Substrates were prepared at 18 uM in ddH2O using 1 mM stock prepared in DMF. 5 uL of substrate were added to each well. The 96-well plates were spun down at 1000 RPM for <30 seconds. The plates were read on Biotek Synergy H1 plate reader, Ex/Em=485/535 with a cycling time of 4 mins 30 seconds using a kinetic read, extended dynamic range for 1 hour.

Figures 34A, 34B:
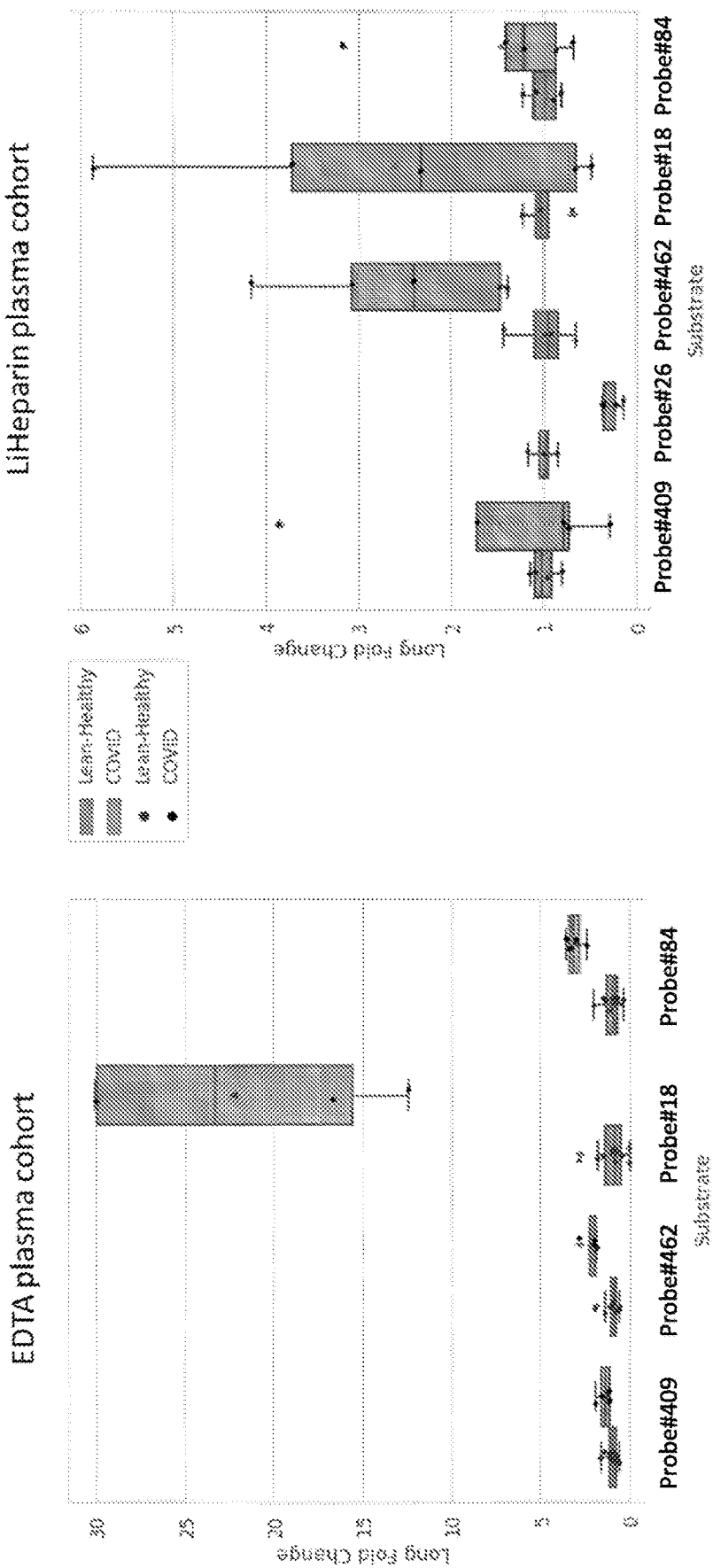
FIG. 34A-B provides experimental evidence that the probes can detect both host response and presence of the COVID virus in plasma under two different conditions of plasma collection.

As shown in FIG. 34A-B, multiple sensors demonstrated differential cleavage between COVID and healthy samples. Probe #462, Probe #18 and Probe #84 demonstrated contrast in both sets and Probe #409, the SARS CoV2 coronavirus substrate, showed modest contrast in the K2 EDTA samples.

Figure 35:
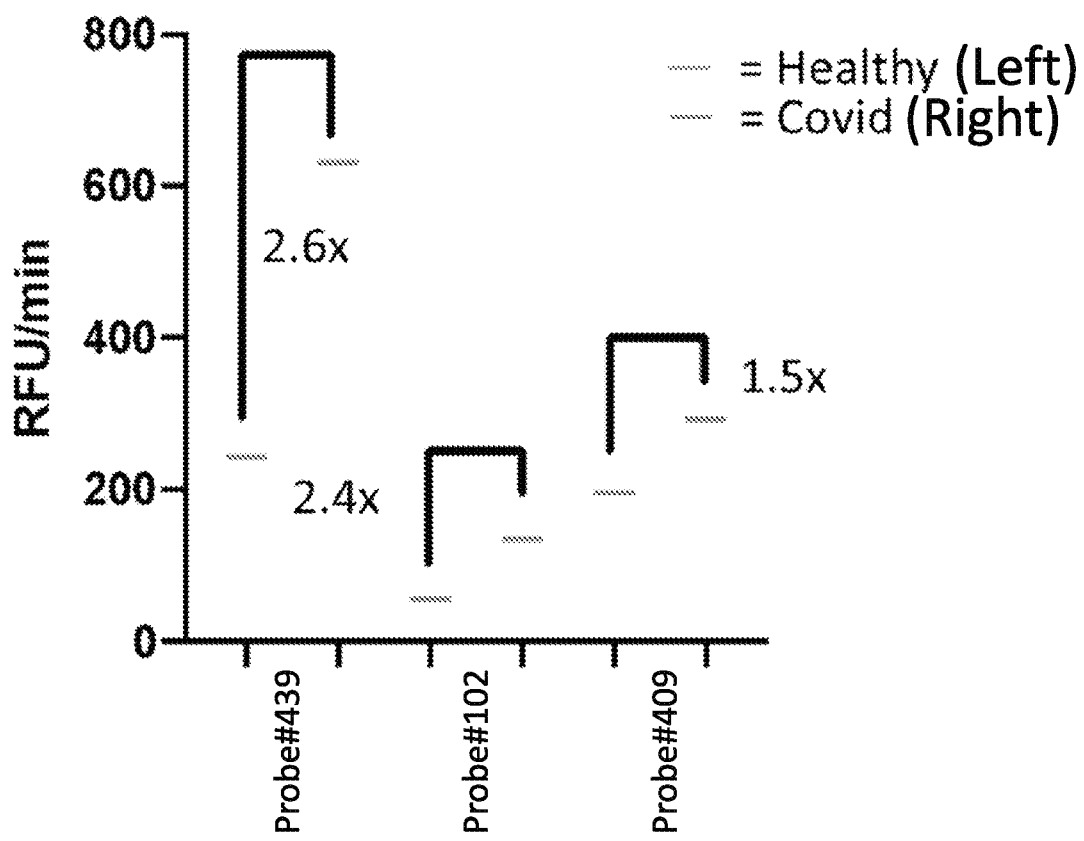
FIG. 35 provides experimental data that the probes can differentiate between healthy swab samples and COVID swab samples.

As shown in FIG. 35, COVID positive and COVID negative swabs (as determined by PCR at the clinical site) were combined with LBx sensors to determine if protease activity can be sensed ex vivo using swabs.

Figures 36A, 36B:
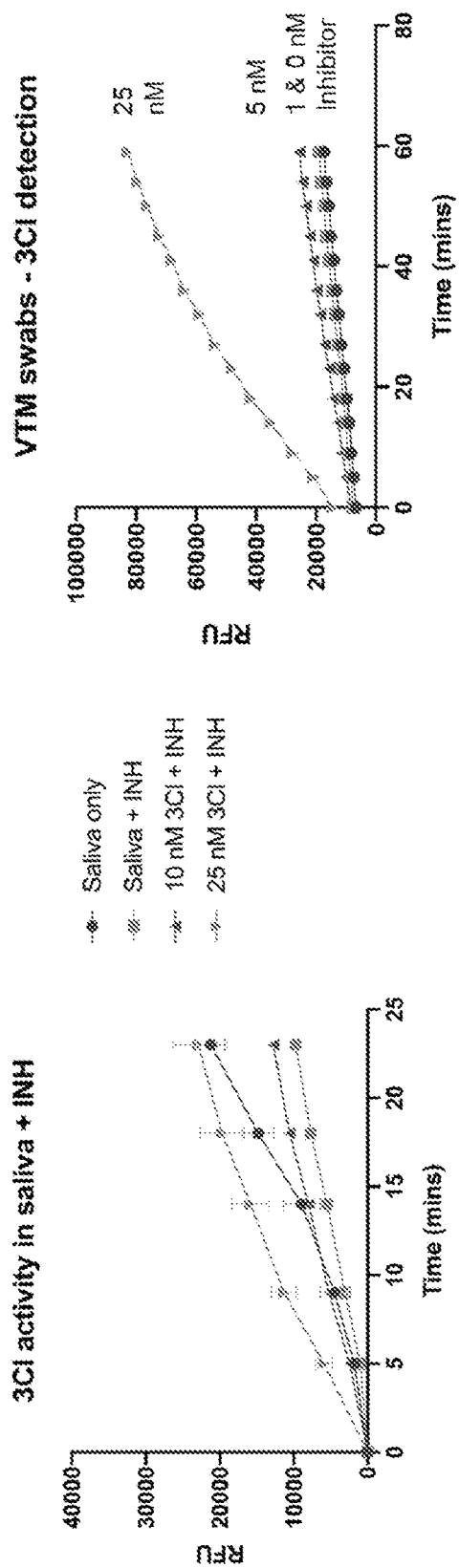
FIG. 36A-B provides experimental data showing that 3C1 protease from SARS-COV2 can be detected when spiked in saliva or swab samples.
Figure 37:
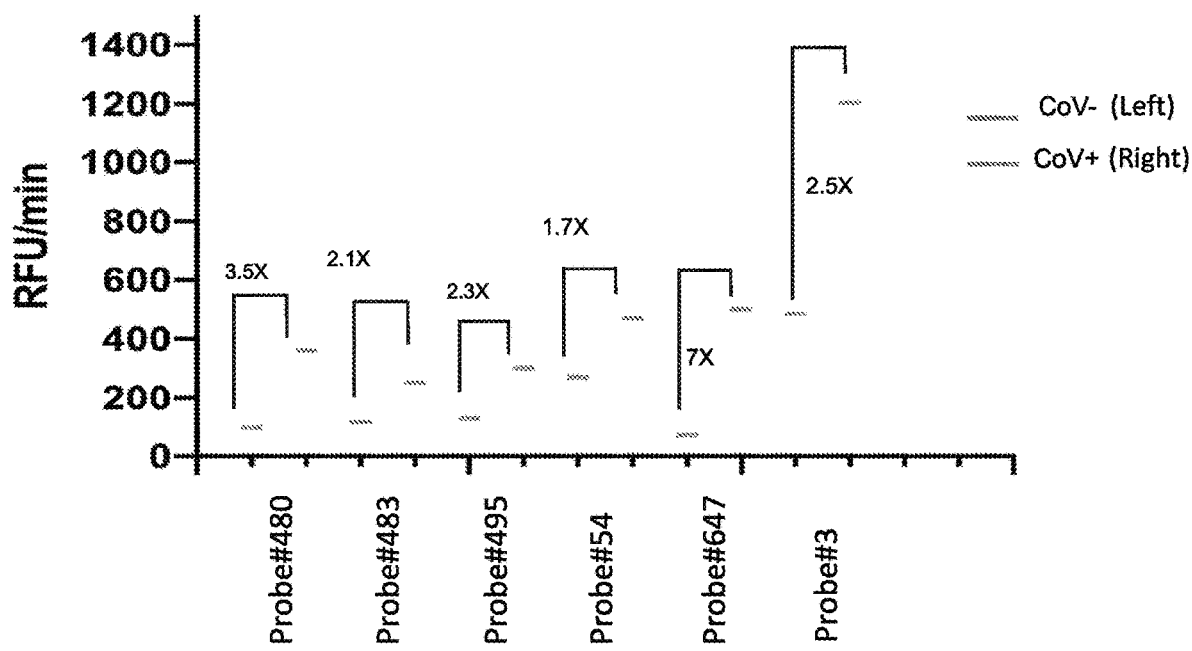
FIG. 37 shows several probes that are capable of differentiating between healthy and COVID samples.

Samples were thawed on ice and then diluted to 10% in DPBS (neutral pH 7.4, Gibco). Where required, samples were pooled according to condition with equal volumes of each sample per condition and then subsequently diluted in DPBS. After the samples are prepared, the volume was split in half and broad protease inhibitors were added to 1 tube—100× dilution final, 67× in the tube. 10 uL of each sample was added into the corresponding wells of a 96-well plate, and the plates were stored on ice. Substrates were prepared at 18 uM in ddH2O using 1 mM stock prepared in DMF. 5 uL of substrate was added to each sample in the 96-well plate, and the plates were spun down at 1000× rpm for <30 seconds. Plates were read on a Biotek Synergy H1 plate reader, Ex/Em=485/535 with a cycling time of 4 mins 30 seconds using a kinetic read, extended dynamic range for 2 hours. FIGS. 36A-B shows both swabs and saliva samples treated with viral transport media (VTM), which contains some proteases in the serum after contact with the probes of the application. However, when swabs were tested using the method from experiment 1 using a saline media instead of VTM, as shown in FIG. 37, clear differences could be seen between COVID− and COVID+samples (as determined by clinical PCR testing). The saline media swabs give superior protease activity signal compared to the VTM swabs as they were collected in saline media with no additives. This shows the application has broad applicability across biofluids.

Figure 38A:
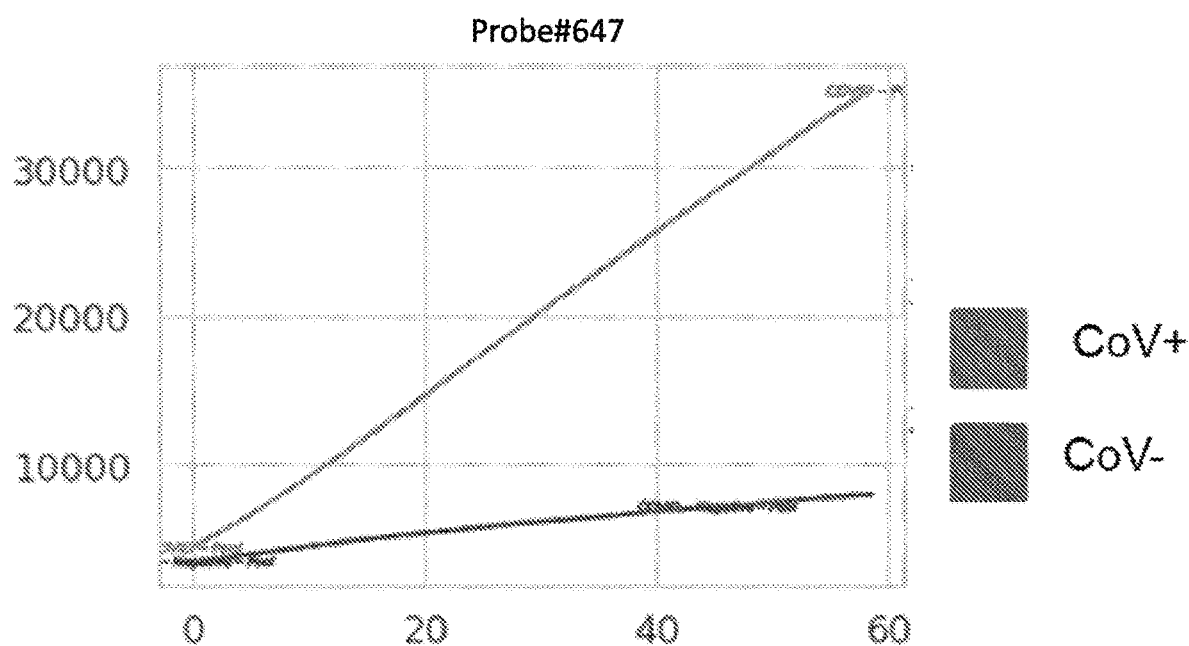
FIG. 38A provides experimental evidence that the Probe #647 can detect the activity of COVID-related proteases to differentiate between healthy and COVID pooled swab samples conditioned in saline.
Figure 38B:
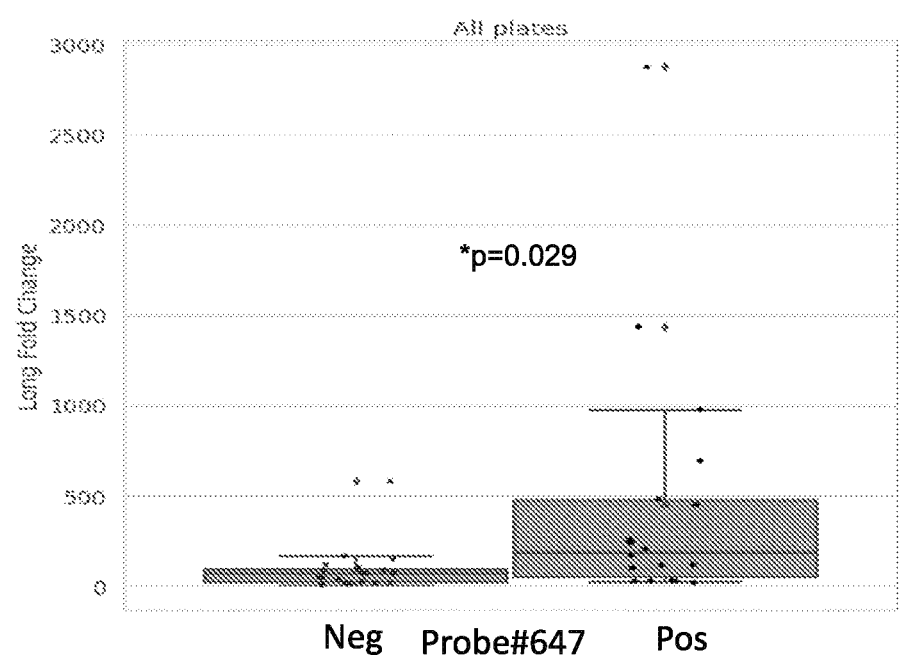
FIG. 38B shows that there are significant differences (p=0.029) between COVID+(n=18) and COVID− (n-19) samples.
Figure 38C:
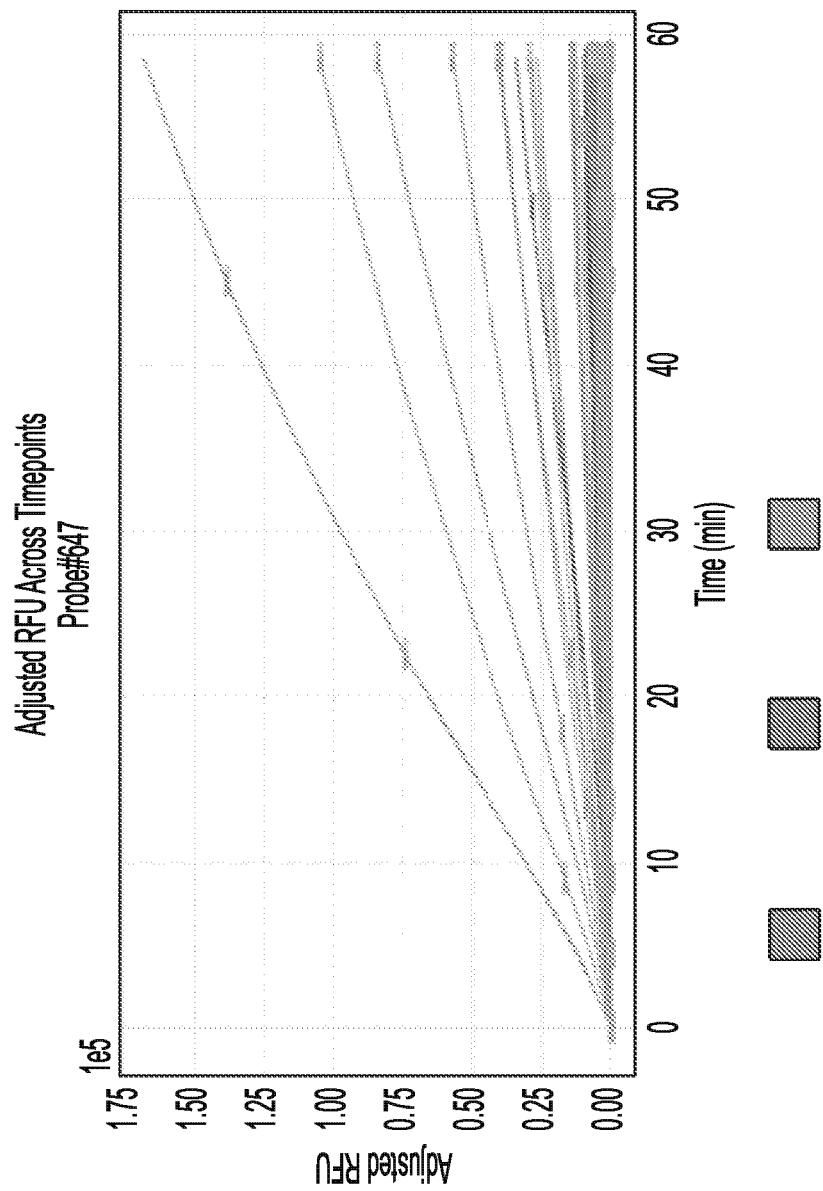
FIG. 38C shows the adjusted RFU across timepoints for COVID+(7 samples were active) and COVID− (1 sample was active) samples.

The specific probe, Probe #647, was shown to be a key differentiator between COVID+ and COVID− samples, as shown in FIG. 38A-C.

Figures 39A, 39B:
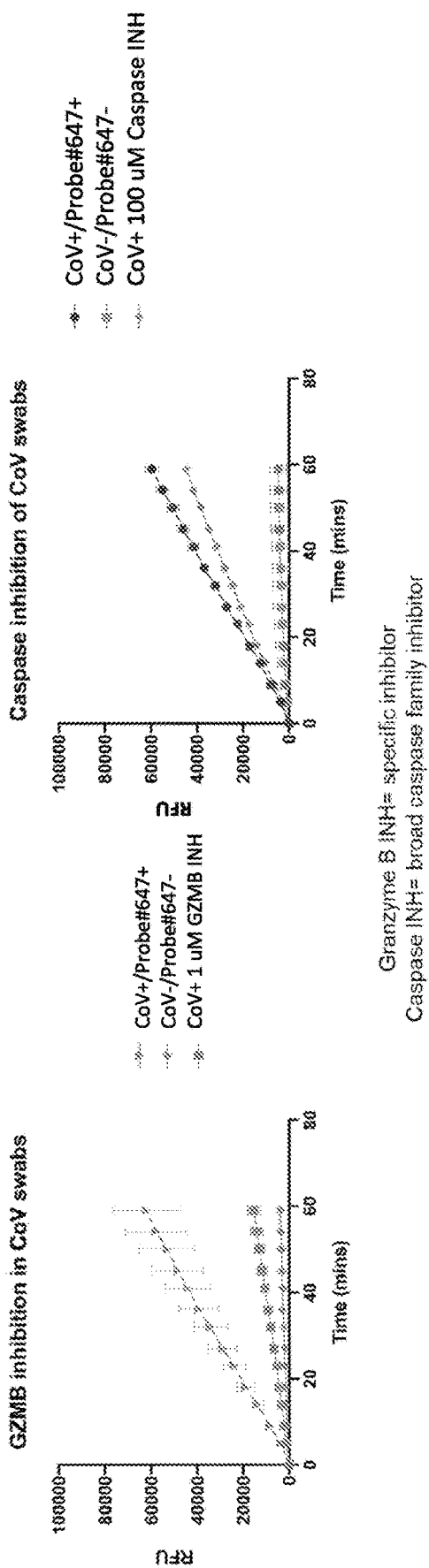
FIG. 39A-B provides experimental evidence that Granzyme B, a protease linked to other autoimmune diseases, is the protease that allows Probe #647 to differentiate between healthy and COVID samples.

As shown in FIGS. 39A-B, Probe #647 signal measures the activity of protease Granzyme B to differentiate between healthy and COVID samples. Granzyme B is a protease that is linked to other autoimmune diseases and viral infections, showing the application can be applied to a wide range of disease biology.

Biotin and Probe #647 were conjugated by dissolving stock Probe #647 powder at 2 mM in 50/50 DMF/PBS. Biotin-Maleimide was reconstituted from powder at 100 mM and diluted to the following concentrations—2 mM, 3 mM and 6 mM in PBS. Three reaction mixtures were created with the following molar equivalents: 1) 1:1-10 uL to 10 uL 2 mM Biotin+2 mM Probe #647, 2) 1:1.5-10 to 10 uL 3 mM Biotin+2 mM Probe #647, and 3) 1:3-10 to 10 uL 6 mM Biotin+2 mM Probe #647. Once mixed, these were inverted on a Hula sample mixer for 2 hours at room temperature. Once the conjugation reactions were completed, recombinant proteases and samples were tested using 100 nM recombinant Granzyme B with 6 uM Probe #647-Biotin conjugate from above 3 reactions. These were then incubated for multiple time points—0 mins, 5 minutes, 30 minutes, 1 hour and optional O/N. They were then diluted up 1:20 and paper strips were dipped into the mixture and the paper strip was read visually. Once the activity was confirmed using recombinant proteases, results were confirmed in strong COVID+ saline swab samples and COVID− saline swab samples (as determined by clinical PCR testing). 10 uL of dilute saline swab sample was combined with 5 uL Probe #647-Biotin conjugate and incubated for multiple time points—0 hours and 2 hours. Post-reaction, the sample was diluted 1:20 and read visually with the paper strip.

The use of a paper strip test to monitor Granzyme B activity using the probes of the application is shown in FIG. 40. This point of care test for the detection of protease cleavage of a biotin-tagged 5FAM sensor has implications for disease monitoring and response in real-time.

Example 8: Liquid Biopsy Applications Towards Pancreatic Ductal Adenocarcinoma

In this example, the application is directed toward diagnosing pancreatic ductal adenocarcinoma (PDAC).

As shown in FIG. 41A-B, when human plasma is contacted with the probes of the application using the method from Experiment 1, one can distinguish between the protease activity of healthy and PDAC human plasma samples.

Furthermore, as shown in FIG. 42, the probes are able to differentiate among healthy, PDAC, and pancreatitis samples.

This experiment continues to show that there is broad applicability for the application regarding different types of diseases that have different protease biology.

Figure 8:
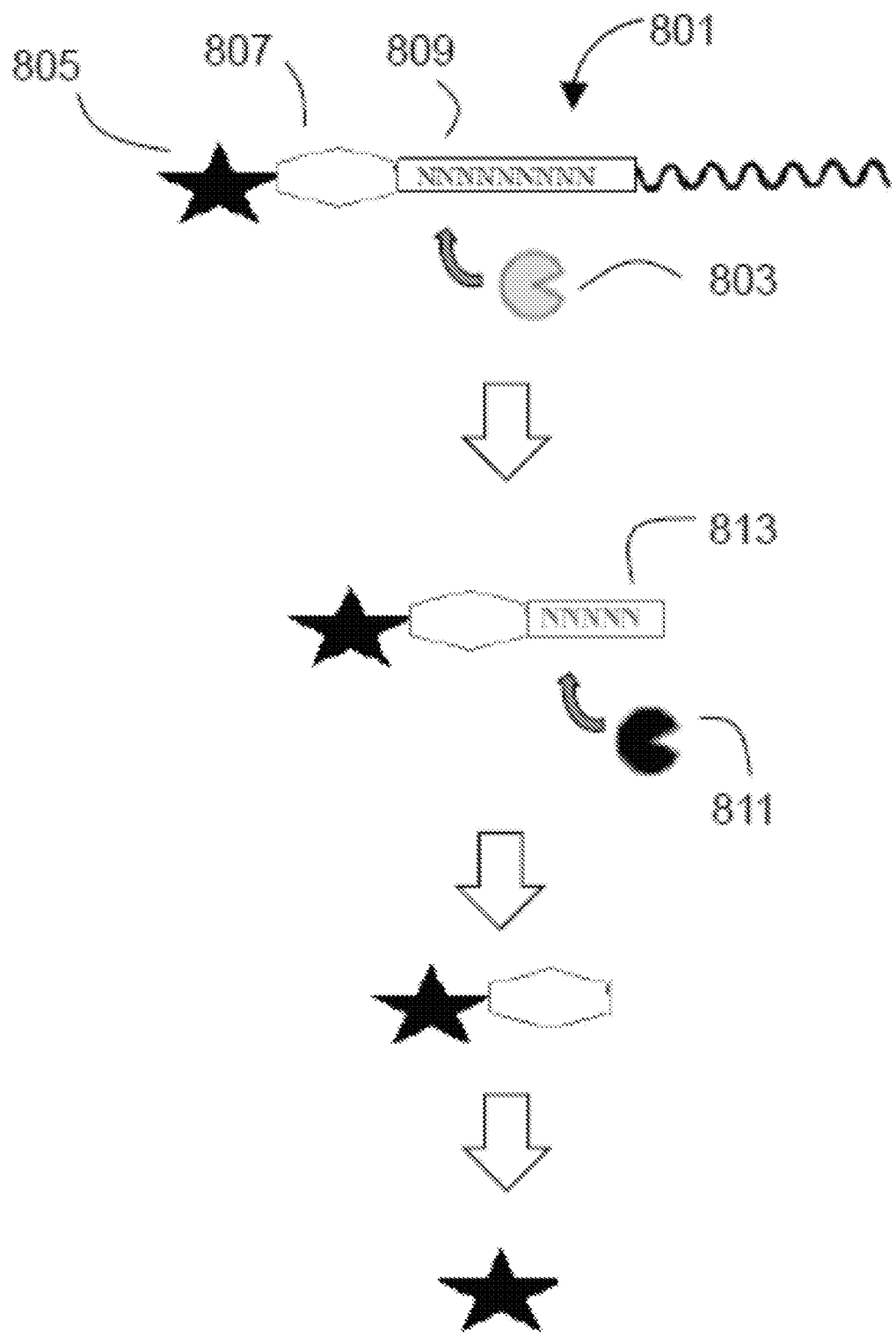
FIG. 8 shows a method using a probe 801 with an auto-immolative spacer 807, precipitating or non precipitating fluorescent reporter 805, and an enzyme/protease substrate 809 cleaved by a predetermined enzyme/endoprotease 803. The probe includes an enzyme/protease substrate 809 that is cleaved by two predetermined enzymes/proteases. The first of these enzymes/proteases, is the enzyme/endoprotease 803 of interest in the sample. The enzyme/endoprotease 803 in the fluid sample cleaves the enzyme/protease substrate 809. However, because 803, cannot cleave completely/the terminal or penultimate amino acids in the protease substrate from the spacer 807. Thus, a predetermined exopeptidase/enzyme 811 is introduced to the sample. The exopeptidase/enzyme can be spiked into the fluid sample, before, after, or during incubation with the endoprotease/enzyme 803. The enzyme/protease substrate 805 is engineered such that cleavage by the enzyme/endoprotease 803 results in a second enzyme/protease substrate 813 that can be cleaved by the predetermined enzyme/exopeptidase 811. Cleavage by 811 causes the spacer 807 to dissociate from the precipitating/non-precipitating fluorophore reporter 805, such the reporter 805 provides an intense fluorescent signal.
Figure 9:
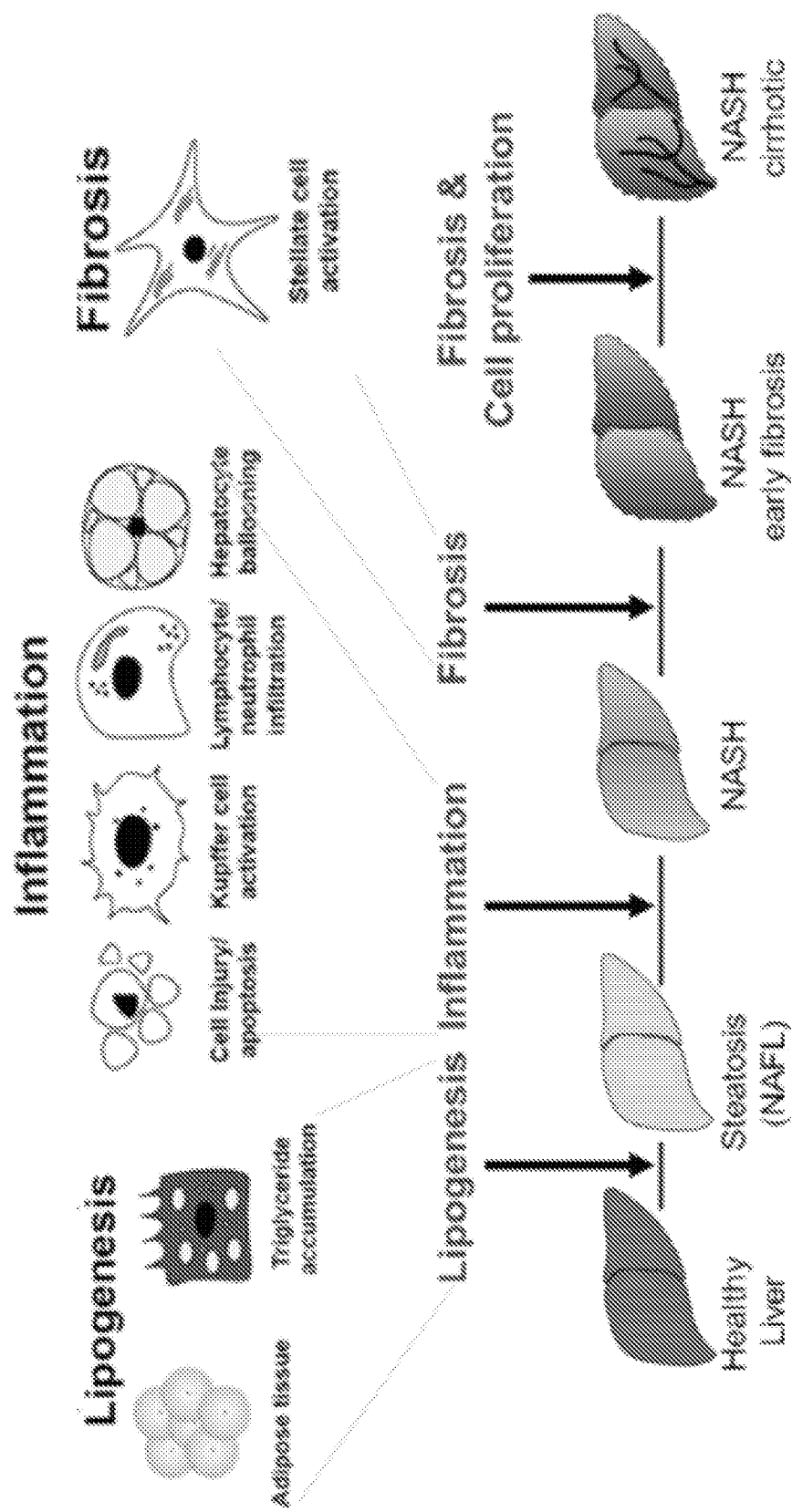
FIG. 9 shows the progression of NASH.

Example 9: Probes with a Fluorescent Reporter Will Accurately Measure NASH-Related Protease Activity Levels in Mice In this prophetic experiment, probes of the present disclosure that include a precipitating fluorescent reporter and a protease substrate cleavable by an endoprotease, like the probes discussed in FIG. 8, will be able to accurately measure the activity levels of NASH-related proteases in healthy mice and NASH mice.

The probes will be engineered such that the protease substrate could be cleaved by a protease such as endoprotease caspase 8, thereby resulting in a second protease substrate linked to a precipitating fluorescent reporter by an auto-immolative spacer. Alternatively, the second protease substrate could be cleaved by the endoprotease CTSD.

Spiking the plasma samples with an excess of CTSD would not result in a measured increase in caspase 8 activity. Thus, in the absence of caspase 8 to cleave the protease substrate, the second substrate will be unavailable for cleavage by CTSD, which will ultimately prevent precipitation of the fluorescent reporter.

However, upon addition of small concentrations of caspase 8 to the fluid sample, a strong signal will be detected by the precipitating fluorophores. Thus, caspase 8 will be able to cleave the protease substrate, thereby resulting in the second protease substrate, which will be cleaved by CTSD. This ultimately will lead to dissociation of the spacer from the precipitating fluorescent reporter, thereby resulting in a fluorescent signal.

Plasma samples with probes having distinguishable precipitating fluorescent reporters will be pooled after incubation with caspase 8 and CTSD. Individually, the plasma samples will be taken from either healthy mice or those with NASH to determine the differences between healthy and NASH samples through detection of caspase 8.

Example 10: Detecting Alternative Enzymes

In this experiment, measurement of alternative enzymes" activities for disease detection is explored. Different enzyme classes include peroxidases, lipases, esterases, phospholipases, amylase etc.

FIG. 43 shows a schematic diagram for detection of Chlorination and peroxidation activity of MPO using the EnzChek® Myeloperoxidase Activity Assay Kit. AH represents the nonfluorescent Amplex® UltraRed substrate, and A represents its fluorescent oxidation product. Hydrogen peroxide converts MPO to MPO-I and MPO is inactive without the presence of hydrogen peroxide. Amplex® UltraRed is then oxidized by MPO-I and creates the fluorescent oxidation product A which can be read at Ex/Em=530/590.

FIG. 44A-C shows the results for detecting peroxidases. FIG. 44A shows that MPO activities are different between healthy mice and mice with NASH. FIG. 44B shows that MPO activities are different between mice fed on a standard ChowDiet (CD), and mice fed on a choline-deficient, L-amino acid-defined, high-fat diet (CDAHFD). FIG. 44C shows that MPO activities are different between healthy subjects and subjects with rheumatoid arthritis. This result shows that we are capable of detecting differential activity in NASH in plasma and rheumatoid arthritis in human pools in synovial fluid.

FIG. 45A-B shows the pooled results of spiked recombinant protease in human plasma using resorufin oleate as substrate. FIG. 46A shows result of 3 recombinant enzymes—carboxylesterase 1, phospholipase A2 and lipoprotein lipase. FIG. 46B shows the result of various concentrations of lipoprotein lipase. This result demonstrates that Resorufin oleate and butyrate were promising for detection of broad range of enzymes.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

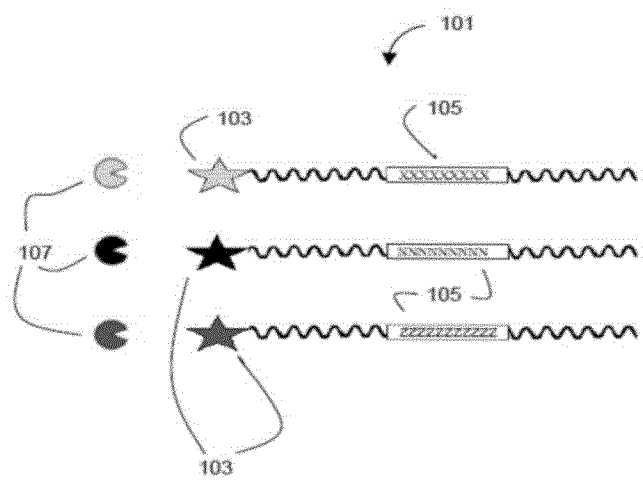

What is claimed is:

1. A method comprising:
contacting a body fluid sample from a subject with a molecule ex vivo,
wherein said molecule comprises a reporter and a cleavable linker, wherein the cleavable linker is directly connected to the reporter through a covalent bond, and
wherein said molecule reacts with a protease from said body fluid, causing said reporter to form a detectable signal,
detecting a rate of formation or an amount of said detectable signal,
determining a disease or condition of said subject based on said detection,
wherein said disease or condition is a certain fibrosis stage or a certain nonalcoholic fatty liver disease activity score (NAS) of Non-alcoholic steatohepatitis (NASH).

2. The method of claim 1, wherein said body fluid sample is selected from the group consisting of blood, plasma, bone marrow fluid, lymphatic fluid, bile, amniotic fluid, mucosal fluid, saliva, urine, cerebrospinal fluid, spinal fluid, synovial fluid, semen, ductal aspirate, feces, stool, vaginal effluent, lachrymal fluid, tissue lysate and patient-derived cell line supernatant.

3. The method of claim 1, wherein said body fluid sample comprises a rinse fluid, a conditioning media or buffer, a swab viral transport media, a saline, a culture media, or a cell culture supernatant.

4. The method of claim 3, wherein said rinse fluid is selected from the group consisting of a mouthwash rinse, a bronchioalveolar rinse, a lavage fluid, a hair wash rinse, a nasal spray effluent, a swab of any bodily surface, orifice, organ structure or solid tumor biopsies applied to saline or any media or any derivatives thereof.

5. The method of claim 1, wherein said protease is an endopeptidase or an exopeptidase.

6. The method of claim 1, wherein said protease is selected from the group consisting of an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase 0, a carboxypeptidase U, a carboxypeptidase X1, a carboxypeptidase X2, a carboxypeptidase Z, a camosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, a DDI-related protease, a DECYSIN, a Der1-like domain family, member 1, a Der1-like domain family, member 2, a Der1-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination thereof.

7. The method of claim 1, wherein said cleavable linker is a peptide.

8. The method of claim 7, wherein said peptide comprises an amino acid sequence selected from the group consisting of SEQ ID Nos: 1-677.

9. The method of claim 1, wherein said reporter comprises a fluorescent label.

10. The method of claim 9, wherein said fluorescent label is selected from a group consisting a 5-carboxyfluorescein (5-FAM), a 7-amino-4-carbamoylmethylcoumarin (ACC), a 7-Amino-4-methylcoumarin (AMC), a 2-Aminobenzoyl (Abz), a Cy7, a Cy5, a Cy3 and a (5-((2-Aminoethyl)amino) naphthalene-1-sulfonic acid) (EDANS).

11. The method of claim 9, wherein said molecule further comprises a fluorescent quencher.

12. The method of claim 11, wherein said fluorescent quencher is selected from the group consisting of BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl] azo)benzoyl), Dnp (2,4-dinitrophenyl) and Eclipse.

13. The method of claim 1, wherein said molecule further comprises a carrier.

14. The method of claim 13, wherein said carrier comprises a native, labeled or synthetic protein, a synthetic chemical polymer of precisely known chemical composition or with a distribution around a mean molecular weight, an oligonucleotide, a phosphorodiamidate morpholino oligomer (PMO), a foldamer, a lipid, a lipid micelle, a nanoparticle, a solid support made of polystyrene, polypropylene or any other type of plastic, or any combination thereof.

15. The method of claim 1, wherein said subject is a human subject.

16. The method of claim 1, wherein said detection comprises a fluorescent detection.

17. The method of claim 16, wherein said fluorescent detection is a fluorescence resonance energy transfer (FRET).

* * * * *

UNITED STATES PATENT AND TRADEMARK OFFICE
CERTIFICATE OF CORRECTION

PATENT NO. : 11,604,193 B2
APPLICATION NO. : 17/573129
DATED : March 14, 2023
INVENTOR(S) : Faycal Touti et al.

It is certified that error appears in the above-identified patent and that said Letters Patent is hereby corrected as shown below:

On the Title Page

Delete the title page and substitute therefore with the attached title page consisting of the corrected illustrative figure.

In the Drawings

Figure 1:
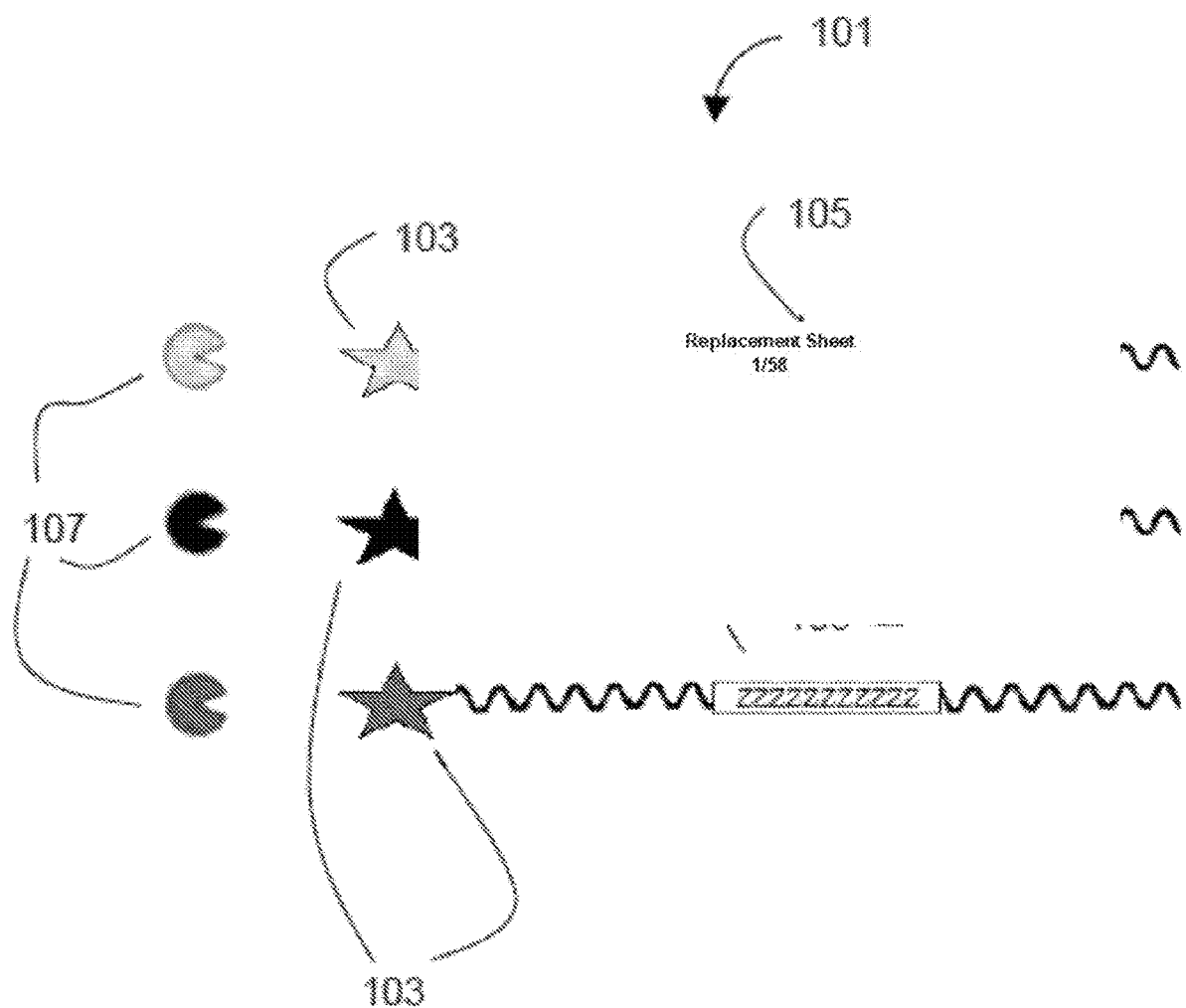
FIG. 1 shows a plurality of probes according to the current application. Each probe 101 includes a reporter 103, shown as a star in FIG. 1. The reporters 103, are linked to a cleavable linker 105, which is a cleavable substrate for an agent 107.
Figure 2:
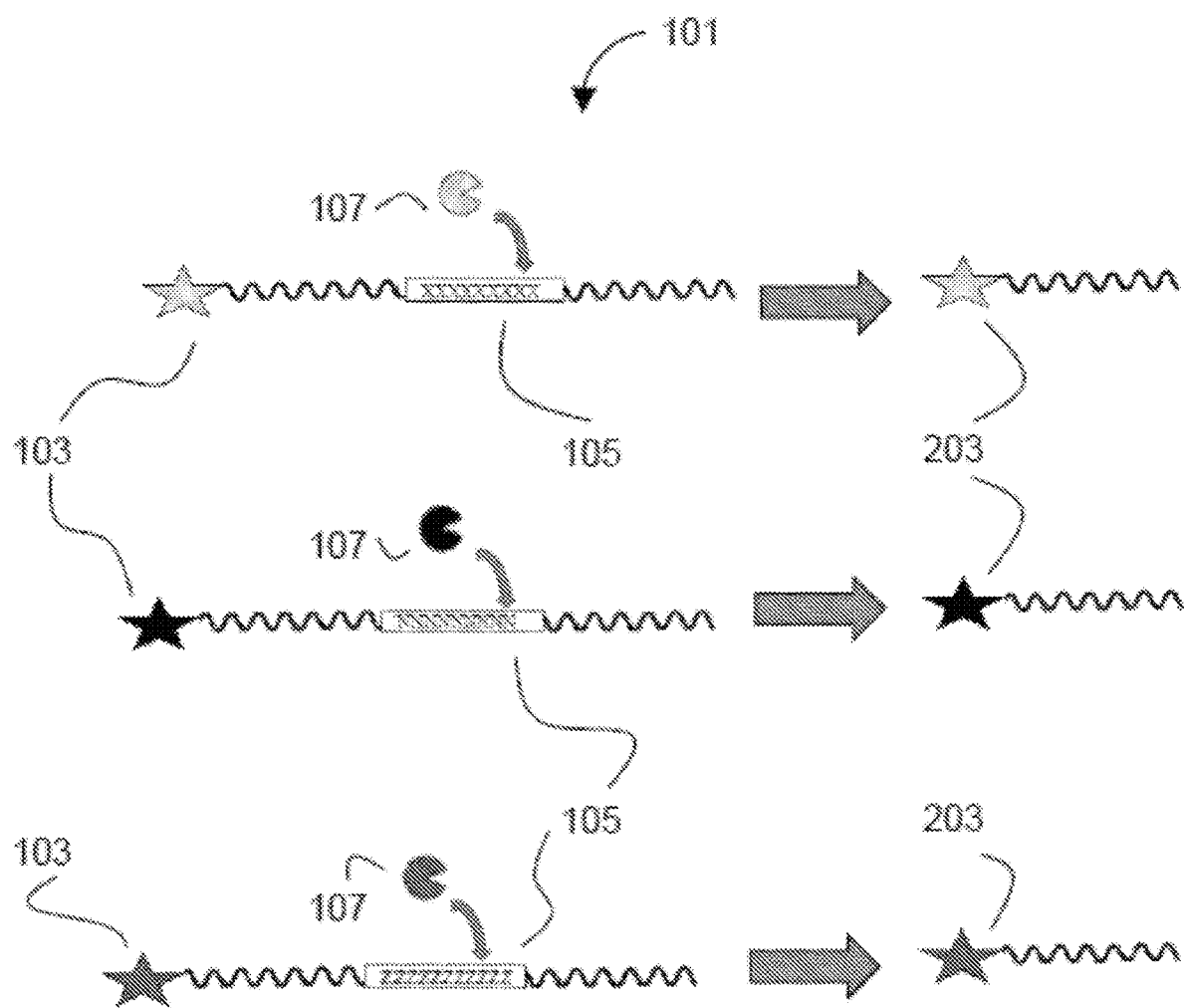
FIG. 2 shows cleavage of the reporter in a plurality of the probes. As shown, cleavage by the agent 107 of the cleavable linker 105 results in the reporters 103 being cleaved from the probe 101. Once cleaved, the cleaved reporters 203 can be detected and/or distinguished from un-cleaved reporters 103. The presence and detection of cleaved reporters 203 indicates that the agents 107 are present and active in a sample. In addition, the absence of an agent activity may be used for detection associated with a decrease in activity. The activity of the agents can be quantified based on, for example, the rate at which the cleavage reaction takes place or the amount of cleaved reporters in a sample or by other means such as a ratio of rates against an appropriate control or a ratio of cleaved reporters against an appropriate control.
Figure 3:
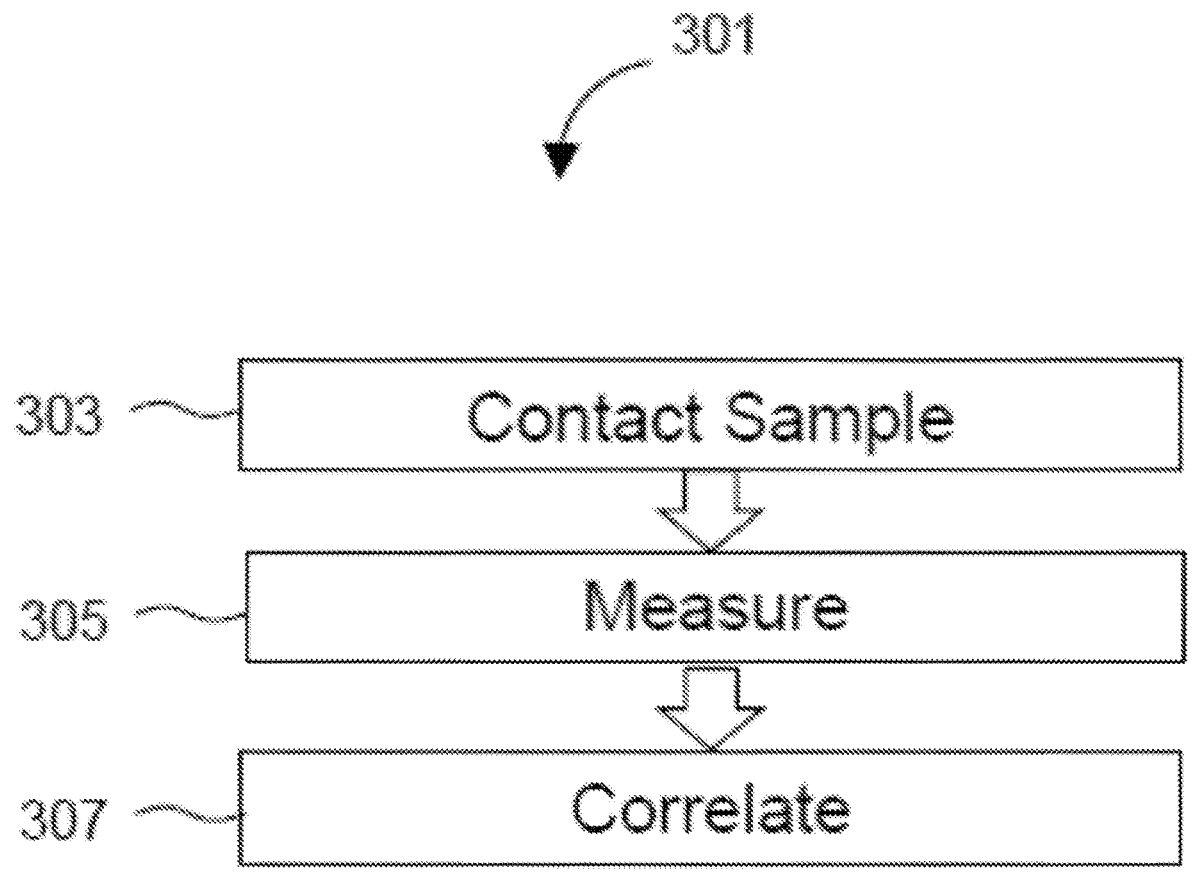
FIG. 3 illustrates a method 301 of evaluating a biological condition in a subject using the probes 101.
Figure 4:
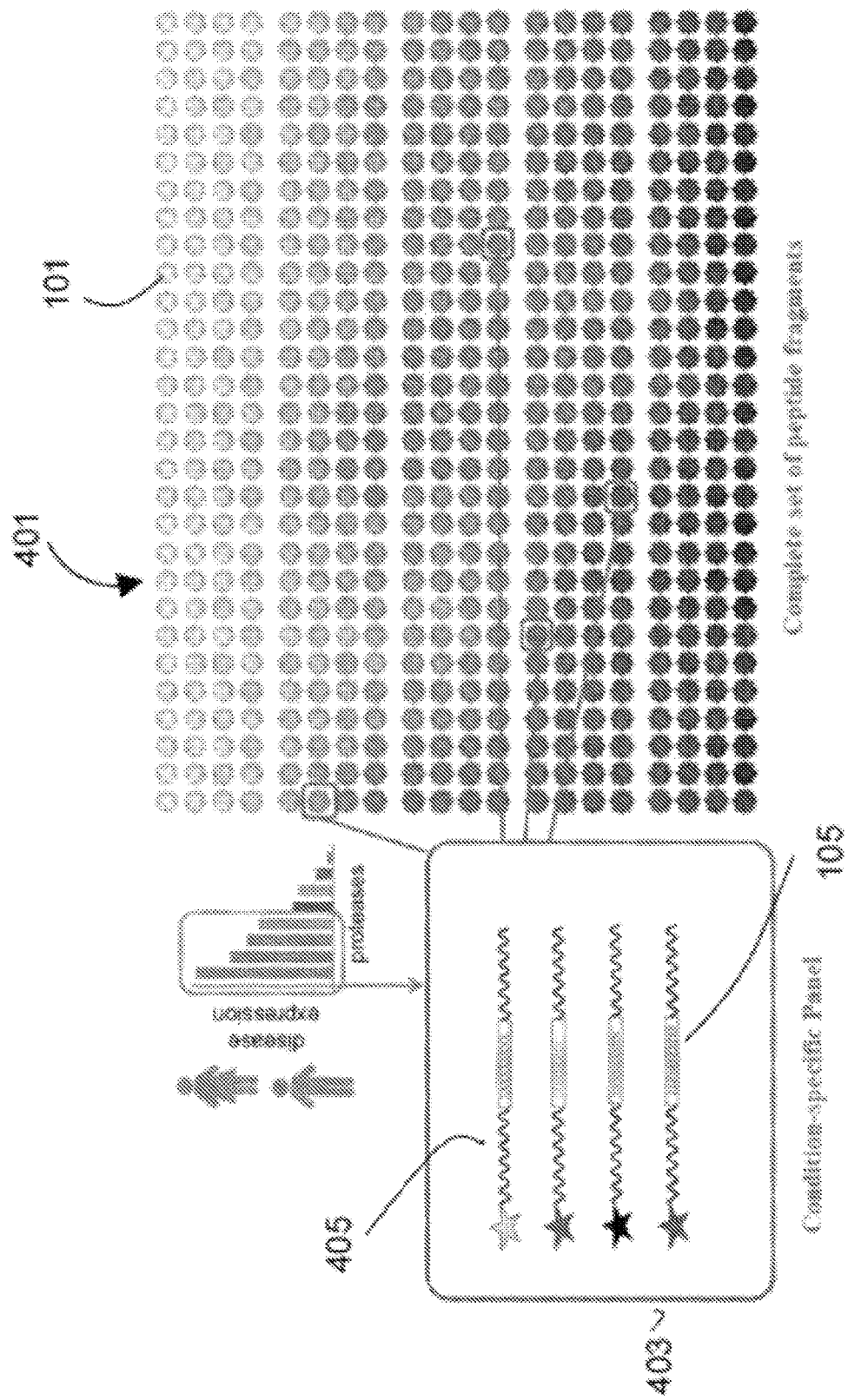
FIG. 4 shows the selection of probes to use in a composition to analyze the activities of agents to analyze one or more particular, biological conditions or disease states. The activity of one or more agents may be associated with a biological condition or disease state. This may include the progression of a particular condition or state over time. Thus, to evaluate a biological condition or disease state in a subject, probes that can be cleaved by agents of interest are selected from the library for inclusion in a condition-specific panel 403. The selected probes 405 of the condition-specific panel are differentially labeled so that the activity of the predetermined proteases can be measured 305. The different probes 101, including those included in library 401, may include features that confer properties to the fragments that ensure accurate, multiplex detection of agent activity. Such properties include, for example improved cleavage, detection, solubility, stability, reproducibility, robustness and/or expanded compatibility with different types of reporter.

Please replace Fig. 1 with Fig. 1 as shown on the attached page.

Signed and Sealed this
Seventeenth Day of October, 2023

Katherine Kelly Vidal
*Director of the United States Patent and Trademark Office*

United States Patent
Touti et al.

(10) Patent No.: US 11,604,193 B2
(45) Date of Patent: Mar. 14, 2023

(54) EX VIVO PROTEASE ACTIVITY DETECTION FOR DISEASE DETECTION/DIAGNOSTIC, STAGING, MONITORING AND TREATMENT

(71) Applicant: Glympse Bio, Inc., Cambridge, MA (US)

(72) Inventors: Fayçal Touti, Belmont, MA (US); Wendy Winckler Adamovich, Melrose, MA (US); Sophie Cazanave, Cambridge, MA (US); Mehar Cheema, Medford, MA (US); Robert S. Langer, Newton, MA (US)

(73) Assignee: GLYMPSE BIO, INC., Cambridge, MA (US)

( * ) Notice: Subject to any disclaimer, the term of this patent is extended or adjusted under 35 U.S.C. 154(b) by 0 days.

(21) Appl. No.: 17/573,129

(22) Filed: Jan. 11, 2022

(65) Prior Publication Data
US 2022/0178935 A1    Jun. 9, 2022

Related U.S. Application Data

(63) Continuation-in-part of application No. PCT/US2021/049948, filed on Sep. 10, 2021.
(Continued)

(51) Int. Cl.
*G01N 33/58*    (2006.01)
*G01N 33/573*   (2006.01)
(Continued)

(52) U.S. Cl.
CPC ....... *G01N 33/573* (2013.01); *G01N 21/6428* (2013.01); *G01N 33/542* (2013.01);
(Continued)

(58) Field of Classification Search
CPC ............. G01N 33/582; G01N 21/6428; G01N 2021/6432; G01N 2021/6441; G01N 2800/085
See application file for complete search history.

(56) References Cited

U.S. PATENT DOCUMENTS 10,100,198 B2 * 10/2018 Kundu ............. C09B 23/083
10,619,219 B2 *  4/2020 McNamara ......... C12Q 1/689
(Continued)

FOREIGN PATENT DOCUMENTS

ES              2325584 T3 *  9/2009  ........ A61K 39/0011
WO    WO-2008018933 A2    2/2008
(Continued)

OTHER PUBLICATIONS

Fluorescent Labeling of (Oligo)Nucleotides by a New Fluoride Cleavable Linker Capable of Versatile Attachment Modes, to Knapp et al., Bioconjugate Chem. 2010, 21, 1043-1055.*
(Continued)

*Primary Examiner* — Mohamed K Amara
(74) *Attorney, Agent, or Firm* — Wilson Sonsini Goodrich & Rosati

(57) ABSTRACT

The present application provides compositions and methods for determining a disease or condition in a subject. The method comprises contacting a body fluid with a molecule comprising a reporter thereof and the reported is cleaved by an agent in the body fluid. Diseases and conditions that can be determined by the method are also described.

17 Claims, 58 Drawing Sheets

Specification includes a Sequence Listing.

SEQUENCE LISTING

```
<160> NUMBER OF SEQ ID NOS: 1362

<210> SEQ ID NO 1
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 1

Ser Gly Arg Ser Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Gly Pro Arg Glu Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Glu Pro Asp Ser Gly Ser Gln
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Val Ala Asp Ser Ser Met Glu Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Thr Ser Tyr
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Arg Phe Lys
1
```

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Val Pro Leu
1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Asp Val Ala Asp
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Glu Thr Asp
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Glu His Asp
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Glu Gln Asp
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 12

Asp Glu Val Asp
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Glu Ile Asp
1

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Gln Val Asp Gly Trp
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Glu Val Asp Gly Trp
1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Glu Val Asp
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Glu Val Glu
1

<210> SEQ ID NO 18
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Pro Val
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Phe Lys Phe
1

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Arg Arg Gly Lys Gly Gly
1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Lys Lys Arg
1

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: p-Nitro phenylalanine

<400> SEQUENCE: 22

Phe Ala Ala Phe Phe Val Leu
1               5

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Val Val Arg
1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Gln Lys Leu Arg
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Pro Gly Phe Ser Ala Phe
1               5

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Pro Arg
1

<210> SEQ ID NO 27
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Arg
1

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Pro Leu Gly Leu
1               5

<210> SEQ ID NO 29
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Pro Leu Gly Leu
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: gamma aminobutyric acid

<400> SEQUENCE: 30

Xaa Pro Gln Gly Leu Glu
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Lys Pro Leu Ala Leu
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Pro Ser Gly Ile His Val
1               5

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Ala His Arg Thr Thr Phe Tyr Arg Arg Gly Ala
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 34

Trp Lys Leu Arg Ser Ser Lys Gln
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Phe Arg
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Tyr Arg Ile Phe
1               5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Pro Tyr
1

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ala Phe Arg Ser Ala Tyr Gly
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Ala Ala Phe Arg Phe Ser Gln Ala
1               5

<210> SEQ ID NO 40
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Pro Arg
1

<210> SEQ ID NO 41
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly
1

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Leu Arg Ser Ser Lys Gln
1               5

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ala Ser Arg
1

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Phe Ala Gln Ala Gln Gln Gln Leu Pro
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 45

Lys Pro Ala Lys Phe Phe Arg Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: L-Homophenylalanine

<400> SEQUENCE: 46

Pro Arg Ala Ala Ala Phe Thr Ser Pro
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Gly Pro Gln Arg Phe Ser Gly Ala Pro
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: L-Homophenylalanine

<400> SEQUENCE: 48

Phe Phe Leu Ala Gln Ala Phe Arg Ser
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Leu Ala Gln Ala Val
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 50

Arg Thr Ala Ala Val Phe Arg Pro
1               5

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Val Gln Glu Phe Arg Gly Val Thr Ala Val Ile Arg
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Glu Gly Glu Ala Arg Gly Ser Val Ile
1               5                   10

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Leucine

<400> SEQUENCE: 53

Leu Thr Arg
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Phe Ala Glu Arg Lys
1               5

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Val Tyr
1
```

```
<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Lys Arg Lys Ile Val Leu
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Ser His Leu Gly Leu Ala Arg
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Pro Ser Arg Ser Ser Lys Ile
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Thr Gly Arg Asn Gly Phe Lys
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Leu Leu Arg Ser Glu Glu Thr
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 61

His Arg Gly Arg Thr Leu Glu Ile
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Leu Gly Arg Ser Tyr Lys Val
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Lys Gln Arg Ile Ile Gly Gly
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Arg Gln Arg Ile Ile Gly Gly
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Gln Arg Ile Tyr Lys
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Leu Gly Arg Lys Ile Gln Ile
1               5

<210> SEQ ID NO 67
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 67

His Ala Ala Pro Arg Ser Ala Asp Ile Gln Ile Asp Ile
1               5                   10

<210> SEQ ID NO 68
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Gly Arg
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Leu Gly Arg
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Leu Gln Arg
1

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Val Ala Arg Thr Leu Leu Val
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Arg Ile Phe Gly
1               5
```

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Pro Lys
1

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Phe Ser Pro Tyr
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Glu Leu Arg His Ala Gly His
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Gln Ser Arg Ile Val Gly Gly Glu
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Gln Ala Val Tyr Gln Thr Ile
1               5

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 78

Val Ala Tyr Ser Gly Glu Asn Thr Phe Gly Phe
1               5                   10

<210> SEQ ID NO 79
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Arg
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Thr Ala Asp
1

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Pro Leu Glu Ser Asn Ala Val
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Pro Leu Gly Leu Ala Arg
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ala Phe Phe
1

<210> SEQ ID NO 84
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Val Lys Arg Gly Leu Ala
1               5

<210> SEQ ID NO 85
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ala Leu
1

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Methionine
<220> FEATURE:
<221> NAME/KEY: MOD_RES
<222> LOCATION: (5)..(5)
<223> OTHER INFORMATION: D-Glutamic acid
<220> FEATURE:
<221> NAME/KEY: MOD_RES
<222> LOCATION: (8)..(8)
<223> OTHER INFORMATION: D-Asparagine
<220> FEATURE:
<221> NAME/KEY: MOD_RES
<222> LOCATION: (9)..(9)
<223> OTHER INFORMATION: D-Aspartic acid
<220> FEATURE:
<221> NAME/KEY: MOD_RES
<222> LOCATION: (10)..(10)
<223> OTHER INFORMATION: D-Asparagine
<220> FEATURE:
<221> NAME/KEY: MOD_RES
<222> LOCATION: (11)..(11)
<223> OTHER INFORMATION: D-Glutamic acid
<220> FEATURE:
<221> NAME/KEY: MOD_RES
<222> LOCATION: (12)..(12)
<223> OTHER INFORMATION: D-Glutamic acid
<220> FEATURE:
<221> NAME/KEY: MOD_RES
<222> LOCATION: (16)..(16)
<223> OTHER INFORMATION: D-Serine
<220> FEATURE:
<221> NAME/KEY: MOD_RES
<222> LOCATION: (18)..(18)
<223> OTHER INFORMATION: D-Arginine

<400> SEQUENCE: 86

Cys Gly Gly Met Glu Gly Val Asn Asp Asn Glu Glu Gly Phe Phe Ser
1               5                   10                  15

Ala Arg

<210> SEQ ID NO 87
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Pro Gln Gly Ile Trp Gly Gln
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Leu Val Pro Arg Gly Ser
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Pro Val Gly Leu Ile
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Pro Trp Gly Ile Trp Gly Gln
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Pro Val Pro Leu Ser Leu Val Met
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

<223> OTHER INFORMATION: D-Phenylalanine
<220> FEATURE:
<221> NAME/KEY: MOD_RES
<222> LOCATION: (3)..(3)
<223> OTHER INFORMATION: piperidine carboxylic acid

<400> SEQUENCE: 92

Gly Phe Xaa Arg Ser Gly Gly
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Pro Leu Gly Met Arg Gly
1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Leu Gly Met Arg Gly
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L-cyclohexylalanine
<220> FEATURE:
<221> NAME/KEY: MOD_RES
<222> LOCATION: (4)..(4)
<223> OTHER INFORMATION: L- Methyl cysteine

<400> SEQUENCE: 95

Pro Xaa Gly Cys His Ala
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Pro Leu Ala Leu Trp Glu Ser Gln
1               5

<210> SEQ ID NO 97
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 97

Ser Gly Lys Gly Pro Arg Gln Ile Thr Ala
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Gly Pro Leu Phe Tyr Ser Val Thr Ala
1               5                   10

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Gly Arg Ile Phe Leu Arg Thr Ala
1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Arg Ser Glu Asn Ile Arg Thr Ala
1               5                   10

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ser Gly Gly Ser
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Pro Ile Leu Phe Phe Arg Leu Lys Gly
1               5                   10
```

```
<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 103

Ala Trp Glu Ser Arg Leu
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 104

Asn Glu Lys Ser Gly Leu
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Ala Thr Ile Val Tyr
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Pro Phe Val Val Ser
1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
```

```
<400> SEQUENCE: 107

Phe His Leu Phe Thr Lys
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine

<400> SEQUENCE: 108

Leu Asn Trp His Lys His
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Phe Ala Arg Arg Trp Gly
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Gly Lys Trp Ser Lys
1               5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Glu Glu Ala Gln Pro
1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Tyr Gly Ala Ile Lys Lys
1               5
```

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 113

Thr Ser Leu Glu Gly Tyr
1               5

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Pro Asn Asn Phe Gly Ser
1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Glu Asp Thr Arg Asn Thr
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Asp Leu Glu Gln Ser
1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Ala Leu His Asn Asp
1               5

<210> SEQ ID NO 118
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 118

Ala Asp Ser Phe Phe Lys
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Thr Phe Trp Arg Ala
1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 120

Leu Ser Asp Leu Arg Leu
1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Glu Val Gly Trp Thr Tyr
1               5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 122

Ile Ala Phe Arg Gln Leu
1               5

<210> SEQ ID NO 123
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 123

Tyr Asn Ile His Thr Leu
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine

<400> SEQUENCE: 124

Leu Leu Trp Ala Asn His
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Leu Tyr Ser Val Gln Val
1               5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 126

Ser His Ile Leu Ser Asn
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Lys Leu Leu Ile Asp Val
1               5

<210> SEQ ID NO 128
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine

<400> SEQUENCE: 128

Glu Leu Gly Val Phe Asp
1               5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

His Gln Ala Tyr Thr Leu
1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Val Arg Lys Ile Gln
1               5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Arg Glu Asn Ser Pro
1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Tyr Asp Lys Pro Arg
1               5

<210> SEQ ID NO 133
<211> LENGTH: 6
<212> TYPE: PRT
<213> ORGANISM: Artificial Sequence
```

```
-continued

<220> FEATURE:
<223> OTHER INFORMATION: Description of Artificial Sequence: Synthetic
      peptide

<400> SEQUENCE: 133

Arg Pro Trp Lys Gln Leu
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Pro Leu Gln Arg Tyr
1               5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 135

Tyr Gln Gly Gln Lys Leu
1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Arg Ile Ser Ser Ile
1               5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

His Ser Leu Thr Asn Val
1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 138

Glu Trp Asp Phe Pro Glu
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 139

Tyr Leu Ala Leu Asp Gly
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 140

Phe Ile Tyr Leu Pro Thr
1               5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly His Glu Thr Trp Val
1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Tyr Ile Gly Asp Glu
1               5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 143

Ala Gly Thr Ala His Pro
1               5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine

<400> SEQUENCE: 144

Val Leu Thr Glu Ile Trp
1               5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Asp Asp Trp Gln Asn
1               5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Leu Asn Gln Glu Tyr
1               5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Tyr Arg Asp Ala Val Ala
1               5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Gly Pro Lys Gly Asn
1               5
```

```
<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp His Val Pro Gln Ile
1               5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Lys Glu Pro Ile Leu
1               5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 151

Val Trp Asn Leu Val His
1               5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Val Ile Ile Glu His
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Phe Gln Thr Asp Asn Leu
1               5

<210> SEQ ID NO 154
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 154

Arg Phe Leu His Gly Ile
1               5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Tyr Ala Glu Arg Thr Thr
1               5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asn Arg Gly Glu Leu Pro
1               5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

His His Tyr Phe Asn Tyr
1               5

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Thr Pro Tyr Tyr His
1               5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 159

Trp Phe Tyr Pro Ser Ala
1               5

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Glu Phe Leu Phe Ser
1               5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Trp Tyr Lys Thr Gln Tyr
1               5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Val Thr His Leu Lys Val
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Asn Gly Gly Phe Ser
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Thr Val Leu Gly Leu Asp
1               5

<210> SEQ ID NO 165
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine

<400> SEQUENCE: 165

Ser Tyr Trp Pro Leu Gln
1               5

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ser Gln Gln His Arg
1               5

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Lys Asn Pro Ala Lys Ala
1               5

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine

<400> SEQUENCE: 168

Leu Tyr Trp Leu Val Glu
1               5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ser Trp Trp Ile Phe Glu
1               5

<210> SEQ ID NO 170
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 170

Val Asn Tyr Glu Gln Asp
1               5

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 171

His Phe Phe Leu Ala Glu
1               5

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asp Ile Pro Pro His Trp
1               5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine

<400> SEQUENCE: 173

Val Asp Gln Trp Leu Trp
1               5

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine

<400> SEQUENCE: 174

Leu Arg Ser Leu Leu Lys
1               5
```

```
<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (2)..(2)
<223> OTHER INFORMATION: Norleucine

<400> SEQUENCE: 175

Leu Leu Ile Arg His Ala
1               5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

His Asp Val Lys Phe Ile
1               5

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Lys Arg Val Gln Phe Leu
1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 178

Arg Asp Leu Tyr Ala Glu
1               5

<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
```

<400> SEQUENCE: 179

Leu Leu Ile Tyr Phe Glu
1               5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Leu Arg Thr Lys Gln Ser
1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Trp His Gly Gln Gln Tyr
1               5

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Pro Glu Gly Thr Ile
1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Glu Leu Asp Pro Ile Pro
1               5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Arg Ala Ala Asp Phe
1               5

<210> SEQ ID NO 185
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

His Phe Ile Asp Tyr Ile
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (3)..(3)
<223> OTHER INFORMATION: Norleucine

<400> SEQUENCE: 186

Ser Leu Leu Arg Val His
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Phe Arg Lys Ile Ile
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 188

Thr Tyr Glu Leu Phe Ser
1               5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

His Leu Leu Gly Phe Tyr
1               5
```

```
<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine

<400> SEQUENCE: 190

Leu Trp Thr Ala Leu Thr
1               5

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 191

Ile Trp Asn Leu Val Tyr
1               5

<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Arg Arg Asn Pro Leu Trp
1               5

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Trp Tyr Gly Gly Ile
1               5

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Lys Thr Gly Asp Ala Arg
1               5
```

```
<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asn Tyr Trp Glu Ala Asn
1               5

<210> SEQ ID NO 196
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine

<400> SEQUENCE: 196

Leu Gln Phe Asp Thr Ser
1               5

<210> SEQ ID NO 197
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Lys Arg Gly Ala Val Glu
1               5

<210> SEQ ID NO 198
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Leu Lys Pro Thr Glu
1               5

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Glu Asn Asp Arg Leu Pro
1               5

<210> SEQ ID NO 200
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 200

Asn Ser Tyr Gln Val Gln
1               5

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Tyr Pro Lys Glu Tyr Leu
1               5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Asn Asn Lys Trp Gln
1               5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine

<400> SEQUENCE: 203

Leu Glu Phe Gln Gly Trp
1               5

<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Pro Val Arg Ser Thr Asn
1               5

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Gln Ala Ile Lys Val
1               5

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 206

Trp Ala Leu Leu Tyr His
1               5

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Ser Trp Ile His Ala
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala His Asp Ile Val
1               5

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Arg His Asn Val Ala Ser
1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ser Val Phe Val Ile Glu
1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Phe Ala Lys Tyr Tyr Lys
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Pro Tyr Asn Thr Leu Gln
1               5

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (6)..(6)
<223> OTHER INFORMATION: Norleucine

<400> SEQUENCE: 213

Leu Asp Trp Gly His Leu
1               5

<210> SEQ ID NO 214
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Asn Arg Glu Trp Phe
1               5

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Lys Ser Glu His Thr
1               5

```
<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 216

Phe Pro Leu Thr Asp Gln
1               5

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 217

Trp Ser Lys Phe Trp Leu
1               5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Arg Phe Thr Arg Pro His
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 219

Gln Glu Thr Leu Lys Asp
1               5

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 220

His Trp Trp Asp Val Leu
1               5

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine

<400> SEQUENCE: 221

Phe Asn Leu Val Leu Ser
1               5

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Ala Trp Arg Gln Arg
1               5

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Thr Phe His Ile Phe Leu
1               5

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Trp Pro Gln His Val Lys
1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
```

```
<400> SEQUENCE: 225

Leu Ile Leu His Lys Asn
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Asp Leu Glu Gln Pro
1               5

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine

<400> SEQUENCE: 227

His Gln Lys Lys Leu Pro
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Val Thr Trp Leu Asn
1               5

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Gly Glu Pro Phe Lys
1               5

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
```

<400> SEQUENCE: 230

Ser Arg Leu Ala Thr Thr
1               5

<210> SEQ ID NO 231
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 231

Leu Ala Phe Leu Asn His
1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Pro Pro Ser Gly Leu Ser
1               5

<210> SEQ ID NO 233
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Tyr Thr His Ser Ser Pro
1               5

<210> SEQ ID NO 234
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Gly Ser His Tyr Arg
1               5

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine

```
<400> SEQUENCE: 235

Tyr Leu Gly Asn Gly Tyr
1               5

<210> SEQ ID NO 236
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asp Ser Ile Thr Val Ser
1               5

<210> SEQ ID NO 237
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gln Thr Pro Asn Ile Gln
1               5

<210> SEQ ID NO 238
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Lys Leu Phe Phe Gly Tyr
1               5

<210> SEQ ID NO 239
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Thr Gln Asn Phe Asn Trp
1               5

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Tyr Ser Asp His Glu Val
1               5

<210> SEQ ID NO 241
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 241

Arg Tyr Val Val Pro Ala
1               5

<210> SEQ ID NO 242
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ile Leu His Arg Ile Arg
1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 243

Glu Ser Asp Asn Gln Leu
1               5

<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 244

Tyr Asp Asp Lys Gly Leu
1               5

<210> SEQ ID NO 245
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 245

Gln Leu Ser Leu Val Trp
1               5
```

```
<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 246

Pro Gly Gly Glu Arg Leu
1               5

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Trp Lys His His Pro Asp
1               5

<210> SEQ ID NO 248
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Trp Val Asp Glu Asp
1               5

<210> SEQ ID NO 249
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asn Ala Tyr Asn Glu Ile
1               5

<210> SEQ ID NO 250
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Glu Lys Ala Pro Arg
1               5

<210> SEQ ID NO 251
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 251

Pro Trp Gln Ile Gly Lys
1               5

<210> SEQ ID NO 252
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ile Ala Gln Val Gly Asn
1               5

<210> SEQ ID NO 253
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine

<400> SEQUENCE: 253

Val Leu Arg Gln Ser Glu
1               5

<210> SEQ ID NO 254
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Thr Glu Arg Val Asp Ala
1               5

<210> SEQ ID NO 255
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Trp Leu Arg Trp Arg Leu
1               5

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 256

Trp Lys Thr Lys Gly Gln
1               5

<210> SEQ ID NO 257
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gln Ser Asn Gly Asp Val
1               5

<210> SEQ ID NO 258
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Thr Leu Phe Tyr Ala Leu
1               5

<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Thr Val Thr Leu Asn Pro
1               5

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Tyr Ala Phe Gly Arg Lys
1               5

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asp Tyr Asn Tyr Trp Asp
1               5

<210> SEQ ID NO 262
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Glu Trp His Glu Ile Ile
1               5

<210> SEQ ID NO 263
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gln Lys Ala Ala Trp Asp
1               5

<210> SEQ ID NO 264
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Asn Thr Ser Ala Asp
1               5

<210> SEQ ID NO 265
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

His Glu Gly Glu Tyr Val
1               5

<210> SEQ ID NO 266
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Trp Ser Pro Ser Phe Lys
1               5

<210> SEQ ID NO 267
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 267

His Asp Glu His Trp Thr
1               5

<210> SEQ ID NO 268
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 268

Tyr Val Trp Leu Arg Asp
1               5

<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (4)..(4)
<223> OTHER INFORMATION: Norleucine

<400> SEQUENCE: 269

Leu Asp Pro Leu Lys Phe
1               5

<210> SEQ ID NO 270
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (3)..(3)
<223> OTHER INFORMATION: Norleucine

<400> SEQUENCE: 270

Leu Arg Leu Phe Trp Asp
1               5

<210> SEQ ID NO 271
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)

```
<223> OTHER INFORMATION: Norleucine

<400> SEQUENCE: 271

Asp Ile Ala Ile Thr Leu
1               5

<210> SEQ ID NO 272
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 272

Pro Ile Leu Arg Phe His
1               5

<210> SEQ ID NO 273
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Val Trp Gln Gly Tyr Ile
1               5

<210> SEQ ID NO 274
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 274

Lys Lys Leu Ser Asn Pro
1               5

<210> SEQ ID NO 275
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gly His Pro Leu Ser Pro
1               5

<210> SEQ ID NO 276
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 276

Val Arg Gln His Lys Pro
1               5

<210> SEQ ID NO 277
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ala Gln Asn Phe Tyr Arg
1               5

<210> SEQ ID NO 278
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Val Ala Gly Lys Ser Ile
1               5

<210> SEQ ID NO 279
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Leu Val Gly Gln Val Asn
1               5

<210> SEQ ID NO 280
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Val Lys His Phe Thr
1               5

<210> SEQ ID NO 281
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Lys Ser Val Val Ser
1               5

<210> SEQ ID NO 282
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine

<400> SEQUENCE: 282

Tyr Leu Gln Glu Trp Leu
1               5

<210> SEQ ID NO 283
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine

<400> SEQUENCE: 283

Gly Leu Tyr Ile Asp Glu
1               5

<210> SEQ ID NO 284
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asn Ala Gly Ser Lys Phe
1               5

<210> SEQ ID NO 285
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Glu Phe Val His Asn Pro
1               5

<210> SEQ ID NO 286
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 286

Trp Glu Leu Val Lys Ile
1               5
```

```
<210> SEQ ID NO 287
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Trp Val Gly Ala Ser His
1               5

<210> SEQ ID NO 288
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 288

Ile Thr Thr Leu Tyr Leu
1               5

<210> SEQ ID NO 289
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gly His Ile Asp Glu Tyr
1               5

<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 290

Lys Val Leu Asp Tyr Gly
1               5

<210> SEQ ID NO 291
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
```

```
<400> SEQUENCE: 291

Gln Glu Lys Gln Thr Leu
1               5

<210> SEQ ID NO 292
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Glu Val Gly His Glu Ala
1               5

<210> SEQ ID NO 293
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Trp Glu Gly Gln Tyr
1               5

<210> SEQ ID NO 294
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Phe Leu Val Gln Trp Thr
1               5

<210> SEQ ID NO 295
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ser Lys Trp Gly Tyr Trp
1               5

<210> SEQ ID NO 296
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine

<400> SEQUENCE: 296

Thr Trp Ile Ser Leu Gln
1               5
```

<210> SEQ ID NO 297
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Val Ile Asp Lys Asp Phe
1               5

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Val Lys Phe Ala Ile Tyr
1               5

<210> SEQ ID NO 299
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 299

His Asn Gln Leu Lys Ser
1               5

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

<400> SEQUENCE: 300

Gln Tyr Val Phe Phe Leu
1               5

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine

```
<400> SEQUENCE: 301

Tyr Asn Pro Arg Glu Leu
1               5

<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine

<400> SEQUENCE: 302

Lys His Gly Leu Pro Glu
1               5

<210> SEQ ID NO 303
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Trp Ser Arg Glu Tyr Trp
1               5

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ile Asp Arg Val Asp Lys
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 305

Gly Asp Arg Glu Asn Ser Pro Lys Leu
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<221> NAME/KEY: MOD_RES
<222> LOCATION: (9)..(9)
<223> OTHER INFORMATION: Lys modified with a CPQ2 quencher

<400> SEQUENCE: 306

Gly Asp Arg Glu Asn Ser Pro Leu Lys
1               5

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 307

Asn Ala Gly Ser Lys Phe Lys Gln
1               5

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 308

Asn Ala Gly Ser Lys Phe Gln Lys
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 309

Gly His Leu Leu Gly Phe Tyr Lys Val
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys modified with a CPQ2 quencher

<400> SEQUENCE: 310

Gly His Leu Leu Gly Phe Tyr Val Lys
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher
<220> FEATURE:
<221> NAME/KEY: MOD_RES
<222> LOCATION: (9)..(9)
<223> OTHER INFORMATION: Norleucine

<400> SEQUENCE: 311

Gly Gln Glu Lys Gln Thr Leu Lys Leu
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 312

Gly Gln Glu Lys Gln Thr Leu Leu Lys
1               5

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 313

Lys Gly Asp Pro Phe Val Val Ser Lys Trp
1               5                   10

```
<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 314

Lys Gly Asp Pro Phe Val Val Ser Trp Lys
1               5                   10

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 315

Asn Ala Tyr Asn Glu Ile Lys Arg
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 316

Asn Ala Tyr Asn Glu Ile Arg Lys
1               5

<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (7)..(7)
<223> OTHER INFORMATION: Lys modified with a CPQ2 quencher
```

```
<400> SEQUENCE: 317

Val Leu Arg Gln Ser Glu Lys Asn
1               5

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher

<400> SEQUENCE: 318

Val Leu Arg Gln Ser Glu Asn Lys
1               5

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (7)..(7)
<223> OTHER INFORMATION: Lys modified with a CPQ2 quencher

<400> SEQUENCE: 319

Tyr Asn Pro Arg Glu Leu Lys Ile
1               5

<210> SEQ ID NO 320
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher

<400> SEQUENCE: 320

Tyr Asn Pro Arg Glu Leu Ile Lys
1               5

<210> SEQ ID NO 321
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 321

Glu Phe Val His Asn Pro Lys Lys
1               5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 322

Glu Phe Val His Asn Pro Lys Lys
1               5

<210> SEQ ID NO 323
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 323

Lys Arg Val Gln Phe Leu Lys His
1               5

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 324

Lys Arg Val Gln Phe Leu His Lys
1               5

<210> SEQ ID NO 325
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
```

```
<221> NAME/KEY: MOD_RES
<222> LOCATION: (7)..(7)
<223> OTHER INFORMATION: Lys modified with a CPQ2 quencher

<400> SEQUENCE: 325

Leu Ile Leu His Lys Asn Lys Gly
1               5

<210> SEQ ID NO 326
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher

<400> SEQUENCE: 326

Leu Ile Leu His Lys Asn Gly Lys
1               5

<210> SEQ ID NO 327
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Lys modified with a CPQ2 quencher

<400> SEQUENCE: 327

Trp Ala Leu Leu Tyr His Lys Ser
1               5

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher

<400> SEQUENCE: 328

Trp Ala Leu Leu Tyr His Ser Lys
1               5

<210> SEQ ID NO 329
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 329

Ala His Asp Ile Val Asn Lys Tyr
1               5

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 330

Ala His Asp Ile Val Asn Tyr Lys
1               5

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 331

Ser Val Phe Val Ile Glu Lys Pro
1               5

<210> SEQ ID NO 332
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 332

Ser Val Phe Val Ile Glu Pro Lys
1               5

<210> SEQ ID NO 333
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
```

```
<223> OTHER INFORMATION: Lys modified with a CPQ2 quencher

<400> SEQUENCE: 333

Pro Pro Ser Gly Leu Ser Lys Glu
1               5

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 334

Pro Pro Ser Gly Leu Ser Glu Lys
1               5

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 335

Arg Trp Tyr Gly Gly Ile Lys Phe
1               5

<210> SEQ ID NO 336
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 336

Arg Trp Tyr Gly Gly Ile Phe Lys
1               5

<210> SEQ ID NO 337
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (7)..(7)
<223> OTHER INFORMATION: Lys modified with a CPQ2 quencher
```

```
<400> SEQUENCE: 337

Gln Tyr Val Phe Phe Leu Lys Asp
1               5

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher

<400> SEQUENCE: 338

Gln Tyr Val Phe Phe Leu Asp Lys
1               5

<210> SEQ ID NO 339
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher

<400> SEQUENCE: 339

Phe Ala Lys Tyr Tyr Lys Lys Thr
1               5

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 340

Phe Ala Lys Tyr Tyr Lys Thr Lys
1               5

<210> SEQ ID NO 341
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys modified with a CPQ2 quencher
```

<400> SEQUENCE: 341

Gln Val Lys His Phe Thr Lys Ala
1               5

<210> SEQ ID NO 342
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys modified with a CPQ2 quencher

<400> SEQUENCE: 342

Gln Val Lys His Phe Thr Ala Lys
1               5

<210> SEQ ID NO 343
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys modified with a CPQ2 quencher

<400> SEQUENCE: 343

Ala Pro Lys
1

<210> SEQ ID NO 344
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 344

His Lys Asp Arg Glu Asn Ser Pro
1               5

<210> SEQ ID NO 345
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 345

Lys His Asp Arg Glu Asn Ser Pro
1               5

```
<210> SEQ ID NO 346
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 346

Trp Lys Asn Ala Gly Ser Lys Phe
1               5

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 347

Lys Trp Asn Ala Gly Ser Lys Phe
1               5

<210> SEQ ID NO 348
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 348

Ser Lys His Leu Leu Gly Phe Tyr
1               5

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 349

Lys Ser His Leu Leu Gly Phe Tyr
1               5

<210> SEQ ID NO 350
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine

<400> SEQUENCE: 350

Lys Lys Gln Glu Lys Gln Thr Leu
1               5

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine

<400> SEQUENCE: 351

Lys Lys Gln Glu Lys Gln Thr Leu
1               5

<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 352

Gly Lys Asp Pro Phe Val Val Ser
1               5

<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 353

Lys Gly Asp Pro Phe Val Val Ser
1               5

<210> SEQ ID NO 354
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 354

Pro Lys Asn Ala Tyr Asn Glu Ile
1               5

<210> SEQ ID NO 355
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 355

Lys Pro Asn Ala Tyr Asn Glu Ile
1               5

<210> SEQ ID NO 356
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (4)..(4)
<223> OTHER INFORMATION: Norleucine

<400> SEQUENCE: 356

Asp Lys Val Leu Arg Gln Ser Glu
1               5

<210> SEQ ID NO 357
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (4)..(4)
<223> OTHER INFORMATION: Norleucine

<400> SEQUENCE: 357

Lys Asp Val Leu Arg Gln Ser Glu
1               5

<210> SEQ ID NO 358
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine

<400> SEQUENCE: 358

Glu Lys Tyr Asn Pro Arg Glu Leu
1               5

<210> SEQ ID NO 359
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine

<400> SEQUENCE: 359

Lys Glu Tyr Asn Pro Arg Glu Leu
1               5

<210> SEQ ID NO 360
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 360

Thr Lys Glu Phe Val His Asn Pro
1               5

<210> SEQ ID NO 361
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 361

Lys Thr Glu Phe Val His Asn Pro
1               5

<210> SEQ ID NO 362
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 362

Gln Lys Lys Arg Val Gln Phe Leu
1               5

<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 363

Lys Gln Lys Arg Val Gln Phe Leu
1               5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine

<400> SEQUENCE: 364

Tyr Lys Leu Ile Leu His Lys Asn
1               5

<210> SEQ ID NO 365
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine

<400> SEQUENCE: 365

Lys Tyr Leu Ile Leu His Lys Asn
1               5

<210> SEQ ID NO 366
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine

<400> SEQUENCE: 366

Phe Lys Trp Ala Leu Leu Tyr His
1               5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine

<400> SEQUENCE: 367

Lys Phe Trp Ala Leu Leu Tyr His
1               5

<210> SEQ ID NO 368
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 368

Ile Lys Ala His Asp Ile Val Asn
1               5

<210> SEQ ID NO 369
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 369

Lys Ile Ala His Asp Ile Val Asn
1               5

<210> SEQ ID NO 370
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 370

Val Lys Ser Val Phe Val Ile Glu
1               5

<210> SEQ ID NO 371
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 371

Lys Val Ser Val Phe Val Ile Glu
1               5

<210> SEQ ID NO 372
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (2)..(2)
<223> OTHER INFORMATION: carboxy-fluorescein-L-lysine

<400> SEQUENCE: 372

Leu Lys Pro Pro Ser Gly Leu Ser
1               5

<210> SEQ ID NO 373
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (2)..(2)
<223> OTHER INFORMATION: Norleucine

<400> SEQUENCE: 373

Lys Leu Pro Pro Ser Gly Leu Ser
1               5
```

```
<210> SEQ ID NO 374
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 374

Leu Lys Arg Trp Tyr Gly Gly Ile
1               5

<210> SEQ ID NO 375
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 375

Lys Leu Arg Trp Tyr Gly Gly Ile
1               5

<210> SEQ ID NO 376
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine

<400> SEQUENCE: 376

Asn Lys Gln Tyr Val Phe Phe Leu
1               5

<210> SEQ ID NO 377
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine

<400> SEQUENCE: 377

Lys Asn Gln Tyr Val Phe Phe Leu
1               5
```

```
<210> SEQ ID NO 378
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 378

Ala Lys Phe Ala Lys Tyr Tyr Lys
1               5

<210> SEQ ID NO 379
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 379

Lys Ala Phe Ala Lys Tyr Tyr Lys
1               5

<210> SEQ ID NO 380
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: carboxy-fluorescein-L-lysine

<400> SEQUENCE: 380

Arg Lys Gln Val Lys His Phe Thr
1               5

<210> SEQ ID NO 381
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 381

Lys Arg Gln Val Lys His Phe Thr
1               5

<210> SEQ ID NO 382
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: carboxy-fluorescein-L-lysine

<400> SEQUENCE: 382

Lys Pro Pro
1

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Proline
<220> FEATURE:
<221> NAME/KEY: MOD_RES
<222> LOCATION: (3)..(3)
<223> OTHER INFORMATION: D-Isoleucine
<220> FEATURE:
<221> NAME/KEY: MOD_RES
<222> LOCATION: (4)..(4)
<223> OTHER INFORMATION: D-Leucine
<220> FEATURE:
<221> NAME/KEY: MOD_RES
<222> LOCATION: (5)..(5)
<223> OTHER INFORMATION: D-Phenylalanine
<220> FEATURE:
<221> NAME/KEY: MOD_RES
<222> LOCATION: (6)..(6)
<223> OTHER INFORMATION: D-Phenylalanine
<220> FEATURE:
<221> NAME/KEY: MOD_RES
<222> LOCATION: (7)..(7)
<223> OTHER INFORMATION: D-Arginine
<220> FEATURE:
<221> NAME/KEY: MOD_RES
<222> LOCATION: (8)..(8)
<223> OTHER INFORMATION: D-Leucine
<220> FEATURE:
<221> NAME/KEY: MOD_RES
<222> LOCATION: (9)..(9)
<223> OTHER INFORMATION: D-Lysine

<400> SEQUENCE: 383

Lys Pro Ile Leu Phe Phe Arg Leu Lys
1               5

<210> SEQ ID NO 384
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Leu Arg Arg
1
```

```
<210> SEQ ID NO 385
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Arg
1

<210> SEQ ID NO 386
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Val Arg
1

<210> SEQ ID NO 387
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Arg Arg
1

<210> SEQ ID NO 388
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gly Arg
1

<210> SEQ ID NO 389
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Phe Arg
1

<210> SEQ ID NO 390
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 390

Arg Gly Lys
1

<210> SEQ ID NO 391
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gly Gly Arg
1

<210> SEQ ID NO 392
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Phe
1

<210> SEQ ID NO 393
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Asp
1

<210> SEQ ID NO 394
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Arg Arg
1

<210> SEQ ID NO 395
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Arg
1

<210> SEQ ID NO 396
<211> LENGTH: 1
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Arg
1

<210> SEQ ID NO 397
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Arg
1

<210> SEQ ID NO 398
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Pro Arg
1

<210> SEQ ID NO 399
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Pro Arg
1

<210> SEQ ID NO 400
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Leu Arg
1

<210> SEQ ID NO 401
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 401

Pro Phe Arg
1

<210> SEQ ID NO 402
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Leu Leu Arg
1

<210> SEQ ID NO 403
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gln Arg Arg
1

<210> SEQ ID NO 404
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Arg
1

<210> SEQ ID NO 405
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Arg Arg
1

<210> SEQ ID NO 406
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Leu Arg Gly Gly
1

<210> SEQ ID NO 407
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Arg Leu Arg Gly Gly
1               5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Arg Glu Leu Asn Gly Gly Ala Pro Ile
1               5

<210> SEQ ID NO 409
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Thr Ser Ala Val Leu Gln Ser Gly Phe Arg Lys
1               5                   10

<210> SEQ ID NO 410
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ser Gly Val Thr Phe Gln Gly Lys Phe Lys Lys
1               5                   10

<210> SEQ ID NO 411
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Ala Ala Phe Ala
1

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 412

His Gly Asp Gln Met Ala Gln Lys Ser
1               5

<210> SEQ ID NO 413
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Gly Pro Leu Gly Met Arg
1               5

<210> SEQ ID NO 414
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: L-homophenylalanine

<400> SEQUENCE: 414

Phe Phe Leu Ala Gln Ala Phe Arg Ser Lys
1               5                   10

<210> SEQ ID NO 415
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Ala His Ala Val Ser Arg Ile Arg Ile Tyr Leu Leu Pro Ala Lys
1               5                   10                  15

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Pro Leu Ala Leu Trp Ala Arg
1               5

<210> SEQ ID NO 417
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: S-para-methoxybenzyl cysteine
```

```
<400> SEQUENCE: 417

Pro Leu Ala Cys Trp Ala Arg
1               5

<210> SEQ ID NO 418
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Ala Pro Arg Trp Ile Gln Asp
1               5

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Leu Arg Glu Gln Gln Arg Leu Lys Ser
1               5

<210> SEQ ID NO 420
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Glu Phe Pro Ile Tyr Val Phe Leu Pro Ala Lys Lys
1               5                   10

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gly Ala Ala Asn Leu Val Arg Gly Gly
1               5

<210> SEQ ID NO 422
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Gly Tyr Ala Glu Leu Arg Met Gly
1               5

<210> SEQ ID NO 423
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 423

Ala Ala Gly Ala Met Phe Leu Glu Ala
1               5

<210> SEQ ID NO 424
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Leu Gly Gly Ser Gly Gln Arg Gly Arg Lys Ala Leu Glu
1               5                   10

<210> SEQ ID NO 425
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Leu Gly Gly Ser Gly His Tyr Gly Arg Ser Gly Leu Glu
1               5                   10

<210> SEQ ID NO 426
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Tyr Gly Arg Ser
1

<210> SEQ ID NO 427
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Phe Arg Gly Arg Lys
1               5

<210> SEQ ID NO 428
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Asp Arg Arg Lys Lys Leu Thr Gln
1               5
```

<210> SEQ ID NO 429
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

His Pro Gly Gly Pro Gln
1               5

<210> SEQ ID NO 430
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Lys Leu Arg Phe Ser Lys Gln
1               5

<210> SEQ ID NO 431
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Ala Ile Lys Phe Phe Ser Ala Gln
1               5

<210> SEQ ID NO 432
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Ile Lys Phe Phe Val Arg Gln
1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Arg Pro Pro Gly Phe Ser Ala Phe Lys
1               5

<210> SEQ ID NO 434
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Phe Ala Pro Gln Leu Ser
1               5

<210> SEQ ID NO 435
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Phe Ala Ala Gln Met Ala
1               5

<210> SEQ ID NO 436
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Gly Met Pro Ala Asn Gln
1               5

<210> SEQ ID NO 437
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Leu Ser Gly Arg Ser Asp Asn His
1               5

<210> SEQ ID NO 438
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Met Ala Ala Leu Ile Thr Arg Pro Asp Phe
1               5                   10

<210> SEQ ID NO 439
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Met Ala Ala Ala Ile Thr Arg Pro Arg Phe
1               5                   10

<210> SEQ ID NO 440
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Met Ala Ala Leu Ile Val Arg Pro Asp Leu
1               5                   10

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Thr Ser Gly Pro Asn Gln Glu Gln Glu
1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Thr Ala Gly Pro Asn Gln Glu Gln Glu
1               5

<210> SEQ ID NO 443
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Gly Pro Gly Pro Asn Gln Ala
1               5

<210> SEQ ID NO 444
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Ala Ser Gly Pro Ala Gly Pro Ala
1               5

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 445

Glu Arg Gly Glu Thr Gly Pro Ser Gly
1               5

<210> SEQ ID NO 446
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Val Ser Gln Glu Leu Gly Gln Arg
1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Thr Gly Pro Pro Gly Tyr Pro Thr Gly
1               5

<210> SEQ ID NO 448
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Thr Arg Leu Pro Val Tyr Gln
1               5

<210> SEQ ID NO 449
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Arg Gln Ala Arg Val Val Gly Gly
1               5

<210> SEQ ID NO 450
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Arg Gln Arg Arg Val Val Gly Gly
1               5

<210> SEQ ID NO 451
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Arg Gln Ala Arg Ala Val Gly Gly
1               5

<210> SEQ ID NO 452
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Arg Lys Arg Arg Gly Ser Arg Gly
1               5

<210> SEQ ID NO 453
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Lys Gln Ser Arg Lys Phe Val Pro
1               5

<210> SEQ ID NO 454
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Val Thr Gly Arg Ser
1               5

<210> SEQ ID NO 455
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Leu Lys Ser Arg Val Lys
1               5

<210> SEQ ID NO 456
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 456

Gly Ile Gly Ala Val Leu Lys Val Leu Thr
1               5                   10

<210> SEQ ID NO 457
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Gly Leu Pro Ala Leu Ile Ser Trp Ile Lys
1               5                   10

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Ser Glu Val Asn Leu Asp Ala Glu Phe
1               5

<210> SEQ ID NO 459
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Glu Glu Lys Pro Ile Cys Phe Phe Arg Leu Gly Lys Glu
1               5                   10

<210> SEQ ID NO 460
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Glu Glu Lys Pro Ile Leu Phe Phe Arg Leu Gly Lys Glu
1               5                   10

<210> SEQ ID NO 461
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Ala Pro Ser Ser Val Ile Ala Ala
1               5

<210> SEQ ID NO 462
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Lys Lys Ala Lys Arg Asn Ala Leu
1               5

<210> SEQ ID NO 463
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Trp Thr Asn Thr Ser Ala Asn Tyr Asn Leu
1               5                   10

<210> SEQ ID NO 464
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Arg Val Arg Arg
1

<210> SEQ ID NO 465
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Glu Arg Thr Lys Arg
1               5

<210> SEQ ID NO 466
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Arg Tyr Gln Ile Lys Pro Leu Lys Ser Thr Asp Glu
1               5                   10

<210> SEQ ID NO 467
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: L-homophenylalanine
```

```
<400> SEQUENCE: 467

Trp Glu Leu Arg His Gln Ala Phe Arg Ser Lys
1               5                   10

<210> SEQ ID NO 468
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: L- Methyl cysteine

<400> SEQUENCE: 468

Ser Gly Ala Phe Lys Cys Leu Lys Asp Gly Ala Gly
1               5                   10

<210> SEQ ID NO 469
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Tyr Val Ala Asp Gly Trp
1               5

<210> SEQ ID NO 470
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Trp Glu His Asp Gly Trp
1               5

<210> SEQ ID NO 471
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Tyr Val Ala Asp Ala Pro Val
1               5

<210> SEQ ID NO 472
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Arg Pro Pro Gly Phe Ser Ala
1               5
```

<210> SEQ ID NO 473
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Gly Ser Pro Ala Phe Leu Ala
1               5

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Ala Gly Phe Ser Leu Pro Ala
1               5

<210> SEQ ID NO 475
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Arg Trp His Thr Val Gly Leu Arg Trp Glu
1               5                   10

<210> SEQ ID NO 476
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Leu Glu Gln
1

<210> SEQ ID NO 477
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Arg Trp Pro Pro Met Gly Leu Pro Trp Glu
1               5                   10

<210> SEQ ID NO 478
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 478

Arg Pro Lys Pro Val Glu
1               5

<210> SEQ ID NO 479
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Ile Glu Thr Asp
1

<210> SEQ ID NO 480
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Val Gly Pro Asp Phe Gly Arg
1               5

<210> SEQ ID NO 481
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Gly Ile Glu Phe Asp Ser Gly Gly Cys
1               5

<210> SEQ ID NO 482
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gly Asp Phe Leu Arg Arg Val
1               5

<210> SEQ ID NO 483
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ala Ala Leu
1

<210> SEQ ID NO 484
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Tyr Ala Thr Trp Ser Met Ile Ala Ala His
1               5                   10

<210> SEQ ID NO 485
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Val Ile Met Trp Arg Leu Thr Val Gly Thr
1               5                   10

<210> SEQ ID NO 486
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Arg Arg Val Leu Ala Leu Gln Gln Glu Leu
1               5                   10

<210> SEQ ID NO 487
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Leu Ala Thr Trp Pro Leu Ser Gly Leu Trp
1               5                   10

<210> SEQ ID NO 488
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Asn Thr Pro Asn Trp Leu Val Asn Ala Val
1               5                   10

<210> SEQ ID NO 489
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 489

Ser Pro Leu Ala Gln Ala Val Arg Ser Ser Ser Arg Lys
1               5                   10

<210> SEQ ID NO 490
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Gln Met Pro Gly Arg Leu Ser Met Ala Phe
1               5                   10

<210> SEQ ID NO 491
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Pro Leu Gly Leu Arg
1               5

<210> SEQ ID NO 492
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Gln Arg Ala Asn Ser Ile Arg Val Thr Trp
1               5                   10

<210> SEQ ID NO 493
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Pro Leu Ala Val Arg
1               5

<210> SEQ ID NO 494
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Leu Leu Ala Val Pro Ala Ala Asn Thr Val
1               5                   10

<210> SEQ ID NO 495
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Gly Pro Gln Gly Leu Arg Gly Gln
1               5

<210> SEQ ID NO 496
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Arg Thr Gly Leu Tyr Leu Tyr Asn Ser Thr
1               5                   10

<210> SEQ ID NO 497
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Arg Lys Lys Leu Thr Gln Ser Lys Phe Val Gly Gly Ala Glu
1               5                   10

<210> SEQ ID NO 498
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Lys His Tyr Arg
1

<210> SEQ ID NO 499
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Gln Ala Arg
1

<210> SEQ ID NO 500
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 500

Pro Arg Pro Phe Asn Tyr Leu
1               5

<210> SEQ ID NO 501
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Ala Pro Phe Glu Met Ser Ala
1               5

<210> SEQ ID NO 502
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Ala Pro Phe Glu Phe Ser Ala
1               5

<210> SEQ ID NO 503
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Pro Leu Gly Phe Arg Val
1               5

<210> SEQ ID NO 504
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Arg Pro Leu Ala Leu Trp Arg Ser
1               5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Arg Pro Leu Ala Leu Glu Glu Ser Gln
1               5

<210> SEQ ID NO 506
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Arg Pro Leu Ala Leu Trp Arg Ser Gln
1               5

<210> SEQ ID NO 507
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Arg Asn Ala Leu Ala Val Glu Arg Thr Ala Ser
1               5                   10

<210> SEQ ID NO 508
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Arg Pro Lys Pro Gln Gln Phe Trp
1               5

<210> SEQ ID NO 509
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Ser Gly Ser Asn Pro Tyr Lys Tyr Thr Ala
1               5                   10

<210> SEQ ID NO 510
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Ser Gly Ser Asn Pro Tyr Gly Tyr Thr Ala
1               5                   10

<210> SEQ ID NO 511
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 511

Ser Gly Thr Leu Ser Glu Leu His Thr Ala
1               5                   10

<210> SEQ ID NO 512
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Ser Gly Thr Ile Ser His Leu His Thr Ala
1               5                   10

<210> SEQ ID NO 513
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: L-Ornithine
<220> FEATURE:
<221> NAME/KEY: MOD_RES
<222> LOCATION: (8)..(8)
<223> OTHER INFORMATION: L-homophenylalanine

<400> SEQUENCE: 513

Ser Gly Xaa Arg Ser His Pro Phe Thr Leu Tyr Thr Ala
1               5                   10

<210> SEQ ID NO 514
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: L-Ornithine
<220> FEATURE:
<221> NAME/KEY: MOD_RES
<222> LOCATION: (8)..(8)
<223> OTHER INFORMATION: L-homophenylalanine

<400> SEQUENCE: 514

Ser Gly Xaa Arg Ser His Gly Phe Phe Leu Tyr Thr Ala
1               5                   10

<210> SEQ ID NO 515
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Ser Gly Glu Ser Leu Ala Tyr Tyr Thr Ala
1               5                   10

```
<210> SEQ ID NO 516
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Ser Gly His Met His Ala Ala Leu Thr Ala
1               5                   10

<210> SEQ ID NO 517
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-isoleucine

<400> SEQUENCE: 517

Ile Leu Ser Arg Ile Val Gly Gly
1               5

<210> SEQ ID NO 518
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (5)..(5)
<223> OTHER INFORMATION: D-Isoleucine
<220> FEATURE:
<221> NAME/KEY: MOD_RES
<222> LOCATION: (6)..(6)
<223> OTHER INFORMATION: D-Valine

<400> SEQUENCE: 518

Ile Leu Ser Arg Ile Val Gly Gly
1               5

<210> SEQ ID NO 519
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Arg Gln Arg Arg Ala Leu Glu Lys
1               5

<210> SEQ ID NO 520
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 520

Lys Pro Ile Ser Leu Ile Ser Ser
1               5

<210> SEQ ID NO 521
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Gln Lys Gly Arg Tyr Lys Gln Glu
1               5

<210> SEQ ID NO 522
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Gly Pro Leu Gly Leu Arg Ser Trp
1               5

<210> SEQ ID NO 523
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Gly Pro Leu Gly Val Arg Gly Lys
1               5

<210> SEQ ID NO 524
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Phenylalanine

<400> SEQUENCE: 524

Gly Phe Pro Arg Ser Gly Gly
1               5

<210> SEQ ID NO 525
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroglutamic acid
```

```
<400> SEQUENCE: 525

Xaa
1

<210> SEQ ID NO 526
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Ser Tyr
1

<210> SEQ ID NO 527
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Gly Phe
1

<210> SEQ ID NO 528
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Tyr
1

<210> SEQ ID NO 529
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: citrulline

<400> SEQUENCE: 529

Xaa
1

<210> SEQ ID NO 530
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Gly Pro
1
```

<210> SEQ ID NO 531
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Thr
1

<210> SEQ ID NO 532
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Ile
1

<210> SEQ ID NO 533
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Gly Ala
1

<210> SEQ ID NO 534
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S-benzyl-L-cysteine

<400> SEQUENCE: 534

Cys
1

<210> SEQ ID NO 535
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Ala
1

<210> SEQ ID NO 536
<211> LENGTH: 1
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 536

Lys
1

<210> SEQ ID NO 537
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Gly Leu Phe
1

<210> SEQ ID NO 538
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Leu
1

<210> SEQ ID NO 539
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Val Ala Asn
1

<210> SEQ ID NO 540
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Ala Ala Ala
1

<210> SEQ ID NO 541
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Lys
1
```

<210> SEQ ID NO 542
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Phe
1

<210> SEQ ID NO 543
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Phe Ser Arg
1

<210> SEQ ID NO 544
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Val Val Arg
1

<210> SEQ ID NO 545
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Lys Ala
1

<210> SEQ ID NO 546
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Pro Arg
1

<210> SEQ ID NO 547
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 547

Met Gly Pro
1

<210> SEQ ID NO 548
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Lys Pro
1

<210> SEQ ID NO 549
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Gln Gly Arg
1

<210> SEQ ID NO 550
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyl-L-glutamate

<400> SEQUENCE: 550

Glu Ala Arg
1

<210> SEQ ID NO 551
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Trp Glu His Asp
1

<210> SEQ ID NO 552
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Gln Ala Arg
1
```

```
<210> SEQ ID NO 553
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Ala Ala Phe
1

<210> SEQ ID NO 554
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Gly Pro Lys
1

<210> SEQ ID NO 555
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Ala Ala Pro Met
1

<210> SEQ ID NO 556
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Ala Glu Pro Phe
1

<210> SEQ ID NO 557
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Gly Gly
1

<210> SEQ ID NO 558
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 558

Val Leu Lys
1

<210> SEQ ID NO 559
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Glu Lys Lys
1

<210> SEQ ID NO 560
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Val Pro Arg
1

<210> SEQ ID NO 561
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Gly Lys Arg
1

<210> SEQ ID NO 562
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyl-L-glutamate

<400> SEQUENCE: 562

Glu Gly Arg
1

<210> SEQ ID NO 563
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Leu Arg
1
```

<210> SEQ ID NO 564
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Ala Phe Lys
1

<210> SEQ ID NO 565
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Leu Gly Arg
1

<210> SEQ ID NO 566
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Pro Phe Arg
1

<210> SEQ ID NO 567
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Ala Ala Pro Val
1

<210> SEQ ID NO 568
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Ala Phe Lys
1

<210> SEQ ID NO 569
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 569

Val Lys Met
1

<210> SEQ ID NO 570
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gly Pro Leu Gly Pro
1               5

<210> SEQ ID NO 571
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Lys Gln Lys Glu Arg
1               5

<210> SEQ ID NO 572
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Arg Val Arg Arg
1

<210> SEQ ID NO 573
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Ile Glu Gly Arg
1

<210> SEQ ID NO 574
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Pro
1

<210> SEQ ID NO 575
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 575

Ala Ala Pro Val
1

<210> SEQ ID NO 576
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Arg Pro Phe His Leu Leu Val Tyr
1               5

<210> SEQ ID NO 577
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: amino-n-butyric acid
<220> FEATURE:
<221> NAME/KEY: MOD_RES
<222> LOCATION: (4)..(4)
<223> OTHER INFORMATION: guamidine-L-phenylalanine

<400> SEQUENCE: 577

Xaa Trp Ser Phe Thr Val Phe
1               5

<210> SEQ ID NO 578
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

His Ser Ser Lys Leu Gln
1               5

<210> SEQ ID NO 579
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Arg Pro Tyr
1

<210> SEQ ID NO 580
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 580

Asp Arg Glu Asn Ser Pro Lys Leu
1               5

<210> SEQ ID NO 581
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: dinitrobenzylation of lysine

<400> SEQUENCE: 581

Lys Lys Asp Arg Glu Asn Ser Pro Leu Lys
1               5                   10

<210> SEQ ID NO 582
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 582

Asn Ala Gly Ser Lys Phe Lys Gln
1               5

<210> SEQ ID NO 583
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 583

Asn Ala Gly Ser Lys Phe Gln Lys
1               5

<210> SEQ ID NO 584
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 584

His Leu Leu Gly Phe Tyr Lys Val
1               5

<210> SEQ ID NO 585
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 585

His Leu Leu Gly Phe Tyr Val Lys
1               5

<210> SEQ ID NO 586
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine
<220> FEATURE:
<221> NAME/KEY: MOD_RES
<222> LOCATION: (8)..(8)
<223> OTHER INFORMATION: Norleucine

<400> SEQUENCE: 586

Gln Glu Lys Gln Thr Leu Lys Leu
1               5

<210> SEQ ID NO 587
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine
```

<400> SEQUENCE: 587

Gln Glu Lys Gln Thr Leu Leu Lys
1               5

<210> SEQ ID NO 588
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 588

Asp Pro Phe Val Val Ser Lys Trp
1               5

<210> SEQ ID NO 589
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 589

Asp Pro Phe Val Val Ser Trp Lys
1               5

<210> SEQ ID NO 590
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 590

Asn Ala Tyr Asn Glu Ile Lys Arg
1               5

<210> SEQ ID NO 591
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 591

Asn Ala Tyr Asn Glu Ile Arg Lys
1               5

<210> SEQ ID NO 592

-continued

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine

<400> SEQUENCE: 592

Val Leu Arg Gln Ser Glu Lys Asn
1               5

<210> SEQ ID NO 593
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine

<400> SEQUENCE: 593

Val Leu Arg Gln Ser Glu Asn Lys
1               5

<210> SEQ ID NO 594
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine

<400> SEQUENCE: 594

Tyr Asn Pro Arg Glu Leu Lys Ile
1               5

<210> SEQ ID NO 595
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (8)..(8)
```

```
<223> OTHER INFORMATION: dinitrobenzylation of lysine

<400> SEQUENCE: 595

Tyr Asn Pro Arg Glu Leu Ile Lys
1               5

<210> SEQ ID NO 596
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 596

Glu Phe Val His Asn Pro Lys Lys
1               5

<210> SEQ ID NO 597
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 597

Glu Phe Val His Asn Pro Lys Lys
1               5

<210> SEQ ID NO 598
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 598

Lys Arg Val Gln Phe Leu Lys His
1               5

<210> SEQ ID NO 599
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 599

Lys Arg Val Gln Phe Leu His Lys
1               5
```

```
<210> SEQ ID NO 600
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine

<400> SEQUENCE: 600

Leu Ile Leu His Lys Asn Lys Gly
1               5

<210> SEQ ID NO 601
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine

<400> SEQUENCE: 601

Leu Ile Leu His Lys Asn Gly Lys
1               5

<210> SEQ ID NO 602
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine

<400> SEQUENCE: 602

Trp Ala Leu Leu Tyr His Lys Ser
1               5

<210> SEQ ID NO 603
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
```

```
<221> NAME/KEY: MOD_RES
<222> LOCATION: (8)..(8)
<223> OTHER INFORMATION: dinitrobenzylation of lysine

<400> SEQUENCE: 603

Trp Ala Leu Leu Tyr His Ser Lys
1               5

<210> SEQ ID NO 604
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 604

Ala His Asp Ile Val Asn Lys Tyr
1               5

<210> SEQ ID NO 605
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 605

Ala His Asp Ile Val Asn Tyr Lys
1               5

<210> SEQ ID NO 606
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 606

Ser Val Phe Val Ile Glu Lys Pro
1               5

<210> SEQ ID NO 607
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine
```

```
<400> SEQUENCE: 607

Ser Val Phe Val Ile Glu Pro Lys
1               5

<210> SEQ ID NO 608
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 608

Pro Pro Ser Gly Leu Ser Lys Glu
1               5

<210> SEQ ID NO 609
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 609

Pro Pro Ser Gly Leu Ser Glu Lys
1               5

<210> SEQ ID NO 610
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 610

Arg Trp Tyr Gly Gly Ile Lys Phe
1               5

<210> SEQ ID NO 611
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 611

Arg Trp Tyr Gly Gly Ile Phe Lys
1               5
```

-continued

```
<210> SEQ ID NO 612
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine

<400> SEQUENCE: 612

Gln Tyr Val Phe Phe Leu Lys Asp
1               5

<210> SEQ ID NO 613
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine

<400> SEQUENCE: 613

Gln Tyr Val Phe Phe Leu Asp Lys
1               5

<210> SEQ ID NO 614
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 614

Phe Ala Lys Tyr Tyr Lys Lys Thr
1               5

<210> SEQ ID NO 615
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 615

Phe Ala Lys Tyr Tyr Lys Thr Lys
1               5
```

```
<210> SEQ ID NO 616
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 616

Gln Val Lys His Phe Thr Lys Ala
1               5

<210> SEQ ID NO 617
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: dinitrobenzylation of lysine

<400> SEQUENCE: 617

Gln Val Lys His Phe Thr Ala Lys
1               5

<210> SEQ ID NO 618
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: dinitrobenzylation of lysine

<400> SEQUENCE: 618

Tyr Val Ala Asp Ala Pro Lys
1               5

<210> SEQ ID NO 619
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Lys Gly Ile Ser Ser Gln Tyr
1               5

<210> SEQ ID NO 620
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 620

Ala Leu Pro Ala Leu Gln Asn
1               5

<210> SEQ ID NO 621
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

His Arg Phe Arg Gly
1               5

<210> SEQ ID NO 622
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Ala Pro Glu Glu Ile Met Asp Gln Gln
1               5

<210> SEQ ID NO 623
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Ser Arg Lys Ser Gln Gln Tyr
1               5

<210> SEQ ID NO 624
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Ser Lys Gly Arg Ser Leu Ile
1               5

<210> SEQ ID NO 625
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Phe Ala Gln Ser Ile Pro Lys
1               5

<210> SEQ ID NO 626
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Arg Gln Arg Arg Val Val Gly
1               5

<210> SEQ ID NO 627
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Glu Arg Gly Glu Thr Gly Pro Ser
1               5

<210> SEQ ID NO 628
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Ala Ser Gly Pro Ser Ser
1               5

<210> SEQ ID NO 629
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Tyr Arg Phe Arg
1

<210> SEQ ID NO 630
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Lys Leu Phe Ser Ser Lys Gln
1               5

<210> SEQ ID NO 631
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 631

Ile Val Pro Arg Gly
1               5

<210> SEQ ID NO 632
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Ile Arg Arg Ser Ser Tyr Phe Lys
1               5

<210> SEQ ID NO 633
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyl-L-histidine
<220> FEATURE:
<221> NAME/KEY: MOD_RES
<222> LOCATION: (2)..(2)
<223> OTHER INFORMATION: L-tert-leucine
<220> FEATURE:
<221> NAME/KEY: MOD_RES
<222> LOCATION: (6)..(6)
<223> OTHER INFORMATION: L-methionine-sulfoxide

<400> SEQUENCE: 633

His Leu Pro Ser Asp Met
1               5

<210> SEQ ID NO 634
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norvaline
<220> FEATURE:
<221> NAME/KEY: MOD_RES
<222> LOCATION: (4)..(4)
<223> OTHER INFORMATION: L-octahydroindole-2-carboxylic acid

<400> SEQUENCE: 634

Val Ile Glu Xaa Asp Phe Gly Arg
1               5

<210> SEQ ID NO 635
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: D-threonine
<220> FEATURE:
<221> NAME/KEY: MOD_RES
<222> LOCATION: (2)..(2)
<223> OTHER INFORMATION: 2,3,4,5,6-pentafluoro-L-penylalanine

<400> SEQUENCE: 635

Thr Phe Arg
1

<210> SEQ ID NO 636
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2,3-diaminopropionic acid
<220> FEATURE:
<221> NAME/KEY: MOD_RES
<222> LOCATION: (2)..(2)
<223> OTHER INFORMATION: L-Ornithine
<220> FEATURE:
<221> NAME/KEY: MOD_RES
<222> LOCATION: (3)..(3)
<223> OTHER INFORMATION: 3-chloro-L-phenylalanine
<220> FEATURE:
<221> NAME/KEY: MOD_RES
<222> LOCATION: (4)..(4)
<223> OTHER INFORMATION: S-para-methoxybenzyl cysteine

<400> SEQUENCE: 636

Xaa Xaa Phe Cys
1

<210> SEQ ID NO 637
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-cyclohexylalanine
<220> FEATURE:
<221> NAME/KEY: MOD_RES
<222> LOCATION: (3)..(3)
<223> OTHER INFORMATION: benzyl homoserine

<400> SEQUENCE: 637

Xaa Leu Ser Arg
1

<210> SEQ ID NO 638
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyl-L-histidine
<220> FEATURE:
<221> NAME/KEY: MOD_RES
<222> LOCATION: (2)..(2)
<223> OTHER INFORMATION: L-tert-leucine
```

```
<220> FEATURE:
<221> NAME/KEY: MOD_RES
<222> LOCATION: (6)..(6)
<223> OTHER INFORMATION: L-methionine-sulfoxide

<400> SEQUENCE: 638

His Leu Pro Ser Asp Met
1               5

<210> SEQ ID NO 639
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: homocyclohexylalnine
<220> FEATURE:
<221> NAME/KEY: MOD_RES
<222> LOCATION: (2)..(2)
<223> OTHER INFORMATION: phenylalanine derivative with a guanidine group
      in the para position
<220> FEATURE:
<221> NAME/KEY: MOD_RES
<222> LOCATION: (3)..(3)
<223> OTHER INFORMATION: L-octahydroindole-2-carboxylic acid

<400> SEQUENCE: 639

Xaa Phe Xaa Arg
1

<210> SEQ ID NO 640
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-alpha-aminobutyric acid
<220> FEATURE:
<221> NAME/KEY: MOD_RES
<222> LOCATION: (2)..(2)
<223> OTHER INFORMATION: benzyloxy-L-norleucine

<400> SEQUENCE: 640

Xaa Leu
1

<210> SEQ ID NO 641
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyloxy-L-norleucine
<220> FEATURE:
<221> NAME/KEY: MOD_RES
<222> LOCATION: (2)..(2)
<223> OTHER INFORMATION: L-methionine sulfone
<220> FEATURE:
<221> NAME/KEY: MOD_RES
<222> LOCATION: (3)..(3)
<223> OTHER INFORMATION: L-octahydroindole-2-carboxylic acid
```

```
<220> FEATURE:
<221> NAME/KEY: MOD_RES
<222> LOCATION: (4)..(4)
<223> OTHER INFORMATION: L-alpha-aminobutyric acid

<400> SEQUENCE: 641

Leu Met Xaa Xaa
1

<210> SEQ ID NO 642
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2,3-diaminopropionic acid
<220> FEATURE:
<221> NAME/KEY: MOD_RES
<222> LOCATION: (2)..(2)
<223> OTHER INFORMATION: L-Ornithine
<220> FEATURE:
<221> NAME/KEY: MOD_RES
<222> LOCATION: (3)..(3)
<223> OTHER INFORMATION: 3-chloro-L-phenylalanine
<220> FEATURE:
<221> NAME/KEY: MOD_RES
<222> LOCATION: (4)..(4)
<223> OTHER INFORMATION: S-para-methoxybenzyl cysteine

<400> SEQUENCE: 642

Xaa Xaa Phe Cys
1

<210> SEQ ID NO 643
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-cyclohexylalanine
<220> FEATURE:
<221> NAME/KEY: MOD_RES
<222> LOCATION: (3)..(3)
<223> OTHER INFORMATION: Homoserine

<400> SEQUENCE: 643

Xaa Leu Ser Arg
1

<210> SEQ ID NO 644
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: guamidine-L-phenylalanine

<400> SEQUENCE: 644

Phe Val Thr Phe Ser Trp
1               5
```

```
<210> SEQ ID NO 645
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: homocyclohexylalnine
<220> FEATURE:
<221> NAME/KEY: MOD_RES
<222> LOCATION: (2)..(2)
<223> OTHER INFORMATION: phenylalanine derivative with a guanidine group
      in the para position
<220> FEATURE:
<221> NAME/KEY: MOD_RES
<222> LOCATION: (3)..(3)
<223> OTHER INFORMATION: L-octahydroindole-2-carboxylic acid

<400> SEQUENCE: 645

Xaa Phe Xaa Arg
1

<210> SEQ ID NO 646
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyloxy-L-norleucine
<220> FEATURE:
<221> NAME/KEY: MOD_RES
<222> LOCATION: (2)..(2)
<223> OTHER INFORMATION: methylsulfonylbutanoic acid
<220> FEATURE:
<221> NAME/KEY: MOD_RES
<222> LOCATION: (3)..(3)
<223> OTHER INFORMATION: L-octahydroindole-2-carboxylic acid
<220> FEATURE:
<221> NAME/KEY: MOD_RES
<222> LOCATION: (4)..(4)
<223> OTHER INFORMATION: L-alpha-aminobutyric acid

<400> SEQUENCE: 646

Leu Met Xaa Xaa
1

<210> SEQ ID NO 647
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Ala Ile Glu Pro Asp Ser Gly
1               5

<210> SEQ ID NO 648
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 648

Ala Ile Glu Phe Asp Ser Gly
1               5

<210> SEQ ID NO 649
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Ala Ala Glu Ala Ile Ser Asp
1               5

<210> SEQ ID NO 650
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Ala Gly Gly Ala Gln Met Gly Ala
1               5

<210> SEQ ID NO 651
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Ala Gln Pro Asp Ala Leu Asn Val
1               5

<210> SEQ ID NO 652
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Ala Thr Asp Val Thr Thr Thr Pro
1               5

<210> SEQ ID NO 653
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Asp Ile Val Thr Val Ala Asn Ala
1               5
```

```
<210> SEQ ID NO 654
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Asp Leu Gly Leu Lys Ser Val Pro
1               5

<210> SEQ ID NO 655
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Asp Val Met Ala Ser Asn Lys Arg
1               5

<210> SEQ ID NO 656
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Glu Ser Asp Glu Leu Asn Thr Ile
1               5

<210> SEQ ID NO 657
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Phe His Pro Leu His Ser Lys Ile
1               5

<210> SEQ ID NO 658
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

His Ala Arg Leu Val His Val
1               5

<210> SEQ ID NO 659
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 659

His Ile Ala Asn Val Glu Arg Val
1               5

<210> SEQ ID NO 660
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Lys Ala Ala Ala Thr Gln Lys Lys
1               5

<210> SEQ ID NO 661
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Leu Ala Thr Ala Ser Thr Met Asp
1               5

<210> SEQ ID NO 662
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Leu Gly Pro Lys Gly Gln Thr
1               5

<210> SEQ ID NO 663
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Leu Ser Leu Pro Glu Thr Gly Glu
1               5

<210> SEQ ID NO 664
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Asn Leu Ala Gly Ile Leu Lys Glu
1               5

<210> SEQ ID NO 665
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Asn Pro Gly Met Ser Glu Pro Val
1               5

<210> SEQ ID NO 666
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Pro Phe Gly Cys His Ala Lys
1               5

<210> SEQ ID NO 667
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Pro Leu Gly Leu Arg Trp Trp
1               5

<210> SEQ ID NO 668
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Gln Met Gly Val Met Gln Gly Val
1               5

<210> SEQ ID NO 669
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Gln Thr Cys Lys Cys Ser Cys Lys
1               5

<210> SEQ ID NO 670
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 670

Gln Trp Ala Gly Leu Val Glu Lys
1               5

<210> SEQ ID NO 671
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Arg Pro Ala Val Met Thr Ser Pro
1               5

<210> SEQ ID NO 672
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Thr Leu Arg Glu Leu His Leu Asp
1               5

<210> SEQ ID NO 673
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Thr Pro Pro Pro Ser Gln Gly Lys
1               5

<210> SEQ ID NO 674
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Thr Ser Glu Asp Leu Val Val Gln
1               5

<210> SEQ ID NO 675
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Val Trp Ala Ala Glu Ala Ile Ser
1               5

<210> SEQ ID NO 676
<211> LENGTH: 1
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Arg
1

<210> SEQ ID NO 677
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Gly Cys
1

<210> SEQ ID NO 678
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 678

Gly Ser Gly Arg Ser Gly Gly Lys
1               5

<210> SEQ ID NO 679
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 679

Gly Pro Gly Pro Arg Glu Gly Gly Lys
1               5

<210> SEQ ID NO 680
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 680

Gly Ile Glu Pro Asp Ser Gly Ser Gln Gly Lys
1               5                   10
```

```
<210> SEQ ID NO 681
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 681

Gly Val Val Ala Asp Ser Ser Met Glu Ser Gly Lys
1               5                   10

<210> SEQ ID NO 682
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 682

Gly Pro Thr Ser Tyr Gly Lys
1               5

<210> SEQ ID NO 683
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 683

Gly Tyr Arg Phe Lys Gly Lys
1               5

<210> SEQ ID NO 684
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 684

Gly Lys Val Pro Leu Gly Lys
1               5

<210> SEQ ID NO 685
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 685

Gly Val Asp Val Ala Asp Gly Lys
1               5

<210> SEQ ID NO 686
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 686

Gly Leu Glu Thr Asp Gly Lys
1               5

<210> SEQ ID NO 687
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 687

Gly Leu Glu His Asp Gly Lys
1               5

<210> SEQ ID NO 688
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 688

Gly Arg Glu Gln Asp Gly Lys
1               5

<210> SEQ ID NO 689
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher
```

-continued

<400> SEQUENCE: 689

Gly Asp Glu Val Asp Gly Lys
1               5

<210> SEQ ID NO 690
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 690

Gly Val Glu Ile Asp Gly Lys
1               5

<210> SEQ ID NO 691
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 691

Gly Val Gln Val Asp Gly Trp Gly Lys
1               5

<210> SEQ ID NO 692
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 692

Gly Tyr Glu Val Asp Gly Trp Gly Lys
1               5

<210> SEQ ID NO 693
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 693

Gly Leu Glu Val Asp Gly Lys
1               5

<210> SEQ ID NO 694

```
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 694

Gly Ile Glu Val Glu Gly Lys
1               5

<210> SEQ ID NO 695
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 695

Gly Ala Ala Pro Val Gly Lys
1               5

<210> SEQ ID NO 696
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 696

Gly Phe Phe Lys Phe Gly Lys
1               5

<210> SEQ ID NO 697
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 697

Gly Gly Arg Arg Gly Lys Gly Gly Gly Lys
1               5                   10

<210> SEQ ID NO 698
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: MOD_RES
<222> LOCATION: (7)..(7)
<223> OTHER INFORMATION: Lys modified with a CPQ2 quencher

<400> SEQUENCE: 698

Gly Val Lys Lys Arg Gly Lys
1               5

<210> SEQ ID NO 699
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: p-Nitro phenylalanine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 699

Gly Phe Ala Ala Phe Phe Val Leu Gly Lys
1               5                   10

<210> SEQ ID NO 700
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 700

Gly Val Val Arg Gly Lys
1               5

<210> SEQ ID NO 701
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 701

Gly Lys Gln Lys Leu Arg Gly Lys
1               5

<210> SEQ ID NO 702
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
```

```
<400> SEQUENCE: 702

Gly Arg Pro Pro Gly Phe Ser Ala Phe Gly Lys
1               5                   10

<210> SEQ ID NO 703
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 703

Gly Gly Pro Arg Gly Lys
1               5

<210> SEQ ID NO 704
<211> LENGTH: 5
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Lys modified with a CPQ2 quencher

<400> SEQUENCE: 704

Gly Phe Arg Gly Lys
1               5

<210> SEQ ID NO 705
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 705

Gly Leu Pro Leu Gly Leu Gly Lys
1               5

<210> SEQ ID NO 706
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 706

Gly Lys Pro Leu Gly Leu Gly Lys
1               5
```

```
<210> SEQ ID NO 707
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: gamma aminobutyric acid
<220> FEATURE:
<221> NAME/KEY: MOD_RES
<222> LOCATION: (9)..(9)
<223> OTHER INFORMATION: Lys modified with a CPQ2 quencher

<400> SEQUENCE: 707

Gly Xaa Pro Gln Gly Leu Glu Gly Lys
1               5

<210> SEQ ID NO 708
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 708

Gly Pro Lys Pro Leu Ala Leu Gly Lys
1               5

<210> SEQ ID NO 709
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 709

Gly Gly Pro Ser Gly Ile His Val Gly Lys
1               5                   10

<210> SEQ ID NO 710
<211> LENGTH: 15
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (15)..(15)
<223> OTHER INFORMATION: Lys modified with a CPQ2 quencher

<400> SEQUENCE: 710

Gly Trp Ala His Arg Thr Thr Phe Tyr Arg Arg Gly Ala Gly Lys
1               5                   10                  15

<210> SEQ ID NO 711
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 711

Gly Trp Lys Leu Arg Ser Ser Lys Gln Gly Lys
1               5                   10

<210> SEQ ID NO 712
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 712

Gly Pro Phe Arg Gly Lys
1               5

<210> SEQ ID NO 713
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 713

Gly Ser Tyr Arg Ile Phe Gly Lys
1               5

<210> SEQ ID NO 714
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 714

Gly Arg Pro Tyr Gly Lys
1               5

<210> SEQ ID NO 715
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
```

```
<223> OTHER INFORMATION: Lys modified with a CPQ2 quencher

<400> SEQUENCE: 715

Gly Thr Ala Phe Arg Ser Ala Tyr Gly Gly Lys
1               5                   10

<210> SEQ ID NO 716
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 716

Gly Trp Ala Ala Phe Arg Phe Ser Gln Ala Gly Lys
1               5                   10

<210> SEQ ID NO 717
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 717

Gly Val Pro Arg Gly Lys
1               5

<210> SEQ ID NO 718
<211> LENGTH: 3
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Lys modified with a CPQ2 quencher

<400> SEQUENCE: 718

Gly Gly Lys
1

<210> SEQ ID NO 719
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 719

Gly Lys Leu Arg Ser Ser Lys Gln Gly Lys
1               5                   10
```

<210> SEQ ID NO 720
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 720

Gly Tyr Ala Ser Arg Gly Lys
1               5

<210> SEQ ID NO 721
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 721

Gly Arg Phe Ala Gln Ala Gln Gln Gln Leu Pro Gly Lys
1               5                   10

<210> SEQ ID NO 722
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 722

Gly Lys Pro Ala Lys Phe Phe Arg Leu Gly Lys
1               5                   10

<210> SEQ ID NO 723
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: L-Homophenylalanine
<220> FEATURE:
<221> NAME/KEY: MOD_RES
<222> LOCATION: (12)..(12)
<223> OTHER INFORMATION: Lys modified with a CPQ2 quencher

<400> SEQUENCE: 723

Gly Pro Arg Ala Ala Ala Phe Thr Ser Pro Gly Lys
1               5                   10

<210> SEQ ID NO 724
<211> LENGTH: 13

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 724

Gly Val Gly Pro Gln Arg Phe Ser Gly Ala Pro Gly Lys
1               5                   10

<210> SEQ ID NO 725
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: L-Homophenylalanine
<220> FEATURE:
<221> NAME/KEY: MOD_RES
<222> LOCATION: (12)..(12)
<223> OTHER INFORMATION: Lys modified with a CPQ2 quencher

<400> SEQUENCE: 725

Gly Phe Phe Leu Ala Gln Ala Phe Arg Ser Gly Lys
1               5                   10

<210> SEQ ID NO 726
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 726

Gly Pro Leu Ala Gln Ala Val Gly Lys
1               5

<210> SEQ ID NO 727
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 727

Gly Arg Thr Ala Ala Val Phe Arg Pro Gly Lys
1               5                   10

<210> SEQ ID NO 728
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (16)..(16)
<223> OTHER INFORMATION: Lys modified with a CPQ2 quencher

<400> SEQUENCE: 728

Gly Asp Val Gln Glu Phe Arg Gly Val Thr Ala Val Ile Arg Gly Lys
1               5                   10                  15

<210> SEQ ID NO 729
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 729

Gly Thr Glu Gly Glu Ala Arg Gly Ser Val Ile Gly Lys
1               5                   10

<210> SEQ ID NO 730
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: D-Leucine
<220> FEATURE:
<221> NAME/KEY: MOD_RES
<222> LOCATION: (6)..(6)
<223> OTHER INFORMATION: Lys modified with a CPQ2 quencher

<400> SEQUENCE: 730

Gly Leu Thr Arg Gly Lys
1               5

<210> SEQ ID NO 731
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 731

Gly Pro Leu Phe Ala Glu Arg Lys Gly Lys
1               5                   10

<210> SEQ ID NO 732
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: MOD_RES
<222> LOCATION: (7)..(7)
<223> OTHER INFORMATION: Lys modified with a CPQ2 quencher

<400> SEQUENCE: 732

Gly Leu Leu Val Tyr Gly Lys
1               5

<210> SEQ ID NO 733
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 733

Gly Gln Gln Lys Arg Lys Ile Val Leu Gly Lys
1               5                   10

<210> SEQ ID NO 734
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 734

Gly Ala Ser His Leu Gly Leu Ala Arg Gly Lys
1               5                   10

<210> SEQ ID NO 735
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 735

Gly Leu Pro Ser Arg Ser Ser Lys Ile Gly Lys
1               5                   10

<210> SEQ ID NO 736
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
```

```
<400> SEQUENCE: 736

Gly Ser Thr Gly Arg Asn Gly Phe Lys Gly Lys
1               5                   10

<210> SEQ ID NO 737
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 737

Gly Ser Leu Leu Arg Ser Glu Glu Thr Gly Lys
1               5                   10

<210> SEQ ID NO 738
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 738

Gly His Arg Gly Arg Thr Leu Glu Ile Gly Lys
1               5                   10

<210> SEQ ID NO 739
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 739

Gly Tyr Leu Gly Arg Ser Tyr Lys Val Gly Lys
1               5                   10

<210> SEQ ID NO 740
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 740

Gly Glu Lys Gln Arg Ile Ile Gly Gly Gly Lys
1               5                   10
```

```
<210> SEQ ID NO 741
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 741

Gly Gln Arg Gln Arg Ile Ile Gly Gly Gly Lys
1               5                   10

<210> SEQ ID NO 742
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 742

Gly Leu Gln Arg Ile Tyr Lys Gly Lys
1               5

<210> SEQ ID NO 743
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 743

Gly Ser Leu Gly Arg Lys Ile Gln Ile Gly Lys
1               5                   10

<210> SEQ ID NO 744
<211> LENGTH: 16
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (16)..(16)
<223> OTHER INFORMATION: Lys modified with a CPQ2 quencher

<400> SEQUENCE: 744

Gly His Ala Ala Pro Arg Ser Ala Asp Ile Gln Ile Asp Ile Gly Lys
1               5                   10                  15

<210> SEQ ID NO 745
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (6)..(6)
<223> OTHER INFORMATION: Lys modified with a CPQ2 quencher

<400> SEQUENCE: 745

Gly Phe Gly Arg Gly Lys
1               5

<210> SEQ ID NO 746
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 746

Gly Ser Leu Gly Arg Gly Lys
1               5

<210> SEQ ID NO 747
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 747

Gly Gly Leu Gln Arg Gly Lys
1               5

<210> SEQ ID NO 748
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 748

Gly Ser Val Ala Arg Thr Leu Leu Val Gly Lys
1               5                   10

<210> SEQ ID NO 749
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher
```

<400> SEQUENCE: 749

Gly Gly Arg Ile Phe Gly Gly Lys
1               5

<210> SEQ ID NO 750
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 750

Gly Ala Pro Lys Gly Lys
1               5

<210> SEQ ID NO 751
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 751

Gly Gly Phe Ser Pro Tyr Gly Lys
1               5

<210> SEQ ID NO 752
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 752

Gly Trp Glu Leu Arg His Ala Gly His Gly Lys
1               5                   10

<210> SEQ ID NO 753
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 753

Gly Arg Gln Ser Arg Ile Val Gly Gly Glu Gly Lys
1               5                   10

-continued

```
<210> SEQ ID NO 754
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 754

Gly Glu Gln Ala Val Tyr Gln Thr Ile Gly Lys
1               5                   10

<210> SEQ ID NO 755
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (14)..(14)
<223> OTHER INFORMATION: Lys modified with a CPQ2 quencher

<400> SEQUENCE: 755

Gly Val Ala Tyr Ser Gly Glu Asn Thr Phe Gly Phe Gly Lys
1               5                   10

<210> SEQ ID NO 756
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 756

Gly Gly Gly Arg Gly Lys
1               5

<210> SEQ ID NO 757
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 757

Gly Ala Thr Ala Asp Gly Lys
1               5

<210> SEQ ID NO 758
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (11)..(11)
<223> OTHER INFORMATION: Lys modified with a CPQ2 quencher

<400> SEQUENCE: 758

Gly Arg Pro Leu Glu Ser Asn Ala Val Gly Lys
1               5                   10

<210> SEQ ID NO 759
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 759

Gly Arg Pro Leu Gly Leu Ala Arg Gly Lys
1               5                   10

<210> SEQ ID NO 760
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 760

Gly Ala Ala Phe Phe Gly Lys
1               5

<210> SEQ ID NO 761
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 761

Gly Arg Val Lys Arg Gly Leu Ala Gly Lys
1               5                   10

<210> SEQ ID NO 762
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher
```

<400> SEQUENCE: 762

Gly Ala Ala Leu Gly Lys
1               5

<210> SEQ ID NO 763
<211> LENGTH: 20
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: D-Methionine
<220> FEATURE:
<221> NAME/KEY: MOD_RES
<222> LOCATION: (5)..(5)
<223> OTHER INFORMATION: D-Glutamic acid
<220> FEATURE:
<221> NAME/KEY: MOD_RES
<222> LOCATION: (8)..(8)
<223> OTHER INFORMATION: D-Asparagine
<220> FEATURE:
<221> NAME/KEY: MOD_RES
<222> LOCATION: (9)..(9)
<223> OTHER INFORMATION: D-Aspartic acid
<220> FEATURE:
<221> NAME/KEY: MOD_RES
<222> LOCATION: (10)..(10)
<223> OTHER INFORMATION: D-Asparagine
<220> FEATURE:
<221> NAME/KEY: MOD_RES
<222> LOCATION: (11)..(11)
<223> OTHER INFORMATION: D-Glutamic acid
<220> FEATURE:
<221> NAME/KEY: MOD_RES
<222> LOCATION: (12)..(12)
<223> OTHER INFORMATION: D-Glutamic acid
<220> FEATURE:
<221> NAME/KEY: MOD_RES
<222> LOCATION: (16)..(16)
<223> OTHER INFORMATION: D-Serine
<220> FEATURE:
<221> NAME/KEY: MOD_RES
<222> LOCATION: (18)..(18)
<223> OTHER INFORMATION: D-Arginine
<220> FEATURE:
<221> NAME/KEY: MOD_RES
<222> LOCATION: (20)..(20)
<223> OTHER INFORMATION: Lys modified with a CPQ2 quencher

<400> SEQUENCE: 763

Cys Gly Gly Met Glu Gly Val Asn Asp Asn Glu Glu Gly Phe Phe Ser
1               5                   10                  15

Ala Arg Gly Lys
            20

<210> SEQ ID NO 764
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

```
<400> SEQUENCE: 764

Gly Gly Pro Gln Gly Ile Trp Gly Gln Lys
1               5                   10

<210> SEQ ID NO 765
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 765

Gly Gly Leu Val Pro Arg Gly Ser Gly Lys
1               5                   10

<210> SEQ ID NO 766
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 766

Gly Gly Pro Val Gly Leu Ile Gly Lys
1               5

<210> SEQ ID NO 767
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 767

Gly Gly Pro Trp Gly Ile Trp Gly Gln Gly Lys
1               5                   10

<210> SEQ ID NO 768
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 768

Gly Gly Pro Val Pro Leu Ser Leu Val Met Lys
1               5                   10
```

```
<210> SEQ ID NO 769
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: D-Phenylalanine
<220> FEATURE:
<221> NAME/KEY: MOD_RES
<222> LOCATION: (4)..(4)
<223> OTHER INFORMATION: piperidine carboxylic acid
<220> FEATURE:
<221> NAME/KEY: MOD_RES
<222> LOCATION: (10)..(10)
<223> OTHER INFORMATION: Lys modified with a CPQ2 quencher

<400> SEQUENCE: 769

Gly Gly Phe Xaa Arg Ser Gly Gly Gly Lys
1               5                   10

<210> SEQ ID NO 770
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: D-Phenylalanine
<220> FEATURE:
<221> NAME/KEY: MOD_RES
<222> LOCATION: (4)..(4)
<223> OTHER INFORMATION: piperidine carboxylic acid
<220> FEATURE:
<221> NAME/KEY: MOD_RES
<222> LOCATION: (10)..(10)
<223> OTHER INFORMATION: Lys modified with a CPQ2 quencher

<400> SEQUENCE: 770

Gly Gly Phe Xaa Lys Ser Gly Gly Gly Lys
1               5                   10

<210> SEQ ID NO 771
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 771

Gly Pro Leu Gly Met Arg Gly Gly Lys
1               5

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
```

```
<222> LOCATION: (3)..(3)
<223> OTHER INFORMATION: L-cyclohexylalanine
<220> FEATURE:
<221> NAME/KEY: MOD_RES
<222> LOCATION: (5)..(5)
<223> OTHER INFORMATION: L- Methyl cysteine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 772

Gly Pro Xaa Gly Cys His Ala Gly Lys
1               5

<210> SEQ ID NO 773
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 773

Gly Arg Pro Leu Ala Leu Trp Glu Ser Gln Gly Lys
1               5                   10

<210> SEQ ID NO 774
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 774

Ser Gly Lys Gly Pro Arg Gln Ile Thr Ala Lys
1               5                   10

<210> SEQ ID NO 775
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 775

Ser Gly Pro Leu Phe Tyr Ser Val Thr Ala Lys
1               5                   10

<210> SEQ ID NO 776
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: MOD_RES
<222> LOCATION: (10)..(10)
<223> OTHER INFORMATION: Lys modified with a CPQ2 quencher

<400> SEQUENCE: 776

Ser Gly Arg Ile Phe Leu Arg Thr Ala Lys
1               5                   10

<210> SEQ ID NO 777
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 777

Ser Gly Arg Ser Glu Asn Ile Arg Thr Ala Lys
1               5                   10

<210> SEQ ID NO 778
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 778

Gly Gly Ser Gly Gly Ser Lys
1               5

<210> SEQ ID NO 779
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 779

Gly Lys Pro Ile Leu Phe Phe Arg Leu Lys Gly Lys
1               5                   10

<210> SEQ ID NO 780
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 780

Gly Ala Trp Glu Ser Arg Leu Gly Lys
1               5

<210> SEQ ID NO 781
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 781

Gly Asn Glu Lys Ser Gly Leu Gly Lys
1               5

<210> SEQ ID NO 782
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 782

Gly Asn Ala Thr Ile Val Tyr Gly Lys
1               5

<210> SEQ ID NO 783
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 783

Gly Asp Pro Phe Val Val Ser Gly Lys
1               5

<210> SEQ ID NO 784
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
```

```
<223> OTHER INFORMATION: Lys modified with a CPQ2 quencher

<400> SEQUENCE: 784

Gly Phe His Leu Phe Thr Lys Gly Lys
1               5

<210> SEQ ID NO 785
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 785

Gly Leu Asn Trp His Lys His Gly Lys
1               5

<210> SEQ ID NO 786
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 786

Gly Phe Ala Arg Arg Trp Gly Gly Lys
1               5

<210> SEQ ID NO 787
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 787

Gly Pro Gly Lys Trp Ser Lys Gly Lys
1               5

<210> SEQ ID NO 788
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

<400> SEQUENCE: 788

Gly Tyr Glu Glu Ala Gln Pro Gly Lys
1               5

<210> SEQ ID NO 789
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 789

Gly Tyr Gly Ala Ile Lys Lys Gly Lys
1               5

<210> SEQ ID NO 790
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 790

Gly Thr Ser Leu Glu Gly Tyr Gly Lys
1               5

<210> SEQ ID NO 791
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 791

Gly Pro Asn Asn Phe Gly Ser Gly Lys
1               5

<210> SEQ ID NO 792
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

```
<400> SEQUENCE: 792

Gly Glu Asp Thr Arg Asn Thr Gly Lys
1               5

<210> SEQ ID NO 793
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 793

Gly Lys Asp Leu Glu Gln Ser Gly Lys
1               5

<210> SEQ ID NO 794
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 794

Gly Ala Ala Leu His Asn Asp Gly Lys
1               5

<210> SEQ ID NO 795
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 795

Gly Ala Asp Ser Phe Phe Lys Gly Lys
1               5

<210> SEQ ID NO 796
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 796

Gly Ile Thr Phe Trp Arg Ala Gly Lys
1               5
```

```
<210> SEQ ID NO 797
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 797

Gly Leu Ser Asp Leu Arg Leu Gly Lys
1               5

<210> SEQ ID NO 798
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 798

Gly Glu Val Gly Trp Thr Tyr Gly Lys
1               5

<210> SEQ ID NO 799
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 799

Gly Ile Ala Phe Arg Gln Leu Gly Lys
1               5

<210> SEQ ID NO 800
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 800

Gly Tyr Asn Ile His Thr Leu Gly Lys
1               5

<210> SEQ ID NO 801
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 801

Gly Leu Leu Trp Ala Asn His Gly Lys
1               5

<210> SEQ ID NO 802
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 802

Gly Leu Tyr Ser Val Gln Val Gly Lys
1               5

<210> SEQ ID NO 803
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 803

Gly Ser His Ile Leu Ser Asn Gly Lys
1               5

<210> SEQ ID NO 804
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
```

<223> OTHER INFORMATION: Lys modified with a CPQ2 quencher

<400> SEQUENCE: 804

Gly Lys Leu Leu Ile Asp Val Gly Lys
1               5

<210> SEQ ID NO 805
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 805

Gly Glu Leu Gly Val Phe Asp Gly Lys
1               5

<210> SEQ ID NO 806
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 806

Gly His Gln Ala Tyr Thr Leu Gly Lys
1               5

<210> SEQ ID NO 807
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 807

Gly Tyr Val Arg Lys Ile Gln Gly Lys
1               5

<210> SEQ ID NO 808
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

```
<400> SEQUENCE: 808

Gly Asp Arg Glu Asn Ser Pro Gly Lys
1               5

<210> SEQ ID NO 809
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 809

Gly Lys Tyr Asp Lys Pro Arg Gly Lys
1               5

<210> SEQ ID NO 810
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 810

Gly Arg Pro Trp Lys Gln Leu Gly Lys
1               5

<210> SEQ ID NO 811
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 811

Gly Ala Pro Leu Gln Arg Tyr Gly Lys
1               5

<210> SEQ ID NO 812
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 812

Gly Tyr Gln Gly Gln Lys Leu Gly Lys
1               5

<210> SEQ ID NO 813
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 813

Gly Gly Arg Ile Ser Ser Ile Gly Lys
1               5

<210> SEQ ID NO 814
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 814

Gly His Ser Leu Thr Asn Val Gly Lys
1               5

<210> SEQ ID NO 815
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 815

Gly Glu Trp Asp Phe Pro Glu Gly Lys
1               5

<210> SEQ ID NO 816
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 816

Gly Tyr Leu Ala Leu Asp Gly Gly Lys
1               5

<210> SEQ ID NO 817
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 817

Gly Phe Ile Tyr Leu Pro Thr Gly Lys
1               5

<210> SEQ ID NO 818
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 818

Gly Gly His Glu Thr Trp Val Gly Lys
1               5

<210> SEQ ID NO 819
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 819

Gly Asp Tyr Ile Gly Asp Glu Gly Lys
1               5

<210> SEQ ID NO 820
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 820

Gly Ala Gly Thr Ala His Pro Gly Lys
1               5

<210> SEQ ID NO 821
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 821

Gly Val Leu Thr Glu Ile Trp Gly Lys
1               5

<210> SEQ ID NO 822
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 822

Gly Pro Asp Asp Trp Gln Asn Gly Lys
1               5

<210> SEQ ID NO 823
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 823

Gly Gly Leu Asn Gln Glu Tyr Gly Lys
1               5

<210> SEQ ID NO 824
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

<400> SEQUENCE: 824

Gly Tyr Arg Asp Ala Val Ala Gly Lys
1               5

<210> SEQ ID NO 825
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 825

Gly Thr Gly Pro Lys Gly Asn Gly Lys
1               5

<210> SEQ ID NO 826
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 826

Gly Asp His Val Pro Gln Ile Gly Lys
1               5

<210> SEQ ID NO 827
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 827

Gly Asn Lys Glu Pro Ile Leu Gly Lys
1               5

<210> SEQ ID NO 828
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

```
<400> SEQUENCE: 828

Gly Val Trp Asn Leu Val His Gly Lys
1               5

<210> SEQ ID NO 829
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 829

Gly Pro Val Ile Ile Glu His Gly Lys
1               5

<210> SEQ ID NO 830
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 830

Gly Phe Gln Thr Asp Asn Leu Gly Lys
1               5

<210> SEQ ID NO 831
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 831

Gly Arg Phe Leu His Gly Ile Gly Lys
1               5

<210> SEQ ID NO 832
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

-continued

```
<400> SEQUENCE: 832

Gly Tyr Ala Glu Arg Thr Thr Gly Lys
1               5

<210> SEQ ID NO 833
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 833

Gly Asn Arg Gly Glu Leu Pro Gly Lys
1               5

<210> SEQ ID NO 834
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 834

Gly His His Tyr Phe Asn Tyr Gly Lys
1               5

<210> SEQ ID NO 835
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 835

Gly Ser Thr Pro Tyr Tyr His Gly Lys
1               5

<210> SEQ ID NO 836
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 836

Gly Trp Phe Tyr Pro Ser Ala Gly Lys
1               5
```

```
<210> SEQ ID NO 837
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 837

Gly Ser Glu Phe Leu Phe Ser Gly Lys
1               5

<210> SEQ ID NO 838
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 838

Gly Trp Tyr Lys Thr Gln Tyr Gly Lys
1               5

<210> SEQ ID NO 839
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 839

Gly Val Thr His Leu Lys Val Gly Lys
1               5

<210> SEQ ID NO 840
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 840

Gly Ile Asn Gly Gly Phe Ser Gly Lys
1               5

<210> SEQ ID NO 841
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (9)..(9)
<223> OTHER INFORMATION: Lys modified with a CPQ2 quencher

<400> SEQUENCE: 841

Gly Thr Val Leu Gly Leu Asp Gly Lys
1               5

<210> SEQ ID NO 842
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 842

Gly Ser Tyr Trp Pro Leu Gln Gly Lys
1               5

<210> SEQ ID NO 843
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 843

Gly Ala Ser Gln Gln His Arg Gly Lys
1               5

<210> SEQ ID NO 844
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 844

Gly Lys Asn Pro Ala Lys Ala Gly Lys
1               5

<210> SEQ ID NO 845
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
```

```
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 845

Gly Leu Tyr Trp Leu Val Glu Gly Lys
1               5

<210> SEQ ID NO 846
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 846

Gly Ser Trp Trp Ile Phe Glu Gly Lys
1               5

<210> SEQ ID NO 847
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 847

Gly Val Asn Tyr Glu Gln Asp Gly Lys
1               5

<210> SEQ ID NO 848
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 848

Gly His Phe Phe Leu Ala Glu Gly Lys
1               5

<210> SEQ ID NO 849
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
```

-continued

```
<222> LOCATION: (9)..(9)
<223> OTHER INFORMATION: Lys modified with a CPQ2 quencher

<400> SEQUENCE: 849

Gly Asp Ile Pro Pro His Trp Gly Lys
1               5

<210> SEQ ID NO 850
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 850

Gly Val Asp Gln Trp Leu Trp Gly Lys
1               5

<210> SEQ ID NO 851
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 851

Gly Leu Arg Ser Leu Leu Lys Gly Lys
1               5

<210> SEQ ID NO 852
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 852

Gly Leu Leu Ile Arg His Ala Gly Lys
1               5
```

```
<210> SEQ ID NO 853
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 853

Gly His Asp Val Lys Phe Ile Gly Lys
1               5

<210> SEQ ID NO 854
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 854

Gly Lys Arg Val Gln Phe Leu Gly Lys
1               5

<210> SEQ ID NO 855
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 855

Gly Arg Asp Leu Tyr Ala Glu Gly Lys
1               5

<210> SEQ ID NO 856
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 856

Gly Leu Leu Ile Tyr Phe Glu Gly Lys
1               5
```

```
<210> SEQ ID NO 857
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 857

Gly Leu Arg Thr Lys Gln Ser Gly Lys
1               5

<210> SEQ ID NO 858
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 858

Gly Trp His Gly Gln Gln Tyr Gly Lys
1               5

<210> SEQ ID NO 859
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 859

Gly Gly Pro Glu Gly Thr Ile Gly Lys
1               5

<210> SEQ ID NO 860
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 860

Gly Glu Leu Asp Pro Ile Pro Gly Lys
1               5

<210> SEQ ID NO 861
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 861

Gly Gly Arg Ala Ala Asp Phe Gly Lys
1               5

<210> SEQ ID NO 862
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 862

Gly His Phe Ile Asp Tyr Ile Gly Lys
1               5

<210> SEQ ID NO 863
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 863

Gly Ser Leu Leu Arg Val His Gly Lys
1               5

<210> SEQ ID NO 864
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 864

Gly Ser Phe Arg Lys Ile Ile Gly Lys
1               5

<210> SEQ ID NO 865
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 865

Gly Thr Tyr Glu Leu Phe Ser Gly Lys
1               5

<210> SEQ ID NO 866
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 866

Gly His Leu Leu Gly Phe Tyr Gly Lys
1               5

<210> SEQ ID NO 867
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 867

Gly Leu Trp Thr Ala Leu Thr Gly Lys
1               5

<210> SEQ ID NO 868
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 868

Gly Ile Trp Asn Leu Val Tyr Gly Lys
1               5
```

```
<210> SEQ ID NO 869
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 869

Gly Arg Arg Asn Pro Leu Trp Gly Lys
1               5

<210> SEQ ID NO 870
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 870

Gly Arg Trp Tyr Gly Gly Ile Gly Lys
1               5

<210> SEQ ID NO 871
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 871

Gly Lys Thr Gly Asp Ala Arg Gly Lys
1               5

<210> SEQ ID NO 872
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 872

Gly Asn Tyr Trp Glu Ala Asn Gly Lys
1               5

<210> SEQ ID NO 873
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 873

Gly Leu Gln Phe Asp Thr Ser Gly Lys
1               5

<210> SEQ ID NO 874
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 874

Gly Lys Arg Gly Ala Val Glu Gly Lys
1               5

<210> SEQ ID NO 875
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 875

Gly Ser Leu Lys Pro Thr Glu Gly Lys
1               5

<210> SEQ ID NO 876
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 876

Gly Glu Asn Asp Arg Leu Pro Gly Lys
1               5

<210> SEQ ID NO 877
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

<221> NAME/KEY: MOD_RES
<222> LOCATION: (9)..(9)
<223> OTHER INFORMATION: Lys modified with a CPQ2 quencher

<400> SEQUENCE: 877

Gly Asn Ser Tyr Gln Val Gln Gly Lys
1               5

<210> SEQ ID NO 878
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 878

Gly Tyr Pro Lys Glu Tyr Leu Gly Lys
1               5

<210> SEQ ID NO 879
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 879

Gly Ile Asn Asn Lys Trp Gln Gly Lys
1               5

<210> SEQ ID NO 880
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 880

Gly Leu Glu Phe Gln Gly Trp Gly Lys
1               5

<210> SEQ ID NO 881
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

```
<400> SEQUENCE: 881

Gly Pro Val Arg Ser Thr Asn Gly Lys
1               5

<210> SEQ ID NO 882
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 882

Gly Ser Gln Ala Ile Lys Val Gly Lys
1               5

<210> SEQ ID NO 883
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 883

Gly Trp Ala Leu Leu Tyr His Gly Lys
1               5

<210> SEQ ID NO 884
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 884

Gly Ile Ser Trp Ile His Ala Gly Lys
1               5

<210> SEQ ID NO 885
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 885

Gly Ala His Asp Ile Val Asn Gly Lys
1               5

<210> SEQ ID NO 886
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 886

Gly Arg His Asn Val Ala Ser Gly Lys
1               5

<210> SEQ ID NO 887
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 887

Gly Ser Val Phe Val Ile Glu Gly Lys
1               5

<210> SEQ ID NO 888
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 888

Gly Phe Ala Lys Tyr Tyr Lys Gly Lys
1               5

<210> SEQ ID NO 889
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 889

Gly Pro Tyr Asn Thr Leu Gln Gly Lys
1               5
```

```
<210> SEQ ID NO 890
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 890

Gly Leu Asp Trp Gly His Leu Gly Lys
1               5

<210> SEQ ID NO 891
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 891

Gly Ser Asn Arg Glu Trp Phe Gly Lys
1               5

<210> SEQ ID NO 892
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 892

Gly Gly Lys Ser Glu His Thr Gly Lys
1               5

<210> SEQ ID NO 893
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher
```

<400> SEQUENCE: 893

Gly Phe Pro Leu Thr Asp Gln Gly Lys
1               5

<210> SEQ ID NO 894
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 894

Gly Trp Ser Lys Phe Trp Leu Gly Lys
1               5

<210> SEQ ID NO 895
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 895

Gly Arg Phe Thr Arg Pro His Gly Lys
1               5

<210> SEQ ID NO 896
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 896

Gly Gln Glu Thr Leu Lys Asp Gly Lys
1               5

<210> SEQ ID NO 897
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)

<223> OTHER INFORMATION: Lys modified with a CPQ2 quencher

<400> SEQUENCE: 897

Gly His Trp Trp Asp Val Leu Gly Lys
1               5

<210> SEQ ID NO 898
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 898

Gly Phe Asn Leu Val Leu Ser Gly Lys
1               5

<210> SEQ ID NO 899
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 899

Gly Ser Ala Trp Arg Gln Arg Gly Lys
1               5

<210> SEQ ID NO 900
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 900

Gly Thr Phe His Ile Phe Leu Gly Lys
1               5

<210> SEQ ID NO 901
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

```
<400> SEQUENCE: 901

Gly Trp Pro Gln His Val Lys Gly Lys
1               5

<210> SEQ ID NO 902
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 902

Gly Leu Ile Leu His Lys Asn Gly Lys
1               5

<210> SEQ ID NO 903
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 903

Gly Gln Asp Leu Glu Gln Pro Gly Lys
1               5

<210> SEQ ID NO 904
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 904

Gly His Gln Lys Lys Leu Pro Gly Lys
1               5

<210> SEQ ID NO 905
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
```

```
<223> OTHER INFORMATION: Lys modified with a CPQ2 quencher

<400> SEQUENCE: 905

Gly Gly Val Thr Trp Leu Asn Gly Lys
1               5

<210> SEQ ID NO 906
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 906

Gly Ala Gly Glu Pro Phe Lys Gly Lys
1               5

<210> SEQ ID NO 907
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 907

Gly Ser Arg Leu Ala Thr Thr Gly Lys
1               5

<210> SEQ ID NO 908
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 908

Gly Leu Ala Phe Leu Asn His Gly Lys
1               5

<210> SEQ ID NO 909
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
```

```
<222> LOCATION: (9)..(9)
<223> OTHER INFORMATION: Lys modified with a CPQ2 quencher

<400> SEQUENCE: 909

Gly Pro Pro Ser Gly Leu Ser Gly Lys
1               5

<210> SEQ ID NO 910
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 910

Gly Tyr Thr His Ser Ser Pro Gly Lys
1               5

<210> SEQ ID NO 911
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 911

Gly Asp Gly Ser His Tyr Arg Gly Lys
1               5

<210> SEQ ID NO 912
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 912

Gly Tyr Leu Gly Asn Gly Tyr Gly Lys
1               5

<210> SEQ ID NO 913
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 913

Gly Asp Ser Ile Thr Val Ser Gly Lys
1               5

<210> SEQ ID NO 914
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 914

Gly Gln Thr Pro Asn Ile Gln Gly Lys
1               5

<210> SEQ ID NO 915
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 915

Gly Lys Leu Phe Phe Gly Tyr Gly Lys
1               5

<210> SEQ ID NO 916
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 916

Gly Thr Gln Asn Phe Asn Trp Gly Lys
1               5

<210> SEQ ID NO 917
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 917

Gly Tyr Ser Asp His Glu Val Gly Lys
1               5

<210> SEQ ID NO 918
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 918

Gly Arg Tyr Val Val Pro Ala Gly Lys
1               5

<210> SEQ ID NO 919
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 919

Gly Ile Leu His Arg Ile Arg Gly Lys
1               5

<210> SEQ ID NO 920
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 920

Gly Glu Ser Asp Asn Gln Leu Gly Lys
1               5

<210> SEQ ID NO 921
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 921

Gly Tyr Asp Asp Lys Gly Leu Gly Lys
1               5
```

```
<210> SEQ ID NO 922
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 922

Gly Gln Leu Ser Leu Val Trp Gly Lys
1               5

<210> SEQ ID NO 923
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 923

Gly Pro Gly Gly Glu Arg Leu Gly Lys
1               5

<210> SEQ ID NO 924
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 924

Gly Trp Lys His His Pro Asp Gly Lys
1               5

<210> SEQ ID NO 925
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 925

Gly Gln Trp Val Asp Glu Asp Gly Lys
1               5
```

```
<210> SEQ ID NO 926
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 926

Gly Asn Ala Tyr Asn Glu Ile Gly Lys
1               5

<210> SEQ ID NO 927
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 927

Gly Glu Glu Lys Ala Pro Arg Gly Lys
1               5

<210> SEQ ID NO 928
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 928

Gly Pro Trp Gln Ile Gly Lys Gly Lys
1               5

<210> SEQ ID NO 929
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 929

Gly Ile Ala Gln Val Gly Asn Gly Lys
1               5

<210> SEQ ID NO 930
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 930

Gly Val Leu Arg Gln Ser Glu Gly Lys
1               5

<210> SEQ ID NO 931
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 931

Gly Thr Glu Arg Val Asp Ala Gly Lys
1               5

<210> SEQ ID NO 932
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 932

Gly Trp Leu Arg Trp Arg Leu Gly Lys
1               5

<210> SEQ ID NO 933
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 933

Gly Trp Lys Thr Lys Gly Gln Gly Lys
1               5

<210> SEQ ID NO 934
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: MOD_RES
<222> LOCATION: (9)..(9)
<223> OTHER INFORMATION: Lys modified with a CPQ2 quencher

<400> SEQUENCE: 934

Gly Gln Ser Asn Gly Asp Val Gly Lys
1               5

<210> SEQ ID NO 935
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 935

Gly Thr Leu Phe Tyr Ala Leu Gly Lys
1               5

<210> SEQ ID NO 936
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 936

Gly Thr Val Thr Leu Asn Pro Gly Lys
1               5

<210> SEQ ID NO 937
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 937

Gly Tyr Ala Phe Gly Arg Lys Gly Lys
1               5

<210> SEQ ID NO 938
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 938

Gly Asp Tyr Asn Tyr Trp Asp Gly Lys
1               5

<210> SEQ ID NO 939
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 939

Gly Glu Trp His Glu Ile Ile Gly Lys
1               5

<210> SEQ ID NO 940
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 940

Gly Gln Lys Ala Ala Trp Asp Gly Lys
1               5

<210> SEQ ID NO 941
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 941

Gly Asp Asn Thr Ser Ala Asp Gly Lys
1               5

<210> SEQ ID NO 942
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 942

Gly His Glu Gly Glu Tyr Val Gly Lys
1               5
```

```
-continued

<210> SEQ ID NO 943
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 943

Gly Trp Ser Pro Ser Phe Lys Gly Lys
1               5

<210> SEQ ID NO 944
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 944

Gly His Asp Glu His Trp Thr Gly Lys
1               5

<210> SEQ ID NO 945
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 945

Gly Tyr Val Trp Leu Arg Asp Gly Lys
1               5

<210> SEQ ID NO 946
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 946

Gly Leu Asp Pro Leu Lys Phe Gly Lys
1               5

<210> SEQ ID NO 947
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 947

Gly Leu Arg Leu Phe Trp Asp Gly Lys
1               5

<210> SEQ ID NO 948
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 948

Gly Asp Ile Ala Ile Thr Leu Gly Lys
1               5

<210> SEQ ID NO 949
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 949

Gly Pro Ile Leu Arg Phe His Gly Lys
1               5

<210> SEQ ID NO 950
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 950

Gly Val Trp Gln Gly Tyr Ile Gly Lys
1               5

<210> SEQ ID NO 951
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 951

Gly Lys Lys Leu Ser Asn Pro Gly Lys
1               5

<210> SEQ ID NO 952
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 952

Gly Gly His Pro Leu Ser Pro Gly Lys
1               5

<210> SEQ ID NO 953
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 953

Gly Val Arg Gln His Lys Pro Gly Lys
1               5

<210> SEQ ID NO 954
<211> LENGTH: 9
<212> TYPE: PRT
<213> ORGANISM: Artificial Sequence
<220> FEATURE:
```

<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 954

Gly Ala Gln Asn Phe Tyr Arg Gly Lys
1               5

<210> SEQ ID NO 955
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 955

Gly Val Ala Gly Lys Ser Ile Gly Lys
1               5

<210> SEQ ID NO 956
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 956

Gly Leu Val Gly Gln Val Asn Gly Lys
1               5

<210> SEQ ID NO 957
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 957

Gly Gln Val Lys His Phe Thr Gly Lys
1               5

<210> SEQ ID NO 958
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher -continued

```
<400> SEQUENCE: 958

Gly Gln Lys Ser Val Val Ser Gly Lys
1               5

<210> SEQ ID NO 959
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 959

Gly Tyr Leu Gln Glu Trp Leu Gly Lys
1               5

<210> SEQ ID NO 960
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 960

Gly Gly Leu Tyr Ile Asp Glu Gly Lys
1               5

<210> SEQ ID NO 961
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 961

Gly Asn Ala Gly Ser Lys Phe Gly Lys
1               5

<210> SEQ ID NO 962
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 962

Gly Glu Phe Val His Asn Pro Gly Lys
1               5

<210> SEQ ID NO 963
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 963

Gly Trp Glu Leu Val Lys Ile Gly Lys
1               5

<210> SEQ ID NO 964
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 964

Gly Trp Val Gly Ala Ser His Gly Lys
1               5

<210> SEQ ID NO 965
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 965

Gly Ile Thr Thr Leu Tyr Leu Gly Lys
1               5

<210> SEQ ID NO 966
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
```

```
<223> OTHER INFORMATION: Lys modified with a CPQ2 quencher

<400> SEQUENCE: 966

Gly Gly His Ile Asp Glu Tyr Gly Lys
1               5

<210> SEQ ID NO 967
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 967

Gly Lys Val Leu Asp Tyr Gly Gly Lys
1               5

<210> SEQ ID NO 968
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 968

Gly Gln Glu Lys Gln Thr Leu Gly Lys
1               5

<210> SEQ ID NO 969
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 969

Gly Glu Val Gly His Glu Ala Gly Lys
1               5

<210> SEQ ID NO 970
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
```

```
<222> LOCATION: (9)..(9)
<223> OTHER INFORMATION: Lys modified with a CPQ2 quencher

<400> SEQUENCE: 970

Gly Ala Trp Glu Gly Gln Tyr Gly Lys
1               5

<210> SEQ ID NO 971
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 971

Gly Phe Leu Val Gln Trp Thr Gly Lys
1               5

<210> SEQ ID NO 972
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 972

Gly Ser Lys Trp Gly Tyr Trp Gly Lys
1               5

<210> SEQ ID NO 973
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 973

Gly Thr Trp Ile Ser Leu Gln Gly Lys
1               5

<210> SEQ ID NO 974
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher
```

```
<400> SEQUENCE: 974

Gly Val Ile Asp Lys Asp Phe Gly Lys
1               5

<210> SEQ ID NO 975
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 975

Gly Val Lys Phe Ala Ile Tyr Gly Lys
1               5

<210> SEQ ID NO 976
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 976

Gly His Asn Gln Leu Lys Ser Gly Lys
1               5

<210> SEQ ID NO 977
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 977

Gly Gln Tyr Val Phe Phe Leu Gly Lys
1               5

<210> SEQ ID NO 978
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
```

```
<220> FEATURE:
<221> NAME/KEY: MOD_RES
<222> LOCATION: (9)..(9)
<223> OTHER INFORMATION: Lys modified with a CPQ2 quencher

<400> SEQUENCE: 978

Gly Tyr Asn Pro Arg Glu Leu Gly Lys
1               5

<210> SEQ ID NO 979
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 979

Gly Lys His Gly Leu Pro Glu Gly Lys
1               5

<210> SEQ ID NO 980
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 980

Gly Trp Ser Arg Glu Tyr Trp Gly Lys
1               5

<210> SEQ ID NO 981
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 981

Gly Ile Asp Arg Val Asp Lys Gly Lys
1               5

<210> SEQ ID NO 982
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
```

```
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 982

Lys Lys Gly Asp Arg Glu Asn Ser Pro Lys Leu
1               5                   10

<210> SEQ ID NO 983
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 983

Lys Lys Gly Asp Arg Glu Asn Ser Pro Leu Lys
1               5                   10

<210> SEQ ID NO 984
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 984

Gly Asn Ala Gly Ser Lys Phe Lys Gln
1               5

<210> SEQ ID NO 985
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 985

Gly Asn Ala Gly Ser Lys Phe Gln Lys
1               5

<210> SEQ ID NO 986
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 986

Lys Lys Gly His Leu Leu Gly Phe Tyr Lys Val
1               5                   10

<210> SEQ ID NO 987
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 987

Lys Lys Gly His Leu Leu Gly Phe Tyr Val Lys
1               5                   10

<210> SEQ ID NO 988
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (9)..(9)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher
<220> FEATURE:
<221> NAME/KEY: MOD_RES
<222> LOCATION: (11)..(11)
<223> OTHER INFORMATION: Norleucine
```

```
<400> SEQUENCE: 988

Lys Lys Gly Gln Glu Lys Gln Thr Leu Lys Leu
1               5                   10

<210> SEQ ID NO 989
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (9)..(9)
<223> OTHER INFORMATION: Norleucine
<220> FEATURE:
<221> NAME/KEY: MOD_RES
<222> LOCATION: (10)..(10)
<223> OTHER INFORMATION: Norleucine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 989

Lys Lys Gly Gln Glu Lys Gln Thr Leu Leu Lys
1               5                   10

<210> SEQ ID NO 990
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 990

Lys Gly Asp Pro Phe Val Val Ser Lys Trp
1               5                   10

<210> SEQ ID NO 991
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher
```

```
<400> SEQUENCE: 991

Lys Gly Asp Pro Phe Val Val Ser Trp Lys
1               5                   10

<210> SEQ ID NO 992
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 992

Gly Asn Ala Tyr Asn Glu Ile Lys Arg
1               5

<210> SEQ ID NO 993
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 993

Gly Asn Ala Tyr Asn Glu Ile Arg Lys
1               5

<210> SEQ ID NO 994
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher

<400> SEQUENCE: 994

Gly Val Leu Arg Gln Ser Glu Lys Asn
1               5

<210> SEQ ID NO 995
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
```

<223> OTHER INFORMATION: Lys modified with a CPQ2 quencher

<400> SEQUENCE: 995

Gly Val Leu Arg Gln Ser Glu Asn Lys
1               5

<210> SEQ ID NO 996
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (8)..(8)
<223> OTHER INFORMATION: Lys modified with a CPQ2 quencher

<400> SEQUENCE: 996

Gly Tyr Asn Pro Arg Glu Leu Lys Ile
1               5

<210> SEQ ID NO 997
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 997

Gly Tyr Asn Pro Arg Glu Leu Ile Lys
1               5

<210> SEQ ID NO 998
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 998

Lys Gly Glu Phe Val His Asn Pro Lys Lys
1               5                   10

<210> SEQ ID NO 999
<211> LENGTH: 10
<212> TYPE: PRT
<213> ORGANISM: Artificial Sequence
<220> FEATURE:

```
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 999

Lys Gly Glu Phe Val His Asn Pro Lys Lys
1               5                   10

<210> SEQ ID NO 1000
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 1000

Gly Lys Arg Val Gln Phe Leu Lys His
1               5

<210> SEQ ID NO 1001
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1001

Gly Lys Arg Val Gln Phe Leu His Lys
1               5

<210> SEQ ID NO 1002
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1002

Lys Gly Leu Ile Leu His Lys Asn Lys Gly
1               5                   10
```

```
<210> SEQ ID NO 1003
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1003

Lys Gly Leu Ile Leu His Lys Asn Gly Lys
1               5                   10

<210> SEQ ID NO 1004
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1004

Lys Lys Gly Trp Ala Leu Leu Tyr His Lys Ser
1               5                   10

<210> SEQ ID NO 1005
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (11)..(11)
<223> OTHER INFORMATION: Lys modified with a CPQ2 quencher
```

```
<400> SEQUENCE: 1005

Lys Lys Gly Trp Ala Leu Leu Tyr His Ser Lys
1               5                   10

<210> SEQ ID NO 1006
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1006

Lys Lys Gly Ala His Asp Ile Val Asn Lys Tyr
1               5                   10

<210> SEQ ID NO 1007
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1007

Lys Lys Gly Ala His Asp Ile Val Asn Tyr Lys
1               5                   10

<210> SEQ ID NO 1008
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1008

Lys Gly Ser Val Phe Val Ile Glu Lys Pro
1               5                   10
```

```
<210> SEQ ID NO 1009
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1009

Lys Gly Ser Val Phe Val Ile Glu Pro Lys
1               5                   10

<210> SEQ ID NO 1010
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1010

Lys Gly Pro Pro Ser Gly Leu Ser Lys Glu
1               5                   10

<210> SEQ ID NO 1011
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1011

Lys Gly Pro Pro Ser Gly Leu Ser Glu Lys
1               5                   10

<210> SEQ ID NO 1012
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
```

-continued

```
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1012

Lys Lys Gly Arg Trp Tyr Gly Gly Ile Lys Phe
1               5                   10

<210> SEQ ID NO 1013
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1013

Lys Lys Gly Arg Trp Tyr Gly Gly Ile Phe Lys
1               5                   10

<210> SEQ ID NO 1014
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1014

Lys Gly Gln Tyr Val Phe Phe Leu Lys Asp
1               5                   10

<210> SEQ ID NO 1015
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
```

```
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1015

Lys Gly Gln Tyr Val Phe Phe Leu Asp Lys
1               5                   10

<210> SEQ ID NO 1016
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1016

Lys Gly Phe Ala Lys Tyr Tyr Lys Lys Thr
1               5                   10

<210> SEQ ID NO 1017
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1017

Lys Gly Phe Ala Lys Tyr Tyr Lys Thr Lys
1               5                   10

<210> SEQ ID NO 1018
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1018

Lys Gly Gln Val Lys His Phe Thr Lys Ala
1               5                   10
```

```
<210> SEQ ID NO 1019
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1019

Lys Gly Gln Val Lys His Phe Thr Ala Lys
1               5                   10

<210> SEQ ID NO 1020
<211> LENGTH: 3
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: Lys modified with a CPQ2 quencher

<400> SEQUENCE: 1020

Ala Pro Lys
1

<210> SEQ ID NO 1021
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1021

His Lys Asp Arg Glu Asn Ser Pro Gly Lys
1               5                   10

<210> SEQ ID NO 1022
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher
```

```
<400> SEQUENCE: 1022

Lys His Asp Arg Glu Asn Ser Pro Gly Lys
1               5                   10

<210> SEQ ID NO 1023
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1023

Trp Lys Asn Ala Gly Ser Lys Phe Gly Lys Lys
1               5                   10

<210> SEQ ID NO 1024
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1024

Lys Trp Asn Ala Gly Ser Lys Phe Gly Lys Lys
1               5                   10

<210> SEQ ID NO 1025
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher
```

<400> SEQUENCE: 1025

Ser Lys His Leu Leu Gly Phe Tyr Gly Lys Lys
1               5                   10

<210> SEQ ID NO 1026
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1026

Lys Ser His Leu Leu Gly Phe Tyr Gly Lys Lys
1               5                   10

<210> SEQ ID NO 1027
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1027

Lys Lys Gln Glu Lys Gln Thr Leu Gly Lys
1               5                   10

<210> SEQ ID NO 1028
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1028

Lys Lys Gln Glu Lys Gln Thr Leu Gly Lys
1               5                   10

<210> SEQ ID NO 1029
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1029

Gly Lys Asp Pro Phe Val Val Ser Gly Lys
1               5                   10

<210> SEQ ID NO 1030
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1030

Lys Gly Asp Pro Phe Val Val Ser Gly Lys
1               5                   10

<210> SEQ ID NO 1031
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1031

Pro Lys Asn Ala Tyr Asn Glu Ile Gly Lys
1               5                   10

<210> SEQ ID NO 1032
<211> LENGTH: 10
<212> TYPE: PRT
<213> ORGANISM: Artificial Sequence
<220> FEATURE:
<223> OTHER INFORMATION: Description of Artificial Sequence: Synthetic
      probe

```
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1032

Lys Pro Asn Ala Tyr Asn Glu Ile Gly Lys
1               5                   10

<210> SEQ ID NO 1033
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1033

Asp Lys Val Leu Arg Gln Ser Glu Gly Lys Lys
1               5                   10

<210> SEQ ID NO 1034
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1034

Lys Asp Val Leu Arg Gln Ser Glu Gly Lys Lys
1               5                   10

<210> SEQ ID NO 1035
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1035

Glu Lys Tyr Asn Pro Arg Glu Leu Gly Lys Lys
1               5                   10

<210> SEQ ID NO 1036
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1036

Lys Glu Tyr Asn Pro Arg Glu Leu Gly Lys Lys
1               5                   10

<210> SEQ ID NO 1037
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher
```

-continued

<400> SEQUENCE: 1037

Thr Lys Glu Phe Val His Asn Pro Gly Lys Lys
1               5                   10

<210> SEQ ID NO 1038
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1038

Lys Thr Glu Phe Val His Asn Pro Gly Lys Lys
1               5                   10

<210> SEQ ID NO 1039
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1039

Gln Lys Lys Arg Val Gln Phe Leu Gly Lys
1               5                   10

<210> SEQ ID NO 1040
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1040

Lys Gln Lys Arg Val Gln Phe Leu Gly Lys
1               5                   10

<210> SEQ ID NO 1041
<211> LENGTH: 10

-continued

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1041

Tyr Lys Leu Ile Leu His Lys Asn Gly Lys
1               5                   10

<210> SEQ ID NO 1042
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1042

Lys Tyr Leu Ile Leu His Lys Asn Gly Lys
1               5                   10

<210> SEQ ID NO 1043
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1043

Phe Lys Trp Ala Leu Leu Tyr His Gly Lys Lys
1               5                   10
```

```
<210> SEQ ID NO 1044
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1044

Lys Phe Trp Ala Leu Leu Tyr His Gly Lys Lys
1               5                   10

<210> SEQ ID NO 1045
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1045

Ile Lys Ala His Asp Ile Val Asn Gly Lys Lys
1               5                   10

<210> SEQ ID NO 1046
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher
```

```
<400> SEQUENCE: 1046

Lys Ile Ala His Asp Ile Val Asn Gly Lys Lys
1               5                   10

<210> SEQ ID NO 1047
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1047

Val Lys Ser Val Phe Val Ile Glu Gly Lys
1               5                   10

<210> SEQ ID NO 1048
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1048

Lys Val Ser Val Phe Val Ile Glu Gly Lys
1               5                   10

<210> SEQ ID NO 1049
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1049

Leu Lys Pro Pro Ser Gly Leu Ser Gly Lys
1               5                   10

<210> SEQ ID NO 1050
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1050

Lys Leu Pro Pro Ser Gly Leu Ser Gly Lys
1               5                   10

<210> SEQ ID NO 1051
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1051

Leu Lys Arg Trp Tyr Gly Gly Ile Gly Lys Lys
1               5                   10

<210> SEQ ID NO 1052
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1052

Lys Leu Arg Trp Tyr Gly Gly Ile Gly Lys Lys
1               5                   10

<210> SEQ ID NO 1053
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1053

Asn Lys Gln Tyr Val Phe Phe Leu Gly Lys
1               5                   10

<210> SEQ ID NO 1054
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1054

Lys Asn Gln Tyr Val Phe Phe Leu Gly Lys
1               5                   10

<210> SEQ ID NO 1055
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1055

Ala Lys Phe Ala Lys Tyr Tyr Lys Gly Lys
1               5                   10

<210> SEQ ID NO 1056
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1056

Lys Ala Phe Ala Lys Tyr Tyr Lys Gly Lys
1               5                   10

<210> SEQ ID NO 1057
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1057

Arg Lys Gln Val Lys His Phe Thr Gly Lys
1               5                   10

<210> SEQ ID NO 1058
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1058

Lys Arg Gln Val Lys His Phe Thr Gly Lys
1               5                   10

<210> SEQ ID NO 1059
<211> LENGTH: 4
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: carboxy-fluorescein-L-lysine
<220> FEATURE:
<221> NAME/KEY: MOD_RES
<222> LOCATION: (4)..(4)
<223> OTHER INFORMATION: Lys modified with a CPQ2 quencher

<400> SEQUENCE: 1059

Lys Pro Pro Lys
1
```

```
<210> SEQ ID NO 1060
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (3)..(3)
<223> OTHER INFORMATION: D-Proline
<220> FEATURE:
<221> NAME/KEY: MOD_RES
<222> LOCATION: (4)..(4)
<223> OTHER INFORMATION: D-Isoleucine
<220> FEATURE:
<221> NAME/KEY: MOD_RES
<222> LOCATION: (5)..(5)
<223> OTHER INFORMATION: D-Leucine
<220> FEATURE:
<221> NAME/KEY: MOD_RES
<222> LOCATION: (6)..(6)
<223> OTHER INFORMATION: D-Phenylalanine
<220> FEATURE:
<221> NAME/KEY: MOD_RES
<222> LOCATION: (7)..(7)
<223> OTHER INFORMATION: D-Phenylalanine
<220> FEATURE:
<221> NAME/KEY: MOD_RES
<222> LOCATION: (8)..(8)
<223> OTHER INFORMATION: D-Arginine
<220> FEATURE:
<221> NAME/KEY: MOD_RES
<222> LOCATION: (9)..(9)
<223> OTHER INFORMATION: D-Leucine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1060

Gly Lys Pro Ile Leu Phe Phe Arg Leu Lys Gly Lys
1               5                   10

<210> SEQ ID NO 1061
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1061

Leu Arg Arg
1

<210> SEQ ID NO 1062
<211> LENGTH: 1
<212> TYPE: PRT
<213> ORGANISM: Artificial Sequence
<220> FEATURE:
<223> OTHER INFORMATION: Description of Artificial Sequence: Synthetic
      probe
```

```
<400> SEQUENCE: 1062

Arg
1

<210> SEQ ID NO 1063
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1063

Val Arg
1

<210> SEQ ID NO 1064
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1064

Arg Arg
1

<210> SEQ ID NO 1065
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1065

Gly Arg
1

<210> SEQ ID NO 1066
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1066

Phe Arg
1

<210> SEQ ID NO 1067
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1067

Arg Gly Lys
1

<210> SEQ ID NO 1068
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1068

Gly Gly Arg
1

<210> SEQ ID NO 1069
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1069

Phe
1

<210> SEQ ID NO 1070
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1070

Asp
1

<210> SEQ ID NO 1071
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1071

Arg Arg
1

<210> SEQ ID NO 1072
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1072

Arg
1

<210> SEQ ID NO 1073
<211> LENGTH: 1
<212> TYPE: PRT
<213> ORGANISM: Artificial Sequence
<220> FEATURE:
<223> OTHER INFORMATION: Description of Artificial Sequence: Synthetic
      probe
```

<400> SEQUENCE: 1073

Arg
1

<210> SEQ ID NO 1074
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1074

Pro Arg
1

<210> SEQ ID NO 1075
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1075

Gly Pro Arg
1

<210> SEQ ID NO 1076
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1076

Leu Arg
1

<210> SEQ ID NO 1077
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1077

Pro Phe Arg
1

<210> SEQ ID NO 1078
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1078

Leu Leu Arg
1

<210> SEQ ID NO 1079
<211> LENGTH: 3

```
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1079

Gln Arg Arg
1

<210> SEQ ID NO 1080
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1080

Gly Arg
1

<210> SEQ ID NO 1081
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1081

Gly Arg Arg
1

<210> SEQ ID NO 1082
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1082

Leu Arg Gly Gly
1

<210> SEQ ID NO 1083
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 1083

Gly Arg Leu Arg Gly Gly Gly Lys
1               5

<210> SEQ ID NO 1084
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1084

Gly Arg Glu Leu Asn Gly Gly Ala Pro Ile Gly Lys
1               5                   10

<210> SEQ ID NO 1085
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (14)..(14)
<223> OTHER INFORMATION: Lys modified with a CPQ2 quencher

<400> SEQUENCE: 1085

Gly Thr Ser Ala Val Leu Gln Ser Gly Phe Arg Lys Gly Lys
1               5                   10

<210> SEQ ID NO 1086
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (14)..(14)
<223> OTHER INFORMATION: Lys modified with a CPQ2 quencher

<400> SEQUENCE: 1086

Gly Ser Gly Val Thr Phe Gln Gly Lys Phe Lys Lys Gly Lys
1               5                   10

<210> SEQ ID NO 1087
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 1087

Gly Ala Ala Phe Ala Gly Lys
1               5

<210> SEQ ID NO 1088
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
```

<400> SEQUENCE: 1088

Gly His Gly Asp Gln Met Ala Gln Lys Ser Lys
1               5                   10

<210> SEQ ID NO 1089
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1089

Gly Gly Pro Leu Gly Met Arg Gly Lys
1               5

<210> SEQ ID NO 1090
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: L-homophenylalanine
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1090

Gly Phe Phe Leu Ala Gln Ala Phe Arg Ser Lys Lys
1               5                   10

<210> SEQ ID NO 1091
<211> LENGTH: 17
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (17)..(17)
<223> OTHER INFORMATION: Lys modified with a CPQ2 quencher

<400> SEQUENCE: 1091

Gly Ala His Ala Val Ser Arg Ile Arg Ile Tyr Leu Leu Pro Ala Lys
1               5                   10                  15

Lys

<210> SEQ ID NO 1092
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

```
<400> SEQUENCE: 1092

Gly Pro Leu Ala Leu Trp Ala Arg Lys
1               5

<210> SEQ ID NO 1093
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: S-para-methoxybenzyl cysteine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1093

Gly Pro Leu Ala Cys Trp Ala Arg Lys
1               5

<210> SEQ ID NO 1094
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1094

Gly Ala Pro Arg Trp Ile Gln Asp Lys
1               5

<210> SEQ ID NO 1095
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1095

Gly Leu Arg Glu Gln Gln Arg Leu Lys Ser Lys
1               5                   10

<210> SEQ ID NO 1096
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (14)..(14)
<223> OTHER INFORMATION: Lys modified with a CPQ2 quencher
```

-continued

```
<400> SEQUENCE: 1096

Gly Glu Phe Pro Ile Tyr Val Phe Leu Pro Ala Lys Lys Lys
1               5                   10

<210> SEQ ID NO 1097
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1097

Gly Gly Ala Ala Asn Leu Val Arg Gly Gly Lys
1               5                   10

<210> SEQ ID NO 1098
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1098

Gly Gly Tyr Ala Glu Leu Arg Met Gly Gly Lys
1               5                   10

<210> SEQ ID NO 1099
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1099

Gly Ala Ala Gly Ala Met Phe Leu Glu Ala Lys
1               5                   10

<210> SEQ ID NO 1100
<211> LENGTH: 16
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (16)..(16)
<223> OTHER INFORMATION: Lys modified with a CPQ2 quencher

<400> SEQUENCE: 1100

Gly Leu Gly Gly Ser Gly Gln Arg Gly Arg Lys Ala Leu Glu Gly Lys
1               5                   10                  15
```

```
<210> SEQ ID NO 1101
<211> LENGTH: 16
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (16)..(16)
<223> OTHER INFORMATION: Lys modified with a CPQ2 quencher

<400> SEQUENCE: 1101

Gly Leu Gly Gly Ser Gly His Tyr Gly Arg Ser Gly Leu Glu Gly Lys
1               5                   10                  15

<210> SEQ ID NO 1102
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 1102

Gly Tyr Gly Arg Ser Gly Lys
1               5

<210> SEQ ID NO 1103
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 1103

Gly Phe Arg Gly Arg Lys Gly Lys
1               5

<210> SEQ ID NO 1104
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1104

Gly Asp Arg Arg Lys Lys Leu Thr Gln Gly Lys
1               5                   10

<210> SEQ ID NO 1105
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1105

Gly His Pro Gly Gly Pro Gln Gly Lys
1               5

<210> SEQ ID NO 1106
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1106

Gly Lys Leu Arg Phe Ser Lys Gln Gly Lys
1               5                   10

<210> SEQ ID NO 1107
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1107

Gly Ala Ile Lys Phe Phe Ser Ala Gln Gly Lys
1               5                   10

<210> SEQ ID NO 1108
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1108

Gly Ala Ile Lys Phe Phe Val Arg Gln Gly Lys
1               5                   10

<210> SEQ ID NO 1109
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher
```

```
<400> SEQUENCE: 1109

Gly Arg Pro Pro Gly Phe Ser Ala Phe Lys Gly Lys
1               5                   10

<210> SEQ ID NO 1110
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1110

Gly Phe Ala Pro Gln Leu Ser Gly Lys
1               5

<210> SEQ ID NO 1111
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1111

Gly Phe Ala Ala Gln Met Ala Gly Lys
1               5

<210> SEQ ID NO 1112
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1112

Gly Gly Met Pro Ala Asn Gln Gly Lys
1               5

<210> SEQ ID NO 1113
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1113

Gly Leu Ser Gly Arg Ser Asp Asn His Gly Lys
1               5                   10
```

```
<210> SEQ ID NO 1114
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1114

Gly Met Ala Ala Leu Ile Thr Arg Pro Asp Phe Gly Lys
1               5                   10

<210> SEQ ID NO 1115
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1115

Gly Met Ala Ala Ala Ile Thr Arg Pro Arg Phe Gly Lys
1               5                   10

<210> SEQ ID NO 1116
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1116

Gly Met Ala Ala Leu Ile Val Arg Pro Asp Leu Gly Lys
1               5                   10

<210> SEQ ID NO 1117
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1117

Gly Thr Ser Gly Pro Asn Gln Glu Gln Glu Gly Lys
1               5                   10

<210> SEQ ID NO 1118
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1118

Gly Thr Ala Gly Pro Asn Gln Glu Gln Glu Gly Lys
1               5                   10

<210> SEQ ID NO 1119
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1119

Gly Gly Pro Gly Pro Asn Gln Ala Gly Lys
1               5                   10

<210> SEQ ID NO 1120
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1120

Gly Ala Ser Gly Pro Ala Gly Pro Ala Gly Lys
1               5                   10

<210> SEQ ID NO 1121
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1121

Gly Glu Arg Gly Glu Thr Gly Pro Ser Gly Gly Lys
1               5                   10

<210> SEQ ID NO 1122
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
```

```
<400> SEQUENCE: 1122

Gly Val Ser Gln Glu Leu Gly Gln Arg Gly Lys
1               5                   10

<210> SEQ ID NO 1123
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1123

Gly Thr Gly Pro Pro Gly Tyr Pro Thr Gly Gly Lys
1               5                   10

<210> SEQ ID NO 1124
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1124

Gly Thr Arg Leu Pro Val Tyr Gln Gly Lys
1               5                   10

<210> SEQ ID NO 1125
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1125

Gly Arg Gln Ala Arg Val Val Gly Gly Gly Lys
1               5                   10

<210> SEQ ID NO 1126
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1126

Gly Arg Gln Arg Arg Val Val Gly Gly Gly Lys
1               5                   10
```

```
<210> SEQ ID NO 1127
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1127

Gly Arg Gln Ala Arg Ala Val Gly Gly Gly Lys
1               5                   10

<210> SEQ ID NO 1128
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1128

Gly Arg Lys Arg Arg Gly Ser Arg Gly Gly Lys
1               5                   10

<210> SEQ ID NO 1129
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1129

Gly Lys Gln Ser Arg Lys Phe Val Pro Gly Lys
1               5                   10

<210> SEQ ID NO 1130
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 1130

Gly Val Thr Gly Arg Ser Gly Lys
1               5

<210> SEQ ID NO 1131
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1131

Gly Leu Lys Ser Arg Val Lys Gly Lys
1               5

<210> SEQ ID NO 1132
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1132

Gly Gly Ile Gly Ala Val Leu Lys Val Leu Thr Gly Lys
1               5                   10

<210> SEQ ID NO 1133
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1133

Gly Gly Leu Pro Ala Leu Ile Ser Trp Ile Lys Gly Lys
1               5                   10

<210> SEQ ID NO 1134
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1134

Gly Ser Glu Val Asn Leu Asp Ala Glu Phe Gly Lys
1               5                   10

<210> SEQ ID NO 1135
<211> LENGTH: 16
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (16)..(16)
<223> OTHER INFORMATION: Lys modified with a CPQ2 quencher
```

```
<400> SEQUENCE: 1135

Gly Glu Glu Lys Pro Ile Cys Phe Phe Arg Leu Gly Lys Glu Gly Lys
1               5                   10                  15

<210> SEQ ID NO 1136
<211> LENGTH: 16
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (16)..(16)
<223> OTHER INFORMATION: Lys modified with a CPQ2 quencher

<400> SEQUENCE: 1136

Gly Glu Glu Lys Pro Ile Leu Phe Phe Arg Leu Gly Lys Glu Gly Lys
1               5                   10                  15

<210> SEQ ID NO 1137
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1137

Gly Ala Pro Ser Ser Val Ile Ala Ala Gly Lys
1               5                   10

<210> SEQ ID NO 1138
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1138

Gly Lys Lys Ala Lys Arg Asn Ala Leu Gly Lys
1               5                   10

<210> SEQ ID NO 1139
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1139

Gly Trp Thr Asn Thr Ser Ala Asn Tyr Asn Leu Gly Lys
1               5                   10
```

```
<210> SEQ ID NO 1140
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 1140

Gly Arg Val Arg Arg Gly Lys
1               5

<210> SEQ ID NO 1141
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 1141

Gly Glu Arg Thr Lys Arg Gly Lys
1               5

<210> SEQ ID NO 1142
<211> LENGTH: 15
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (15)..(15)
<223> OTHER INFORMATION: Lys modified with a CPQ2 quencher

<400> SEQUENCE: 1142

Gly Arg Tyr Gln Ile Lys Pro Leu Lys Ser Thr Asp Glu Gly Lys
1               5                   10                  15

<210> SEQ ID NO 1143
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: L-homophenylalanine
<220> FEATURE:
<221> NAME/KEY: MOD_RES
<222> LOCATION: (14)..(14)
<223> OTHER INFORMATION: Lys modified with a CPQ2 quencher

<400> SEQUENCE: 1143

Gly Trp Glu Leu Arg His Gln Ala Phe Arg Ser Lys Gly Lys
1               5                   10

<210> SEQ ID NO 1144
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: L- Methyl cysteine
<220> FEATURE:
<221> NAME/KEY: MOD_RES
<222> LOCATION: (15)..(15)
<223> OTHER INFORMATION: Lys modified with a CPQ2 quencher

<400> SEQUENCE: 1144

Gly Ser Gly Ala Phe Lys Cys Leu Lys Asp Gly Ala Gly Gly Lys
1               5                   10                  15

<210> SEQ ID NO 1145
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1145

Gly Tyr Val Ala Asp Gly Trp Gly Lys
1               5

<210> SEQ ID NO 1146
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1146

Gly Trp Glu His Asp Gly Trp Gly Lys
1               5

<210> SEQ ID NO 1147
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1147

Gly Tyr Val Ala Asp Ala Pro Val Gly Lys
1               5                   10

<210> SEQ ID NO 1148
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1148

Gly Arg Pro Pro Gly Phe Ser Ala Gly Lys
1               5                   10

<210> SEQ ID NO 1149
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1149

Gly Gly Ser Pro Ala Phe Leu Ala Gly Lys
1               5                   10

<210> SEQ ID NO 1150
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1150

Gly Ala Gly Phe Ser Leu Pro Ala Gly Lys
1               5                   10

<210> SEQ ID NO 1151
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1151

Gly Arg Trp His Thr Val Gly Leu Arg Trp Glu Gly Lys
1               5                   10

<210> SEQ ID NO 1152
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher
```

```
<400> SEQUENCE: 1152

Gly Leu Glu Gln Gly Lys
1               5

<210> SEQ ID NO 1153
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1153

Gly Arg Trp Pro Pro Met Gly Leu Pro Trp Glu Gly Lys
1               5                   10

<210> SEQ ID NO 1154
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1154

Gly Arg Pro Lys Pro Val Glu Gly Lys
1               5

<210> SEQ ID NO 1155
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 1155

Gly Ile Glu Thr Asp Gly Lys
1               5

<210> SEQ ID NO 1156
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1156

Gly Val Gly Pro Asp Phe Gly Arg Gly Lys
1               5                   10

<210> SEQ ID NO 1157
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1157

Gly Gly Ile Glu Phe Asp Ser Gly Gly Cys Gly Lys
1               5                   10

<210> SEQ ID NO 1158
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1158

Gly Gly Asp Phe Leu Arg Arg Val Gly Lys
1               5                   10

<210> SEQ ID NO 1159
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 1159

Gly Ala Ala Leu Gly Lys
1               5

<210> SEQ ID NO 1160
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1160

Gly Tyr Ala Thr Trp Ser Met Ile Ala Ala His Gly Lys
1               5                   10

<210> SEQ ID NO 1161
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

<221> NAME/KEY: MOD_RES
<222> LOCATION: (13)..(13)
<223> OTHER INFORMATION: Lys modified with a CPQ2 quencher

<400> SEQUENCE: 1161

Gly Val Ile Met Trp Arg Leu Thr Val Gly Thr Gly Lys
1               5                   10

<210> SEQ ID NO 1162
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1162

Gly Arg Arg Val Leu Ala Leu Gln Gln Glu Leu Gly Lys
1               5                   10

<210> SEQ ID NO 1163
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1163

Gly Leu Ala Thr Trp Pro Leu Ser Gly Leu Trp Gly Lys
1               5                   10

<210> SEQ ID NO 1164
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1164

Gly Asn Thr Pro Asn Trp Leu Val Asn Ala Val Gly Lys
1               5                   10

<210> SEQ ID NO 1165
<211> LENGTH: 16
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (16)..(16)
<223> OTHER INFORMATION: Lys modified with a CPQ2 quencher

```
<400> SEQUENCE: 1165

Gly Ser Pro Leu Ala Gln Ala Val Arg Ser Ser Ser Arg Lys Gly Lys
1               5                   10                  15

<210> SEQ ID NO 1166
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1166

Gly Gln Met Pro Gly Arg Leu Ser Met Ala Phe Gly Lys
1               5                   10

<210> SEQ ID NO 1167
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 1167

Gly Pro Leu Gly Leu Arg Gly Lys
1               5

<210> SEQ ID NO 1168
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1168

Gly Gln Arg Ala Asn Ser Ile Arg Val Thr Trp Gly Lys
1               5                   10

<210> SEQ ID NO 1169
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher

<400> SEQUENCE: 1169

Gly Pro Leu Ala Val Arg Gly Lys
1               5
```

```
<210> SEQ ID NO 1170
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1170

Gly Leu Leu Ala Val Pro Ala Ala Asn Thr Val Gly Lys
1               5                   10

<210> SEQ ID NO 1171
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1171

Gly Gly Pro Gln Gly Leu Arg Gly Gln Gly Lys
1               5                   10

<210> SEQ ID NO 1172
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (13)..(13)
<223> OTHER INFORMATION: Lys modified with a CPQ2 quencher

<400> SEQUENCE: 1172

Gly Arg Thr Gly Leu Tyr Leu Tyr Asn Ser Thr Gly Lys
1               5                   10

<210> SEQ ID NO 1173
<211> LENGTH: 17
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (17)..(17)
<223> OTHER INFORMATION: Lys modified with a CPQ2 quencher

<400> SEQUENCE: 1173

Gly Arg Lys Lys Leu Thr Gln Ser Lys Phe Val Gly Gly Ala Glu Gly
1               5                   10                  15

Lys

<210> SEQ ID NO 1174
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: Lys modified with a CPQ2 quencher

<400> SEQUENCE: 1174

Gly Lys His Tyr Arg Gly Lys
1               5

<210> SEQ ID NO 1175
<211> LENGTH: 6
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Lys modified with a CPQ2 quencher

<400> SEQUENCE: 1175

Gly Gln Ala Arg Gly Lys
1               5

<210> SEQ ID NO 1176
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1176

Gly Pro Arg Pro Phe Asn Tyr Leu Gly Lys
1               5                   10

<210> SEQ ID NO 1177
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1177

Gly Ala Pro Phe Glu Met Ser Ala Gly Lys
1               5                   10

<210> SEQ ID NO 1178
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher
```

```
<400> SEQUENCE: 1178

Gly Ala Pro Phe Glu Phe Ser Ala Gly Lys
1               5                   10

<210> SEQ ID NO 1179
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1179

Gly Pro Leu Gly Phe Arg Val Gly Lys
1               5

<210> SEQ ID NO 1180
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1180

Gly Arg Pro Leu Ala Leu Trp Arg Ser Gly Lys
1               5                   10

<210> SEQ ID NO 1181
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1181

Gly Arg Pro Leu Ala Leu Glu Glu Ser Gln Gly Lys
1               5                   10

<210> SEQ ID NO 1182
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (12)..(12)
<223> OTHER INFORMATION: Lys modified with a CPQ2 quencher

<400> SEQUENCE: 1182

Gly Arg Pro Leu Ala Leu Trp Arg Ser Gln Gly Lys
1               5                   10

<210> SEQ ID NO 1183
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (14)..(14)
<223> OTHER INFORMATION: Lys modified with a CPQ2 quencher

<400> SEQUENCE: 1183

Gly Arg Asn Ala Leu Ala Val Glu Arg Thr Ala Ser Gly Lys
1               5                   10

<210> SEQ ID NO 1184
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1184

Gly Arg Pro Lys Pro Gln Gln Phe Trp Gly Lys
1               5                   10

<210> SEQ ID NO 1185
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1185

Ser Gly Ser Asn Pro Tyr Lys Tyr Thr Ala Lys
1               5                   10

<210> SEQ ID NO 1186
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1186

Ser Gly Ser Asn Pro Tyr Gly Tyr Thr Ala Lys
1               5                   10

<210> SEQ ID NO 1187
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: MOD_RES
<222> LOCATION: (11)..(11)
<223> OTHER INFORMATION: Lys modified with a CPQ2 quencher

<400> SEQUENCE: 1187

Ser Gly Thr Leu Ser Glu Leu His Thr Ala Lys
1               5                   10

<210> SEQ ID NO 1188
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1188

Ser Gly Thr Ile Ser His Leu His Thr Ala Lys
1               5                   10

<210> SEQ ID NO 1189
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: L-Ornithine
<220> FEATURE:
<221> NAME/KEY: MOD_RES
<222> LOCATION: (8)..(8)
<223> OTHER INFORMATION: L-homophenylalanine
<220> FEATURE:
<221> NAME/KEY: MOD_RES
<222> LOCATION: (14)..(14)
<223> OTHER INFORMATION: Lys modified with a CPQ2 quencher

<400> SEQUENCE: 1189

Ser Gly Xaa Arg Ser His Pro Phe Thr Leu Tyr Thr Ala Lys
1               5                   10

<210> SEQ ID NO 1190
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: L-Ornithine
<220> FEATURE:
<221> NAME/KEY: MOD_RES
<222> LOCATION: (8)..(8)
<223> OTHER INFORMATION: L-homophenylalanine
<220> FEATURE:
<221> NAME/KEY: MOD_RES
<222> LOCATION: (14)..(14)
<223> OTHER INFORMATION: Lys modified with a CPQ2 quencher

<400> SEQUENCE: 1190

Ser Gly Xaa Arg Ser His Gly Phe Phe Leu Tyr Thr Ala Lys
1               5                   10
```

```
<210> SEQ ID NO 1191
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1191

Ser Gly Glu Ser Leu Ala Tyr Tyr Thr Ala Lys
1               5                   10

<210> SEQ ID NO 1192
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1192

Ser Gly His Met His Ala Ala Leu Thr Ala Lys
1               5                   10

<210> SEQ ID NO 1193
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: D-isoleucine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1193

Gly Ile Leu Ser Arg Ile Val Gly Gly Gly Lys
1               5                   10

<210> SEQ ID NO 1194
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (5)..(5)
<223> OTHER INFORMATION: D-arginine
<220> FEATURE:
<221> NAME/KEY: MOD_RES
<222> LOCATION: (6)..(6)
<223> OTHER INFORMATION: D-isoleucine
<220> FEATURE:
<221> NAME/KEY: MOD_RES
<222> LOCATION: (7)..(7)
<223> OTHER INFORMATION: D-valine
<220> FEATURE:
```

```
<221> NAME/KEY: MOD_RES
<222> LOCATION: (11)..(11)
<223> OTHER INFORMATION: Lys modified with a CPQ2 quencher

<400> SEQUENCE: 1194

Gly Ile Leu Ser Arg Ile Val Gly Gly Gly Lys
1               5                   10

<210> SEQ ID NO 1195
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1195

Gly Arg Gln Arg Arg Ala Leu Glu Lys Gly Lys
1               5                   10

<210> SEQ ID NO 1196
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1196

Gly Lys Pro Ile Ser Leu Ile Ser Ser Gly Lys
1               5                   10

<210> SEQ ID NO 1197
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1197

Gly Gln Lys Gly Arg Tyr Lys Gln Glu Gly Lys
1               5                   10

<210> SEQ ID NO 1198
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher
```

<400> SEQUENCE: 1198

Gly Gly Pro Leu Gly Leu Arg Ser Trp Lys
1               5                   10

<210> SEQ ID NO 1199
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1199

Gly Gly Pro Leu Gly Val Arg Gly Lys Lys
1               5                   10

<210> SEQ ID NO 1200
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: D-Phenylalanine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1200

Gly Gly Phe Pro Arg Ser Gly Gly Gly Lys
1               5                   10

<210> SEQ ID NO 1201
<211> LENGTH: 1
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: pyroglutamic acid

<400> SEQUENCE: 1201

Xaa
1

<210> SEQ ID NO 1202
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1202

Ser Tyr
1

```
<210> SEQ ID NO 1203
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1203

Gly Phe
1

<210> SEQ ID NO 1204
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1204

Tyr
1

<210> SEQ ID NO 1205
<211> LENGTH: 1
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: citrulline

<400> SEQUENCE: 1205

Xaa
1

<210> SEQ ID NO 1206
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1206

Gly Pro
1

<210> SEQ ID NO 1207
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1207

Thr
1

<210> SEQ ID NO 1208
<211> LENGTH: 1
<212> TYPE: PRT
<213> ORGANISM: Artificial Sequence
<220> FEATURE:
```

<223> OTHER INFORMATION: Description of Artificial Sequence: Synthetic
      probe

<400> SEQUENCE: 1208

Ile
1

<210> SEQ ID NO 1209
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1209

Gly Ala
1

<210> SEQ ID NO 1210
<211> LENGTH: 1
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: S-benzyl-L-cysteine

<400> SEQUENCE: 1210

Cys
1

<210> SEQ ID NO 1211
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1211

Ala
1

<210> SEQ ID NO 1212
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1212

Lys
1

<210> SEQ ID NO 1213
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1213

Gly Leu Phe
1

<210> SEQ ID NO 1214
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1214

Leu
1

<210> SEQ ID NO 1215
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1215

Val Ala Asn
1

<210> SEQ ID NO 1216
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1216

Ala Ala Ala
1

<210> SEQ ID NO 1217
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1217

Lys
1

<210> SEQ ID NO 1218
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1218

Phe
1

<210> SEQ ID NO 1219
<211> LENGTH: 3

```
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1219

Phe Ser Arg
1

<210> SEQ ID NO 1220
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1220

Val Val Arg
1

<210> SEQ ID NO 1221
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1221

Lys Ala
1

<210> SEQ ID NO 1222
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1222

Pro Arg
1

<210> SEQ ID NO 1223
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1223

Met Gly Pro
1

<210> SEQ ID NO 1224
<211> LENGTH: 2
<212> TYPE: PRT
<213> ORGANISM: Artificial Sequence
<220> FEATURE:
<223> OTHER INFORMATION: Description of Artificial Sequence: Synthetic
      probe
```

```
<400> SEQUENCE: 1224

Lys Pro
1

<210> SEQ ID NO 1225
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1225

Gln Gly Arg
1

<210> SEQ ID NO 1226
<211> LENGTH: 3
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: benzyl-L-glutamate

<400> SEQUENCE: 1226

Glu Ala Arg
1

<210> SEQ ID NO 1227
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1227

Trp Glu His Asp
1

<210> SEQ ID NO 1228
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1228

Gln Ala Arg
1

<210> SEQ ID NO 1229
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1229

Ala Ala Phe
1
```

<210> SEQ ID NO 1230
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1230

Gly Pro Lys
1

<210> SEQ ID NO 1231
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1231

Ala Ala Pro Met
1

<210> SEQ ID NO 1232
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1232

Ala Glu Pro Phe
1

<210> SEQ ID NO 1233
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1233

Gly Gly
1

<210> SEQ ID NO 1234
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1234

Val Leu Lys
1

<210> SEQ ID NO 1235
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

```
<400> SEQUENCE: 1235

Glu Lys Lys
1

<210> SEQ ID NO 1236
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1236

Val Pro Arg
1

<210> SEQ ID NO 1237
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1237

Gly Lys Arg
1

<210> SEQ ID NO 1238
<211> LENGTH: 3
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: benzyl-L-glutamate

<400> SEQUENCE: 1238

Glu Gly Arg
1

<210> SEQ ID NO 1239
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1239

Leu Arg
1

<210> SEQ ID NO 1240
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1240

Ala Phe Lys
1
```

```
<210> SEQ ID NO 1241
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1241

Leu Gly Arg
1

<210> SEQ ID NO 1242
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1242

Pro Phe Arg
1

<210> SEQ ID NO 1243
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1243

Ala Ala Pro Val
1

<210> SEQ ID NO 1244
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1244

Ala Phe Lys
1

<210> SEQ ID NO 1245
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1245

Val Lys Met
1

<210> SEQ ID NO 1246
<211> LENGTH: 5
<212> TYPE: PRT
<213> ORGANISM: Artificial Sequence
<220> FEATURE:
<223> OTHER INFORMATION: Description of Artificial Sequence: Synthetic
      probe
```

-continued

<400> SEQUENCE: 1246

Gly Pro Leu Gly Pro
1               5

<210> SEQ ID NO 1247
<211> LENGTH: 5
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1247

Lys Gln Lys Leu Arg
1               5

<210> SEQ ID NO 1248
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1248

Arg Val Arg Arg
1

<210> SEQ ID NO 1249
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1249

Ile Glu Gly Arg
1

<210> SEQ ID NO 1250
<211> LENGTH: 2
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1250

Gly Pro
1

<210> SEQ ID NO 1251
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1251

Ala Ala Pro Val
1

<210> SEQ ID NO 1252
<211> LENGTH: 8

```
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1252

Arg Pro Phe His Leu Leu Val Tyr
1               5

<210> SEQ ID NO 1253
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: amino-n-butyric acid
<220> FEATURE:
<221> NAME/KEY: MOD_RES
<222> LOCATION: (4)..(4)
<223> OTHER INFORMATION: guamidine-L-phenylalanine

<400> SEQUENCE: 1253

Xaa Trp Ser Phe Thr Val Phe
1               5

<210> SEQ ID NO 1254
<211> LENGTH: 6
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1254

His Ser Ser Lys Leu Gln
1               5

<210> SEQ ID NO 1255
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1255

Arg Pro Tyr
1

<210> SEQ ID NO 1256
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
```

```
<222> LOCATION: (9)..(9)
<223> OTHER INFORMATION: dinitrobenzylation of lysine

<400> SEQUENCE: 1256

Lys Lys Asp Arg Glu Asn Ser Pro Lys Leu
1               5                   10

<210> SEQ ID NO 1257
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: dinitrobenzylation of lysine

<400> SEQUENCE: 1257

Lys Lys Asp Arg Glu Asn Ser Pro Leu Lys
1               5                   10

<210> SEQ ID NO 1258
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: dinitrobenzylation of lysine

<400> SEQUENCE: 1258

Asn Ala Gly Ser Lys Phe Lys Gln
1               5

<210> SEQ ID NO 1259
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: dinitrobenzylation of lysine

<400> SEQUENCE: 1259

Asn Ala Gly Ser Lys Phe Gln Lys
1               5

<210> SEQ ID NO 1260
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine

<400> SEQUENCE: 1260

Lys Lys His Leu Leu Gly Phe Tyr Lys Val
1               5                   10

<210> SEQ ID NO 1261
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: dinitrobenzylation of lysine

<400> SEQUENCE: 1261

Lys Lys His Leu Leu Gly Phe Tyr Val Lys
1               5                   10

<210> SEQ ID NO 1262
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (9)..(9)
<223> OTHER INFORMATION: dinitrobenzylation of lysine
<220> FEATURE:
<221> NAME/KEY: MOD_RES
<222> LOCATION: (10)..(10)
<223> OTHER INFORMATION: Norleucine

<400> SEQUENCE: 1262

Lys Lys Gln Glu Lys Gln Thr Leu Lys Leu
1               5                   10

<210> SEQ ID NO 1263
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (9)..(9)
<223> OTHER INFORMATION: Norleucine
<220> FEATURE:
<221> NAME/KEY: MOD_RES
<222> LOCATION: (10)..(10)
<223> OTHER INFORMATION: dinitrobenzylation of lysine

<400> SEQUENCE: 1263

Lys Lys Gln Glu Lys Gln Thr Leu Leu Lys
1               5                   10

<210> SEQ ID NO 1264
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: dinitrobenzylation of lysine

<400> SEQUENCE: 1264

Lys Asp Pro Phe Val Val Ser Lys Trp
1               5

<210> SEQ ID NO 1265
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine

<400> SEQUENCE: 1265

Lys Asp Pro Phe Val Val Ser Trp Lys
1               5

<210> SEQ ID NO 1266
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: dinitrobenzylation of lysine

<400> SEQUENCE: 1266

Asn Ala Tyr Asn Glu Ile Lys Arg
1               5

<210> SEQ ID NO 1267
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: dinitrobenzylation of lysine

<400> SEQUENCE: 1267

Asn Ala Tyr Asn Glu Ile Arg Lys
1               5

<210> SEQ ID NO 1268
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine

<400> SEQUENCE: 1268

Val Leu Arg Gln Ser Glu Lys Asn
1               5

<210> SEQ ID NO 1269
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine

<400> SEQUENCE: 1269

Val Leu Arg Gln Ser Glu Asn Lys
1               5

<210> SEQ ID NO 1270
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (7)..(7)
<223> OTHER INFORMATION: dinitrobenzylation of lysine

<400> SEQUENCE: 1270

Tyr Asn Pro Arg Glu Leu Lys Ile
1               5

<210> SEQ ID NO 1271
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine

<400> SEQUENCE: 1271

Tyr Asn Pro Arg Glu Leu Ile Lys
1               5

<210> SEQ ID NO 1272
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: dinitrobenzylation of lysine

<400> SEQUENCE: 1272

Lys Glu Phe Val His Asn Pro Lys Lys
1               5

<210> SEQ ID NO 1273
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
```

```
<223> OTHER INFORMATION: dinitrobenzylation of lysine

<400> SEQUENCE: 1273

Lys Glu Phe Val His Asn Pro Lys Lys
1               5

<210> SEQ ID NO 1274
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: dinitrobenzylation of lysine

<400> SEQUENCE: 1274

Lys Arg Val Gln Phe Leu Lys His
1               5

<210> SEQ ID NO 1275
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: dinitrobenzylation of lysine

<400> SEQUENCE: 1275

Lys Arg Val Gln Phe Leu His Lys
1               5

<210> SEQ ID NO 1276
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine

<400> SEQUENCE: 1276

Lys Leu Ile Leu His Lys Asn Lys Gly
1               5

<210> SEQ ID NO 1277
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
```

```
<222> LOCATION: (1)..(1)
<223> OTHER INFORMATION: D-Lysine
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (9)..(9)
<223> OTHER INFORMATION: dinitrobenzylation of lysine

<400> SEQUENCE: 1277

Lys Leu Ile Leu His Lys Asn Gly Lys
1               5

<210> SEQ ID NO 1278
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: dinitrobenzylation of lysine

<400> SEQUENCE: 1278

Lys Lys Trp Ala Leu Leu Tyr His Lys Ser
1               5                   10

<210> SEQ ID NO 1279
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (10)..(10)
<223> OTHER INFORMATION: dinitrobenzylation of lysine

<400> SEQUENCE: 1279

Lys Lys Trp Ala Leu Leu Tyr His Ser Lys
1               5                   10

<210> SEQ ID NO 1280
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine

<400> SEQUENCE: 1280

Lys Lys Ala His Asp Ile Val Asn Lys Tyr
1               5                   10

<210> SEQ ID NO 1281
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: dinitrobenzylation of lysine

<400> SEQUENCE: 1281

Lys Lys Ala His Asp Ile Val Asn Tyr Lys
1               5                   10

<210> SEQ ID NO 1282
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: dinitrobenzylation of lysine

<400> SEQUENCE: 1282

Lys Ser Val Phe Val Ile Glu Lys Pro
1               5

<210> SEQ ID NO 1283
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine

<400> SEQUENCE: 1283

Lys Ser Val Phe Val Ile Glu Pro Lys
1               5

<210> SEQ ID NO 1284
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: dinitrobenzylation of lysine

<400> SEQUENCE: 1284

Lys Pro Pro Ser Gly Leu Ser Lys Glu
1               5

<210> SEQ ID NO 1285
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine

<400> SEQUENCE: 1285

Lys Pro Pro Ser Gly Leu Ser Glu Lys
1               5

<210> SEQ ID NO 1286
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine
```

```
<400> SEQUENCE: 1286

Lys Lys Arg Trp Tyr Gly Gly Ile Lys Phe
1               5                   10

<210> SEQ ID NO 1287
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (2)..(2)
<223> OTHER INFORMATION: D-Lysine
<220> FEATURE:
<221> NAME/KEY: MOD_RES
<222> LOCATION: (10)..(10)
<223> OTHER INFORMATION: dinitrobenzylation of lysine

<400> SEQUENCE: 1287

Lys Lys Arg Trp Tyr Gly Gly Ile Phe Lys
1               5                   10

<210> SEQ ID NO 1288
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (8)..(8)
<223> OTHER INFORMATION: dinitrobenzylation of lysine

<400> SEQUENCE: 1288

Lys Gln Tyr Val Phe Phe Leu Lys Asp
1               5

<210> SEQ ID NO 1289
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: dinitrobenzylation of lysine
```

```
<400> SEQUENCE: 1289

Lys Gln Tyr Val Phe Phe Leu Asp Lys
1               5

<210> SEQ ID NO 1290
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: dinitrobenzylation of lysine

<400> SEQUENCE: 1290

Lys Phe Ala Lys Tyr Tyr Lys Lys Thr
1               5

<210> SEQ ID NO 1291
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine

<400> SEQUENCE: 1291

Lys Phe Ala Lys Tyr Tyr Lys Thr Lys
1               5

<210> SEQ ID NO 1292
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: dinitrobenzylation of lysine

<400> SEQUENCE: 1292

Lys Gln Val Lys His Phe Thr Lys Ala
1               5

<210> SEQ ID NO 1293
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (9)..(9)
<223> OTHER INFORMATION: dinitrobenzylation of lysine

<400> SEQUENCE: 1293

Lys Gln Val Lys His Phe Thr Ala Lys
1               5

<210> SEQ ID NO 1294
<211> LENGTH: 8
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
<220> FEATURE:
<221> NAME/KEY: MOD_RES
<222> LOCATION: (8)..(8)
<223> OTHER INFORMATION: dinitrobenzylation of lysine

<400> SEQUENCE: 1294

Lys Tyr Val Ala Asp Ala Pro Lys
1               5

<210> SEQ ID NO 1295
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: dinitrobenzylation of lysine

<400> SEQUENCE: 1295

Gly Lys Gly Ile Ser Ser Gln Tyr Lys
1               5

<210> SEQ ID NO 1296
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: dinitrobenzylation of lysine

<400> SEQUENCE: 1296

Gly Ala Leu Pro Ala Leu Gln Asn Lys
1               5

<210> SEQ ID NO 1297
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: dinitrobenzylation of lysine

<400> SEQUENCE: 1297

Gly His Arg Phe Arg Gly Lys
1               5

<210> SEQ ID NO 1298
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: dinitrobenzylation of lysine

<400> SEQUENCE: 1298

Gly Ala Pro Glu Glu Ile Met Asp Gln Gln Lys
1               5                   10

<210> SEQ ID NO 1299
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: dinitrobenzylation of lysine

<400> SEQUENCE: 1299

Gly Ser Arg Lys Ser Gln Gln Tyr Lys
1               5

<210> SEQ ID NO 1300
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: dinitrobenzylation of lysine

<400> SEQUENCE: 1300

Gly Ser Lys Gly Arg Ser Leu Ile Gly Lys
1               5                   10

<210> SEQ ID NO 1301
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: dinitrobenzylation of lysine
```

```
<400> SEQUENCE: 1301

Gly Phe Ala Gln Ser Ile Pro Lys Lys
1               5

<210> SEQ ID NO 1302
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: dinitrobenzylation of lysine

<400> SEQUENCE: 1302

Gly Arg Gln Arg Arg Val Val Gly Gly Lys
1               5                   10

<210> SEQ ID NO 1303
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: dinitrobenzylation of lysine

<400> SEQUENCE: 1303

Gly Glu Arg Gly Glu Thr Gly Pro Ser Gly Lys
1               5                   10

<210> SEQ ID NO 1304
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: dinitrobenzylation of lysine

<400> SEQUENCE: 1304

Gly Ala Ser Gly Pro Ser Ser Gly Lys
1               5

<210> SEQ ID NO 1305
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: dinitrobenzylation of lysine

<400> SEQUENCE: 1305

Gly Tyr Arg Phe Arg Gly Lys
1               5
```

```
<210> SEQ ID NO 1306
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (9)..(9)
<223> OTHER INFORMATION: dinitrobenzylation of lysine

<400> SEQUENCE: 1306

Gly Lys Leu Phe Ser Ser Lys Gln Lys
1               5

<210> SEQ ID NO 1307
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (7)..(7)
<223> OTHER INFORMATION: dinitrobenzylation of lysine

<400> SEQUENCE: 1307

Gly Ile Val Pro Arg Gly Lys
1               5

<210> SEQ ID NO 1308
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: dinitrobenzylation of lysine

<400> SEQUENCE: 1308

Gly Ile Arg Arg Ser Ser Tyr Phe Lys Lys
1               5                   10

<210> SEQ ID NO 1309
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: benzyl-L-histidine
<220> FEATURE:
<221> NAME/KEY: MOD_RES
<222> LOCATION: (3)..(3)
<223> OTHER INFORMATION: L-tert-leucine
<220> FEATURE:
<221> NAME/KEY: MOD_RES
<222> LOCATION: (7)..(7)
<223> OTHER INFORMATION: L-methionine-sulfoxide
<220> FEATURE:
<221> NAME/KEY: MOD_RES
<222> LOCATION: (9)..(9)
<223> OTHER INFORMATION: dinitrobenzylation of lysine
```

```
<400> SEQUENCE: 1309

Gly His Leu Pro Ser Asp Met Gly Lys Gly
 1               5                  10

<210> SEQ ID NO 1310
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: Norvaline
<220> FEATURE:
<221> NAME/KEY: MOD_RES
<222> LOCATION: (4)..(4)
<223> OTHER INFORMATION: L-octahydroindole-2-carboxylic acid
<220> FEATURE:
<221> NAME/KEY: MOD_RES
<222> LOCATION: (9)..(9)
<223> OTHER INFORMATION: dinitrobenzylation of lysine

<400> SEQUENCE: 1310

Val Ile Glu Xaa Asp Phe Gly Arg Lys
 1               5

<210> SEQ ID NO 1311
<211> LENGTH: 4
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: D-threonine
<220> FEATURE:
<221> NAME/KEY: MOD_RES
<222> LOCATION: (3)..(3)
<223> OTHER INFORMATION: 2,3,4,5,6-pentafluoro-L-penylalanine

<400> SEQUENCE: 1311

His Thr Phe Arg
 1

<210> SEQ ID NO 1312
<211> LENGTH: 4
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: 2,3-diaminopropionic acid
<220> FEATURE:
<221> NAME/KEY: MOD_RES
<222> LOCATION: (2)..(2)
<223> OTHER INFORMATION: L-Ornithine
<220> FEATURE:
<221> NAME/KEY: MOD_RES
<222> LOCATION: (3)..(3)
<223> OTHER INFORMATION: 3-chloro-L-phenylalanine
<220> FEATURE:
<221> NAME/KEY: MOD_RES
<222> LOCATION: (4)..(4)
<223> OTHER INFORMATION: S-para-methoxybenzyl cysteine
```

```
<400> SEQUENCE: 1312

Xaa Xaa Phe Cys
1

<210> SEQ ID NO 1313
<211> LENGTH: 4
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: L-cyclohexylalanine
<220> FEATURE:
<221> NAME/KEY: MOD_RES
<222> LOCATION: (3)..(3)
<223> OTHER INFORMATION: benzyl homoserine

<400> SEQUENCE: 1313

Xaa Leu Ser Arg
1

<210> SEQ ID NO 1314
<211> LENGTH: 4
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: homocyclohexylalnine
<220> FEATURE:
<221> NAME/KEY: MOD_RES
<222> LOCATION: (2)..(2)
<223> OTHER INFORMATION: phenylalanine derivative with a guanidine group
      in the para position
<220> FEATURE:
<221> NAME/KEY: MOD_RES
<222> LOCATION: (3)..(3)
<223> OTHER INFORMATION: L-octahydroindole-2-carboxylic acid

<400> SEQUENCE: 1314

Xaa Phe Xaa Arg
1

<210> SEQ ID NO 1315
<211> LENGTH: 2
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: L-alpha-aminobutyric acid
<220> FEATURE:
<221> NAME/KEY: MOD_RES
<222> LOCATION: (2)..(2)
<223> OTHER INFORMATION: benzyloxy-L-norleucine

<400> SEQUENCE: 1315

Xaa Leu
1

<210> SEQ ID NO 1316
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: benzyloxy-L-norleucine
<220> FEATURE:
<221> NAME/KEY: MOD_RES
<222> LOCATION: (2)..(2)
<223> OTHER INFORMATION: L-methionine sulfone
<220> FEATURE:
<221> NAME/KEY: MOD_RES
<222> LOCATION: (3)..(3)
<223> OTHER INFORMATION: L-octahydroindole-2-carboxylic acid
<220> FEATURE:
<221> NAME/KEY: MOD_RES
<222> LOCATION: (4)..(4)
<223> OTHER INFORMATION: L-alpha-aminobutyric acid

<400> SEQUENCE: 1316

Leu Met Xaa Xaa
1

<210> SEQ ID NO 1317
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: 2,3-diaminopropionic acid
<220> FEATURE:
<221> NAME/KEY: MOD_RES
<222> LOCATION: (3)..(3)
<223> OTHER INFORMATION: L-Ornithine
<220> FEATURE:
<221> NAME/KEY: MOD_RES
<222> LOCATION: (4)..(4)
<223> OTHER INFORMATION: 3-chloro-L-phenylalanine
<220> FEATURE:
<221> NAME/KEY: MOD_RES
<222> LOCATION: (5)..(5)
<223> OTHER INFORMATION: S-para-methoxybenzyl cysteine
<220> FEATURE:
<221> NAME/KEY: MOD_RES
<222> LOCATION: (7)..(7)
<223> OTHER INFORMATION: dinitrobenzylation of lysine

<400> SEQUENCE: 1317

Gly Xaa Xaa Phe Cys Gly Lys
1               5

<210> SEQ ID NO 1318
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: L-cyclohexylalanine
<220> FEATURE:
<221> NAME/KEY: MOD_RES
<222> LOCATION: (4)..(4)
<223> OTHER INFORMATION: Homoserine
<220> FEATURE:
<221> NAME/KEY: MOD_RES
```

```
<222> LOCATION: (7)..(7)
<223> OTHER INFORMATION: dinitrobenzylation of lysine

<400> SEQUENCE: 1318

Gly Xaa Leu Ser Arg Gly Lys
1               5

<210> SEQ ID NO 1319
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: guamidine-L-phenylalanine
<220> FEATURE:
<221> NAME/KEY: MOD_RES
<222> LOCATION: (7)..(7)
<223> OTHER INFORMATION: dinitrobenzylation of lysine

<400> SEQUENCE: 1319

Phe Val Thr Phe Ser Trp Lys
1               5

<210> SEQ ID NO 1320
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: homocyclohexylalnine
<220> FEATURE:
<221> NAME/KEY: MOD_RES
<222> LOCATION: (3)..(3)
<223> OTHER INFORMATION: phenylalanine derivative with a guanidine group
      in the para position
<220> FEATURE:
<221> NAME/KEY: MOD_RES
<222> LOCATION: (4)..(4)
<223> OTHER INFORMATION: L-octahydroindole-2-carboxylic acid
<220> FEATURE:
<221> NAME/KEY: MOD_RES
<222> LOCATION: (7)..(7)
<223> OTHER INFORMATION: dinitrobenzylation of lysine

<400> SEQUENCE: 1320

Gly Xaa Phe Xaa Arg Gly Lys
1               5

<210> SEQ ID NO 1321
<211> LENGTH: 7
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(2)
<223> OTHER INFORMATION: benzyloxy-L-norleucine
<220> FEATURE:
<221> NAME/KEY: MOD_RES
<222> LOCATION: (3)..(3)
<223> OTHER INFORMATION: methylsulfonylbutanoic acid
<220> FEATURE:
<221> NAME/KEY: MOD_RES
```

```
<222> LOCATION: (4)..(4)
<223> OTHER INFORMATION: L-octahydroindole-2-carboxylic acid
<220> FEATURE:
<221> NAME/KEY: MOD_RES
<222> LOCATION: (5)..(5)
<223> OTHER INFORMATION: L-alpha-aminobutyric acid
<220> FEATURE:
<221> NAME/KEY: MOD_RES
<222> LOCATION: (7)..(7)
<223> OTHER INFORMATION: dinitrobenzylation of lysine

<400> SEQUENCE: 1321

Gly Leu Met Xaa Xaa Gly Lys
1               5

<210> SEQ ID NO 1322
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1322

Gly Ala Ile Glu Pro Asp Ser Gly Gly Lys
1               5                   10

<210> SEQ ID NO 1323
<211> LENGTH: 14
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher
<220> FEATURE:
<221> NAME/KEY: MOD_RES
<222> LOCATION: (11)..(11)
<223> OTHER INFORMATION: D-Lysine
<220> FEATURE:
<221> NAME/KEY: MOD_RES
<222> LOCATION: (12)..(12)
<223> OTHER INFORMATION: D-Lysine

<400> SEQUENCE: 1323

Gly Ala Ile Glu Phe Asp Ser Gly Gly Lys Lys Lys Gly Cys
1               5                   10

<210> SEQ ID NO 1324
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
```

```
<223> OTHER INFORMATION: D-Lysine

<400> SEQUENCE: 1324

Gly Gly Ala Ala Glu Ala Ile Ser Asp Ala Lys Lys Lys
1               5                   10

<210> SEQ ID NO 1325
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1325

Gly Gly Ala Gly Gly Ala Gln Met Gly Ala Lys Lys Lys
1               5                   10

<210> SEQ ID NO 1326
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1326

Gly Gly Ala Gln Pro Asp Ala Leu Asn Val Lys Lys Lys
1               5                   10

<210> SEQ ID NO 1327
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine
```

-continued

<400> SEQUENCE: 1327

Gly Gly Ala Thr Asp Val Thr Thr Thr Pro Lys Lys Lys
1               5                   10

<210> SEQ ID NO 1328
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1328

Gly Gly Asp Ile Val Thr Val Ala Asn Ala Lys Lys Lys
1               5                   10

<210> SEQ ID NO 1329
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1329

Gly Gly Asp Leu Gly Leu Lys Ser Val Pro Lys Lys Lys
1               5                   10

<210> SEQ ID NO 1330
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1330

Gly Gly Asp Val Met Ala Ser Asn Lys Arg Lys Lys Lys
1               5                   10

<210> SEQ ID NO 1331
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1331

Gly Gly Glu Ser Asp Glu Leu Asn Thr Ile Lys Lys Lys
1               5                   10

<210> SEQ ID NO 1332
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1332

Gly Gly Phe His Pro Leu His Ser Lys Ile Lys Lys Lys
1               5                   10

<210> SEQ ID NO 1333
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1333

Gly Gly Gly His Ala Arg Leu Val His Val Lys Lys Lys
1               5                   10

<210> SEQ ID NO 1334
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1334

Gly Gly His Ile Ala Asn Val Glu Arg Val Lys Lys Lys
1               5                   10

<210> SEQ ID NO 1335
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1335

Gly Gly Lys Ala Ala Ala Thr Gln Lys Lys Lys Lys Lys
1               5                   10

<210> SEQ ID NO 1336
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

```
<400> SEQUENCE: 1336

Gly Gly Leu Ala Thr Ala Ser Thr Met Asp Lys Lys Lys
1               5                   10

<210> SEQ ID NO 1337
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1337

Gly Gly Leu Gly Pro Lys Gly Gln Thr Gly Lys Lys Lys
1               5                   10

<210> SEQ ID NO 1338
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1338

Gly Gly Leu Ser Leu Pro Glu Thr Gly Glu Lys Lys Lys
1               5                   10

<210> SEQ ID NO 1339
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine
```

<400> SEQUENCE: 1339

Gly Gly Asn Leu Ala Gly Ile Leu Lys Glu Lys Lys Lys
1               5                   10

<210> SEQ ID NO 1340
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1340

Gly Gly Asn Pro Gly Met Ser Glu Pro Val Lys Lys Lys
1               5                   10

<210> SEQ ID NO 1341
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher
<220> FEATURE:
<221> NAME/KEY: MOD_RES
<222> LOCATION: (11)..(11)
<223> OTHER INFORMATION: D-Lysine
<220> FEATURE:
<221> NAME/KEY: MOD_RES
<222> LOCATION: (12)..(12)
<223> OTHER INFORMATION: D-Lysine

<400> SEQUENCE: 1341

Gly Gly Pro Phe Gly Cys His Ala Lys Lys Lys Lys
1               5                   10

<210> SEQ ID NO 1342
<211> LENGTH: 12
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (10)..(10)
<223> OTHER INFORMATION: Lys modified with a CPQ2 quencher
<220> FEATURE:
<221> NAME/KEY: MOD_RES
<222> LOCATION: (11)..(11)
<223> OTHER INFORMATION: D-Lysine
<220> FEATURE:
<221> NAME/KEY: MOD_RES
<222> LOCATION: (12)..(12)
<223> OTHER INFORMATION: D-Lysine

```
<400> SEQUENCE: 1342

Gly Gly Pro Leu Gly Leu Arg Trp Trp Lys Lys Lys
1               5                   10

<210> SEQ ID NO 1343
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1343

Gly Gly Gln Met Gly Val Met Gln Gly Val Lys Lys Lys
1               5                   10

<210> SEQ ID NO 1344
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1344

Gly Gly Gln Thr Cys Lys Cys Ser Cys Lys Lys Lys Lys
1               5                   10

<210> SEQ ID NO 1345
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine
```

```
<400> SEQUENCE: 1345

Gly Gly Gln Trp Ala Gly Leu Val Glu Lys Lys Lys Lys
1               5                   10

<210> SEQ ID NO 1346
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1346

Gly Gly Arg Pro Ala Val Met Thr Ser Pro Lys Lys Lys
1               5                   10

<210> SEQ ID NO 1347
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1347

Gly Gly Thr Leu Arg Glu Leu His Leu Asp Lys Lys Lys
1               5                   10

<210> SEQ ID NO 1348
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine
```

<400> SEQUENCE: 1348

Gly Gly Thr Pro Pro Ser Gln Gly Lys Lys Lys Lys
1               5                   10

<210> SEQ ID NO 1349
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1349

Gly Gly Thr Ser Glu Asp Leu Val Val Gln Lys Lys Lys
1               5                   10

<210> SEQ ID NO 1350
<211> LENGTH: 13
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (11)..(11)
<223> OTHER INFORMATION: Lys modified with a CPQ2 quencher
<220> FEATURE:
<221> NAME/KEY: MOD_RES
<222> LOCATION: (12)..(12)
<223> OTHER INFORMATION: D-Lysine
<220> FEATURE:
<221> NAME/KEY: MOD_RES
<222> LOCATION: (13)..(13)
<223> OTHER INFORMATION: D-Lysine

<400> SEQUENCE: 1350

Gly Gly Val Trp Ala Ala Glu Ala Ile Ser Lys Lys Lys
1               5                   10

<210> SEQ ID NO 1351
<211> LENGTH: 1
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1351

Arg
1

<210> SEQ ID NO 1352
<211> LENGTH: 3
<212> TYPE: PRT
<213> ORGANISM: Artificial Sequence
<220> FEATURE:
<223> OTHER INFORMATION: Description of Artificial Sequence: Synthetic
      probe

```
<400> SEQUENCE: 1352

Gly Gly Cys
1

<210> SEQ ID NO 1353
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: R or K
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1353

Gly Trp Tyr Xaa Thr Gln Tyr Gly Lys
1               5

<210> SEQ ID NO 1354
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: R or K
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1354

Gly Phe Ala Xaa Arg Trp Gly Gly Lys
1               5

<210> SEQ ID NO 1355
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: F, Y, L or W
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1355

Gly Ser Tyr Xaa Pro Leu Gln Gly Lys
1               5

<210> SEQ ID NO 1356
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: F or Y
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1356

Gly Phe Ile Xaa Leu Pro Thr Gly Lys
1               5

<210> SEQ ID NO 1357
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (3)..(3)
<223> OTHER INFORMATION: T, I or V
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1357

Gly Val Xaa Asp Lys Asp Phe Gly Lys
1               5

<210> SEQ ID NO 1358
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (4)..(4)
<223> OTHER INFORMATION: R or K
<220> FEATURE:
<221> NAME/KEY: MOD_RES
<222> LOCATION: (9)..(9)
<223> OTHER INFORMATION: Lys modified with a CPQ2 quencher

<400> SEQUENCE: 1358

Gly Phe Ala Xaa Arg Trp Gly Gly Lys
1               5

<210> SEQ ID NO 1359
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: D-Lysine
```

```
<220> FEATURE:
<221> NAME/KEY: MOD_RES
<222> LOCATION: (9)..(9)
<223> OTHER INFORMATION: Lys modified with a CPQ2 quencher
<220> FEATURE:
<221> NAME/KEY: MOD_RES
<222> LOCATION: (10)..(10)
<223> OTHER INFORMATION: K or R

<400> SEQUENCE: 1359

Lys Gly Glu Phe Val His Asn Pro Lys Xaa
1               5                   10

<210> SEQ ID NO 1360
<211> LENGTH: 9
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (8)..(8)
<223> OTHER INFORMATION: Lys modified with a CPQ2 quencher
<220> FEATURE:
<221> NAME/KEY: MOD_RES
<222> LOCATION: (9)..(9)
<223> OTHER INFORMATION: K, R or H

<400> SEQUENCE: 1360

Gly Asn Ala Tyr Asn Glu Ile Lys Xaa
1               5

<210> SEQ ID NO 1361
<211> LENGTH: 11
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: W, G or F
<220> FEATURE:
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: D-Lysine
<220> FEATURE:
<221> NAME/KEY: MOD_RES
<222> LOCATION: (11)..(11)
<223> OTHER INFORMATION: Lys modified with a CPQ2 quencher

<400> SEQUENCE: 1361

Xaa Lys Asn Ala Gly Ser Lys Phe Gly Lys Lys
1               5                   10

<210> SEQ ID NO 1362
<211> LENGTH: 10
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(1)
<223> OTHER INFORMATION: Q or K
<220> FEATURE:
```

-continued

```
<221> NAME/KEY: MOD_RES
<222> LOCATION: (2)..(2)
<223> OTHER INFORMATION: carboxy-fluorescein-L-lysine
<220> FEATURE:
<221> NAME/KEY: MOD_RES
<222> LOCATION: (10)..(10)
<223> OTHER INFORMATION: Lys modified with a CPQ2 quencher

<400> SEQUENCE: 1362

Xaa Lys Lys Arg Val Gln Phe Leu Gly Lys
1               5                   10
```